(12) United States Patent
Engelhardt et al.

(10) Patent No.: US 7,749,491 B2
(45) Date of Patent: Jul. 6, 2010

(54) COMPOUNDS AND METHODS TO ENHANCE RAAV TRANSDUCTION

(75) Inventors: John F. Engelhardt, Iowa City, IA (US); Keith L. Munson, Seattle, WA (US); Ziying Yan, Iowa City, IA (US)

(73) Assignees: University of Iowa Research Foundation, Iowa City, IA (US); Targeted Genetics Corporation, Seattle, WA (US)

( * ) Notice: Subject to any disclaimer, the term of this patent is extended or adjusted under 35 U.S.C. 154(b) by 682 days.

(21) Appl. No.: 10/815,262

(22) Filed: Mar. 31, 2004

(65) Prior Publication Data
US 2005/0037497 A1 Feb. 17, 2005

Related U.S. Application Data

(60) Provisional application No. 60/459,323, filed on Mar. 31, 2003, provisional application No. 60/512,347, filed on Oct. 16, 2003.

(51) Int. Cl.
*A01N 25/28* (2006.01)
*A61K 38/06* (2006.01)
*A61K 48/00* (2006.01)
*C07H 15/24* (2006.01)
*C12N 15/00* (2006.01)
*C12N 15/86* (2006.01)

(52) U.S. Cl. .............. 424/93.1; 424/93.6; 424/417; 435/455; 435/456; 514/18; 530/331; 536/6.4

(58) Field of Classification Search ............. 424/93.1, 424/93.6, 417; 435/455, 456; 514/18; 530/331; 536/6.4
See application file for complete search history.

(56) References Cited

U.S. PATENT DOCUMENTS

| 4,501,729 | A | 2/1985 | Boucher et al. |
|---|---|---|---|
| 5,292,498 | A | 3/1994 | Boucher, Jr. |
| 5,512,269 | A | 4/1996 | Molina y Vedia et al. |
| 5,604,090 | A | 2/1997 | Alexander et al. |
| 5,628,984 | A | 5/1997 | Boucher, Jr. |
| 5,635,160 | A | 6/1997 | Stutts, III et al. |
| 5,651,957 | A | 7/1997 | Molina y Vedia et al. |
| 5,656,256 | A | 8/1997 | Boucher et al. |
| 5,683,675 | A | 11/1997 | Molina y Vedia et al. |
| 5,691,176 | A | 11/1997 | Lebkowski et al. |
| 5,716,931 | A | 2/1998 | Molina y Vedia et al. |
| 5,725,842 | A | 3/1998 | Boucher, Jr. et al. |
| 5,801,030 | A | 9/1998 | McVey et al. |
| 5,831,068 | A | 11/1998 | Nair et al. |
| 5,834,182 | A | 11/1998 | Alexander et al. |
| 5,843,742 | A | 12/1998 | Natsoulis et al. |
| 5,849,706 | A | 12/1998 | Molina y Vedia et al. |
| 5,855,918 | A | 1/1999 | Mrsny et al. |
| 5,876,700 | A | 3/1999 | Boucher, Jr. et al. |
| 5,902,567 | A | 5/1999 | Boucher, Jr. |
| 5,935,555 | A | 8/1999 | Stutts, III et al. |
| 6,022,527 | A | 2/2000 | Boucher, Jr. et al. |
| 6,033,688 | A | 3/2000 | Mrsny et al. |
| 6,037,177 | A | 3/2000 | Snyder |
| 6,083,702 | A | 7/2000 | Mitchell et al. |
| 6,133,247 | A | 10/2000 | Boucher, Jr. |
| 6,143,279 | A | 11/2000 | Boucher, Jr. et al. |
| 6,156,303 | A | 12/2000 | Russell et al. |
| 6,200,560 | B1 | 3/2001 | Couto et al. |
| 6,214,536 | B1 | 4/2001 | Boucher, Jr. |
| 6,221,349 | B1 | 4/2001 | Couto et al. |
| 6,235,266 | B1 | 5/2001 | Stutts, III et al. |
| 6,264,975 | B1 | 7/2001 | Boucher, Jr. |
| 6,270,996 | B1 | 8/2001 | Wilson et al. |
| 6,287,569 | B1 | 9/2001 | Kipps et al. |
| 6,290,951 | B1* | 9/2001 | Mikulski .............. 424/94.1 |
| 6,323,187 | B1 | 11/2001 | Yerxa et al. |
| 6,416,759 | B1 | 7/2002 | Firestone et al. |
| 6,420,347 | B1 | 7/2002 | Jacobus et al. |
| 6,436,392 | B1 | 8/2002 | Engelhardt et al. |
| 6,451,288 | B1 | 9/2002 | Boucher, Jr. et al. |
| 6,475,509 | B1 | 11/2002 | Boucher, Jr. |
| 6,475,537 | B1* | 11/2002 | King et al. ............ 424/778 |
| 6,544,786 | B1 | 4/2003 | Xiao et al. |
| 6,586,416 | B2 | 7/2003 | Bubien |
| 6,607,741 | B2 | 8/2003 | Boucher, Jr. |
| 6,613,345 | B2 | 9/2003 | Boucher, Jr. |
| 6,855,549 | B1 | 2/2005 | McCray, Jr. et al. |
| 7,060,497 | B2 | 6/2006 | Nakai et al. |
| 7,241,447 | B1 | 7/2007 | Engelhardt et al. |
| 2001/0034349 | A1 | 10/2001 | Boucher, Jr. |
| 2001/0041682 | A1 | 11/2001 | Stutts, III et al. |
| 2002/0076754 | A1 | 6/2002 | Sun et al. |
| 2002/0099023 | A1 | 7/2002 | Boucher, Jr. |

(Continued)

FOREIGN PATENT DOCUMENTS

AU    4091299    12/1999

(Continued)

OTHER PUBLICATIONS

Kapturczak et al, Curr. Mol. Med. 1:245-258, 2001.*
Mah et al, Molecular Therapy 6(1):106-112, 2001.*
Goncalves, Virology J. 2: 43; 17 pages, 2005.*
Tenenbaum et al, Gene Therapy 6: 1045-1053, 1999.*
Yan et al, J. Virology 78(6):2863-2874, 2004.*
Duan et al, J. Clin. Invest. 105:1573-1587, 2000.*
Schwarzbach et al, Int. J. Oncology 20: 1211-1218, 2002.*
Yalkinoglu et al, Int. J. Cancer 45(6): 1195-1203, 1990, Abstract only.*
Zhang et al, J. Biol. Chem. 282(31):22460-22471, 2007.*
Maitra et al, Am. J. Physiol. Cell Physiol. 280:C1031-C1037, 2001.*
Voinea et al, J. Cell. Mol. Med. 6(4):465-474, 2002.*
Oberdorf et al, Biochemistry 40(44):13397-13405, 2001.*

(Continued)

*Primary Examiner*—Kevin K. Hill
(74) *Attorney, Agent, or Firm*—Schwegman, Lundberg & Woessner, P.A.

(57) ABSTRACT

Agents and methods to alter rAAV transduction are provided.

38 Claims, 35 Drawing Sheets

U.S. PATENT DOCUMENTS

| | | | |
|---|---|---|---|
| 2002/0115619 A1 | 8/2002 | Rubenstein et al. | |
| 2002/0128203 A1 | 9/2002 | Schild | |
| 2002/0131956 A1 | 9/2002 | Walsh et al. | |
| 2002/0132770 A1 | 9/2002 | Caplan et al. | |
| 2002/0156057 A1 | 10/2002 | Bubien | |
| 2002/0158255 A1 | 10/2002 | Boucher, Jr. | |
| 2002/0165239 A1 | 11/2002 | Boucher, Jr. | |
| 2002/0197237 A1 | 12/2002 | Engelhardt et al. | |
| 2003/0003583 A1* | 1/2003 | Hirsch et al. | 435/456 |
| 2003/0087818 A1 | 5/2003 | Jiang et al. | |
| 2003/0103939 A1 | 6/2003 | Engelhardt et al. | |
| 2004/0248301 A1 | 12/2004 | Engelhardt et al. | |
| 2005/0037497 A1 | 2/2005 | Engelhardt et al. | |
| 2005/0095225 A1 | 5/2005 | Engelhardt et al. | |
| 2005/0158281 A1 | 7/2005 | Chamberlain et al. | |
| 2005/0181423 A1 | 8/2005 | Barak et al. | |
| 2005/0255087 A1 | 11/2005 | Engelhardt et al. | |
| 2008/0206198 A1 | 8/2008 | Engelhardt et al. | |
| 2008/0213221 A1 | 9/2008 | Engelhardt et al. | |
| 2008/0249050 A1 | 10/2008 | Engelhardt et al. | |
| 2009/0017062 A1 | 1/2009 | Engelhardt et al. | |

FOREIGN PATENT DOCUMENTS

| | | |
|---|---|---|
| CA | 2302627 | 9/2001 |
| EP | 0041682 A1 | 12/1981 |
| EP | 0132770 A1 | 2/1985 |
| EP | 0158255 A2 | 10/1985 |
| EP | 1153612 A1 | 11/2001 |
| EP | 1486567 A1 | 12/2004 |
| WO | WO-94/13788 A1 | 6/1994 |
| WO | WO-95/07351 A1 | 3/1995 |
| WO | WO-95/15384 A1 | 6/1995 |
| WO | WO-9610402 A1 | 4/1996 |
| WO | WO-97/22250 A1 | 6/1997 |
| WO | WO-98/09657 A2 | 3/1998 |
| WO | WO-98/24479 A1 | 6/1998 |
| WO | WO-9853839 A2 | 12/1998 |
| WO | WO-99/60146 A1 | 11/1999 |
| WO | WO-00/47220 A1 | 2/2000 |
| WO | WO-00/75365 A2 | 12/2000 |
| WO | WO-0075365 A1 | 12/2000 |
| WO | WO-0075365 A3 | 12/2000 |
| WO | WO-01/25465 A1 | 4/2001 |
| WO | WO-0125465 A1 | 4/2001 |
| WO | WO-01/83692 A2 | 11/2001 |
| WO | WO-0224172 A1 | 3/2002 |
| WO | WO-0224177 A2 | 3/2002 |
| WO | WO-02087306 A2 | 11/2002 |
| WO | WO-03006616 A2 | 1/2003 |
| WO | WO-03057847 A2 | 7/2003 |
| WO | WO-03095667 A2 | 11/2003 |
| WO | WO-2004/090145 A2 | 10/2004 |
| WO | WO-2004089423 A2 | 10/2004 |
| WO | WO-2004089423 A3 | 10/2004 |
| WO | WO-2004090145 A2 | 10/2004 |
| WO | WO-2004090145 A3 | 10/2004 |
| WO | WO-2004112727 A2 | 12/2004 |
| WO | WO-2005116224 A2 | 12/2005 |
| WO | WO-2005119251 A2 | 12/2005 |
| WO | WO-2007127464 A2 | 11/2007 |

OTHER PUBLICATIONS

"(S)-(+)-Camptothecin; 4-Ethyl-4-hydroxy-1H-pyrano[3', 4':6,7] indolizino [1,2-b] quinoline-3, 14 (4H, 12H) dione", *Calbiochem®*, Camptothecin, Camptotheca acuminata, (Oct. 2, 2000), 2 pgs.

"Adriamycin; 14-Hydroxydaunomycin, HCl", *Calbiochem®*, Doxorubicin, Hydrochloride, Catalog No. 324380, (Oct. 21, 1998), 2 pgs.

"Aminoglycoside antibiotic. Inhibits myeloperoxidase-dependent oxidant cell injury", *Calbiochem®*, Tobramycin, Free Base, Catalog No. 614005, (Aug. 26, 1999), 1 pg.

"Cancer Research", *Contribution to Society*, http://www.bikaken.or.jp/mcrf_e/contributiion, (Dec. 4, 2000), 2 pages.

"Carbobenzoxy-L-leucyl-L-leucinal", *Calbiochem®*, MG-132, Catalog No. 474790, (Oct. 15, 1999), 2 pgs.

"Drugs for Selection of Genetic Markers—Reagents for Positive and Negative Selection of Genes Involved in Nucleotide Metabolism", *Calbiochem®*, (Mar. 2002), 6 pgs.

"EPA; 20:5 w-3; 5,8, 11, 14, 17-Eicosapentaenoic Acid", *Calbiochem®*, Eicosapentaenoic Acid, Catalog No. 324875, (Dec. 7, 1998), 2 pgs.

"Epoxomicin- a potent and selective proteasome inhibitor", *Affiniti Research Products Limited*, (2001) 2 pgs.

International Search Report for corresponding PCT Application No. PCT/US2004/010045 (Jan. 10, 2005), 6 pgs.

"LDP-341", *Millennium Pharmaceuticals*, http://www.biospace.com/ct/detail.cfm?ClinicalID=266404,(2001), 1 pg.

"Mevinolin; MK-803", *Calbiochem®*, Lovastatin, Catalolg No. 438185,(Jun. 29, 2001), 2 pgs.

"MK-733", *Calbiochem®*, Simvastatin, Catalog No. 567020,(Oct. 25, 2001), 2 pgs.

"Polymer Vectors Endosomal release and cytoplasmic delivery", *Endosomal Release*, http://web.bham.ac.uk/can4psd4/nonviral/endosome.html,(Jun. 3, 2001), 1 pg.

"Product Data Sheet", *Moravek Biochemicals, Inc.*, M-1535, Ritonavir, (Jul. 12, 2001), 1 pg.

"Product Information", *Sigma®*, Cyclosporin A, Sigma Product No. C3662, (Oct. 28, 1996), 3 pgs.

"Product Information", *Sigma®*, Bleomycin Sulfate, Sigma Prod. No. B5507, (Nov. 25, 1996), 2 pgs.

"Proteasome Inhibitors", *Peptides International, Inc.*, (Apr. 16, 2001), 2 pgs.

"Tannic Acid, A.C.S. reagent", *Sigma*, www.sigma-aldrich.com/sacatolog.nsf/productlookup/Aldrich403040?OpenDocument,1 pg.

Adams, J., et al., "Chapter 28. Novel Inhibitors of the Proteasome and Their Theraputic Use in Inflammation", *Annual Reports in Medicinal Chemistry*, Academic Press, Inc., (1996), 279-288.

Adams, J., "Proteasome inhibition: a Novel Approach to Cancer Therapy", *Trends in Molecular Medicine*, 8(4), (2002), S49-S54.

Alberts, B., et al., *Molecular Biology of the Cell*, (Garland Publishing, New York, NY, 3rd Edition, 1994), 618-626.

Alexander, I. E., et al., "DNA-Damaging Agents Greatly Increase the Transduction of Nondividing Cells by Adeno-Associated Virus Vectors", *Journal of Virology*, 68 (12), (Dec. 1994),8282-8287.

Alexander, I. E., et al., "Effects of Gamma Irradiation on the Transduction of Dividing and Nondviding Cells in Brain and Muscle of Rats by Adeno-Associated Virus Vectors", *Human Gene Therapy*, 7(7), (May 1, 1996), 841-850.

Andre, P., et al., "An Inhibitor of HIV-1 Protease Modulates Proteasome Activity, Antigen Presentation, and T Cell Responses", *Proc. National Academy of Science USA*, 95, (Oct. 1998), 13120-13124.

Arcamone, F M., "From the Pigments of the Actinomycetes to Third Generation Antitumor Anthracyclines", *Biochimie* (Paris), 80(3), (Mar. 1998), 201-206.

Banerjee, D., et al., "The Treatment of Respiratory Pseudomonas Infection in Cystic Fibrosis: What Drug and Which Way?", *Drugs*, 60(5), (Abstract Only), (Nov. 2000), 1 pg.

Bartlett, J. S., et al., "Infectious Entry Pathway of Adeno-Associated Virus and Adeno-Associated Virus Vectors", *Journal of Virology*, 74(6), (Mar. 2000), 2777-2785.

Bartlett, J S., et al., "Targeted Adeno-Associated Virus Vector Transduction of Nonpermissive Cells Mediated by a Bispecific F(ab'γ)$_2$ Antibody", *Nature Biotechnology*, 17, (1999),pp. 181-186.

Basak, S , et al., "Infectious Entry Pathways for Canine Parvovirus", *Virology*, 186(2), (Feb. 1992), 368-376.

Berns, K. I., et al., "Biology of Adeno-associated Virus", *In: Current Topics in Microbiology and Immunology*, 218, Springer-Verlag, Berlin: R.W. Compans, et al., Editors, (1996), 1-23.

Berns, K. I., "Parvovirus Replication", *Microbiological Reviews*, 54(3), (Sep. 1990), 316-329.

Bies, J., et al., "Oncogenic Activation of c-Myb by Carboxyl-Terminal Truncation Leads to Decreased Proteolysis by the Ubiquitin-26S Proteasome Pathway", *Oncogene*, 14(2), (Abstract Only), (Jan. 16, 1997), 1 pg.

Bokkala, S., et al., "Angiotensin Il-induced Down-regulation of Inositol Trisphosphate Receptors in WB Rat Liver Epithelial Cells", *Journal of Biological Chemistry*, 272(19), (May 9, 1997), 12454-12461.

Bonacorsi, S., et al., "Comparative In Vitro Activities of Meropenem, Impenem, Temocillin, Piperacillin, and Ceftazidime in Combination with Tobramycin, Rifampin, or Ciprofloxacin against *Burkholderia cepacia* Isolates From Patients With Cystic Fibrosis", *Antimicrobial Agents and Chemotherapy*, 43(2), (1999), 213-217.

Brand, S., et al., "Role of the Proteasome in Rat Indomethacin-Induced Gastropathy", *Gastroenterology*, 116(4), (1999), 865-873.

Bravo, L., "Polyphenols: Chemistry, Dietary Sources, Metabolism and Nutritional Significance", *Nutrition Reviews*, 56 (11) (Nov. 1998), 317-333.

Bugg, C., et al., "SRI6975 Increases Adenovirus Mediated Gene Transfer Through the Apical Surface of Polarized MDCK Cell Monolayers", *Cystic Fibrosis Foundation: 2000 North American CF Conference*, (Nov. 2000), 1 pg.

Cantin, A. M., et al., "Aerosolized Prolastin Suppresses Bacterial Proliferation in a Model of Chronic *Pseudomonas aeruginosa* Lung Infection", *American Journal of Respiratory and Critical Care Medicine*, vol. 160, (1999), 1130-1135.

Chu, Q, et al., "Binding and Uptake of Cationic Lipid: pDNA Complexes by Polarized Airway Epithelial Cells", *Human Gene Therapy*, 10, (1999), 25-36.

Chung, K.-T., et al., "Tannis and Human Health: A Review", *Critical Reviews in Food Science and Nutrition*, 38(6), (1998),421-464.

Coonrod, A, et al., "On the Mechanism of DNA Transfection: Efficent Gene Transfer Without Viruses", *Gene Therapy*, 4, (1997), 1313-1321.

Desai, S D., et al., "Ubiquitin-Dependent Destruction of Topoisomerase I Is Stimulated by the Antitumor Drug Camptothecin", *Journal of Biological Chemistry*, 272(39), (Sep. 26, 1997),24159-24164.

Dietrich, C., et al., "p53-Dependent Cell Cycle Arrest Induced by N-acetyl-L-leucinyl-L-leucinyl-L-norleucinal in Platelet-Derived Growth Factor-Stimulated Human Fibroblasts", *Proc. Natl. Acad. Sci. USA*, 93(20), (1996), 10815-10819.

Ding, W., et al., "Proteasome Inhibitor LLnL (MG101) Augments AAV5 Transduction in Polarized Human Airway Epithelia", *American Society of Gene Therapy*, Abstracts of Scientific Presentations (Abstract No. 571), (Jun. 5, 2002), 1 pg.

Duan, D, et al., "Circular Intermediates of Recombinant Adeno-Associated Virus Have Defined Structural Characteristics Responsible for Long-Term Episomal Persistence in Muscle Tissue", *Journal of Virology*, 72 (11), (1998), 8568-8577.

Duan, D., et al., "Dynamin is Required for Recombinant Adeno-Associated Virus Type 2 Infection", *Journal of Virology*, 73(12), (1999), 10371-10376.

Duan, D., et al., "Endosomal Processing limits Gene Transfer to Polarized Airway Epithelia by Adeno-Associated Virus", *Journal of Clinical Investigation*, 105, (Jun. 2000), 1573-1587.

Duan, D., "Formation of Adeno-Associated Virus Circular Genomes is Differentially Regulated by Adenovirus E4 ORF6 and E2a Gene Expression", *Journal of Virology*, 73 (1), (Jan. 1999), 161-169.

Duan, D., "Polarity Influences the Efficiency of Recombinant Adenoassociated Virus Infection in Differentiated Airway Epithelia", *Human Gene Therapy*, 9, (Dec. 10, 1998), 2761-2776.

Duan, D, et al., "Response to "Polarity Influences the Efficiency of Recombinant Adenoassociated Virus Infection in Differentiated Airway Epithelia"", *Human Gene Therapy*, 10, (1999), 1553-1557.

Duan, D., et al., "Structural Analysis of Adeno-Associated Virus Transduction Circular Intermediates", *Virology*, 261(1), (Aug. 1999), 8-14.

Duan, D., et al., "Structural and Functional Heterogeneity of Intregrated Recombinant AAV Genomes", *Virus Research*, 48(1), (1997), 41-56.

Elliott, P J., et al., "Recent Advances in Understanding Proteasome Function", *Current Opinion in Drug Discovery and Development*, 5 (2), (1999), 484-490.

Everett, R. D., et al., "A Viral Activator of Gene Expression Functions via the Ubiquitin-Proteasome Pathway", *The EMBO Journal*, 17(24), (1998), 7161-7169.

Fasbender, A., et al., "Complexes of Adenovirus With Polycationic Polymers and Cationic Lipids Increase the Efficiency of Gene Transfer in vitro and in Vivo", *The Journal of Biological Chemistry*, 272(10), (Mar. 7, 1997), 6479-6489.

Fayadat, L., et al., "Degradation of Human Thyroperoxidase in the Endoplasmic Reticulum Involves Two Different Pathways Depending on the Folding State of the Protein", *Journal of Biological Chemistry*, 275(21), (2000), 15948-15954.

Fenteany, G., et al., "Inhibition of Proteasome Activities and Subunit-Specific Amino-Terminal Threonine Modification by Lactacystin", *Science*, 268, (1995), 726-731.

Fenteany, G., et al., "Lactacystin, Proteasome Function, and Cell Fate", *Journal of Biological Chemistry*, 273(15), (1998), 8545-8548.

Ferrari, F K., et al., "Second-Strand Synthesis Is a Rate-Limiting Step for Efficient Transduction by Recombinant Adeno-Associated Virus Vectors", *Journal of Virology*, 70 (5), (1996), 3227-3234.

Figueiredo-Pereira, M. E., et al., "The Antitumor Drug Aclacinomycin A, Which Inhibits the Degradation of Ubiquitinated Proteins, Shows Selectivity for the Chymotrypsin-Like Activity of the Bovine Pituitary 20 S Proteasome", *Journal of Biological Chemistry*, 271(28), (Jul. 12, 1996), 16455-16459.

Fisher, K., et al., "Recombinant Adeno-Associated Virus for Muscle Directed Gene Therapy", *Nature Medicine*, 3 (3), (1997), 306-312.

Fisher, K J., et al., "Transduction With Recombinant Adeno-Associated Virus for Gene Therapy Is Limited by Leading-Strand Synthesis", *Journal of Virology*, 70 (1), (1996), 520-532.

Gabizon, A., "Long-Circulating Liposomes for Drug Delivery in Cancer Therapy: a Review of Biodistribution Studies in Tumor-Bearing Animals", *Advanced Drug Delivery Reviews*, (1997), 337-344.

Gabizon, A., et al., "Preclinical Studies with Doxorubicin Encapsulated in Polyethyleneglycol-Coated Liposomes", *Journal of Liposome Research*, 3(3), (1993), 517-528.

Garber, K., "Taking Garbage In, Taking Cancer Out?", *Science*, 295, (Jan. 25, 2002), 612-613.

Goldberg, A L., et al., "New Insights Into Proteasome Function: From Archaebacteria to Drug Development", *Chemistry & Biology*, 2 (8), (1995), 503-508.

Gottlieb, T A., et al., "Actin Microfilaments Play a Critical Role in Endocytosis at the Apical but not the Basolateral Surface of Polarized Epithelial Cells", *The Journal of Cell Biology*, 120 (3), (1993), 695-710.

Halbert, C. L., "Transduction by Adeno-Associated Virus Vectors in the Rabbit Airway: Efficiency, Persistence, and Readministration", *Journal of Virology*, 71 (8), (Aug. 1997), 5932-5941.

Hasegawa, S., et al., "Microtubule Involvement in the Intracellular Dynamics for Gene Transfection Mediated by Cationic Liposomes", *Gene Therapy*, 8, (2001), 1669-1673.

Hong, J., et al., "Identification of SRI6975, A Compound that Enhances Adenovirus-Mediated Gene Expression in Polarized Epithelial Cells", *Cystic Fibrosis Foundation: 2000 North American CF Conference*, (Nov. 2000), 2 pgs.

Hsu, A., et al., "Ritonavir. Clinical Pharmacokinetics and Interactions With Other Anti-HIV Agents", *Clin Pharmacokinet*, 35(6), (Abstract Only), (Dec. 1998), 1 pg.

Huang, L., et al., "Efficient Lipofection With Cisplatin-Resistant Human Tumor Cells", *Cancer Gene Therapy*, 3(2), (1996), 107-112.

Iqbal, M., et al., "Potent Inhibitors of Proteasome", *Journal of Medicinal Chemistry*, 38(13), (1995), 2276-2277.

Jensen, T J., et al., "Multiple Proteolytic Systems, Including the Proteasome, Contribute to CFTR Processing", *Cell*, 83, (1995), 129-135.

Kaplan, J. M., et al., "Potentiation of Gene Transfer to the Mouse Lung by Complexes of Adenovirus Vector and Polycations Improves Therapeutic Potential", *Human Gene Therapy*, 9(10) (Jul. 1, 1998), 1469-1479.

Kazi, A., et al., "Inhibition of the Proteasome Activity, a Novel Mechanism Associated with the Tumor Cell Apoptosis-Inducing Ability of Genistein", *Biochemical Pharmacology*, 66, (2003), 965-976.

Kessler, P., et al., "Sodium Butyrate Greatly Enhances the Efficiency of Viral Transduction in Adult Ventricular Cardiomyocytes by Adeno-Associated Viral Vectors", *Circulation* 92(8), (Oct. 15, 1995), 296.

Kim, K. B., et al., "Proteasome Inhibition by the Natural Products Epoxomicin and Dihydroeponemycin: Insights into Specificity and Potency", *Bioorganic & Medicinal Chemistry Letters*, (1999), 3335-3340.

Kim, K., "Proteasome Inhibitors Sensitize Human Vascular Smooth Muscle Cells to Fas (CD95)—Mediated Death", *Biochemical and Biophysical Research Communications*, 281(2), (2001), 305-310.

Kiyomiya, K.-I., et al., "The Role of the Proteasome in apoptosis Induced by Anthracycline Anticancer Agents", *International Journal of Oncology*, 20(6), (Jun. 2002), 1205-1209.

Kloetzel, P M., "The Proteasome System: A Neglected Tool for Improvement of Novel Therapeutic Strategies?", *Gene Therapy*, 5, (1998), 1297-1298.

Kumar, G., "Side-Stepping the Side Effects", *BioCentury, The Bernstein Report on BioBusiness*, (Dec. 17, 2001), p. A7.

Lebkowski, J., "Adeno-Associated Virus: A Vector System for Efficient Introduction and Integration of DNA into a Variety of Mammalian Cell Types", *Molecular and Cell Biology* 8(10), (1988), 3988-3996.

Lee, S. G., et al., "Enhancement of Adenoviral Transduction With Polycationic Liposomes in vivo", *Cancer Gene Therapy*, 7(10), (2000), 1329-1335.

Lee, D. H., et al., "Proteasome Inhibitors: Valuable New Tools for Cell Biologists", *Trends in Cell Biology*, 8, (Oct. 1998), 397-403.

Lee, D. H., et al., "Selective Inhibitors of the Proteasome-Dependent and Vacuolar Pathways of Protein Degradation in *Saccharomyces cerevisiae*", *Journal of Biological Chemistry*, (Nov. 1, 1996), 27280-27284.

Lee, D. H., et al., "Chapter 10—The Proteasome Inhibitors and Their Uses", *In Proteasomes: The World of Regulatory Proteolysis*, Landes Bioscience, (2000), 154-175.

Liang, E., et al., "Oligonucleotide Delivery: A Cellular Prospective", *Pharmazie*, 54(8), (Aug. 1999), 559-566.

Lu, W., et al., "HIV Protease Inhibitors Restore Impaired T-Cell Proliferative Response in vivo and in vitro: A Viral-Suppression-Independent Mechanism", *Blood*, 96(1), (Jul. 1, 2000), 250-258.

Luo, H. et al., "A Proteasome Inhibitor Effectively Prevents Mouse Heart Allograft Rejection", *Transplantation*, 72(2), (Jul. 27, 2001), 196-202.

Mah, C., et al., "Adeno-Associated Virus Type 2—Mediated Gene Transfer: Role of Epidermal Growth Factor Receptor Protein Tyrosine Kinase in Transgene Expression", *Journal of Virology*, 72(12), (1998), 9835-9843.

Mastroianni, C. M., et al., "Ex Vivo and In Vitro Effect of Human Immunodeficiency Virus Protease Inhibitors on Neutrophil Apoptosis", *Journal of Infectious Diseases*, 182, (Nov. 2000), 1536-1539.

Meng, L., et al., "Eponemycin Exerts Its Antitumor Effect through the Inhibition of Proteasome Function", *Cancer Research*, 59, (Jun. 15, 1999), 2798-2801.

Meng, L., et al., "Epoxomicin, a Potent and Selective Proteasome Inhibitor, Exhibits in vivo Antiinflammatory Activity", *Proc. Natl. Acad. Sci. USA*, 96, (Aug. 1999), 10403-10408.

Meyer, S., et al., "Cyclosporine A is an Uncompetitive Inhibitor of Proteasome Activity and Prevents NF-κB Activation", *FEBS Letters*, 413, (1997), 354-358.

Mosnaim, A. D., et al., "Degradation Kinetics of Leucine[5] —Enkephalin by Plasma Samples from Healthy Controls and Various Patient Populations: In Vitro Drug Effects", *American Journal of Therapeutics*, 7, (2000), 185-194.

Nam, S.; et al., "Tannic Acid Potently Inhibits Tumor Cell Proteasome Activity, Increases p27 and Bax Expression, and Induces $G_1$ Arrest and Apoptosis", *Cancer Epidemiology, Biomarkers & Prevention*, (Oct. 2001), 1083-1088.

Nepka, C., et al., "Chemopreventive Activity of Very Low Dose Dietary Tannic Acid Administration in Hepatoma Bearing C3H Male Mice", *Cancer Letters*, 141, (1999), 57-62.

Nepka, C. H., et al., "Tannins, Xenobiotic Metabolism and Cancer Chemo-Prevention in Experimental Animals", *European Journal of Drug Metabolism and Pharmacokinetics*, 24(2) (1999), 183-189.

Obin, M., et al., "Neurite Outgrowth in PC12 Cells. Distinguishing the Roles of Ubiquitylation and Ubiquitin-Dependent Proteolysis", *The Journal of Biological Chemistry*, 274(17), (1999), 11789-11795.

Palombella, V. J., et al., "Role of the Proteasome and NF-κB in Streptococcal Cell Wall-Induced Polyarthritis", *Proc. Natl. Acad. Sci. USA*, 95, (Dec. 1998), 15671-15676.

Paolini, R., et al., "Ubiquitination and Degradation of Syk and ZAP-70 Protein Tyrosine Kinases in Human NK Cells Upon CD16 Engagement", *Proc. Natl. Acad. Sci. USA*, 98(17), (Aug. 14, 2001), 9611-9616.

Petrov, V., et al., "Effect of Protease Inhibitors on Angiotensin-Converting Enzyme Activity in Human T-Lymphocytes", *American Journal of Hypertension*, 13(5), (May 2000), 535-539.

Piccinini, M. , et al., "The Human 26S Proteasome is a Target of Antiretroviral Agents", *AIDS*, 16(5), (Abstract Only), Mar. 29, 2002), 1 pg.

Pickles, R J., et al., "Limited Entry of Adenovirus Vectors into Well-Differentiated Airway Epithelium Is Responsible for Inefficient Gene Transfer", *Journal of Virology*, 72 (7), (1998), 6014-6023.

Princiotta, M. F., et al., "Cells Adapted to the Proteasome Inhibitor 4-hydroxy-5-iodo-3-nitrophenylacetyl-Leu-Leu-leucinal-vinyl sulfone Require Enzymatically Active Proteasomes for Continued Survival", *Proc. Natl. Acad. Sci. USA*, 98(2), (Jan. 16, 2001), 513-518.

Prydz, K , et al., "Effects of Brefeldin A on Endocytosis, and Transport to the Golgi Complex in Polarized MDCK Cells", *The Journal of Cell Biology*, 119(2), (1992),pp. 259-272.

Puttaraju, M., et al., "Spliceosome-Mediated RNA *Trans*-Splicing as a Tool for Gene Therapy", *Nature Biotechnology*, 17(3), (Mar. 1999), 246-252.

Qing, K. , et al.; "Adeno-Associated Virus Type 2-Mediated Gene Transfer: Correlation of Tyrosine Phosphorylation of the Cellular Single-Stranded D Sequence-Binding Protein with Transgene Expression in Human Cells In Vitro and Murine Tissues In Vivo", *Journal of Virology*, 72(2), (Feb. 1998), 1593-1599.

Qing, K., et al., "Human Fibroblast Growth Factor Receptor 1 is a Co-Receptor for Infection by Adeno-Associated Virus 2", *Nature Medicine*, 5 (1), (Jan. 1999), 71-77.

Qing, K., et al., "Role of Tyrosine Phosphorylation of a Cellular Protein in Adeno-Associated Virus 2-Mediated Transgene Expression", *Proc. Natl. Acad. Sci. USA*, 94, (Sep. 1997), 10879-10884.

Rao, S., et al., "Lovastatin-Mediated $G_1$ Arrest is Through Inhibition of the Proteasome, Independent of Hydroxymethyl Glutaryl-CoA Reductase", *Proc. Natl. Acad. Sci. USA*, 96, (Jul. 1999), 7797-7802.

Rendahl, K. G., et al., "Regulation of Gene Expression in vivo Following Transduction by Two Separate rAAv Vectors", *Nature Biotechnology*, 16, (1998), 757-761.

Richards, R. G., et al., "E2-Induced Degradation of Uterine Insulin Receptor Substrate-2: Requirement for an IGF-I-Stimulated, Proteasome-Dependent Pathway", *Endocrinology*, 142(9), (Sep. 2001), 3842-3849.

Rock, K L., et al., "Inhibitors of the Proteasome Block the Degradation of Most Cell Proteins and the Generation of Peptides Presented on MHC Class I Molecules", *Cell*, 78, (1994), 761-771.

Russell, D W., et al., "DNA Synthesis and Topoisomerase Inhibitors Increase Transduction by Adeno-Associated Virus Vectors", *Proc. Natl. Acad. Sci. USA*, 92, (1995), 5719-5723.

Sanlioglu, S , et al., "Cellular Redox State Alters Recombinant Adeno-Associated Virus Transduction Through Tyrosine Phosphatase Pathways", *Gene Therapy*, 6, (1999), 1427-1437.

Schwartz, O., et al., "Antiviral Activity of the Proteasome on Incoming Human Immunodeficiency Virus Type 1", *Journal of Virology*, 72 (5), (1998), 3845-3850.

Schwartz, D., et al., "The Neutral Cysteine Protease Bleomycin Hydrolase is Essential for Epidermal Integrity and Bleomycin Resistance", *Proc. Natl. Acad. Sci. USA* 96, (Apr. 1999), 4680-4685.

Schwarz, K., et al., "The Selective Proteasome Inhibitors Lactacystin and Epoxomicin can be used to either Up- or Down-Regulate Antigen Presentation at Nontoxic Doses", *Journal of Immunology*, (2000), 6147-6157.

Shah, S., et al., "26S Proteasome Inhibition Induces Apoptosis and Limits Growth of Human Pancreatic Cancer", *Journal of Cellular Biochemistry*, 82, (2001), 110-122.

Smith, H. J., et al., "Effect of a Cancer Cachectic Factor on Protein Synthesis/Degradation in Murine C2C12 Myoblasts: Modulation by Eicosapentaenoic Acid", *Cancer Research.*, 59(21), (Abstract Only), (Nov. 1999), 1 pg.

Smith, A., et al., "The Role of the Epidermal Growth Factor Receptor in Recombinant Adeno-Associated Virus Type-2 Mediated Transgene Expression in Lung Epithelial Cells", *Molecular Therapy*, 5(5), (Abstract Only), (May 2002), S186.

Son, K., et al., "Exposure of Human Ovarian Carcinoma to Cisplatin Transiently Sensitizes the Tumor Cells for Liposome-Mediated Gene Transfer", *Proc. Natl. Acad. Sci. USA*, 91, (Dec. 1994), 12669-12672.

Son, K, et al., "Factors influencing the Drug Sensitization of Human Tumor Cells for in situ Lipofection", *Gene Therapy* (3), (1996), 630-634.

Son, K., et al., "Nitric Oxide-Mediated Tumor Cell Killing of Cisplatin-Based Interferon-γ Gene Therapy in Murine Ovarian Carcinoma", *Cancer Gene Therapy*, 7(10). 10, (2000), 1324-1328.

Swinney, D. C., et al., "Targeting Protein Ubiquitination for Drug Discovery. What is in the Drug Discovery Toolbox?", *DDT*, 6(5), (Mar. 2001), 244-250.

Tajima, K., et al., "The Proteasome Inhibitor MG132 Promotes Accumulation of the Steroidogenic Acute Regulatory Protein (StAR) and Steriodogenesis", *Federation of European Biochemical Societies*, 490,(Jan. 24, 2001), 59-64.

Teodori, L., et al., "Reduction of 1-beta-D-arabinofuranosylcytosine and adriamycin cytotoxicity Following Cell Cycle Arrest by Anguidine", *Cancer Research*, 41(4), (Abstract Only), (Apr. 1981), 1 pg.

Teramoto, S., et al., "Factors Influencing Adeno-Associated Virus-Mediated Gene Transfer to Human Cystic Fibrosis Airway Epithelial Cells: Comparison With Adenovirus Vectors", *Journal of Virology*, 72, (Nov. 1998), 8904-8912.

Tweedale, T., "[Dioxin-l] Inhibits Estrogen-Induced Breast Cancer Cell Proliferation", *Reuters Health*, http://lists.essential.org/pipermail/dioxin-l/Week-of-Mon-2000103/000096.html, (Dec. 1999), 1 pg.

Van Kerkhof, P., et al., "Proteasome Inhibitors Block a Late Step in Lysosomal Transport of Selected Membrane but not Soluble Proteins", *Molecular Biology of the Cell*, 12, (Aug. 2001), 2556-2566.

Vihinen-Ranta, M., et al., "Intracellular Route of Canine Parvovirus Entry", *Journal of Virology*, 72 (1), (1998), 802-806.

Villani, P., et al., "Antiretrovirals: Simultaneous Determination of Five Protease Inhibitors and Three Nonnucleoside Transcriptase Inhibitors in Human Plasma by a Rapid High-Performance Liquid Chromatography-Mass Spectrometry Assay", *The Drug Monit.*, 23 (4), (Abstract Only), (Aug. 2001), 1 pg.

Walters, R W., et al., "Basolateral Localization of Fiber Receptors Limits Adenovirus Infection From the Apical Surface of Airway Epithelia", *The Journal of Biological Chemistry*, 274(15), Apr. 9, 1999), 10219-10226.

Walters, R W., et al., "Incorporation of Adeno-Associated Virus in a Calcium Phosphate Coprecipitate Improves Gene Transfer to Airway Epithelia In Vitro and In Vivo", *Journal of Virology*, 74 (1), (2000),pp. 535-540.

Westfall, T. D., et al., "The Ecto-ATPase Inhibitor ARL 67156 Enhances Parasympathetic Neurotransmission in the Guinea-Pig Urinary Bladder", *European Journal of Pharmacology*, 329, (1997), 169-173.

Whitehouse, A., et al., "Downregulation of Ubiquitin-Dependent Proteolysis by Eicosapentaenoic Acid in Acute Starvation", *Biochemical and Biophysical Research Communications*, 285(3), (2001), 598-602.

Wickham, T. J., et al., "Adenovirus Targeted to Heparan-Containing Receptors Increases its Gene Delivery Efficiency to Multiple Cell Types", *Nature Biotechnology*, 14, (1996), 1570-1573.

Wickham, T. J., et al., "Targeted Adenovirus Gene Transfer to Endothelial and Smooth Muscle Cells by Using Bispecific Antibodies", *Journal of Virology*, 70 (10), (1996), 6831-6838.

Woessner, Richard , et al., "Comparison of Three Approaches to Doxorubicin Therapy: Free Doxorubicin, Liposomal Doxorubicin, and β-Glucuronidase-Activated Prodrug (HMR 1826)", *Anticancer Research*, 20, (2000), 2289-2296.

Wójcik, C., "Inhibition of the Proteasome as a Therapeutic Approach", *Drug Discovery Today*, 4(4), (Apr. 1999), 188-189.

Wójcik, C., et al., "Lovastatin and Simvastatin are Modulators of the Proteasome", *International Journal of Biochemistry & Cell Biology*, 32, (2000), 957-965.

Working, Peter , et al., "Pharmacological-Toxicological Expert Report CAELYX™ (Stealth Liposomal Doxorubicin HCI)", *Human & Experimental Toxicology*, (1996), 752-785.

Xiao, W., et al., "Adeno-Associated Virus as a Vector for Liver-Directed Gene Therapy", *Journal of Virology*, 72(12), (1998), 10222-10226.

Yan, Z., et al., "A Common Theme for Ubiquitination-Dependent Transduction of rAAV Type 2 and 5", *American Society of Gene Therapy*, Abstracts of Scientific Presentations (Abstract No. 569), (Jun. 5, 2002), 1 Pg.

Yan, Z., et al., "Distinct Classes of Proteasome-Modulating Agents Cooperatively Augment Recombinant Adeno-Associated Virus Type 2 and Type 5-Mediated Transduction From the Apical Surfaces of Human Airway Epithelia", *Journal of Virology*, 78(6), (Mar. 2004), 2863-2874.

Yan, Z ., et al., "Trans-Splicing Vectors Expand the Utility of Adeno-Associated Virus for Gene Therapy", *Proc. Natl. Acad. Sci. USA*, 97, (Jun. 6, 2000), 6716-6721.

Yang, J., et al., "Concatamerization of Adeno-Associated Virus Circular Genomes Occurs Through Intermolecular Recombination", *Journal of Virology*, 73 (11), (Nov. 1999), 9468-9477.

Zabner, J , et al., "Adenovirus-Mediated Gene Transfer to Ciliated Airway Epithelia Requires Prolonged Incubation Time", *Journal of Virology*, 70(10), (1996), 6994-7003.

Zabner, J, et al., "Adenovirus-Mediated Generation of cAMP-Stimulated CI—Transport in Cystic Fibrosis Airway Epithelia in vitro: Effect of Promoter and Administration Method", *Gene Therapy*, 3, (1996), 458-465.

Zhou, L., et al., "Improvement of Transduction Efficiency from Split AAV Vectors", *American Society of Gene Therapy*, Abstracts of Scientific Presentations (Abstract No. 584), (Jun. 5, 2002), 1 pg.

Bank, U., "Review: Peptidases and Peptidase Inhibitors in the Pathogenesis of Diseases", *Cellular Peptidases in Immune Functions and Diseases 2*, (Edited by Jurgen Langner, et al., Kluwer Academic / Plenum Publishers),(2000),349-378.

Brötz, H., "The Lantibiotic Mersacidin Inhibits Peptidoglycan Biosynthesis and the Level of Transglycosylation", *Eur. J. Biochem.*, 246(1), (1997), 193-199.

Conrad, C. K., et al., "Safety of Single-Dose Administration of an Adeno-Associated Virus (AAV)-CFTR Vector in the Primate Lung", *Gene Therapy*, 3(8), (Aug. 1996),658-668.

Croyle, M., et al., "Development of Novel Formulations that Enhance Adenoviral-Mediated Gene Expression in the Lung in Vitro and in Vivo", *Molecular Therapy*, 4(1), (2001),22-28.

Ding, W., et al., "Second-Strand Genome Conversion of Adeno-Associated Virus Type 2 (AAV-2) and AAV-5 is Not Rate Limiting Following Apical Infection of Polarized Human Airway Epithelia", *Journal of Virology*, 77(13), (2003),7361-7366.

Dishart, K., et al., "Recombinant Adeno-Associated Virus-2 as a Candidate Gene Delivery Vector for Vein Grafts", *American Society of Gene Therapy*, Abstracts of Scientific Presentations (Abstract No. 1107), (2002), 1 pg.

Donaldson, S. H., et al., "Regulation of the Epithelial Sodium Channel by Serine Proteases in Human Airways", *The Journal of Biological Chemistry*, 277(10), (2002),8338-8345.

Douar, A.-M. , et al., "Intracellular Trafficking of Adeno-Associated Virus Vectors: Routing to the Late Endosomal Compartment and Proteasome Degration", *Journal of Virology*, 75 (4), (2001),1824-1833.

Duan, D., et al., "A New Dual-Vector Approach to Enhance Recombinant Adeno-Associated Virus-Mediated Gene Expression Through Intermolecular cis Activation", *Nature Medicine*, 6(5), (2000),595-598.

Duan, D., et al., "Chapter 15: *Trans*-Splicing Vectors Expand the Packaging Limits of Adeno-Associated Virus for Gene Therapy Applications", *Methods in Molecular Medicine, vol. 76: Viral Vectors for Gene Therapy: Methods and Protocols*, (2003),287-307.

Duan, D., et al., "Chapter 3—Adeno-Associated Virus", *In: Lung Biology in Health and Disease, vol. 169—Gene Therapy in Lung Disease*, Albelda, S. M., Editor, Marcel Dekker, Inc.,(2002),51-92.

Duan, D., et al., "Chapter 3—Dual Vector Expansion of the Recombinant AAV Packaging Capacity", *In: Methods in Molecular Biology, vol. 219: Cardiac Cell and Gene Transfer*, Metzger, J. M., Editor, Human Press,-Inc., Totowa, NJ,(2003),29-51.

Duan, D., et al., "Consequences of DNA-Dependent Protein Kinase Catalytic Subunit Deficiency on Recombinant Adeno-Associated Virus Genome Circularization and Heterodimerization in Muscle Tissue", *Journal of Virology*, 77(8), (2003),4751-4759.

Duan, D., et al., "Enhancement of Muscle Gene Delivery With Pseudotyped Adeno-Associated Virus Type 5 Correlates With Myoblast Differentiation", *Journal of Virology*, 75(16), (2001),7662-7671.

Duan, D., et al., "Expanding AAV Packaging Capacity With *Trans*-splicing or Overlapping Vectors: A Quantitative Comparison", *Molecular Therapy*, 4(4), (2001),383-391.

Engelhardt, J. F., et al., "Direct Gene Transfer of Human CFTR Into Human Bronchial Epithelia of Xenografts With E1-Deleted Adenoviruses", *Nature Genetics*, 4, (1993),27-34.

Engelhardt, J. F., "The Lung as a Metabolic Factory for Gene Therapy", *The Journal of Clinical Investigation*, 110(4), (2002),429-432.

Flotte, T. R., et al., "Adeno-Associated Virus Vector Gene Expression Occurs in Nondividing Cells in the Absence of Vector DNA Integration", *American Journal of Respiratory Cell and Molecular Biology*, 11, (1994), 517-521.

Flotte, T. R., et al., "Chapter 40—Adeno-Associated Viral Vectors for CF Gene Therapy", *In: Methods in Molecular Medicine*, 70, (2002),599-608.

Gruchala, M., et al., "Adeno-Associated Virus-Mediated Gene Transfer into Normal Rabbit Arteries. Assessment of the Tie and CMV Promoters and the Antiproteasome Treatment with MG-132", *American Society of Gene Therapy*, Abstracts of Scientific Presentations—abstract No. 1110,(Jun. 5, 2002), 1 page.

Hansen, J., et al., "Adeno-Associated Virus Type 2-Mediated Gene Transfer: Altered Endocytic Processing Enhances Transduction Efficiency in Murine Fibroblasts", *Journal of Virology*, 75(9), (2001),4080-4090.

Hansen, J., et al., "Impaired Intracellular Trafficking of Adeno-Associated Virus Type 2 Vectors Limits Efficient Transduction of Murine Fibroblasts", *Journal of Virology*, 74(2), (2000),992-996.

Hosseini, H., et al., "Protection Against Experimental Autoimmune Encephalomyelitis by a Proteasome Modulator", *Journal of Neuroimmunology*, 188, (2001),233-244.

Itani, O. A., et al., "Cycloheximide Increases Glucocorticoid-Stimulated α-ENaC mRNA in Collecting Duct Cells by p38 MAPK-dependent Pathway", *Am. J. Physiol. Renal Physiol.*, 284, (2002),F778-F787.

Kiyomiya, K.-I., et al., "Mechanism of Specific Nuclear Transport of Adriamycin: The Mode of Nuclear Translocation of Adriamycin-Proteasome Complex", *Cancer Research*, (2001),2467-2471.

Mattsson, K., et al., "Proteins Associated With the Promyelocytic Leukemia Gene Product (PML)-Containing Nuclear Body Move to the Nucleolus Upon Inhibition of Proteaseome-Dependent Protein Degradation", *Proc. National Academy of Science*, 98(3), (2001), 1012-1017.

McAuliffe, O., et al., "Lantibiotics: Structure, Biosynthesis and Mode of Action", *FEMS Microbiology Reviews*, 25(3), (2001),285-308.

Nielsen, J., et al., "Spironolactone-Mediated Downregulation of the Epithelial Sodium Channel (eNaC) in Rat Kidney", *FASEB Journal*, 15 (1) (Abstracts Part I), (Abstract No. 393.11), (2001), A432.

Parker, J. S., et al., "Cellular Uptake and Infection by Canine Parvovirus Involves Rapid Dynamin-Regulated Clathrin-Mediated Endocytosis, Followed by Slower Intracellular Trafficking", *Journal of Virology*, 74(4), (2000),1919-1930.

Sanlioglu, S., et al., "Endocytosis and Nuclear Traffickling of Adeno-Associated Virus Type 2 Are Controlled by Rac1 and Phosphatidylinositol-3 Kinase Activation", *Journal of Virology*, 74(19), (2000),9184-9196.

Sanlioglu, S., et al., "Lipopoolysaccharide Induces Rac1-Dependent Reactive Oxygen Species Formation and Coordinates Tumor Necrosis Factor-alpha Secretion Through IKK Regulation of NF-κB", *The Journal of Biological Chemistry*, 276(32), (2001),30188-30198.

Sanlioglu, S., et al., "Loss of ATM Function Enhances Recombinant Adeno-Associated Virus Transduction and Integration Through Pathways Similar to UV Irradiation", *Virology*, 268, (2000),68-78.

Sanlioglu, S., et al., "Rate Limiting Steps of AAV Transduction and Implications for Human Gene Therapy", *Current Gene Therapy* 1, (2001), 137-147.

Sanlioglu, S., et al., "Two Independent Molecular Pathways for Recombinant Adeno-Associated Virus Genome Conversion Occur After UV-C and E4orf6 Augmentation of Transduction", *Human Gene Therapy*, 10(4), (1999),591-602.

Sasaki, T., et al., "Inhibitory Effect of di- and Tripeptidyl Aldehydes on Calpains and Cathepsins", *Journal of Enzyme Inhibition*, 3(3), (1990),195-201.

Staub, O., "Chapter 5 Regulation of ENaC by Interacting Proteins and by Ubiquitination", *Current Topics in Membranes, 47—Amiloride-Sensitive Sodium Channels—Physiology and Functional Diversity*, Edited by Dale J. Benos, Academic Press, Publisher,(1999),65-87.

Staub, O., "Regulation of Stability and Functional of the Epithelial $Na^+$ Channel (ENaC) by Ubiquitination", *The EMBO Journal*, 16(21), (1997),6325-6336.

Stockand, J. D., et al., "Targeted Degradation of the Epithelial Na Channel (ENaC) in Response to PKC Activation of the MAPK 1/2 Cascade", *The FASEB Journal*, 17(5), Abstracts (Part II), (Abstract No. 585.7),(2003),A913.

Stokes, J. B., "Regulation of rENac mRNA by Dietary NaCl and Steroids: Organ, Tissue, and Steroid Heterogeneity", *American Journal of Physiology, Cell Physiology*, 274, (1998),C1699-C1707.

Yan, Z., et al., "[20] Recombinant AAV-Mediated Gene Delivery Using Dual Vector Heterodimerizatiion", *In: Methods in Enzmology, vol. 346: Gene Therapy Methods*, Phillips, M. I., Editor, Academic Press, San Diego, CA,(2002),334-357.

"U.S. Appl. No. 11/796,605, Preliminary Amendment Sep. 11, 2007", 6 pgs.

"Application Serial No. 04749597.3, Office Action Nov. 20, 2006", 3 pgs.

"Application Serial No. 04749597.3, Office Action mailed Mar. 28, 2006", 9 pgs.

"Application Serial No. 04749597.3, Response filed Sep. 6, 2007 to Office Action Nov. 20, 2006", 6 pgs.

"Application Serial No. 04749597.3, Response filed Oct. 6, 2006 to Office Action mailed Mar. 28, 2006", 28 pgs.

"Application Serial No. 782966, Response filed Jul. 7, 2005 to Foreign Office Action Nov. 18, 2004", 15 pgs.

"Application Serial No. 782966 Report", 3 pgs.

"Application Serial No. 782966, Foreign office Action Jul. 18, 2005", 2 pgs.

"Application Serial No. 00944624.6, Foreign Office Action Mar. 4, 2005", 5 pgs.

"Application Serial No. 00944624.6, Foreign Office Action Aug. 5, 2003", 3 pgs.

"Application Serial No. 00944624.6, Response filed Feb. 16, 2004 to Office Action Mailed Aug. 5, 2003", 25 pgs.

"Application Serial No. 00944624.6, Response filed Aug. 26, 2005 to Office Action mailed Mar. 4, 2005", 31 pgs.

"Application Serial No. 04749619.5, Office Action mailed Mar. 28, 2006", 8 pgs.

"Application Serial No. 04749619.5, Office Action mailed Nov. 20, 2006", 4 pgs.

"Application Serial No. 04749619.5, Response filed Sep. 7, 2007 to Office Action mailed Nov. 20, 2006", 28 pgs.

"Application Serial No. 04749619.5, Response filed Oct. 17, 2006 to Office Action mailed Mar. 28, 2006", 17 pgs.

"U.S. Appl. No. 09/689,136 Advisory Action mailed Nov. 3, 2004", 3 pgs.

"U.S. Appl. No. 09/689,136 Amendment filed Aug. 3, 2005", 13 pgs.

"U.S. Appl. No. 09/689,136 Amendment filed Nov. 18, 2004", 11 pgs.

"U.S. Appl. No. 09/689,136 Final Office Action mailed Feb. 24, 2003", 11 pgs.

"U.S. Appl. No. 09/689,136 Final Office Action mailed Jun. 18, 2004", 8 pgs.

"U.S. Appl. No. 09/689,136 Non Final Office Action mailed Jan. 7, 2005", 10 pgs.

"U.S. Appl. No. 09/689,136 Non Final Office Action mailed Jun. 26, 2002", 13 pgs.

"U.S. Appl. No. 09/689,136 Non Final Office Action mailed Aug. 12, 2003", 8 pgs.

"U.S. Appl. No. 09/689,136 Notice of Allowance mailed Sep. 12, 2005", 10 pgs.

"U.S. Appl. No. 09/689,136 Preliminary Amendment filed Oct. 12, 2000", 2 pgs.

"U.S. Appl. No. 09/689,136 Response filed Jan. 12, 2004 to Non Final Office Action mailed Aug. 12, 2003", 12 pgs.

"U.S. Appl. No. 09/689,136, Response filed May 18, 2005 to Non Final Office Action mailed Jan. 7, 2005", 14 pgs.

"U.S. Appl. No. 09/689,136 Response filed May 30, 2003 to Final Office Action mailed Feb. 24, 2003", 13 pgs.

"U.S. Appl. No. 09/689,136 Response filed Oct. 18, 2004 to Final Office Action mailed Jun. 18, 2004", 13 pgs.

"U.S. Appl. No. 09/689,136 Response filed Nov. 26, 2002 to Non Final Office Action mailed Jun. 26, 2002", 14 pgs.

"U.S. Appl. No. 10/815,557 Non Final Office Action mailed May 21, 2007", 24 pgs.

"U.S. Appl. No. 10/815,557 Response filed Aug. 21, 2007 to Non Final Office Action mailed May 21, 2007", 22 pgs.

"U.S. Appl. No. 10/815,557, Final-Office Action Mailed Nov. 14, 2007", 29 pgs.

"U.S. Appl. No. 11/301,601, Non-Final Office Action mailed Jul. 12, 2007", 29 pgs.

"U.S. Appl. No. 11/301,601, Response filed Oct. 11, 2007 to Non-Final Office Action mailed Jul. 12, 2007", 14 pages.

"U.S. Appl. No. 11/301,601 Preliminary Amendment filed Aug. 7, 2007", 9 pgs.

"U.S. Appl. No. 11/301,601, Preliminary Amendment filed Dec. 13, 2005", 9 pgs.

"U.S. Appl. No. 11/301,601, Response filed Aug. 11, 2007 Non-Final Office Action mailed Jul. 12, 2007", 14 pgs.

"U.S. Appl. No. 11/301,601 Final Office Action mailed Dec. 13, 2007", 15 pgs.

"U.S. Appl. No. 11/890,777, Preliminary Amendment filed Aug. 7, 2007", 9 pgs.

"Application Serial No. 501645/01, Preliminary Amendment filed May 31, 2007", 12 pgs.

"Enzyme database entry for EC No. 3.4.22", ,, [online}. Retrieved from the Internet: <http://ca.expasy.org/enzyme/3.4.22>, (Jun. 19, 2007),2 pgs.

"International Application Serial No. PCT/US 00/15700, International Search Report Dec. 21, 2000",9 pgs.

"International Application Serial No. PCT/US 00/15700, Written Opinion Aug. 1, 2001", 7 pgs.

"International Application Serial No. PCT/US2007/010434, International Search Report mailed Dec. 5, 2007", 11 pgs.

"International Application Serial No. PCT/US2007/010434, Written Opinion mailed Dec. 5, 2007", 19 pgs.

"International Search Report for corresponding PCT Application No. PCT/US2004/009950 mailed Mar. 8, 2005", 8 pgs.

"Written Opinion for corresponding PCT Application No. PCT/US2004/009950", (Mar. 8, 2005), 15 pgs.

"Written Opinion for corresponding PCT Application No. PCT/US2004/010045", (Jan. 10, 2005), 15 pgs.

Audige, A., et al., "Epithelial sodium channel (ENaC) subunit mRNA and protein expression in rats with puromycin aminonucleoside-induced nephrotic syndrome.", *Clincial Sci.*, 104(4), (2003),389-395.

Auerbach, S. D., et al., "Human Amiloride-Sensitive Epithelial $Na^+$ Channel y Subunit Promoter: Functional Analysis and Identification of a Polypurine-Polypyrimidine Tract With the Potential for Triplex DNA Formation", *Biochem. J.*, 347, (2000), 105-114.

Baines, D. L., et al., "Effect of LPS-Induced NF-κB Activity on the Transcriptional Response of a 5' Flanking Region of the alphaENaC Gene", *Experimental Biology 2003—Translating the Genome*, Abstract No. 5860 (http://www.biosis-select.org/faseb/data/FASEB005860.html,(2003), 1 pg.

Baruchel, S., et al., "The role of oxidative stress in disease progression in individuals infected by the human immunodeficiency virus.", *J Leukoc Biol.*, 52(1), (Jul. 1992), 111-4.

Beutler, K. T., et al., "Long-Term Regulation of ENaC Expression in Kidney by Angiotensin II", *Hypertension*, 41, (2003),1143-1150.

Billington, D., et al., "Dissection of hepatic receptor-mediated endocytic pathways using self-generated gradients of iodixanol (Optiprep).", *Anal. Biochem.*, 258(8), (1998),251-258.

Bohl, D., et al., "Control of erythropoietin delivery by doxycycline in mice after intramuscular injection of adeno-associated vector.", *Blood*, 92(5), (1998),1512-1517.

Booth, R. E., et al., "Targeted Degradation of ENaC in Response to PKC Activation of the ERK1/2 Cascade", *Am. J. Physiol. Renal Physiol.*, 284, (2003),F938-F947.

Bruno, T. , et al., "Levels of Expression of hRPB11, a core subassembly subunit of human RNA polymerase II, affect doxorubicin sensitivity and cellular differentiation", *FEBS Letters 427*, (1998),241-246.

Bubien, J. K., et al., "Expression and regulation of normal and polymorphic epithelial sodium channel by human lymphocytes", *J. Biol. Chem.*, 276(11), (2001),8557-8566.

Buffinton, G. D., et al., "Oxidative stress in lungs of mice infected with influenza A virus", *Free Radic Res Commun.*, 16(2), (1992),99-110.

Cai, J., et al., "Inhibition of influenza infection by glutathione.", *Free Radic Biol Med.*, 34(7), (Apr. 1, 2003),928-36.

Dollard, S. C., et al., "Enhanced responsiveness to nuclear factor kappa B contributes to the unique phenotype of simian immunodeficiency virus variant SIVsmmPBj14.", *J Virol.*, 68(12), (Dec. 1994),7800-9.

Droge, W. , et al., "HIV-induced cysteine deficiency and T-cell dysfunction—a rationale for treatment with N-acetylcysteine", *Immunol Today.*, 13(6), (Jun. 1992),211-4.

Ecelbarger, C. A., et al., "Regulation of the Abudance of Renal Sodium Transporters and Channels by Vasopressin", *Experimental Neurology*, 171, (2001),227-234.

Eck, et al., *Goodman & Gilman's The Pharmacological Basis of Therapeutics*, 9th Edition, Chapter 5, McGraw-Hill,NY.

Engelhardt, J. , et al., "Adeno-Associated Virus Vectors", U.S. Appl. No. 60/086,166, filed May 20, 1998.

Engelhardt, John, et al., "Compounds and Methods to Enhance Adeno-Associated Virus Transduction", U.S. Appl. No. 60/138,188, filed Jun. 8, 1999.

Engelhardt, John, et al., "Compounds and Methodsd to Enhance Adeno-Associated Virus Transduction", U.S. Appl. No. 60/201,089, filed May 2, 2000.

Engelhardt, John , et al., "Enhancement of Muscle Gene Delivery With Pseudotyped AAV-5 Correlates With Myoblast Differentiation", U.S. Appl. No. 60/305,204, filed Jul. 13, 2001.

Englehardt, John , "Compounds and Methods for Pharmico-Gene Therapy of Epithelial Sodium Channel Associated Disorders" U.S. Appl. No. 60/512,347, filed Oct. 16, 2003.

Englehardt, John , et al., "Compounds and Methods to Enhance rAAV Transduction", U.S. Appl. No. 60/459,323, filed Mar. 31, 2003.

Englehardt, John , et al., "Pseudotyped Adeno-Associated Viruses and Uses Thereof", U.S. Appl. No. 10/194,421, filed Jul. 12, 2002.

Fallin, R. A., et al., "PMA-Induced Inhibition of Amiloride-Sensitive Sodium Absorption is Partially Mediated by ERK1/2 Activation", *The FASEB Journal*, 17(5) (Abstracts Part II), Abstract No. 585-19,(2003),A915.

Gadallah, M. F., et al., "Epithelial Sodium Channel-Dependent Hyptertension: An Emerging Syndrome", *Journal of the American Society of Nephrology*, 10 (Abstracts Issue), Abstract No. A1842,(1999),365A.

Gadallah, M. F., et al., "Preservation of Renal Function in Patients With Hypertension and Chronic Renal Impairment; Revisited", *Journal of the American Society of Nephrology*, 10 (Abstracts Issue), Abstract No. A1841,(1999),365A.

Gormley, K., et al., "Regulation of the Epithelial Sodium Channel by Accessory Proteins", *Biochem. J.*, 371 (2003),1-14.

Graham, J. M., et al., "Iodixanol—a new density gradient medium for the dissection of the endosomal compartment", *Z Gastroenterol.*, 34 Suppl 3, (1996),76-8.

Graham, J., "Purification of peroxisomes using a density barrier in a swinging-bucket rotor.", *ScientificWorldJournal*, 2, (May 22, 2002),1400-3.

Graham, J., et al., "The preparation of subcellular organelles from mouse liver in self-generated gradients of iodixanol", *Anal. Biochem.*, 220(2), (1994),367-73.

Hummler, E., et al., "Genetic Disorders of Membrane Transport—V. The Epithelial Sodium Channel and its Implication in Human Diseases", *American Journal of Physiology, Gastrointensinal and Liver Physiology*, 276, (1999),G567-G571.

Hunziker, et al., "Review—Perspectives: toward a peptide-based vaccine against hepatitis C virus", *Molecular Immunol*, 38, (2001),475-484.

Jiang, Q., et al., "Cellular Heterogeneity of CFTR Expression and Function in the Lung: Implications for Gene Therapy of Cystic Fibrosis", *European Journal of Human Genetics*, 6, (Jan. 1998),12-31.

Johnson, L. G., et al., "Efficiency of gene transfer for restoration of normal airway epithelial function in Cystic Fibrosis", *Nature Genetics 2*, (1992),21-25.

Jorgensen, M. J., et al., "Expression of Completely y-Carboxylated Recombinant Human Prothrombin", *The Journal of Biological Chemistry*, 262(14), (1987),6729-6734.

Kamynina, E., et al., "Concerted Action of ENaC, Nedd4-2, and Sgk1 in Transepithelial Na$^+$ Transport", *Am. J. Physiol. Renal Physiol.*, 283, (2002),F377-F387.

Kannan, R., et al., "Impairment of conjunctival glutathione secretion and ion transport by oxidative stress in an adenovirus type 5 ocular infection model of pigmented rabbits.", *Free Radic Biol Med.*, 37(2), (Jul. 15, 2004),229-38.

Kellenberger, et al., "Epithelial Sodium Channel/Degenerin Family of Ion Channels: A Variety fo Functions for a Shared Structure", *Physiological Review*, 82, (2002),735-767.

Lambeth, David J., "Nox enzymes and the biology of reactive oxygen", *Nature Reviews, Immunology* Mar. 2004, vol. 4, No. 3, Mar. 2004, pp. 181-189, XP002450232, 9.

Lechardeur, et al., "Intracellular Barriers to Non-Viral Gene Transfer", *Curr. Gene Therapy*, 2, (2002),183-194.

Li, Q., et al., "Nox2 and Rac1 regulate H2O2-dependent recruitment of TRAF6 to endosomal interleukin-1 receptor complexes", *Mol Cell Biol.*, 26(1), (Jan. 2005),140-54.

Lin, H. C., et al., "Prediction of tyrosine sulfation sites in animal virus", *Biochemical And Biophysical Research Communications*,312(4), (Dec. 26, 2003),1154-1158.

Loguercio, C., et al., "Oxidative stress in viral and alcoholic hepatitis.", *Free Radic Biol Med.*, 34(1), (Jan. 1, 2003),1-10.

Maitra, R., et al., "Increased Functional Cell Surface Expression of CFTR and deltaF508-CFTR by the Anthracycline doxorubicin", *Am. J. Physiol. Cell Physiol.*, 280, (May 2001),C1031-C1037.

Malik, B., et al., "ENaC Degradation in A6 Cells by the Ubiquitin-Proteosome Proteolytic Pathway", *The Journal of Biological Chemistry*, 276(16), (Apr. 20, 2001),12903-12910.

Marshall, E., "Gene Therapy's Growing Plans", *Science 269*(5227), (1995),1050-1055.

Matalon, S., et al., "Lung Edema Clearance: 20 Years of Progress—Invited Review: Biophysical Properties of Sodium Channels in Lung Alveolar Epithelial Cells", *J. Appl. Physiol.*, 93, (2002),1852-1859.

McFadden, G., "Even viruses can learn to cope with stress.", *Science*, 279(5347), (Jan. 2, 1998),40-1.

Mihm, S., et al., "Inhibition of HIV-1 replication and NF-kappa B activity by cysteine and cysteine derivatives.", *AIDS*, 5(5), (May, 1991),497-503.

Mirshahi, M., et al., "Paradoxical Effects of Mineralocorticoids on the Ion Gated Sodium Channel in Embryologically Diverse Cells", *Biochemical and Biophysical Research Communications*, 270, (2000),811-815.

Nakamura, H., et al., "Redox imbalance and its control in HIV infection", *Antioxid Redox Signal.*, 4(3), (Jun. 2002),455-64.

Nakayama, M., et al., "Hypomethylation Status of CpG Sites at the Promoter Region and Overexpression of the Human MDR1 Gene in Acute Myeloid Leukemias", *Blood*, 92(11), (1998),4296-4307.

Newman, G. W., et al., "Opposing regulatory effects of thioredoxin and eosinophil cytotoxicity-enhancing factor on the development of human immunodeficiency virus 1.", *J Exp Med.*, 180(1), (Jul. 1, 1994),359-63.

Oda, T., et al., "Oxygen radicals in influenza-induced pathogenesis and treatment with pyran polymer-conjugated SOD.", *Science*, 244(4907), (May 26, 1989),974-6.

Orkin, S. H., et al., "Report and recommendation of the Panel to Assess the NIH Investment in Research on Gene Therapy", [on-line]. [retrieved Jul. 6, 2007]. Retrieved from the Internet: <URL: file://E:\Enablement Rejections\Generally usefu art\wwwnihgov-newspanelrephtm.htm>,(Dec. 7, 1995),39 pgs.

Plonne, D., et al., "Separation of the intracellular secretory compartment of rat liver and isolated rat hepatocytes in a single step using self-generating gradients of iodixanol.", *Anal Biochem.*, 276(1), (Dec. 1, 1999),88-96.

Ross, G., et al., "Gene Therapy in the United States: A Five-Year Status Report", *Human Gene Therapy*, 7, (1996),1781-1790.

Rotin, D., "Regulation of the Epithelial Sodium Channel (ENaC) by Accessory Proteins", *Current Opinion in Nephrology and Hypertension*, 9, (2000),529-534.

Rotin, D., et al., "Trafficking and Cell Surface Stability of ENaC", *Am. J. Physiol. Renal Physiol.*, 281, (2001),F391-F399.

Rubanyi, G. M., "The Future of Human Gene Therapy", *2001 Mol Aspects Med.* 22, 113-142.

Sakai, et al., "Cloning and functional expression of a novel degenerin-like Na$^+$ channel gene in mammals", *J. Physiol 519*, (1999),323-333.

Sanlioglu, S, et al., "Cellular redox state alters recombinant adeno-associated virus transduction through tyrosine phosphate pathways", *Gene Therapy* Aug. 1999. vol. 6, No. 8 pp. 1427-1437, XP002450231, (Aug. 1999),11.

Sanlioglu, S., et al., "Endocytosis and nuclear trafficking of adeno-associated virus type 2 are controlled by rac1 and phosphatidylinositol-3 knase activation", *Journal of Virology*, 74(9), (Oct. 2000),9184-9196.

Sanlioglu, et al., "Novel Approaches to Augment Adeno-Associated Virus Type-2 Endocytosis and Transduction", *Virus Research and Transduction*,104(1), (Aug. 2004),51-59.

Schaefer, et al., "Molecular cloning, functional expression and chromosomal localization of an amiloride-sensitive Na$^+$ channel from human small intestine", *FEBS Letters 471*, (2000),205-210.

Schreck, R., et al., "Antioxidants selectively suppress activation of NF-kappa B by human T-cell leukemia virus type I Tax protein", *J Virol.*, 66(11), (Nov. 1992),6288-93.

Schwarz, K., "Oxidative stress during viral infection: a review.", *Free Radic Biol Med.*, 21(5), (1996),641-9.

Shisler, J. L., et al., "Ultraviolet-induced cell death blocked by a selenoprotein from a human dermatotropic poxvirus", *Science*,279(5347), (Jan. 2, 1998), 102-5.

Snyder, P. M., et al., "Serum and Glucocorticoid-Regulated Kinase Modulates Nedd4-2-Mediated Inhibition of the Epithelial NA+ Channel", *The Journal of Biological Chemistry*,277(1), (2002),5-8.

Sonntag, Florian, et al., "Adeno-associated Virus Type 2 Capsids with Externalized VP1/VP2 Trafficking Domains Are Generated Prior to Passage through the Cytoplasm and Are Maintained until Uncoating Occurs", *Journal of Virology*, vol. 80, No. 22,(Nov. 2006),11040-11054.

Spindler, B., et al., "Characterization of Early Aldosterone-induced RNAs identified in A6 Kidney Epithelia", *Pfluegers Archiv*, vol. 434, Springer Verlag, Berlin, DE XP001025924 ISSN: 0031-6768,(1997),323-331.

Stutts, M. J., et al., "Cystic fibrosis transmembrane conductance regulator inverts protein kinase A-mediated regulation of epithelial sodium channel single channel kinetics.", *J. Biol. Chem.*, 272(22), (1997),14037-14040.

Teoh, M. L., et al., "Tumorigenic poxviruses up-regulate intracellular superoxide to inhibit apoptosis and promote cell proliferation", *J Virol.*, 79(9), (May 2005),5799-811.

Thomas, C. P., et al., "Genomic Organization of the 5' End of Human B-ENaC and Preliminary Characterization of its Promoter", *Am. J. Physiol. Renal Physiol.* 282, (2002),F898-F909.

Thrasher, A J., et al., "Generation of recombinant adeno-associated virus (rAAV) from an adenoviral vector and functional reconstitution of the NADPH-oxidase", *Gene Therapy*, Macmillan Press Ltd., Basinstoke, GB, Vo. 2, 1995, pp. 481-485, XP000651495, (1995),5.

Trischler, M., et al., "Biochemical analysis of distinct Rab5- and Rab11-positive endosomes along the transferrin pathway.", *J Cell Sci.*, 112 ( Pt 24), (Dec. 1999),4773-4783.

Vema, I. M., et al., "Gene Therapy—Promises, Problems and Prospects", *Nature*, 389, (1997),239-242.

Xia, W., et al., "Presenilin 1 regulates the processing of beta-amyloid precursor protein C-terminal fragments and the generation of amyloid beta-protein in endoplasmic reticulum and Golgi", *Biochemistry*, 37(47), (Nov. 24, 1998),16465-71.

Yan, Z., et al., "Distinct Classes of Proteasome-Modulating Agents Cooperatively Augment Recombinant Adeno-Associated Virus Type 2 and Type 5-Mediated Transduction from the Apical Surfaces of Human Airway Epithelia", *Journal of Virology*, 78, (Mar. 2004),2863-2874.

Zentner, M. D., "The Amiloride-Sensitive Epithelial Sodium Channel a-Subunit is Transcriptionally Down-Regulated in Rat Parotid Cells by the Extracellular Signal-Regulated Protein Kinase Pathway", *The Journal of Biological Chemistry*, 273(46), (1998),30770-30776.

U.S. Appl. No. 09/689,136, Response filed Apr. 11, 2002 to Restriction requirement mailed Oct. 11, 2001, 12 pgs.

U.S. Appl. No. 09/689,136, Restriction requirement mailed Oct. 11, 2001, 9 pgs.

U.S. Appl. No. 10/815,557, Amendment and Response mailed May 14, 2008 to Final Office Action mailed Nov. 14, 2007, 18 pages.

U.S. Appl. No. 10/815,557, Non-Final Office Action mailed Aug. 13, 2008, 25 pgs.

U.S. Appl. No. 11/890,761, Preliminary Amendment mailed May 19, 2008, 8 pgs.

Djaldetti, M., et al., "SEM observations on the effect of anthracycline drugs on cultured newborn rat cardiomyocytes (Abstract Only)", *Basic Res Cardiol.*, vol. 6, (1988), 627-627.

Gross, R., "Clinical problems of optimum bioavailability, in particular in cytostatic therapy (Abstract Only)", *Arzneimittelforschung*, vol. 26(1A), (1976), 130-135.

Patel, et al., "identification of Yeast DNA Topoisomerase II Mutants Resistant to the Antitumor Drug Doxorubcin: Implications for the Mechanisms of Doxorubicin Action and Cytotoxicity", *Pharmacol. 52*(4), (1997), 658-666.

"U.S. Appl. No. 10/815,557 Non-Final Office Action mailed Feb. 3, 2009", 23 pgs.

"U.S. Appl. No. 10/815,557 Response filed Nov. 13, 2008 to Non-Final Office Action mailed Aug. 13, 2008", 19 pgs.

"U.S. Appl. No. 10/837,029 Final Office Action mailed Jan. 8, 2009", 9 pgs.

"U.S. Appl. No. 10/837,029 Response filed Oct. 15, 2008 to Non-Final Office Action mailed Jul. 15, 2008", 13 pgs.

"U.S. Appl. No. 10/837,029 Response filed Apr. 17, 2009 to Final Office Action mailed Jan. 8, 2009", 13 pgs.

"U.S. Appl. No. 10/837,029, Supplemental Amendment filed Oct. 16, 2007 to Non-Final Office Action mailed Apr. 11, 2007", 16 pgs.

"U.S. Appl. No. 11/301,601 Advisory Action mailed Mar. 24, 2008", 6 pgs.

"U.S. Appl. No. 11/301,601 Final Office Action mailed Apr. 3, 2009", 16 pgs.

"U.S. Appl. No. 11/301,601 Non-Final Office Action mailed Oct. 2, 2008", 15 pgs.

"U.S. Appl. No. 11/301,601 Response filed Mar. 13, 2008 to Final Office Action mailed Dec. 13, 2007", 10 pgs.

"U.S. Appl. No. 11/301,601 Second Preliminary Amendment filed Jan. 25, 2006", 3 pgs.

"U.S. Appl. No. 11/890,777 Preliminary Amendment filed Aug. 7, 2007", 9 pgs.

"U.S. Appl. No. 11/890,776 Preliminary Amendment filed May 9, 2008", 6 pgs.

"Australia application No. 2004/227358 Office Action mailed Sep. 23, 2008", 4 pgs.

"U.S. Appl. No. 10/837,029, Non-Final Office Action mailed Jun. 23, 2009", 11 pgs.

"U.S. Appl. No. 10/837,029, Response filed Nov. 19, 2009 to Non Final Office Action mailed Jun. 23, 2009", 14 pgs.

"U.S. Appl. No. 11/301,601 Response filed Jul. 1, 2009 to Final Office Action mailed Apr. 3, 2009", 12 pgs.

"U.S. Appl. No. 11/301,601, Non-Final Office Action mailed Sep. 28, 2009", 13 pgs.

"U.S. Appl. No. 11/796,605 Restriction Requirement mailed Jul. 7, 2009", 7 pgs.

"U.S. Appl. No. 11/890,761, Non-Final Office Action mailed Jul. 16, 2009", 16 pgs.

"U.S. Appl. No. 11/890,761, Response filed Oct. 29, 2009 to Non Final Office Action mailed Jul. 16, 2009", 19 pgs.

"Australian Application No. 2004227915, Report mailed Dec. 5, 2008", 2 pgs.

"Australian Application Serial No. 2004227358, Report No. 2 mailed Aug. 27, 2009", 2 pgs.

"Australian Application Serial No. 2004227358, Response filed Jul. 10, 2009 to First Report dated Sep. 23, 2008", 10 pgs.

"Canadian Application Serial No. 2,376,400, Office Action mailed Apr. 7, 2008", 4 pgs.

"Canadian Application Serial No. 2,376,400, Response filed Oct. 7, 2008 to Office Action mailed Apr. 7, 2008", 49 pgs.

"European Application Serial No. 04749619.5, Office Action mailed Mar. 11, 2009", 4 pgs.

Adams, J., et al., "Proteasome inhibition: a new strategy in cancer treatment.", *Invest New Drugs*, 18(2), (May 2000), 109-21.

Almond, J. B., et al., "The proteasome: a novel target for cancer chemotherapy", *Leukemia*, 16, (2002), 443-443.

Wu, J., "On the role of proteasomes in cell biology and proteasome inhibition as a novel frontier in the development of immunosuppressants.", *Am J Transplant.*, 2(10), (Nov. 2002), 904-12.

"U.S. Appl. No. 09/689,136, Interview Summary mailed Apr. 18, 2005", 3 pgs.

"U.S. Appl. No. 09/689,136, Interview Summary mailed May 15, 2005", 3 pgs.

"U.S. Appl. No. 09/689,136, Interview Summary mailed Sep. 28, 2004", 3 pgs.

"U.S. Appl. No. 10/815,557, Interview Summary mailed Feb. 6, 2007", 4 pgs.

"U.S. Appl. No. 10/837,029, Interview Summary mailed Nov. 15, 2007", 3 pgs.

"U.S. Appl. No. 10/837,029, Response filed Nov. 19, 2009 to Non-Final Office Action mailed Jun. 23, 2009", 14 pgs.

"U.S. Appl. No. 11/301,601. Response filed Jan. 4, 2010 to Non-Final Office Action mailed Sep. 28, 2009", 12 pgs.

"U.S. Appl. No. 11/890,761, Final Office Action mailed Dec. 22, 2009", 15 pgs.

"U.S. Appl. No. 11/890,761, Response filed Apr. 14, 2009 to Restriction Requirement mailed Oct. 14, 2008", 7 pgs.

"U.S. Appl. No. 11/890,776, Restriction Requirement mailed Dec. 17, 2008", 8 pgs.

"Australian Application Serial No. 2004227358, Response filed Oct. 22, 2009 to Second Report dated Aug. 27, 2009", 16 pgs.

"European Application Serial No. 04749619.5, Communication dated Apr. 14, 2008", 5 pgs.

"European Application Serial No. 04749619.5, Communication dated Mar. 11, 2009", 4 pgs.

"European Application Serial No. 04749619.5, Communication dated Sep. 13, 2007", 1 pg.

"European Application Serial No. 04749619.5, Communication dated Nov. 9, 2009", 3 pgs.
"European Application Serial No. 04749619.5, Communication Noting Loss of Rights dated Nov. 28, 2008", 1 pg.
"European Application Serial No. 04749619.5, Response filed Feb. 6, 2009 to Communication dated Nov. 28, 2008", 14 pgs.
"European Application Serial No. 04749619.5, Response filed Oct. 4, 2007 to Communication dated Sep. 13, 2007", 3 pgs.
"European Application Serial No. 04749619.5, Response filed Sep. 21, 2009 to Office Action mailed Mar. 11, 2009", 19 pgs.
"International Application Serial No. PCT/US2004/010045, International Search Report mailed Jan. 10, 2005", 6 pgs.
Denby, L., et al., "Adeno-associated virus (AAV)-7 and -8 poorly transduce vascular endothelial cells and are sensitive to proteasomal degradation.", *Gene Therapy*, 12(20), (Oct. 2005), 1534-8.

Jennings, K., et al., "Proteasome Inhibition Enhances AAV-Mediated Transgene Expression in Human Synoviocytes in Vitro and in Vivo", *Molecular Therapy*, 11(4), (Apr. 2005), 600-607.
Johnson, J. S., et al., "Enhancement of Adeno-Associated Virus Infection by Mobilizing Capsids into and Out of the Nucleolus", *Journal of Virology*, 83(6), (2009), 2632-2644.
Kiyomiya, K-I, et al., "Proteasome is a Carrier to Translocate Doxorubicin From Cytoplasm into Nucleus", *Life Sciences*, 62(20), (1998), 1853-1860.
Yan, Z., et al., "Ubiquitination of Both Adeno-Associated Virus Type 2 and 5 Capsid Proteins Affects the Transduction Efficiency of Recombinant Vectors", *Journal of Virology*, 76(5), (2002), 2043-2053.

* cited by examiner

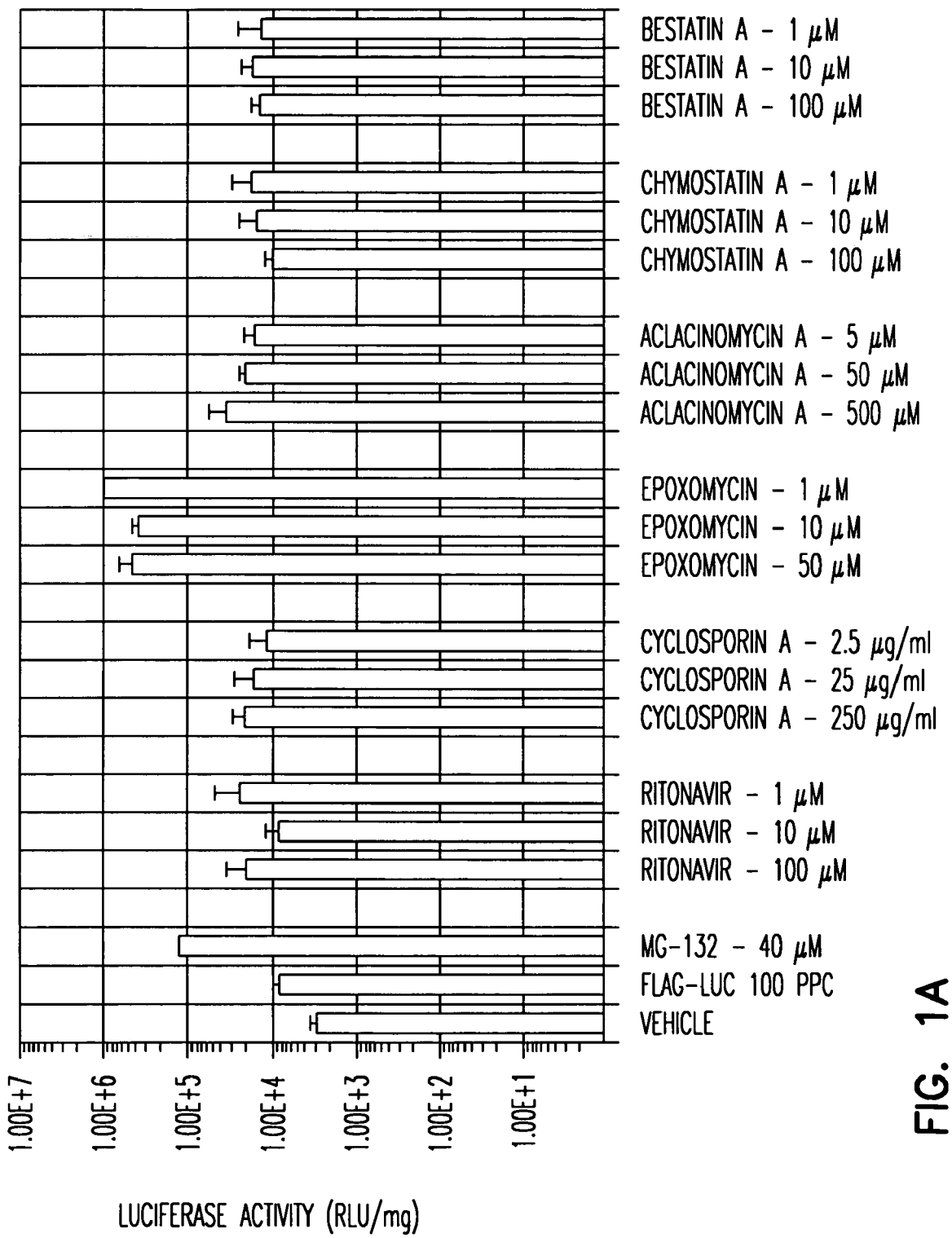

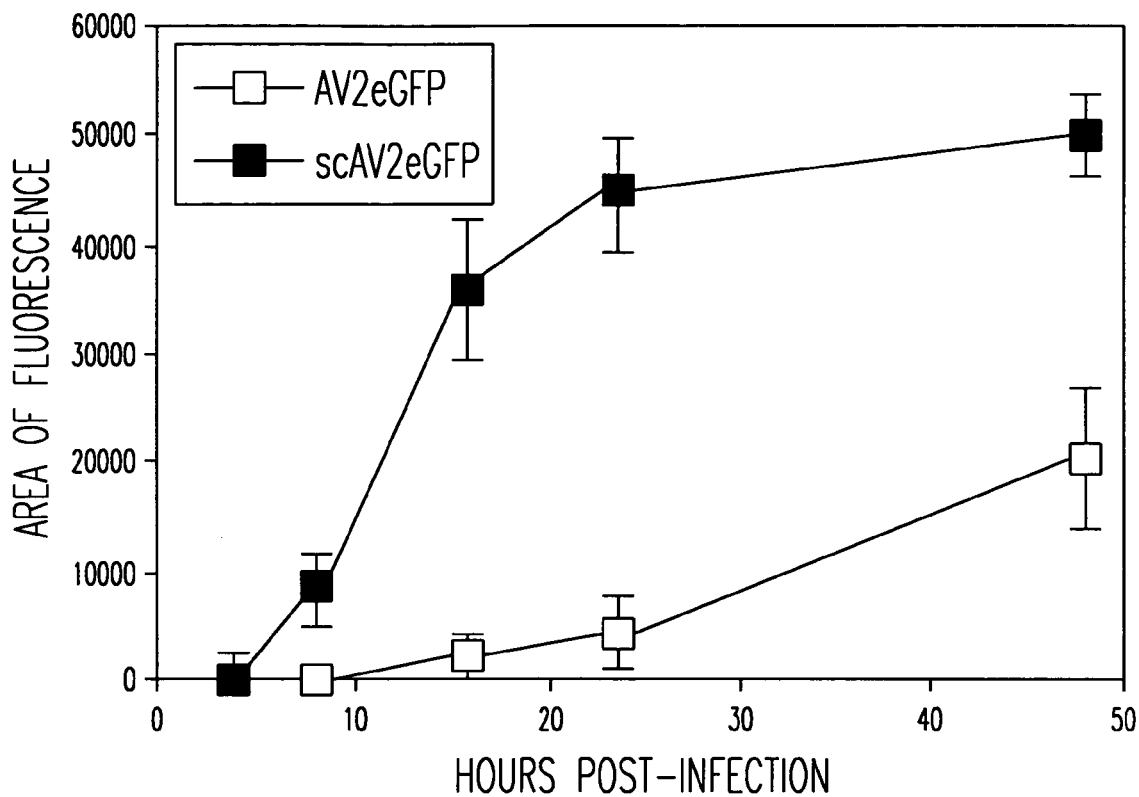
FIG. 15A
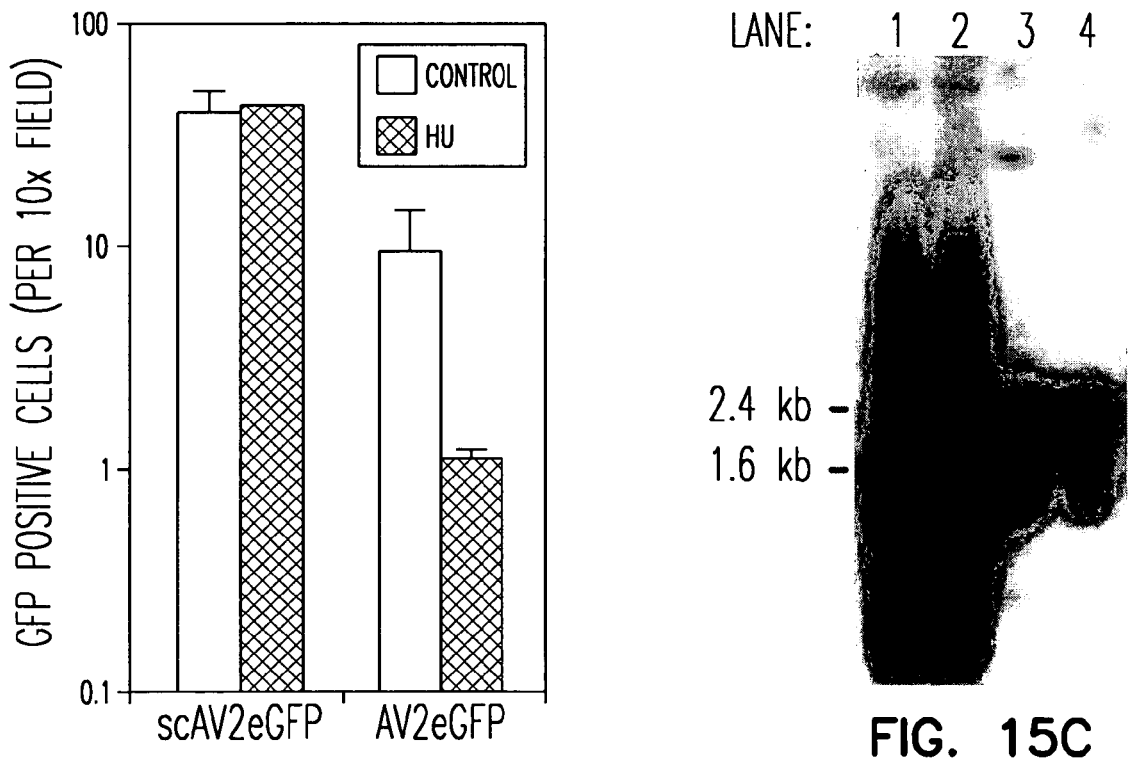
FIG. 15B
FIG. 15C

| SAMPLE | AVG RLU/mg | STDEV | FOLD CHANGE |
|---|---|---|---|
| VEHICLE | 2.95E+03 | 9.01E+02 | |
| AAV2 FLAG-LUCIFERASE | 1.11E+05 | 3.77E+04 | 1.00 |
| | | | |
| MG-132 - 20 μM | 1.43E+06 | 1.72E+06 | 12.90 |
| | | | |
| DOXORUBICIN 6 μg/ML | 2.10E+07 | 4.57E+06 | 189.36 |
| DOXORUBICIN 3 μg/ML | 6.55E+06 | 1.15E+05 | 58.99 |
| DOXORUBICIN 0.6 μg/ML | 2.55E+05 | 1.30E+05 | 2.30 |
| | | | |
| DAUNORUBICIN 6 μg/ML | 3.17E+08 | 1.41E+08 | 2855.65 |
| DAUNORUBICIN 3 μg/ML | 2.40E+07 | 2.72E+06 | 216.42 |
| DAUNORUBICIN 0.6 μg/ML | 4.09E+05 | 6.41E+04 | 3.69 |
| | | | |
| ELLENCE 6 μg/ML | 1.06E+08 | 4.85E+07 | 952.50 |
| ELLENCE 3 μg/ML | 1.33E+07 | 2.70E+06 | 120.13 |
| ELLENCE 0.6 μg/ML | 3.81E+05 | 1.78E+05 | 3.43 |
| | | | |
| IDAMYCIN 6 μg/ML | 3.87E+04 | 2.00E+04 | 0.35 |
| IDAMYCIN 3 μg/ML | 5.99E+08 | 1.91E+08 | 5396.31 |
| IDAMYCIN 0.6 μg/ML | 5.30E+07 | 1.48E+07 | 477.76 |

FIG. 20B

COMPOUNDS AND METHODS TO ENHANCE RAAV TRANSDUCTION

CROSS-REFERENCE TO RELATED APPLICATIONS

The present application claims the benefit of the filing date of U.S. application Ser. No. 60/459,323, filed Mar. 31, 2003, and U.S. application Ser. No. 60/512,347, filed Oct. 16, 2003, the disclosures of which are incorporated by reference herein.

STATEMENT OF GOVERNMENT RIGHTS

This invention was made, at least in part, with a grant from the Government of the United States of America (grant HL58340 from the National Institutes of Health). The Government may have certain rights in the invention.

BACKGROUND OF THE INVENTION

Recombinant adeno-associated virus (rAAV) has several characteristics that underscore its potential as a gene therapy vector for numerous target organs and inherited or acquired diseases, a vaccine vector or for diagnostics. Moreover, rAAV vector systems potentially offer major advantages over other gene delivery vehicles, including adenoviruses and retroviruses. These include the ability of rAAV to readily transduce non dividing or slowly dividing cells and persist essentially for the lifetime of the cell, the lack of undesirable cellular immune responses since all viral genes can be deleted from the vector, and the fact that AAV has never been associated with human disease.

A serotype 2 rAAV (rAAV-2) vector expressing the CFTR gene was the first AAV vector to be utilized in clinical trials. This vector has demonstrated promise in patients with cystic fibrosis and has advanced to phase II trials (Flotte et al., 1996; Wagner et al., 1999; Wagner et al., 2002; Aitken et al., 2001). In recent years, additional rAAV 2 vectors have been or are currently being advanced to clinical trials to treat a number of disease states including a rAAV2 factor IX vector in phase I clinical trials in patients with hemophilia B (Kay et al., 2000), and a rAAV2 sarcoglycan vector in phase I clinical trials of patients with CNS disease. Additionally, clinical trials for rAAV expressing proteins to treat Parkinsons disease (RDAC, 2001), and Canavan's disease (Janson et al., 2001), have been proposed.

Other serotypes of AAV are known to exist, although they are all closely related at the functional, structural, and genetic level (see, e.g., Blacklow, 1988; and Rose, 1974). All AAV serotypes exhibit very similar replication properties mediated by homologous rep genes; all bear three related capsid proteins such as those expressed in AAV-2, and all contain 5'-3' ITR sequences. Currently, 8 serotypes of AAV have been described with the complete genome sequence information available for AAV-1-AAV-6 (Srivastava et al., 1983; Miramatsu et al., 1996; Chiorini et al., 1967; Xiao et al., 1999; Chiorini et al., 1999; Bantel-Schaal et al., 1999; Rutledge et al., 1998) and capsid gene sequence for AAV-7 and AAV-8 (Gao et al., 2002). AAV-6 has been shown to be a recombinant between AAV-1 and AAV-2. In addition, there are two isolates and sequences of AAV-3 that differ from each other in a number of amino acids in both rep and cap (Rutledge et al., 1998). AAV-5 is the most distantly related of the serotypes, and displays a serotype-specific terminal resolution site (trs) in its ITR (Chiorini et al., 1999). Even though rep proteins from other serotypes bind the AAV-5 ITR, they do not efficiently cleave at the trs. In addition to recent developments in AAV and rAAV serotypes, numerous groups are experimenting with rAAV pseudotypes.

Variations in cell surface receptor usage for binding of rAAV to cell membranes exists among various serotypes and may be in part responsible for the differences in transduction efficiencies in various tissue and cell types. Although conflicting data exists, it has become apparent that there are differences among the serotypes in the efficiency of transgene expression in various tissues and cell types. For example, rAAV-1 and rAAV-7 overall appear several orders of magnitude superior for transduction of murine muscle tissue although rAAV-5 also demonstrates enhancement compared to rAAV-2 (Gao et al., 2002; Chao et al., 2000; Rabinowitz et al., 2002; Hildinger et al., 2001). rAAV-8 transduces murine liver up to 100-fold higher (Gao et al., 2002) than rAAV-2, and rAAV-5 appears superior in transduction of cells of the murine respiratory tract (Zabner et al., 2000; Aurichio et al., 2002). rAAV-5 generally appears to be superior to rAAV-2-based vectors in all tissue types tested so far including CNS, muscle, liver and retina (Chao et al., 2000; Rabinowitz et al., 2002; Hildinger et al., 2001; Aurichio et al., 2002; Davidson et al., 2000; Mingozzi et al., 2002). Similarly, rAAV-6 is more efficient than rAAV-2 in transducing murine airway epithelia and alveoli, while rAAV-3 is superior in transducing smooth muscle cells (Halbert et al., 2001; Halbert et al., 2000). rAAV-4 transduces ependymal cells in the murine CNS almost exclusively, while rAAV-5 transduces both neurons and astrocytes (Davidson et al., 2000). In retina, a number of studies have demonstrated large differences among serotypes in the ability to transduce photoreceptor cells and the retinal pigmented epithelium (Walters et al., 2001; Aurricchio et al., 2001; Yang et al., 2002).

Despite the fact that rAAV has a very broad host tropism in a variety of human, simian, and rodent cell lines (Lebkowski et al., 1988; Muzyczka, 1992), the overall transduction efficiency in human airway epithelia and other tissues seems to be quite low. Previous studies have suggested that single to double strand conversion of the rAAV genome may be the rate-limiting step for AAV-mediated gene transfer (Ferrari et al., 1996; Fisher et al., 1996). These studies demonstrated that adenovirus E4orf6 enhances the conversion of single-stranded DNA genomes to linear, double-stranded replication form dimers (Rfd) and monomers (Rfm), through a pathway characteristic of the lytic phase of rAAV replication. The structure of these replication forms consists of head-to-head and tail-to-tail orientated linear concatamers with one covalently linked end (Ferrari et al., 1996; Fisher et al., 1996). In contrast, recent studies have elucidated an alternative pathway for the conversion of rAAV genomes to double-stranded circular intermediates with head-to-tail monomer and concatamer structures (Duan et al., 1999; Duan et al., 1998; Sanlioglu et al., 1999). The distinct pathways leading to the formation of either circular AAV genomes or Rf intermediates appear to be regulated by different cellular factors. For example, adenoviral E4orf6 expression decreases circular genome formation while adenovirus E2a enhances its formation (Duan et al., 1999). Similarly, UV irradiation also enhances AAV circular intermediate formation but not Rf intermediates (Sanlioglu et al., 1999).

More recently, when cellular binding protein FK506-(FKBP-52) was phosphorylated at tyrosine residues (by the epidermal growth factor receptor protein tyrosine kinase), FKBP-52 was demonstrated to be bound to the single-stranded D-sequence of the AAV ITR causing an impairment in second strand synthesis (Qing et al., 2001; Qing et al., 2003. The efficiency of rAAV transduction in a number of cell types in vitro and in vivo correlates with the phosphorylation state of FKBP-52. For example, in HeLa cells, overexpression of a cellular phosphatase (TC-PTP), led to dephosphorylation of the FKBP-52, an increase in AAV second-strand DNA synthesis, and an increase in transgene expression. Transgenic mice expressing either the wild type (wt) or a catalytically mutant form of TC-PTP, were created. Hematopoietic stem cells from transgenic mice expressing the wt TC-PTP phosphatase were transduced by a rAAV2, but those from the phosphatase-negative mutant were not. These results suggest that the block to second-strand DNA synthesis is due to binding of FKBP-52 to the D-sequence of infecting vector genomic DNA and that this binding is regulated by phosphorylation. Thus, numerous strategies aimed at increasing the transduction frequency for AAV have focused on enhancing the molecular conversion of nonfunctional viral genomes to expressible forms (Fisher et al., 1996; Sanlioglu et al., 1999) or by increasing transcription and translation efficiencies by altering the transgene expression cassettes (Zabner et al., 1996; Xiao et al., 1998).

A second approach aimed at improving transduction efficiencies of rAAV has focused on the binding of rAAV to cell surface receptors. Many primary and secondary cell surface receptor molecules have been identified for the various AAV serotypes. The primary receptors identified (heparin sulfate and sialic acid) are found on many cell types and are also utilized by a large number of viruses besides AAV. This suggests that additional receptors that lend more specificity to attachment and penetration of cells might exist and several such co-receptors have been identified. Thus, additional strategies to improve rAAV transduction efficiency have focused on manipulation of cell surface receptors (Qing et al., 1997) and/or receptor ligands in the virus coat proteins (Wickham et al., 1996a; Wickham et al., 1996b; Bartlett et al., 1999).

While binding to the cell surface membrane and successful conversion to a double stranded DNA genome are important, the efficiency of these events does not necessarily correlate with the overall ability or efficiency of rAAV to transduce a given cell type. This has been increasingly apparent in recent years as a more detailed understanding of the trafficking and uncoating of rAAV has been accumulated (Duan et al., 1998; Seisenberger et al., 2001; Hanson et al., 2001; Bantel-Schaal et al., 2002; Yan et al., 2002). For example, polarized human airway epithelial cells are transduced with varying efficiencies by rAAV-2 depending on the route of delivery; entry from the basolateral surface results in about a 200-fold increase in gene expression in the cells compared to vector administered from the apical surface (Duan et al., 1998; Duan et al., 2000). Surprisingly, the difference in rAAV cell surface binding between two cell surfaces is only about 5-fold. This finding led to the discovery that the vectors traffic differently in these cells depending on the route of delivery (Duan et al., 1998; Duan et al., 2000).

Previous reports have clearly demonstrated that intracellular trafficking to the nucleus for rAAV-2 and canine parvovirus is a slow, rate-limiting process for certain cell types (Parker et al., 2000; Hanson et al., 2001; Hanson et al., 2000; Duan et al., 2000). Canine parvovirus and rAAV-2 have also been demonstrated to be endocytosed through clathrin-dependent receptor endocytosis and processed through endosomal compartments in a similar fashion to transferrin, but not a fluid phase marker such as dextran (Parker et al., 2000; Bartlett et al., 2000; Benson et al., 2000; Duan et al., 1999). Transferrin trafficking has been extensively studied and shown to move through the early endosome to perinuclear recycling endosome (PNRE) (Sonnichsen et al., 2000; Ren et al., 1998). The recycling of transferrin through the PNRE requires the coordinated interactions of several small GTPases (Rab5, Rab4, and Rab11) which direct the movement and fusion of early endosomes to the PNRE compartment (Sonnichsen et al., 2000).

Studies designed to develop agents to improve the efficiency of rAAV transduction have demonstrated that proteosome inhibitors such as the tripeptides LLnL and Z-LLL can enhance transduction of rAAV. Agents of this class affect ubiquitination of rAAV by inhibiting calpains, cathepsins, cysteine proteases as well as the chymotrypsin-like protease activity of proteasomes in polarized cell types (Duan et al., 2000; Yan et al., 2002). Additionally, agents affecting DNA metabolism including hydroxyurea, novobiocin, amsacrine, and etopside were tested for the ability to enhance rAAV transduction based on the hypothesis that these drugs would increase the rate of conversion of the single stranded rAAV genome to a double stranded form. Results demonstrated that etoposide, hydroxyurea, and campothecin were effective at enhancing rAAV transduction when utilized singularly but when used in combination produced no additive or synergistic effects (Russel et al., 1995). Furthermore, these agents were only stated as effective in enhancing rAAV transduction in cell types for which gene conversion is rate limiting. Steps which proceed gene conversion (i.e., intracellular trafficking and processing of virions) appear to be critical rate-limiting steps in primary cells and differentiated tissues such as the airway (Hansen et al., 2000; Duan et al., 2000).

There exists a need for improved transduction efficiencies for rAAV vectors. Thus, what is needed is the identification of agents that can alter, e.g., increase or enhance, rAAV transduction or rAAV transduction frequencies in vivo. What is also needed is the identification of agents that increase or enhance the expression of a rAAV heterologous transgene in non-dividing or slowly dividing cells or tissues, such as those in the liver and the airway.

SUMMARY OF THE INVENTION

The invention provides a method to identify an agent, or a combination of agents, that alters adeno-associated virus (AAV) transduction of a eukaryotic cell, e.g., a mammalian cell such as a mammalian lung or liver cell, or a population of eukaryotic cells, e.g., in tissues or organs. For example, the invention provides a method to identify agents that enhance rAAV transduction, e.g., enhance rAAV endocytosis, enhance trafficking and processing of the rAAV through the intracellular compartments, including without limitation proteosomes, endosomes, and trans-golgi, decrease viral nucleic acid or protein degradation, increase viral uncoating and/or increase nuclear transport of virus or the viral genome, e.g., via cytoskeletal components such as microtubules or microfilaments. The method comprises contacting the cell or population of cells with one or more agents and virus. Then it is determined whether virus transduction is altered. Preferred cells include those of mammals, birds, fish, and reptiles, especially domesticated mammals and birds such as humans, non-human primates, cattle, sheep, pigs, horses, dogs, cats, mice, rats, rabbits, chickens, and turkeys. For example, polarized human airway epithelial cells grown at an air-liquid interface or human bronchial xenografts are useful to identify agents which alter viral transduction.

In one embodiment, agents to be tested are selected from agents including those having desirable properties, e.g., therapeutic properties or functional and/or structural properties of other agents identified as altering rAAV transduction. An agent or library of agents may be randomly screened in the methods of the invention. Alternatively, agents to be tested may be selected from agents having desirable properties for a particular cell type, tissue type or disease type to be treated with rAAV. Moreover, agents may be selected from agents that modulate the proteosome, e.g., agents that bind to a proteosome, alter the interaction of virus and the proteosome, alter a function of the proteosome, stabilize the proteosome, or alter the trafficking of the proteosome, but do not inhibit the proteolytic activity of the proteosome. As used herein, agents that are "proteosome modulating agents" do not include agents that inhibit the proteolytic activity of the proteosome. For example, to identify an agent useful to enhance transduction of a CFTR rAAV vector for delivery to the lungs of patients with cystic fibrosis, agents may be selected from agents used or approved for use in cystic fibrosis patient populations, agents in clinical trials or having FDA approval, and/or agents associated with viral transduction, e.g., rAAV endocytosis, trafficking and processing of the rAAV through intracellular compartment(s), e.g., endosomal compartments, decreased viral nucleic acid or protein degradation, increased viral uncoating, or increased nuclear transport of virus or the viral genome, agents that interact with cytoskeletal elements, e.g., microtubules or microfilaments. In one embodiment, the agent is not an agent inhibits proteolytic activity of the proteosome. In one embodiment, the agent alters, e.g., enhances, transduction of a mammalian cell by rAAV after viral binding to the cell membrane and before second strand synthesis which yields an expressible form of the viral genome. Randomized screening may be performed using a transgene expressing rAAV, e.g., a reporter transgene encoding GFP, or high throughput screening of chemical libraries on indicator cell lines. Transduction may be assessed using expression of the rAAV encoded reporter transgene. In one embodiment, chemical libraries are selected based on chemical structures known to interact with the proteasome, virus, or other intracellular processing pathways, e.g., endosomal compartments, through which virus is processed. Alternatively, peptide libraries may be screened to identify agents that enhance rAAV transduction, for instance, via an interaction with a proteosome that affects rAAV transduction.

The agents of the inventions may be tested and/or used with any serotype or pseudotype of rAAV vectors. It is envisioned that agents identified as enhancing rAAV transduction may function with all AAV serotypes and pseudotypes although there may be variations in the degree of enhancement, cell or tissue type specificities or concentrations employed for enhancement.

Agents of the invention may be used alone or in combination to produce additive or synergistic transduction effects, to increase the efficiency of transduction for multiple cell or tissue types, to increase the time period of rAAV heterologous transgene expression, to shorten the time period to expression of the transgene, or to reduce the amount of virus needed to achieve a therapeutic or prophylactic effect compared to transduction by or expression of the same vector in the absence of the agent or agents, or when an agent is used singularly. It is also contemplated that one or more agents of invention may be used in combination with agents that increase binding to cellular receptors, promote conversion of the single stranded rAAV vector to the double stranded form, or inhibit proteosome proteolytic functions, to produce additive or synergistic transduction effects, to increase the efficiency of transduction for multiple cell or tissue types, to increase the time period of rAAV heterologous transgene expression, to decrease lag time between contact of the host cell with rAAV and expression of the transgene, or to reduce the amount of virus needed to achieve a desired effect, compared to transduction by or expression of the same vector in the absence of the agent, a single agent or less than all of the agents. Agents of the invention used in combination may be synergistic or additive in enhancing rAAV transduction. Examples of additive effects of rAAV transduction include, e.g., a shortened lag time between infection and expression of the transgene and an overall longer time period of expression.

Accordingly the invention provides a method to enhance rAAV transduction of a mammalian cell. The method includes contacting the mammalian cell with at least one rAAV and at least two agents, e.g., in an amount effective to additively or synergistically enhance rAAV transduction.

Agents of the invention may be employed with a rAAV vector that contains only a single heterologous transgene, i.e., one not derived from AAV sequences, e.g., not encoding a AAV protein, or with dual vector strategies wherein the rAAV vectors contain more than one heterologous transgene and/or transcriptional regulatory elements as described in Duan et al. (2000); Yan et al. (2000); and Duan et al. (2001). The gene being expressed can be either a DNA segment encoding a polypeptide, catalytic RNA, or antisense RNA, with whatever control elements (e.g., promoters, operators) are desired.

The invention includes agents that modulate proteosomes including agents that bind to, and/or alter one or more activities of a proteosome, the association of virus with the proteasome, and/or subcellular positioning of the proteasome. Proteosomes are the main proteolytic complex in the cytosol and nucleus, and can be transported between the cytoplasm and nucleus. For instance, the 26S proteosome complex comprises a 19S regulatory unit and a 20S catalytic core which has chymotrypsin-like activity, i.e., cleavage after large hydrophobic residues, trypsin-like activity, i.e., cleavage after basic residues, post-glutamyl hydrolase activity, i.e., cleavage after acidic residues, branched amino acid cleavage activity and small neutral amino acid cleavage activity. As described herein, doxorubicin, an approved antibiotic, also enhances rAAV transduction. Doxorubin may facilitate viral binding to the proteasome and/or subsequent transportation into the nucleus. In contrast, proteasome inhibitors such as LLnL and Z-LLL more significantly inhibit core proteolytic activity of the proteasome.

Hence, the combined use of agents that individually have different or overlapping properties that alter rAAV transduction, as well as agents with similar or identical properties, can result in an additive and/or synergistic effect and so enhance rAAV transduction. Thus, agents that enhance virus transduction are particularly useful in gene therapy that employs rAAV to introduce and/or express a therapeutic peptide or polypeptide, or in vaccines that employ rAAV to introduce and/or express an immunogenic prophylactic polypeptide or peptide, such as one from a virus, fungus, bacterium, yeast or cancer cell, so as to induce an immune response to that polypeptide or peptide. The agents of the invention are also useful for the development of diagnostic markers to aide in in vivo cellular marking of cells or tissue, or to track and/or target chemotherapeutic strategies. Further, agents of the invention may enhance rAAV transduction of cells, tissues, or animals employed for the production of therapeutic proteins, e.g., growth hormone, cytokines or other recombinant proteins.

Further, the cells to be transduced may be contacted with one or more agents prior to viral infection, concurrently with viral infection, subsequent to viral infection, or any combination thereof. Cells to be transduced may be contacted with one or more agents at a single time point, e.g., a single dose of one agent or a single dose of two or more agents, or at multiple time points, as described above, e.g., multiple doses of one agent, multiple doses of a combination of two or more agents, sequential or alternating doses of two or more agents.

As described hereinbelow, virus binding, e.g., the restricted distribution of viral receptors, and endocytosis of AAV-2 at the apical membrane of airway epithelia is not the major rate limiting step in transduction of this tissue type. In fact, differentiated human airway epithelia internalize rAAV-2 quite efficiently from the apical surface. Rather, endosomal processing and trafficking of internalized virus to the nucleus is the major obstacle encountered by AAV-2 following infection from the apical membrane of the airway. In contrast to basolateral infection that led to the efficient conversion of single stranded AAV DNA to circular form genomes, apical infection gave rise to persistent intracellular single stranded viral DNA in a transcriptionally inactive state for up to 50 days. Using proteasome inhibitors which increase the efficiency of endosomal processing of AAV-2 and intracellular routing to the nucleus, a significantly enhanced transduction from the apical surface of more than 200-fold was observed, to nearly that of transduction from the basolateral surface. It was also found that AAV capsid proteins are ubiquitinated following endocytosis, and that ubiquitin-mediated proteasome degradation of incoming virus can be blocked by treatment with either proteasome or ubiquitin ligase inhibitors.

Moreover, importantly, in vivo application of proteasome inhibitor in mouse lung augmented rAAV gene transfer from undetectable levels to a mean of 10.4+/−1.6% of the epithelial cells in large bronchioles. Thus, the use of one or more agents that alter rAAV endocytosis, trafficking and processing of the rAAV through the intracellular compartments, including without limitation proteasomes, endosomes, and trans-golgi, viral nucleic acid or protein degradation, viral uncoating and/or nuclear transport of virus or viral genome, e.g., via cytoskeletal components such as microtubules or microfilaments, to circumvent the major endosomal processing barriers to transduction in the airway may provide clinically useful strategies for in vivo AAV-mediated gene therapy of respiratory disorders such as cystic fibrosis, as well as for other tissues in which viral processing appears to be a rate limiting event, or strategies for in vivo rAAV-mediated vaccines.

As also described hereinbelow, the transduction efficiency of a recombinant AAV-2 construct with an RSV LTR promoter driving a luciferase reporter that was packaged into both AAV-2 and AAV-5 capsid particles was compared in a number of cell lines and in lung in vivo. Co-administration of the viruses with agents of the invention including a proteosome modulator and/or a proteosome inhibitor in vitro not only increased the transduction efficiency of AAV-2, it also augmented AAV-5 mediated gene transfer although often to a slightly lower extent. Increased transgene expression in the presence of proteasome inhibitor was independent of viral genome degradation since no significant difference of the amount of internalized viral DNA was detected 24 hours after infection. Western blot assays of immunoprecipitated viral proteins from infected HeLa cell lysates and in vitro reconstitution experiments revealed evidence for ubiquitin conjugation of both AAV-2 and AAV-5 capsids. These studies suggest that the previously reported barrier involving the ubiquitin/proteasome pathway for rAAV-2 is also active for rAAV-5 capsid entry pathways. In vivo co-administration of a pseudotyped rAAV and the proteosome inhibitor Z-LLL induced whole lung luciferase expression 17.2- and 2.1-fold at 14 and 42 days post-infection, respectively, while co-administration of rAAV and a different rAAV transduction enhancing agent, doxorubicin, induced tracheal and bronchial luciferase expression at higher levels at 14, 42 and 90 days post-infection relative to expression levels induced by Z-LLL. Surprisingly, at 42 days, luciferase expression in trachea and bronchi in mice co-administered virus and Z-LLL and doxorubicin was more than additive when administered by endotracheal instillation. In human polarized airway epithelia, combined doxorubicin and LLnL enhanced luciferase expression from rAAV synergistically more that 1000-fold while individually doxorubicin and LLnL enhanced transduction by 100- and 10-fold, respectively. As also described herein, other agents that bind to proteosomes and/or modulate proteosome activity, can alter rAAV transduction efficiency.

Further, the activity of agents that alter virus transduction, e.g., a modulator of rAAV endocytosis, trafficking and processing of rAAV through the intracellular compartment, viral nucleic acid or protein degradation, viral uncoating and nuclear transport, may be enhanced by the addition of agents, such as EDTA or EGTA, which may alter molecules in pathways associated with virus transduction, e.g., agents such as calcium chelators or modulators of intracellular calcium levels. Thus, one or more agents that alter virus transduction may be employed with an agent that enhances the activity of, or acts synergistically with, the one or more agents that alter virus transduction. Thus, the invention also provides for compositions or kits comprising two or more agents, e.g., a first agent that alters virus transduction and a second agent which enhances the activity of the first agent or acts synergistically with the first agent.

Therefore, the invention also provides a method to alter adeno-associated virus transduction of a eukaryotic cell or a population of cells. The method comprises contacting the cell or a population of cells with an amount of virus and an amount of at least one agent of the invention effective to alter virus transduction. The agent may be contacted with the cell concurrently with the virus, prior to contacting the cell with virus or after contacting the cell with virus. In one embodiment, the invention provides a method in which a mammalian cell is contacted with at least one rAAV and at least one agent that alters rAAV endocytosis, rAAV trafficking or processing in intracellular compartments, viral nucleic acid or protein degradation, and/or nuclear transport of virus or viral genomes. In one embodiment, the agent is not an inhibitor of proteosome proteolytic activity. The agent(s) and/or virus may each be administered once, or in repeated dosing, so as to achieve the desired effect, i.e., to enhance rAAV transduction. Since AAV has been shown to have a broad host range (e.g., for pulmonary expression) and persists in muscle, rAAV may be employed to express a gene in any animal, and particularly in mammals, birds, fish, and reptiles, especially domesticated mammals and birds such as cattle, sheep, pigs, horses, dogs, cats, chickens, and turkeys. Both human and veterinary uses are particularly preferred.

In one embodiment, at least one rAAV and/or pseudotyped rAAV and one or more agents of the invention may be employed in methods to alter, e.g., increase, transduction efficiency and transgene expression, methods to detect or determine transgene expression efficiency, methods to screen for promoter strength and/or RNA stability, as well as in therapeutic or prophylactic therapies in which the vectors are useful include blood disorders (e.g., sickle cell anemia, thalassemias, hemophilias, and Fanconi anemias), neurological disorders, such as Alzheimer's disease and Parkinson's disease, and muscle disorders involving skeletal, cardiac or smooth muscle, as well as diseases of the lung, e.g., cystic fibrosis and asthma. In particular, therapeutic genes useful in the vectors of the invention include a α-globin gene, β-globin gene, γ-globin gene, Factor VIII gene, Factor IX gene, cystic fibrosis transmembrane conductance regulator gene (CFTR), Fanconi anemia complementation group, dystrophin gene, an antisense gene, low density lipoprotein (LDL) gene, tyrosine hydroxylase gene (Parkinson's disease), glucocerebrosidase gene (Gaucher's disease), arylsulfatase A gene (metachromatic leukodystrophies), erythropoietin gene, as well as genes encoding immunogenic polypeptides or peptide, such as those useful for vaccines, or genes encoding other gene products such as other peptides, polypeptides or proteins. In one embodiment, the rAAV encodes a catalytic RNA, e.g., a ribozyme or siRNA, e.g., one useful to decrease expression of a particular RNA expressed in a cell.

Also within the scope of the invention is the inclusion of more than one open reading frame in a rAAV vector, i.e., a plurality of genes may be present in an individual vector. Further, as rAAV may form concatamers after infection, each monomer of that concatamer may comprise a different gene, or a portion thereof. Circularized intermediates of recombinant adeno-associated virus may impart episomal persistence to linked sequences.

Further, co-infection with two or more different rAAV may, through intermolecular recombination, yield a concatamer having one or more copies of any particular rAAV. The implications of intermolecular recombination of rAAV genomes to form a single molecule, e.g., a nuclear episome, which may be a concatamer comprising at least two different rAAV genomes, is particularly relevant for gene therapy with rAAV, as large regulatory elements and genes beyond the packaging capacity of rAAV can be brought together by co-infecting cells or tissue of an organism with two independent rAAV vectors. For example, enhancers and/or promoters may be introduced into one vector while DNA comprising an open reading frame, e.g., a gene of interest, with or without a minimal promoter, is introduced into a second vector. Thus, after co-infection with the two vectors, the transgene cassette size is increased beyond that for a single AAV vector alone and the DNA comprising the opening reading frame is linked to the enhancer and/or promoter. In another embodiment of the invention, vectors encoding two independent regions of a gene are brought together to form an intact splicing unit. Without being bound by theory, agents of the invention may increase concatamerization and/or intermolecular recombination of rAAV by increasing the steady state abundance of viral genomes resulting in enhanced transduction frequencies of rAAV compared to cells not treated with agents of the invention. Agents of the invention that alter processing of rAAV virions in the cytoplasm and/or nucleus may also influence the presentation of viral DNA in the nucleus and hence alter gene conversion products. Such altered presentation may affect concatamerization by allowing for more localized accumulation of virions at specific sites within the nucleus. Alternatively, ubiquitination of associated factors with viral DNA (i.e., Rep or host cell proteins) may affect the biologic properties of these associated factors and influence linear, circular, and/or concatamerization processes. Thus, agents of this invention may influence intramolecular concatamerization and the efficiency of multiple vector technologies by the mechanisms discussed above.

Accordingly, the use of multiple rAAV vectors is useful to overcome the current size limitation for transgenes within rAAV vectors, and allows for the incorporation of a larger transcriptional regulatory region, e.g., a stronger heterologous promoter or an endogenous promoter, e.g., the CFTR endogenous promoter, or one or more enhancer sequences.

Therefore, two or more, e.g., a plurality, of DNA segments, each in an individual rAAV vector, may be delivered to a cell, so as to result in a single DNA molecule having DNA segments from more than one rAAV. In one embodiment of the invention, one rAAV may comprise a first recombinant DNA molecule comprising linked: a first DNA segment comprising a 5' ITR of AAV; a second DNA segment which does not comprise AAV sequences (nonAAV sequences), i.e., heterologous sequences; and a third DNA segment comprising a 3' ITR of AAV. A second recombinant AAV comprises a second recombinant DNA molecule comprising linked: a first DNA segment comprising a 5' ITR of AAV; a second DNA segment which does not comprise AAV sequences and which second DNA segment has sequences which are different than the sequences in the second DNA segment of the first recombinant DNA molecule; and a third DNA segment comprising a 3' ITR of AAV. One of the rAAV may be a pseudotype.

In one embodiment of the invention, one rAAV vector comprises a first DNA segment comprising a 5' ITR linked to a second DNA segment comprising the 5' end of an open reading frame (but optionally not an entire open reading frame), optionally operably linked to a promoter, e.g., a heterologous promoter, and a 5' splice site linked to a third DNA segment comprising a 3' ITR. The second rAAV vector comprises a first DNA segment comprising a 5' ITR linked to a second DNA segment comprising a 3' splice site and the 3' end (the remainder) of an open reading frame, i.e., the second DNA segment of the second vector together with the second DNA segment of the first vector encodes a functional gene product linked to a third DNA segment comprising a 3' ITR. A "functional" gene product is one which has a detectable activity or is capable of having a detectable activity when present in an appropriate cell, tissue or organism, e.g., has at least one activity, and preferably substantially the same activity, as a reference, e.g., corresponding, gene product, for example, a wild-type (full-length) polypeptide or ribozyme. Preferably, the second DNA segments together comprise DNA encoding, for example, CFTR, factor VIII, dystrophin, or erythropoietin. The second DNA segments may be obtained or derived from cDNA, genomic DNA or a combination thereof. For example, the second DNA segment of the first vector may comprise one or more, but not all of the exons of a gene comprising more than one exon and the second DNA segment of the second vector may comprise at least one exon of the gene that is not present in the first vector, or one or more exons from a different gene (thereby coding for a chimeric polypeptide). The second DNA segment of the first vector may comprise the endogenous promoter of the respective gene, e.g., the epo promoter, or a heterologous promoter.

In another embodiment, one rAAV vector comprises a first DNA segment comprising a 5' ITR linked to a second DNA segment comprising a promoter and/or enhancer linked to a third DNA segment comprising a 3' ITR. Optionally, the first rAAV vector does not include a splice donor and/or a splice acceptor. A second rAAV vector comprises a first DNA segment comprising a 5' ITR linked to a second DNA segment comprising at least a portion of an open reading frame optionally linked to a promoter (a different promoter than in the first vector or a second copy of the promoter in the first vector) linked to a third DNA segment comprising a 3' ITR. For example, the second DNA segment of the first recombinant DNA molecule comprises at least one heterologous enhancer and/or at least one heterologous promoter, i.e., the enhancer and/or promoter sequences are not derived from AAV sequences. Preferably, the second DNA segment of the second recombinant DNA molecule comprises a portion of an open reading frame which encodes a functional gene product.

In one embodiment, co-infection of a cell with at least one pseudotyped rAAV, e.g., a transgene containing vector, and a second vector comprising at least one, preferably at least two or more, enhancer sequences, may result in an enhancement of transgene expression from a minimal promoter. Furthermore, an enhancement can also be achieved by cis-activation of ITRs in transgene-containing vectors without a promoter. Thus, large regulatory elements including tissue-specific enhancers can be introduced into cells by a separate rAAV vector to regulate the expression of a second transgene-containing AAV vector in cis following intracellular concatamerization.

In yet another embodiment of the invention, the second DNA segment of the first recombinant DNA molecule comprises a cis-acting integration sequence(s) for a recombinase and also encodes a recombinase or integrase that is specific for the integration sequence(s), e.g., Cre/lox system of bacteriophage P1 (U.S. Pat. No. 5,658,772), the FLP/FRT system of yeast, the Gin recombinase of phage Mu, the Pin recombinase of E. coli, the R/RS system of the pSR1 plasmid, a retrotransposase or the integrase from a lentivirus or retrovirus. The second DNA segment in the second recombinant DNA molecule comprises at least a portion of an open reading frame, and preferably a promoter operably linked to the open reading frame. The formation of a concatamer comprising the first and the second recombinant DNA molecules, and the expression of the recombinase or integrase, will enhance the integration of the concatamer, or a portion thereof, into the host genome. Also, rAAV vectors comprising cis-acting integration sequences and the corresponding recombinase or integrase are useful to drive directional recombination, which, as discussed above, may be particularly useful when employing two or more rAAV vectors.

Accordingly, the vectors of the invention are useful in a method of delivering and/or expressing one or more genes in a host cell, to prepare host cells having the vector(s), and in the preparation of a composition comprising rAAV(s). A host cell may be contacted with each rAAV individually, e.g., sequentially, with or without an agent of the invention. To deliver the gene(s) to the host cell, a recombinant adenovirus helper virus may be employed.

Thus, the invention also provides a method to express a gene product in a host cell. The host cell is preferably a mammalian host cell, e.g., a murine, canine, feral or human cell, and may be a lung, neuron or muscle cell. The method comprises contacting the host cell with at least one rAAV vector and at least one agent of the invention. In one embodiment, the host cell is contacted with at least two different rAAV vectors. In one embodiment, one of the rAAV vectors is a pseudotyped rAAV. The host cell is preferably contacted with the vectors concurrently, although it is envisioned that the host cell may be contacted with each vector at a different time relative to the contact with the other vector(s), as discussed herein. Two or more agents of the invention may also be employed in the method, and may be contacted with the cell prior to, concurrent with, or subsequent to contact of the cell with the vector(s). In one embodiment, the agent modulates microfilament or microtubule synthesis, formation or degradation, modulates rAAV endocytosis, modulates rAAV trafficking in a cell, modulates rAAV processing in a cell, modulates rAAV nucleic acid degradation in a cell, modulates rAAV protein degradation in a cell, modulates rAAV transport to the nucleus and/or modulates viral genome transport to the nucleus. In one embodiment, two agents that modulate microfilament or microtubule synthesis, formation or degradation, rAAV endocytosis, rAAV trafficking in a cell, rAAV processing in a cell, rAAV nucleic acid degradation in a cell, rAAV protein degradation in a cell, rAAV transport to the nucleus and/or viral genome transport to the nucleus, are employed.

Also provided is a method to detect expression of a transgene in a cell. The method comprises contacting a host cell with a rAAV of the invention which comprises a transgene comprising a non-AAV promoter linked to an open reading frame, e.g., a marker gene or an open reading frame having one or more genetic modifications relative to a corresponding wild-type open reading frame. One or more agents of the invention may also be employed in the method, and may be contacted with the cell prior to, concurrent with, or subsequent to contact of the cell with the vector(s). The expression of the transgene is then detected or determined, e.g., relative to a host cell contacted with a rAAV comprising a transgene linked to a different promoter or a transgene with the same promoter but linked to a wild-type open reading frame or one not contacted with an agent of the invention.

Thus, one embodiment, the invention provides a method to prevent, inhibit or treat a condition associated with aberrant expression of an endogenous gene product. The method includes contacting a mammal at risk of or having the condition, with an effective amount of at least one agent that enhances AAV transduction and an effective amount at least one rAAV comprising a transgene encoding at least a portion of a functional gene product, the expression of which in the mammal inhibits the aberrant expression of the corresponding endogenous gene product, e.g., via a dominant negative, antisense or catalytic RNA, or encodes a functional gene product, thereby preventing or inhibiting one or more symptoms of the condition. In one embodiment, the agent is a chemotherapeutic, a lipid lowering agent, an antibiotic or a food additive. In one embodiment, the agent is not campthothecin. In another embodiment, the agent is not cisplatin.

BRIEF DESCRIPTION OF THE FIGURES

FIGS. 1A-E. Luciferase activity in HeLa cells transfected with rAAV FLAG-Luc in the presence or absence of various agents. HeLa cells were contacted with 100 ppc AAV FLAG-Luc for 2 hours, and cells were harvested 48 hours later. N=3, average±standard deviation.

FIG. 15. Analysis of full-length and self-complementary eGFP-expressing AAV vectors. HeLa cells were infected at an MOI=1000 particles/cell. (A) Quantification of relative eGFP-expressing area for AV2eGFP and scAV2eGFP vectors. The values represent the mean (+/−SEM) for three independent infections and quantification of 10 random fields for each experimental point. (B) Response of AV2eGFP and scAV2eGFP vectors to treatment with hydroxyurea (5 mM) with gene expression analyzed at 24 hours post-infection. (C) Southern blot analysis of Hirt DNA harvested from AV2eGFP-infected (lanes 1 and 2) and scAV2eGFP-infected (lanes 3 and 4) Hela cells at 24 hours post-infection. A $^{32}$P-labeled eGFP DNA probe was used for Southern blots.

DETAILED DESCRIPTION OF THE INVENTION

Definitions

Figure 1B:
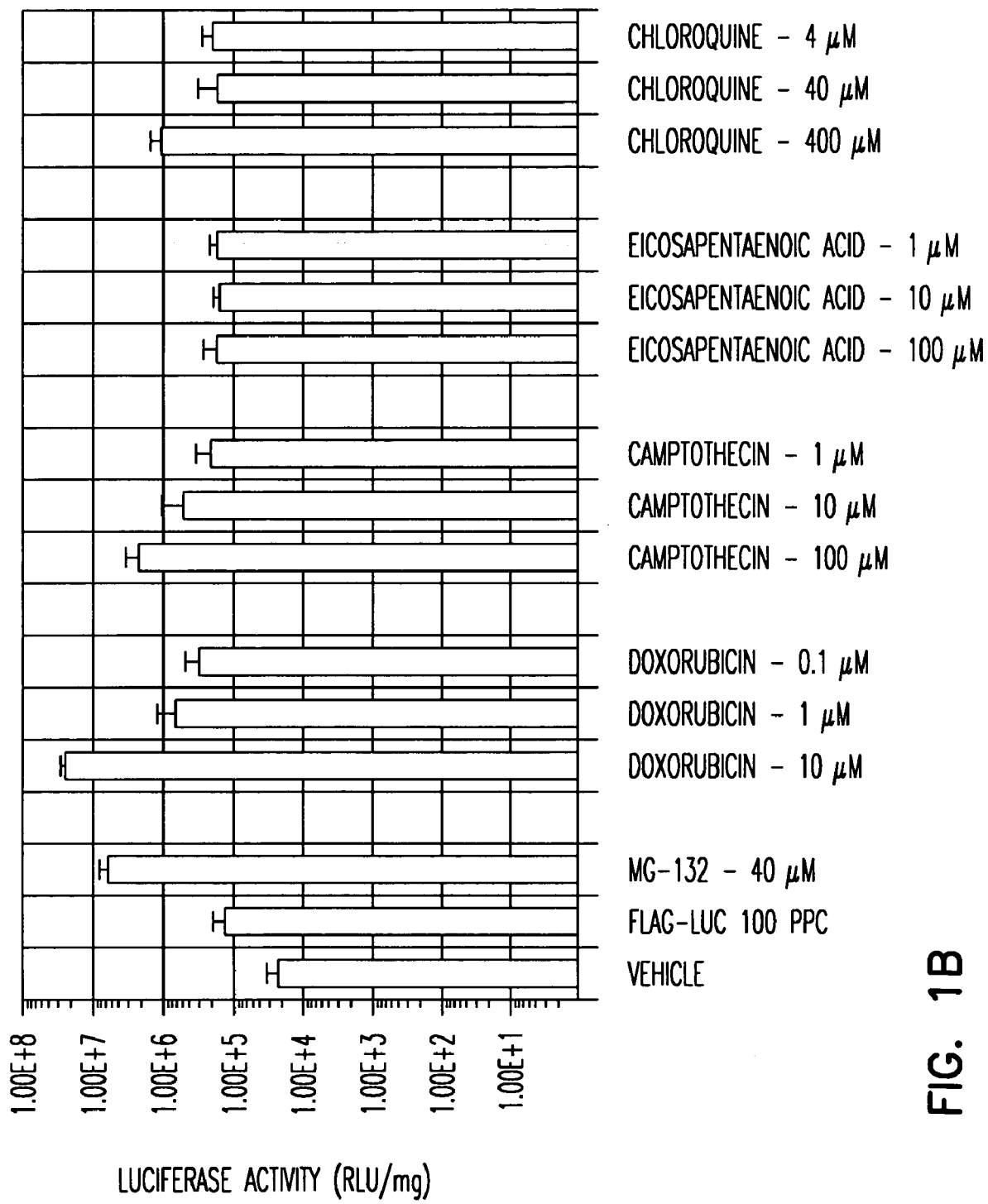
Figure 1C:
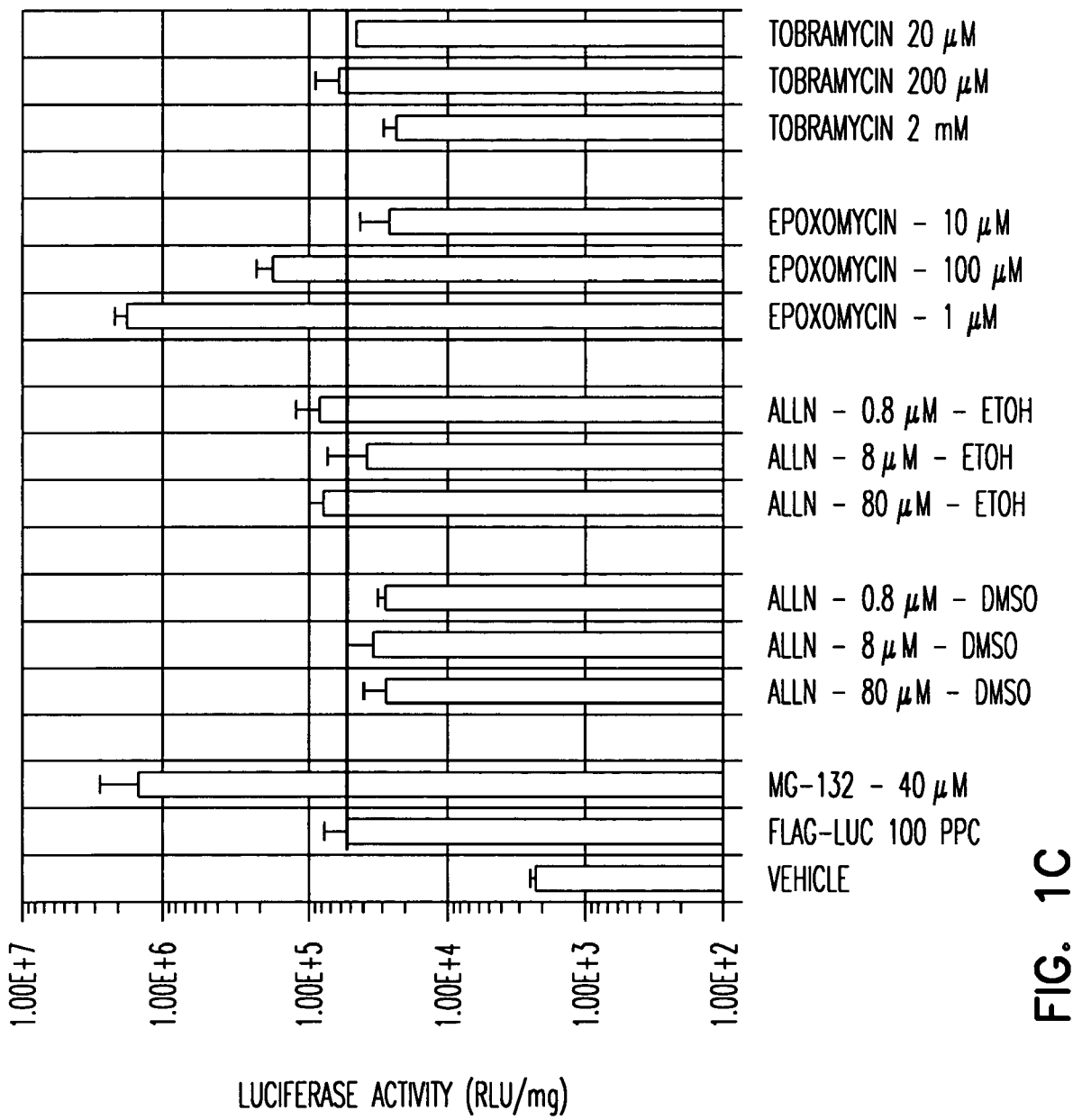
Figure 1D:
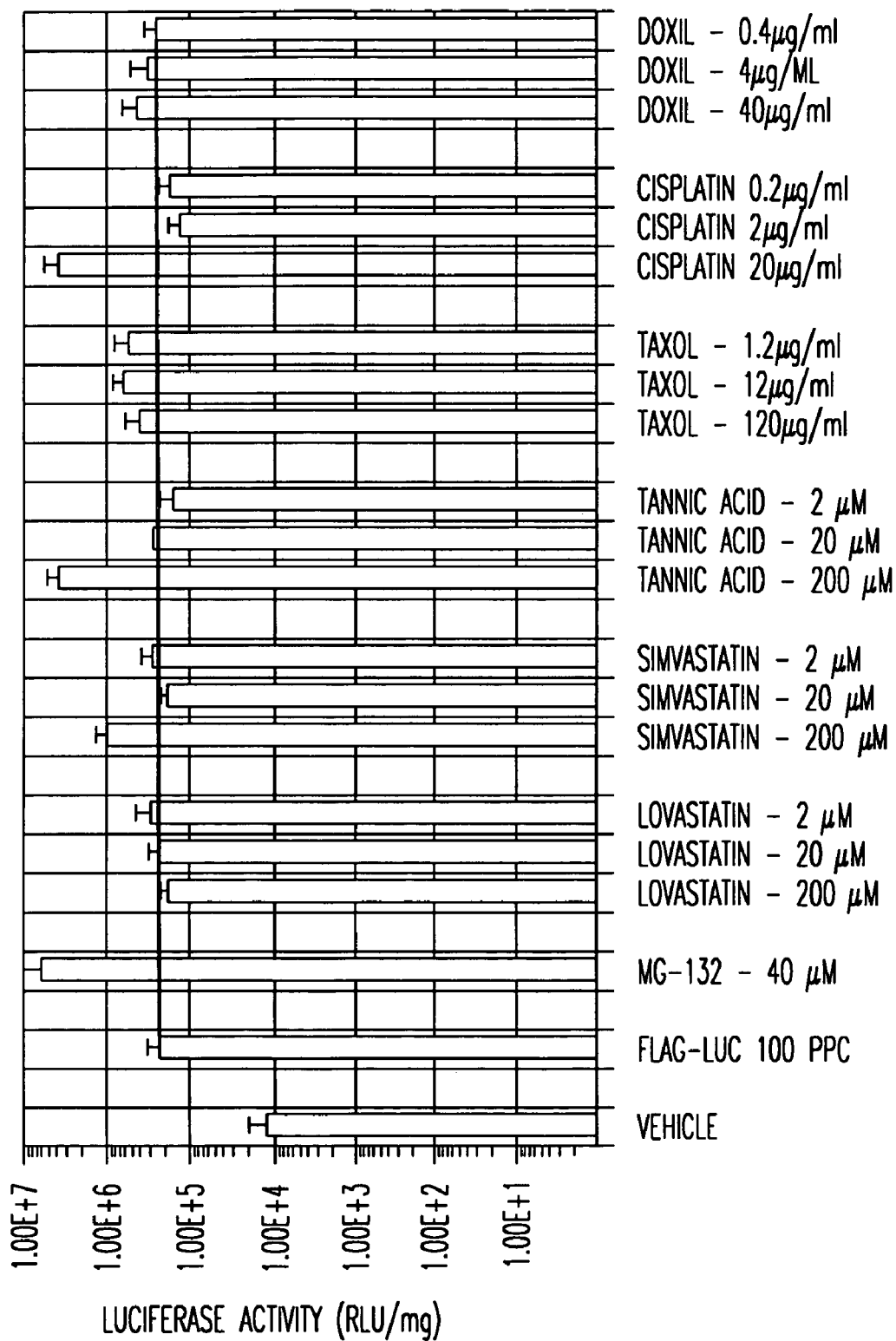
Figure 1E:
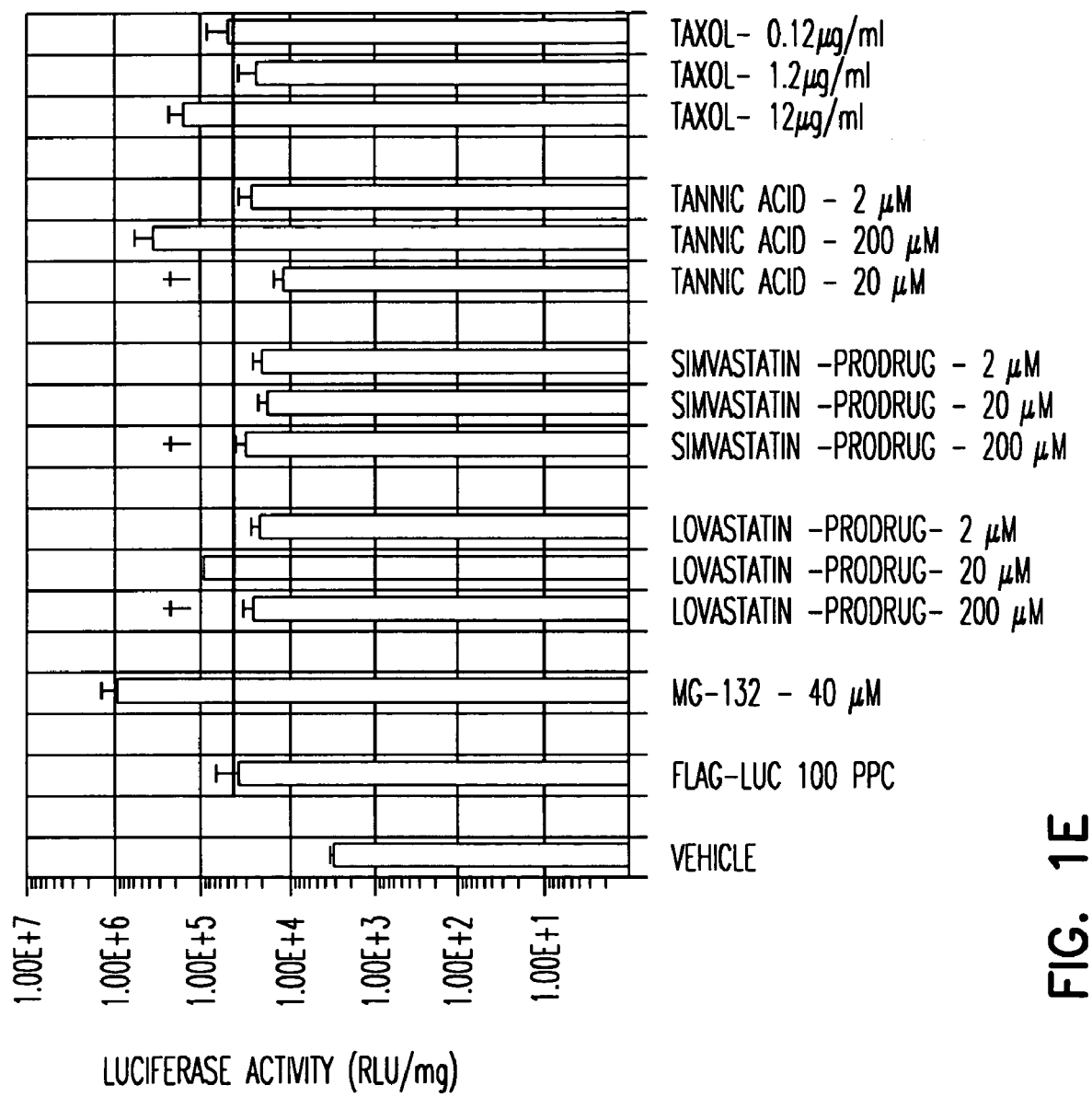
Figure 2:
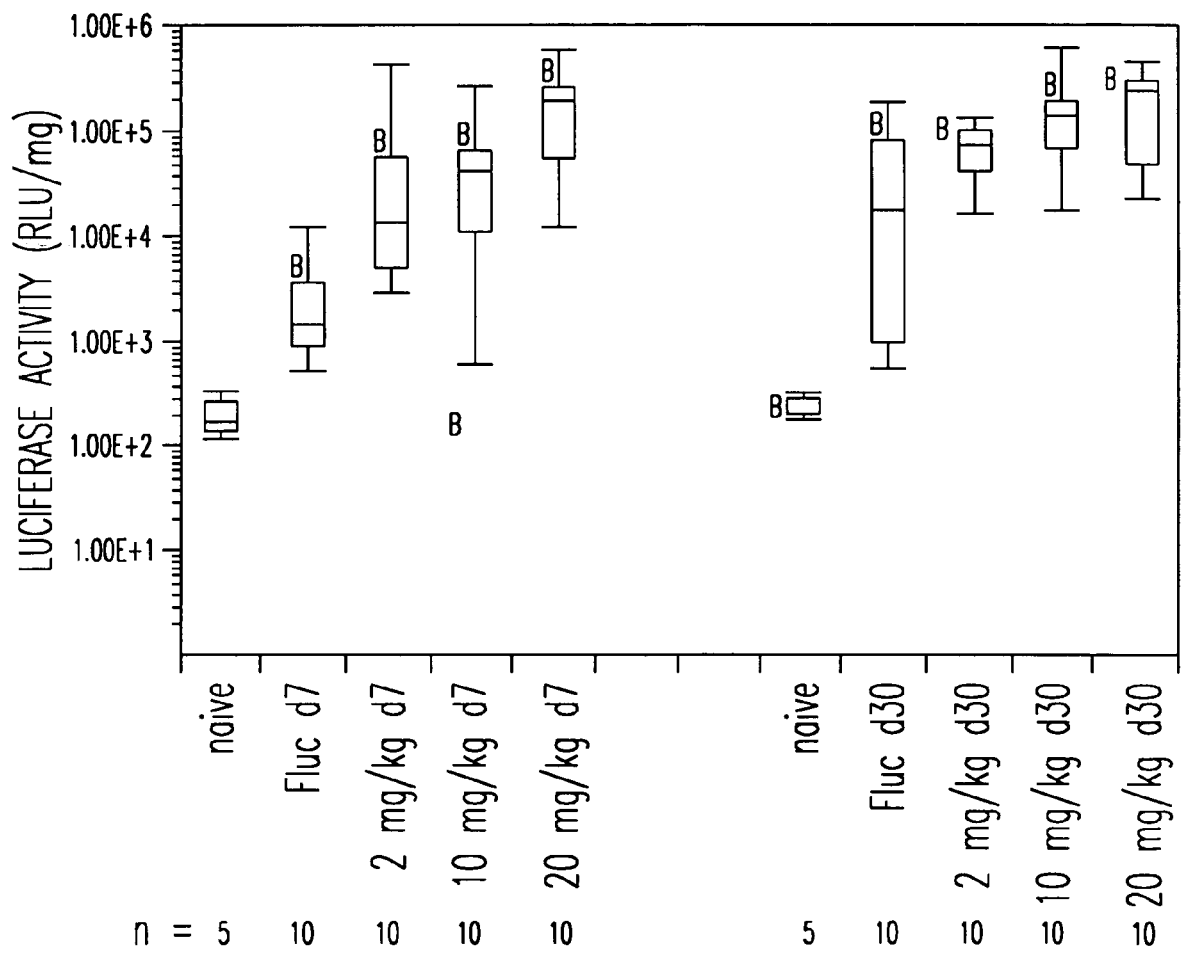
FIG. 2. In vivo enhancement of rAAV transduction with DOXIL®. Male Balb/c mice intravenously administered DOXIL® were endotracheally instilled with $1\times10^{11}$ DRP AAV2FLAG-Luc (01:004). A) Effect on rAAV lung transduction. B) Effect on rAAV tracheal and bronchial transduction.

A "vector" as used herein refers to a macromolecule or association of macromolecules that comprises or associates with a polynucleotide and which can be used to mediate delivery of the polynucleotide to a cell, either in vitro or in vivo. Illustrative vectors include, for example, plasmids, viral vectors, liposomes and other gene delivery vehicles. The polynucleotide to be delivered, sometimes referred to as a "target polynucleotide" or "transgene," may comprise a coding sequence of interest in gene therapy (such as a gene encoding a protein of therapeutic or interest), a coding sequence of interest in vaccine development (such as a polynucleotide expressing a protein, polypeptide or peptide suitable for eliciting an immune response in a mammal), and/or a selectable or detectable marker.

"AAV" is adeno-associated virus, and may be used to refer to the naturally occurring wild-type virus itself or derivatives thereof. The term covers all subtypes, serotypes and pseudotypes, and both naturally occurring and recombinant forms, except where required otherwise. As used herein, the term "serotype" refers to an AAV which is identified by and distinguished from other AAVs based on capsid protein reactivity with defined antisera, e.g., there are eight serotypes of primate AAVs, AAV-1 to AAV-8. For example, serotype AAV2 is used to refer to an AAV which contains capsid proteins encoded from the cap gene of AAV 2 and a genome containing 5' and 3' ITR sequences from the same AAV2 serotype. Pseudotyped AAV as refers to an AAV that contains capsid proteins from one serotype and a viral genome including 5'-3' ITRs of a second serotype. Pseudotyped rAAV would be expected to have cell surface binding properties of the capsid serotype and genetic properties consistent with the ITR serotype. Pseudotyped rAAV are produced using standard techniques described in the art. As used herein, for example, rAAV5 may be used to refer an AAV having both capsid proteins and 5'-3' ITRs from the same serotype or it may refer to an AAV having capsid proteins from serotype 5 and 5'-3' ITRs from a different AAV serotype, e.g., AAV serotype 2. For each example illustrated herein the description of the vector design and production describes the serotype of the capsid and 5'-3' ITR sequences. The abbreviation "rAAV" refers to recombinant adeno-associated virus, also referred to as a recombinant AAV vector (or "rAAV vector").

"Transduction" or "transducing" as used herein, are terms referring to a process for the introduction of an exogenous polynucleotide, e.g., a transgene in rAAV vector, into a host cell leading to expression of the polynucleotide, e.g., the transgene in the cell. The process includes 1) endocytosis of the AAV after it has bound to a cell surface receptor, 2) escape from endosomes or other intracellular compartments in the cytosol of a cell, 3) trafficking of the viral particle or viral genome to the nucleus, 4) uncoating of the virus particles, and generation of expressible double stranded AAV genome forms, including circular intermediates. The rAAV expressible double stranded form may persist as a nuclear episome or optionally may integrate into the host genome. The alteration of any or a combination of endocytosis of the AAV after it has bound to a cell surface receptor, escape from endosomes or other intracellular compartments to the cytosol of a cell, trafficking of the viral particle or viral genome to the nucleus, or uncoating of the virus particles, and generation of expressive double stranded AAV genome forms, including circular intermediates, by an agent of the invention, may result in altered expression levels or persistence of expression, or altered trafficking to the nucleus, or altered types or relative numbers of host cells or a population of cells expressing the introduced polynucleotide. Altered expression or persistence of a polynucleotide introduced via rAAV can be determined by methods well known to the art including, but not limited to, protein expression, e.g., by ELISA, flow cytometry and Western blot, measurement of and DNA and RNA production by hybridization assays, e.g., Northern blots, Southern blots and gel shift mobility assays. The agents of the invention preferably alter, enhance or increase viral endocytosis, escape from endosomes or other intracellular cytosolic compartments, and trafficking into or to the nucleus, uncoating of the viral particles in the nucleus, and/or increasing concatamerization or generation of double stranded expressible forms of the rAAV genome in the nucleus, so as to alter expression of the introduced polynucleotide, e.g., a transgene in a rAAV vector, in vitro or in vivo. Methods used for the introduction of the exogenous polynucleotide include well-known techniques such as transfection, lipofection, viral infection, transformation, and electroporation, as well as non-viral gene delivery techniques. The introduced polynucleotide may be stably or transiently maintained in the host cell.

"Increased transduction or transduction frequency", "altered transduction or transduction frequency", or "enhanced transduction or transduction frequency" refers to an increase in one or more of the activities described above in a treated cell relative to an untreated cell. Agents of the invention which increase transduction efficiency may be determined by measuring the effect on one or more transduction activities, which may include measuring the expression of the transgene, measuring the function of the transgene, or determining the number of rAAV vector particles necessary to yield the same transgene effect compared to host cells not treated with the agents.

"Proteosome modulator" refers to an agent or class of agents which alter or enhance rAAV transduction or rAAV transduction frequencies by interacting with, binding to, or altering the function of, and/or trafficking or location of the proteosome. Proteosome modulators may have other cellular functions as described in the art, e.g., such as doxyrubicin, an antibiotic. Proteosome modulators of the current invention do not include proteosome inhibitors, e.g., such as tripeptidyl aldehydes (Z-LLL or LLnL), agents that inhibit calpains, cathepsins, cysteine proteases, and/or chymotrypsin-like protease activity of proteasomes (Wagner et al., 2002; Young et al., 2000; Seisenberger et al., 2001).

"Generation of double stranded expressible forms" or "conversion of single to double strand rAAV genomes" refers to the process of replicating in the nucleus of an rAAV infected host cell a complimentary strand of the rAAV single stranded vector DNA genome and annealing of the complimentary strand to the vector genome to produce a double stranded DNA rAAV genome. Agents of the invention described herein to increase, alter, or enhance rAAV transduction include agents which increase the rate of nuclear transport or the steady state of single stranded viral DNA genomes in the nucleus which can drive gene conversion events via steady state mechanisms. For the purposes of the invention described herein, agents which enhance conversion of single to double strands do not include agents which increase the concentration of DNA repair enzymes or activate alternate DNA repair mechanism described by Russel et al. (1995).

"Gene delivery" refers to the introduction of an exogenous polynucleotide into a cell for gene transfer, and may encompass targeting, binding, uptake, transport, localization, replicon integration and expression.

"Gene transfer" refers to the introduction of an exogenous polynucleotide into a cell which may encompass targeting, binding, uptake, transport, localization and replicon integration, but is distinct from and does not imply subsequent expression of the gene.

"Gene expression" or "expression" refers to the process of gene transcription, translation, and post-translational modification.

A "detectable marker gene" is a gene that allows cells carrying the gene to be specifically detected (e.g., distinguished from cells which do not carry the marker gene). A large variety of such marker genes are known in the art.

A "selectable marker gene" is a gene that allows cells carrying the gene to be specifically selected for or against, in the presence of a corresponding selective agent. By way of illustration, an antibiotic resistance gene can be used as a positive selectable marker gene that allows a host cell to be positively selected for in the presence of the corresponding antibiotic. A variety of positive and negative selectable markers are known in the art, some of which are described below.

An "rAAV vector" as used herein refers to an AAV vector comprising a polynucleotide sequence not of AAV origin (i.e., a polynucleotide heterologous to AAV), typically a sequence of interest for the genetic transformation of a cell. In preferred vector constructs of this invention, the heterologous polynucleotide is flanked by at least one, preferably two AAV inverted terminal repeat sequences (ITRs). The term rAAV vector encompasses both rAAV vector particles and rAAV vector plasmids.

An "AAV virus" or "AAV viral particle" refers to a viral particle composed of at least one AAV capsid protein (preferably by all of the capsid proteins of a wild-type AAV) and an encapsidated polynucleotide. If the particle comprises a heterologous polynucleotide (i.e., a polynucleotide other than a wild-type AAV genome such as a transgene to be delivered to a mammalian cell), it is typically referred to as "rAAV".

A "rAAV vaccine" as used herein refers to an AAV vector comprising a polynucleotide sequence not of AAV origin (i.e., a polynucleotide heterologous to AAV), that encodes a peptide, polypeptide, or protein capable of eliciting an immune response in a host contacted with the vector. Expression of the polynucleotide may result in generation of a neutralizing antibody response and/or a cell mediated response, e.g., a cytotoxic T cell response. In preferred vector constructs of this invention, the heterologous polynucleotide is flanked by at least one, preferably two AAV inverted terminal repeat sequences (ITRs).

A "helper virus" for AAV refers to a virus that allows AAV (e.g., wild-type AAV) to be replicated and packaged by a mammalian cell. A variety of such helper viruses for AAV are known in the art, including adenoviruses, herpes viruses and poxviruses such as vaccinia. The adenoviruses encompass a number of different subgroups, although Adenovirus type 5 of subgroup C is most commonly used. Numerous adenoviruses of human, non-human mammalian and avian origin are known and available from depositories such as the ATCC. Viruses of the herpes family include, for example, herpes simplex viruses (HSV) and Epstein-Barr viruses (EBV), as well as cytomegaloviruses (CMV) and pseudorabies viruses (PRV); which are also available from depositories such as ATCC.

An "infectious" virus or viral particle is one that comprises a polynucleotide component which it is capable of delivering into a cell for which the viral species is trophic. The term does not necessarily imply any replication capacity of the virus. A "replication-competent" virus (e.g., a replication-competent AAV, sometimes abbreviated as "RCA") refers to a phenotypically wild-type virus that is infectious, and is also capable of being replicated in an infected cell (i.e., in the presence of a helper virus or helper virus functions). In the case of AAV, replication competence generally requires the presence of functional AAV packaging genes. Preferred rAAV vectors as described herein are replication-incompetent in mammalian cells (especially in human cells) by virtue of the lack of one or more AAV packaging genes. Preferably, such rAAV vectors lack any AAV packaging gene sequences in order to minimize the possibility that RCA are generated by recombination between AAV packaging genes and an incoming rAAV vector. Preferred rAAV vector preparations as described herein are those which contain few if any RCA (preferably less than about 1 RCA per $10^2$ rAAV particles, more preferably less than about 1 RCA per $10^4$ rAAV particles, still more preferably less than about 1 RCA per $10^8$ rAAV particles, even more preferably less than about 1 RCA per $10^{12}$ rAAV particles, most preferably no RCA).

The term "polynucleotide" refers to a polymeric form of nucleotides of any length, including deoxyribonucleotides or ribonucleotides, or analogs thereof. A polynucleotide may comprise modified nucleotides, such as methylated or capped nucleotides and nucleotide analogs, and may be interrupted by non-nucleotide components. If present, modifications to the nucleotide structure may be imparted before or after assembly of the polymer. The term polynucleotide, as used herein, refers interchangeably to double- and single-stranded molecules. Unless otherwise specified or required, any embodiment of the invention described herein that is a polynucleotide encompasses both the double-stranded form and each of two complementary single-stranded forms known or predicted to make up the double-stranded form.

A "transcriptional regulatory sequence" or "TRS," as used herein, refers to a genomic region that controls the transcription of a gene or coding sequence to which it is operably linked. Transcriptional regulatory sequences of use in the present invention generally include at least one transcriptional promoter and may also include one or more enhancers and/or terminators of transcription.

"Operably linked" refers to an arrangement of two or more components, wherein the components so described are in a relationship permitting them to function in a coordinated manner. By way of illustration, a transcriptional regulatory sequence or a promoter is operably linked to a coding sequence if the TRS or promoter promotes transcription of the coding sequence. An operably linked TRS is generally joined in cis with the coding sequence, but it is not necessarily directly adjacent to it.

"Heterologous" means derived from a genotypically distinct entity from that of the rest of the entity to which it is compared. For example, a polynucleotide introduced by genetic engineering techniques into a different cell type is a heterologous polynucleotide (and, when expressed, can encode a heterologous polypeptide). Similarly, a TRS or promoter that is removed from its native coding sequence and operably linked to a different coding sequence is a heterologous TRS or promoter.

"Packaging" as used herein refers to a series of subcellular events that results in the assembly and encapsidation of a viral vector, particularly an AAV vector. Thus, when a suitable vector is introduced into a packaging cell line under appropriate conditions, it can be assembled into a viral particle. Functions associated with packaging of viral vectors, particularly AAV vectors, are described herein and in the art.

A "terminator" refers to a polynucleotide sequence that tends to diminish or prevent read-through transcription (i.e., it diminishes or prevent transcription originating on one side of the terminator from continuing through to the other side of the terminator). The degree to which transcription is disrupted is typically a function of the base sequence and/or the length of the terminator sequence. In particular, as is well known in numerous molecular biological systems, particular DNA sequences, generally referred to as "transcriptional termination sequences" are specific sequences that tend to disrupt read-through transcription by RNA polymerase, presumably by causing the RNA polymerase molecule to stop and/or disengage from the DNA being transcribed. Typical example of such sequence-specific terminators include polyadenylation ("polyA") sequences, e.g., SV40 polyA. In addition to or in place of such sequence-specific terminators, insertions of relatively long DNA sequences between a promoter and a coding region also tend to disrupt transcription of the coding region, generally in proportion to the length of the intervening sequence. This effect presumably arises because there is always some tendency for an RNA polymerase molecule to become disengaged from the DNA being transcribed, and increasing the length of the sequence to be traversed before reaching the coding region would generally increase the likelihood that disengagement would occur before transcription of the coding region was completed or possibly even initiated. Terminators may thus prevent transcription from only one direction ("uni-directional" terminators) or from both directions ("bi-directional" terminators), and may be comprised of sequence-specific termination sequences or sequence-nonspecific terminators or both. A variety of such terminator sequences are known in the art; and illustrative uses of such sequences within the context of the present invention are provided below.

"Host cells," "cell lines," "cell cultures," "packaging cell line" and other such terms denote higher eukaryotic cells, preferably mammalian cells, most preferably human cells, useful in the present invention. These cells can be used as recipients for recombinant vectors, viruses or other transfer polynucleotides, and include the progeny of the original cell that was transduced. It is understood that the progeny of a single cell may not necessarily be completely identical (in morphology or in genomic complement) to the original parent cell.

A "therapeutic gene," "prophylactic gene," "target polynucleotide," "transgene," "gene of interest" and the like generally refer to a gene or genes to be transferred using a vector. Typically, in the context of the present invention, such genes are located within the rAAV vector (which vector is flanked by inverted terminal repeat (ITR) regions and thus can be replicated and encapsidated into rAAV particles). Target polynucleotides can be used in this invention to generate rAAV vectors for a number of different applications. Such polynucleotides include, but are not limited to: (i) polynucleotides encoding proteins useful in other forms of gene therapy to relieve deficiencies caused by missing, defective or suboptimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as E1A tumor suppressor genes or p53 tumor suppressor genes for the treatment of various cancers. To effect expression of the transgene in a recipient host cell, it is preferably operably linked to a promoter, either its own or a heterologous promoter. A large number of suitable promoters are known in the art, the choice of which depends on the desired level of expression of the target polynucleotide; whether one wants constitutive expression, inducible expression, cell-specific or tissue-specific expression, etc. The rAAV vector may also contain a selectable marker.

A "gene" refers to a polynucleotide containing at least one open reading frame that is capable of encoding a particular protein after being transcribed and translated.

"Recombinant," as applied to a polynucleotide means that the polynucleotide is the product of various combinations of cloning, restriction and/or ligation steps, and other procedures that result in a construct that is distinct from a polynucleotide found in nature. A recombinant virus is a viral particle comprising a recombinant polynucleotide. The terms respectively include replicates of the original polynucleotide construct and progeny of the original virus construct.

A "control element" or "control sequence" is a nucleotide sequence involved in an interaction of molecules that contributes to the functional regulation of a polynucleotide, including replication, duplication, transcription, splicing, translation, or degradation of the polynucleotide. The regulation may affect the frequency, speed, or specificity of the process, and may be enhancing or inhibitory in nature. Control elements known in the art include, for example, transcriptional regulatory sequences such as promoters and enhancers. A promoter is a DNA region capable under certain conditions of binding RNA polymerase and initiating transcription of a coding region usually located downstream (in the 3' direction) from the promoter. Promoters include AAV promoters, e.g., P5, P19, P40 and AAV ITR promoters, as well as heterologous promoters.

An "expression vector" is a vector comprising a region which encodes a polypeptide of interest, and is used for effecting the expression of the protein in an intended target cell. An expression vector also comprises control elements operatively linked to the encoding region to facilitate expression of the protein in the target. The combination of control elements and a gene or genes to which they are operably linked for expression is sometimes referred to as an "expression cassette," a large number of which are known and available in the art or can be readily constructed from components that are available in the art.

"Genetic alteration" refers to a process wherein a genetic element is introduced into a cell other than by mitosis or meiosis. The element may be heterologous to the cell, or it may be an additional copy or improved version of an element already present in the cell. Genetic alteration may be effected, for example, by transfecting a cell with a recombinant plasmid or other polynucleotide through any process known in the art, such as electroporation, calcium phosphate precipitation, or contacting with a polynucleotide-liposome complex. Genetic alteration may also be effected, for example, by transduction or infection with a DNA or RNA virus or viral vector. Preferably, the genetic element is introduced into a chromosome or mini-chromosome in the cell; but any alteration that changes the phenotype and/or genotype of the cell and its progeny is included in this term.

A cell is said to be "stably" altered, transduced or transformed with a genetic sequence if the sequence is available to perform its function during extended culture of the cell in vitro. In preferred examples, such a cell is "inheritably" altered in that a genetic alteration is introduced which is also inheritable by progeny of the altered cell.

The terms "polypeptide" and "protein" are used interchangeably herein to refer to polymers of amino acids of any length. The terms also encompass an amino acid polymer that has been modified; for example, disulfide bond formation, glycosylation, acetylation, phosphonylation, lipidation, or conjugation with a labeling component. Polypeptides such as "CFTR" and the like, when discussed in the context of gene therapy and compositions therefor, refer to the respective intact polypeptide, or any fragment or genetically engineered derivative thereof, that retains the desired biochemical function of the intact protein. Similarly, references to CFTR, and other such genes for use in gene therapy (typically referred to as "transgenes" to be delivered to a recipient cell), include polynucleotides encoding the intact polypeptide or any fragment or genetically engineered derivative possessing the desired biochemical function.

An "isolated" plasmid, virus, or other substance refers to a preparation of the substance devoid of at least some of the other components that may also be present where the substance or a similar substance naturally occurs or is initially prepared from. Thus, for example, an isolated substance may be prepared by using a purification technique to enrich it from a source mixture. Enrichment can be measured on an absolute basis, such as weight per volume of solution, or it can be measured in relation to a second, potentially interfering substance present in the source mixture. Increasing enrichments of the embodiments of this invention are increasingly more preferred. Thus, for example, a 2-fold enrichment is preferred, 10-fold enrichment is more preferred, 100-fold enrichment is more preferred, 1000-fold enrichment is even more preferred.

A preparation of AAV is said to be "substantially free" of helper virus if the ratio of infectious AAV particles to infectious helper virus particles is at least about $10^2:1$; preferably at least about $10^4:1$, more preferably at least about $10^6:1$; still more preferably at least about $10^8:1$. Preparations are also preferably free of equivalent amounts of helper virus proteins (i.e., proteins as would be present as a result of such a level of helper virus if the helper virus particle impurities noted above were present in disrupted form). Viral and/or cellular protein contamination can generally be observed as the presence of Coomassie staining bands on SDS gels (e.g., the appearance of bands other than those corresponding to the AAV capsid proteins VP1, VP2 and VP3).

"Efficiency" when used in describing viral production, replication or packaging refers to useful properties of the method: in particular, the growth rate and the number of virus particles produced per cell. "High efficiency" production indicates production of at least 100 viral particles per cell; preferably at least about 10,000 and more preferably at least about 100,000 particles per cell, over the course of the culture period specified.

An "individual" or "subject" treated in accordance with this invention refers to vertebrates, particularly members of a mammalian species, and includes but is not limited to domestic animals, sports animals, and primates, including humans.

"Treatment" of an individual or a cell is any type of intervention in an attempt to alter the natural course of the individual or cell at the time the treatment is initiated, e.g., eliciting a prophylactic, curative or other beneficial effect in the individual. For example, treatment of an individual may be undertaken to decrease or limit the pathology caused by any pathological condition, including (but not limited to) an inherited or induced genetic deficiency, infection by a viral, bacterial, or parasitic organism, a neoplastic or aplastic condition, or an immune system dysfunction such as autoimmunity or immunosuppression. Treatment includes (but is not limited to) administration of a composition, such as a pharmaceutical composition, and administration of compatible cells that have been treated with a composition. Treatment may be performed either prophylactically or therapeutically; that is, either prior or subsequent to the initiation of a pathologic event or contact with an etiologic agent.

The practice of the present invention will employ, unless otherwise indicated, conventional techniques of molecular biology, virology, microbiology, recombinant DNA, and immunology, which are within the skill of the art. Such techniques are explained fully in the literature. See, e.g., Sambrook et al., 1989; Gait, 1984; Freshney, 1987; the series *Methods in Enzymology* (Academic Press, Inc.); Miller et al., 1987; Weir et al., 1996; Ausubel et al., 1998; Coligan et al., 1991; Coligan et al., 1995; and Scopes 1994.

I. rAAV Vectors

Recombinant AAV vectors are potentially powerful tools for human gene therapy, particularly for diseases such as cystic fibrosis and sickle cell anemia. A major advantage of rAAV vectors over other approaches to gene therapy is that they generally do not require ongoing replication of the target cell in order to become stably integrated into the host cell.

rAAV vectors and/or viruses are also potentially powerful for the development of therapeutic or prophylactic vaccines to prevent infection, progression, and/or severity of disease. A major advantage of rAAV vectors for vaccine development is that they are capable of persisting for essentially the lifetime of the cell as a nuclear episome and therefore provide long term expression of the peptide, polypeptide, or protein of immunologic interest. Transgenes of interest include viral gene e.g. the envelope (env) or gag genes of HIV; bacterial genes e.g., streptococcal cell wall proteins; fungi, e.g., cocidomycosis; parasites, e.g., Leischmaniosis, or cancer genes, e.g. p53.

rAAV vectors and/or viruses may also contain one or more detectable markers. A variety of such markers are known, including, by way of illustration, the bacterial beta-galactosidase (lacZ) gene; the human placental alkaline phosphatase (AP) gene and genes encoding various cellular surface markers which have been used as reporter molecules both in vitro and in vivo. The rAAV vectors and/or viruses may also contain one or more selectable markers.

Recombinant AAV vectors and/or viruses can also comprise polynucleotides that do not encode proteins, including, e.g., polynucleotides encoding for antisense mRNA (the complement of mRNA) which can be used to block the translation of normal mRNA by forming a duplex with it, and polynucleotides that encode ribozymes (RNA catalysts).

II. Selection and Preparation of AAV Vector

Adeno-associated viruses of any serotype are suitable to prepare rAAV, since the various serotypes are functionally and structurally related, even at the genetic level (see, e.g., Blacklow, 1988; and Rose, 1974). All AAV serotypes apparently exhibit similar replication properties mediated by homologous rep genes; and all generally bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to ITRs. The similar infectivity patterns also suggest that the replication functions in each serotype are under similar regulatory control. Among the various AAV serotypes, AAV2 is most commonly employed.

An AAV vector of the invention typically comprises a polynucleotide that is heterologous to AAV. The polynucleotide is typically of interest because of a capacity to provide a function to a target cell in the context of gene therapy, such as up- or down-regulation of the expression of a certain phenotype. Such a heterologous polynucleotide or "transgene," generally is of sufficient length to provide the desired function or encoding sequence.

Where transcription of the heterologous polynucleotide is desired in the intended target cell, it can be operably linked to its own or to a heterologous promoter, depending for example on the desired level and/or specificity of transcription within the target cell, as is known in the art. Various types of promoters and enhancers are suitable for use in this context. Constitutive promoters provide an ongoing level of gene transcription, and are preferred when it is desired that the therapeutic or prophylactic polynucleotide be expressed on an ongoing basis. Inducible promoters generally exhibit low activity in the absence of the inducer, and are up-regulated in the presence of the inducer. They may be preferred when expression is desired only at certain times or at certain locations, or when it is desirable to titrate the level of expression using an inducing agent. Promoters and enhancers may also be tissue-specific: that is, they exhibit their activity only in certain cell types, presumably due to gene regulatory elements found uniquely in those cells.

Illustrative examples of promoters are the SV40 late promoter from simian virus 40, the Baculovirus polyhedron enhancer/promoter element, Herpes Simplex Virus thymidine kinase (HSV tk), the immediate early promoter from cytomegalovirus (CMV) and various retroviral promoters including LTR elements. Inducible promoters include heavy metal ion inducible promoters (such as the mouse mammary tumor virus (MMTV) promoter or various growth hormone promoters), and the promoters from T7 phage which are active in the presence of T7 RNA polymerase. By way of illustration, examples of tissue-specific promoters include various surfactin promoters (for expression in the lung), myosin promoters (for expression in muscle), and albumin promoters (for expression in the liver). A large variety of other promoters are known and generally available in the art, and the sequences of many such promoters are available in sequence databases such as the GenBank database.

Where translation is also desired in the intended target cell, the heterologous polynucleotide will preferably also comprise control elements that facilitate translation (such as a ribosome binding site or "RBS" and a polyadenylation signal). Accordingly, the heterologous polynucleotide generally comprises at least one coding region operatively linked to a suitable promoter, and may also comprise, for example, an operatively linked enhancer, ribosome binding site and poly-A signal. The heterologous polynucleotide may comprise one encoding region, or more than one encoding regions under the control of the same or different promoters. The entire unit, containing a combination of control elements and encoding region, is often referred to as an expression cassette.

The heterologous polynucleotide is integrated by recombinant techniques into or preferably in place of the AAV genomic coding region (i.e., in place of the AAV rep and cap genes), but is generally flanked on either side by AAV inverted terminal repeat (ITR) regions. This means that an ITR appears both upstream and downstream from the coding sequence, either in direct juxtaposition, preferably (although not necessarily) without any intervening sequence of AAV origin in order to reduce the likelihood of recombination that might regenerate a replication-competent AAV genome. However, a single ITR may be sufficient to carry out the functions normally associated with configurations comprising two ITRs (see, for example, WO 94/13788), and vector constructs with only one ITR can thus be employed in conjunction with the packaging and production methods of the present invention.

The native promoters for rep are self-regulating, and can limit the amount of AAV particles produced. The rep gene can also be operably linked to a heterologous promoter, whether rep is provided as part of the vector construct, or separately. Any heterologous promoter that is not strongly down-regulated by rep gene expression is suitable; but inducible promoters are preferred because constitutive expression of the rep gene can have a negative impact on the host cell. A large variety of inducible promoters are known in the art; including, by way of illustration, heavy metal ion inducible promoters (such as metallothionein promoters); steroid hormone inducible promoters (such as the MMTV promoter or growth hormone promoters); and promoters such as those from T7 phage which are active in the presence of T7 RNA polymerase. An especially preferred sub-class of inducible promoters are those that are induced by the helper virus that is used to complement the replication and packaging of the rAAV vector. A number of helper-virus-inducible promoters have also been described, including the adenovirus early gene promoter which is inducible by adenovirus E1A protein; the adenovirus major late promoter; the herpesvirus promoter which is inducible by herpesvirus proteins such as VP16 or 1CP4; as well as vaccinia or poxvirus inducible promoters.

Methods for identifying and testing helper-virus-inducible promoters have been described (see, e.g., WO 96/17947). Thus, methods are known in the art to determine whether or not candidate promoters are helper-virus-inducible, and whether or not they will be useful in the generation of high efficiency packaging cells. Briefly, one such method involves replacing the p5 promoter of the AAV rep gene with the putative helper-virus-inducible promoter (either known in the art or identified using well-known techniques such as linkage to promoter-less "reporter" genes). The AAV rep-cap genes (with p5 replaced), preferably linked to a positive selectable marker such as an antibiotic resistance gene, are then stably integrated into a suitable host cell (such as the HeLa or A549 cells exemplified below). Cells that are able to grow relatively well under selection conditions (e.g., in the presence of the antibiotic) are then tested for their ability to express the rep and cap genes upon addition of a helper virus. As an initial test for rep and/or cap expression, cells can be readily screened using immunofluorescence to detect Rep and/or Cap proteins. Confirmation of packaging capabilities and efficiencies can then be determined by functional tests for replication and packaging of incoming rAAV vectors. Using this methodology, a helper-virus-inducible promoter derived from the mouse metallothionein gene has been identified as a suitable replacement for the p5 promoter, and used for producing high titers of rAAV particles (as described in WO 96/17947).

Given the relative encapsidation size limits of various AAV genomes, insertion of a large heterologous polynucleotide into the genome necessitates removal of a portion of the AAV sequence. Removal of one or more AAV genes is in any case desirable, to reduce the likelihood of generating replication-competent AAV ("RCA"). Accordingly, encoding or promoter sequences for rep, cap, or both, are preferably removed, since the functions provided by these genes can be provided in trans.

The resultant vector is referred to as being "defective" in these functions. In order to replicate and package the vector, the missing functions are complemented with a packaging gene, or a plurality thereof, which together encode the necessary functions for the various missing rep and/or cap gene products. The packaging genes or gene cassettes are preferably not flanked by AAV ITRs and preferably do not share any substantial homology with the rAAV genome. Thus, in order to minimize homologous recombination during replication between the vector sequence and separately provided packaging genes, it is desirable to avoid overlap of the two polynucleotide sequences. The level of homology and corresponding frequency of recombination increase with increasing length of homologous sequences and with their level of shared identity. The level of homology that will pose a concern in a given system can be determined theoretically and confirmed experimentally, as is known in the art. Typically, however, recombination can be substantially reduced or eliminated if the overlapping sequence is less than about a 25 nucleotide sequence if it is at least 80% identical over its entire length, or less than about a 50 nucleotide sequence if it is at least 70% identical over its entire length. Of course, even lower levels of homology are preferable since they will further reduce the likelihood of recombination. It appears that, even without any overlapping homology, there is some residual frequency of generating RCA. Even further reductions in the frequency of generating RCA (e.g., by nonhomologous recombination) can be obtained by "splitting" the replication and encapsidation functions of AAV, as described by Allen et al., WO 98/27204).

The rAAV vector construct, and the complementary packaging gene constructs can be implemented in this invention in a number of different forms. Viral particles, plasmids, and stably transformed host cells can all be used to introduce such constructs into the packaging cell, either transiently or stably.

In certain embodiments of this invention, the AAV vector and complementary packaging gene(s), if any, are provided in the form of bacterial plasmids, AAV particles, or any combination thereof. In other embodiments, either the AAV vector sequence, the packaging gene(s), or both, are provided in the form of genetically altered (preferably inheritably altered) eukaryotic cells. The development of host cells inheritably altered to express the AAV vector sequence, AAV packaging genes, or both, provides an established source of the material that is expressed at a reliable level.

A variety of different genetically altered cells can thus be used in the context of this invention. By way of illustration, a mammalian host cell may be used with at least one intact copy of a stably integrated rAAV vector. An AAV packaging plasmid comprising at least an AAV rep gene operably linked to a promoter can be used to supply replication functions (as described in U.S. Pat. No. 5,658,776). Alternatively, a stable mammalian cell line with an AAV rep gene operably linked to a promoter can be used to supply replication functions (see, e.g., Trempe et al., WO 95/13392); Burstein et al. (WO 98/23018); and Johnson et al. (U.S. Pat. No. 5,656,785). The AAV cap gene, providing the encapsidation proteins as described above, can be provided together with an AAV rep gene or separately (see, e.g., the above-referenced applications and patents as well as Allen et al. (WO 98/27204). Other combinations are possible and included within the scope of this invention.

III. Generating rAAV

To generate recombinant AAV particles useful for such purposes as gene therapy, the packaging cell line is preferably supplied with a recombinant AAV vector comprising AAV inverted terminal repeat (ITR) regions surrounding one or more polynucleotides of interest (or "target" polynucleotides).

The target polynucleotide is generally operably linked to a promoter, either its own or a heterologous promoter. A large number of suitable promoters are known in the art, the choice of which depends on the desired level of expression of the target polynucleotide (i.e., whether one wants constitutive expression, inducible expression, cell-specific or tissue-specific expression, etc.).

Preferably, the rAAV vector also contains a positive selectable marker in order to allow for selection of cells that have been infected by the rAAV vector. Negative selectable markers can also be included; as a means of selecting against those same cells should that become necessary or desirable. In a preferred embodiment, one can make use of the "bifunctional selectable fusion genes" described by S. D. Lupton; see, e.g., PCT/US91/08442 and PCT/US94/05601. Briefly, those constructs involve direct translational fusions between a dominant positive selectable marker and a negative selectable marker. Preferred positive selectable markers are derived from genes selected from the group consisting of hph, neo, and gpt, and preferred negative selectable markers are derived from genes selected from the group consisting of cytosine deaminase, HSV-I TK, VZV TK, HPRT, APRT and gpt. Especially preferred markers are bifunctional selectable fusion genes wherein the positive selectable marker is derived from hph or neo, and the negative selectable marker is derived from cytosine deaminase or a TK gene.

Useful target polynucleotides can be employed in rAAV vectors for a number of different applications. Such polynucleotides include, but are not limited to: (i) polynucleotides encoding proteins useful in other forms of gene therapy to relieve deficiencies caused by missing, defective or sub-optimal levels of a structural protein or enzyme; (ii) polynucleotides that are transcribed into anti-sense molecules; (iii) polynucleotides that are transcribed into decoys that bind transcription or translation factors; (iv) polynucleotides that encode cellular modulators such as cytokines; (v) polynucleotides that can make recipient cells susceptible to specific drugs, such as the herpes virus thymidine kinase gene; and (vi) polynucleotides for cancer therapy, such as the wild-type p53 tumor suppressor cDNA for replacement of the missing or damaged p53 gene associated with some lung and breast cancers, or the E1A tumor suppressor gene which is capable of inhibiting tumorigenesis and/or metastasis of a variety of different cancers including breast and ovarian cancers.

Since the therapeutic or prophylactic specificity of the resulting recombinant AAV particle is determined by the particular vector or pro-vector introduced, the same basic packaging cell line can be modified for any of these applications. For example, a vector comprising a specific target polynucleotide can be introduced into the packaging cell for production of the AAV vector by any of several possible methods; including, for example, electroporation or transfection of a plasmid comprising an rAAV pro-vector, or infection with an rAAV or helper virus comprising an rAAV vector or pro-vector.

Helper virus can be introduced before, during or after introduction of the rAAV vector. For example, the plasmid can be co-infected into the culture along with the helper virus; and the cells can then be cultured for a sufficient period, typically 2-5 days, in conditions suitable for replication and packaging as known in the art (see references above and examples below). Lysates are prepared, and the recombinant AAV vector particles are purified by techniques known in the art.

In a preferred embodiment, also illustrated in the Examples below, a recombinant AAV vector is itself stably integrated into a mammalian cell to be used for packaging. Such rAAV "producer cells" can then be grown and stored until ready for use. To induce production of rAAV particles from such producer cells, the user need only infect the cells with helper virus and culture the cells under conditions suitable for replication and packaging of AAV (as described below).

Alternatively, one or more of the AAV split-packaging genes or the rAAV vector can be introduced as part of a recombinant helper virus. For example, the E1, E3 and/or the E4 genes of adenovirus can be replaced with one or more split-packaging genes or an rAAV vector. Techniques for facilitating cloning into adenovirus vectors, e.g., into the E1 and/or E3 regions, are known in the art (see, e.g., Bett, A. J. et al., *Proc. Natl. Acad. Sci. USA*, 91, 8802-8806 (1994)). Thus, a helper virus such as a recombinant adenovirus, can be used to provide helper virus functions as well as AAV packaging genes and/or an rAAV pro-vector, since (as is known in the art) a number of genes in such a helper virus (e.g., the E3 gene of adenovirus) can be replaced without eliminating helper virus activity. Additional genes can be inserted into such a helper virus by providing any necessary helper virus functions in trans. For example, human 293 cells contain adenoviral genes that can complement adenoviral E1 mutants. Thus, heterologous genes can also be cloned into an adenovirus in which the E1 genes have been deleted, for use in cells that can effectively provide such adenoviral functions in trans. Alternatively, the use of a helper virus can be eliminated by providing all necessary helper virus functions in the packaging cell.

IV. Introduction of Genetic Material into Cells

As is described in the art, and illustrated both herein and in the references cited above, genetic material can be introduced into cells (such as mammalian "producer" cells for the production of AAV) using any of a variety of means to transform or transduce such cells. By way of illustration, such techniques include, for example, transfection with bacterial plasmids, infection with viral vectors, electroporation, calcium phosphate precipitation, and introduction using any of a variety of lipid-based compositions (a process often referred to as "lipofection"). Methods and compositions for performing these techniques have been described in the art and are widely available.

Selection of suitably altered cells may be conducted by any technique in the art. For example, the polynucleotide sequences used to alter the cell may be introduced simultaneously with or operably linked to one or more detectable or selectable markers as is known in the art. By way of illustration, one can employ a drug-resistance gene as a selectable marker. Drug-resistant cells can then be picked and grown, and then tested for expression of the desired sequence, i.e., a packaging gene product, or a product of the heterologous polynucleotide, as appropriate. Testing for acquisition, localization and/or maintenance of an introduced polynucleotide can be performed using DNA hybridization-based techniques (such as Southern blotting and other procedures as is known in the art). Testing for expression can be readily performed by Northern analysis of RNA extracted from the genetically altered cells, or by indirect immunofluorescence for the corresponding gene product. Testing and confirmation of packaging capabilities and efficiencies can be obtained by introducing to the cell the remaining functional components of AAV and a helper virus, to test for production of AAV particles. Where a cell is inheritably altered with a plurality of polynucleotide constructs, it is generally more convenient (though not essential) to introduce them to the cell separately, and validate each step seriatim. References describing such techniques include those cited herein.

V. Selection and Preparation of Helper Virus

As discussed above, AAV is a parvovirus that is defective for self-replication, and must generally rely on a helper virus to supply certain replicative functions. A number of such helper viruses have been identified, including adenoviruses, herpes viruses (including but not limited to HSV1, cytomegalovirus and HHV-6), and pox viruses (particularly vaccinia). Any such virus may be used with this invention.

Frequently, the helper virus is an adenovirus of a type and subgroup that can infect the intended host cell. Human adenovirus of subgroup C, particularly serotypes 1, 2, 4, 6, and 7, are commonly used. Serotype 5 is generally preferred.

The features and growth patterns of adenovirus are known in the art. The reader may refer, for example, to Horowitz (1985). The packaged adenovirus genome is a linear DNA molecule, linked through adenovirus ITRs at the left- and right-hand termini through a terminal protein complex to form a circle. Control and encoding regions for early, intermediate, and late components overlap within the genome. Early region genes are implicated in replication of the adenovirus genome, and are grouped depending on their location into the E1, E2, E3, and E4 regions.

Although not essential, in principle it is desirable that the helper virus strain be defective for replication in the subject ultimately to receive the genetic therapy. Thus, any residual helper virus present in an rAAV preparation will be replication-incompetent. Adenoviruses from which the E1A or both the E1A and the E3 region have been removed are not infectious for most human cells. They can be replicated in a permissive cell line (e.g., the human 293 cell line) which is capable of complementing the missing activity. Regions of adenovirus that appear to be associated with helper function, as well as regions that do not, have been identified and described in the art (see, e.g., P. Colosi et al., WO97/17458, and references cited therein).

VI. Uses of rAAV for Gene Therapy

AAV vectors can be used for administration to an individual for purposes of gene therapy or vaccination. Suitable diseases for rAAV therapy include but are not limited to those induced by viral, bacterial, or parasitic infections, various malignancies and hyperproliferative conditions, autoimmune conditions, and congenital deficiencies.

Gene therapy can be conducted to enhance the level of expression of a particular protein either within or secreted by the cell. Vectors of this invention may be used to genetically alter cells either for gene marking, replacement of a missing or defective gene, or insertion of a therapeutic gene. Alternatively, a polynucleotide may be provided to the cell that decreases the level of expression. This may be used for the suppression of an undesirable phenotype, such as the product of a gene amplified or overexpressed during the course of a malignancy, or a gene introduced or overexpressed during the course of a microbial infection. Expression levels may be decreased by supplying a therapeutic or prophylactic polynucleotide comprising a sequence capable, for example, of forming a stable hybrid with either the target gene or RNA transcript (antisense therapy), capable of acting as a ribozyme to cleave the relevant mRNA or capable of acting as a decoy for a product of the target gene.

The introduction of rAAV vectors by the methods of the present invention may involve use of any number of delivery techniques (both surgical and non-surgical) which are available and well known in the art. Such delivery techniques, for example, include vascular catheterization, cannulization, injection, inhalation, endotracheal, subcutaneous, inunction, topical, oral, percutaneous, intra-arterial, intravenous, and/or intraperitoneal administrations. Vectors can also be introduced by way of bioprostheses, including, by way of illustration, vascular grafts (PTFE and dacron), heart valves, intravascular stents, intravascular paving as well as other nonvascular prostheses. General techniques regarding delivery, frequency, composition and dosage ranges of vector solutions are within the skill of the art.

In particular, for delivery of a vector of the invention to a tissue, any physical or biological method that will introduce the vector to a host animal can be employed. Vector means both a bare recombinant vector and vector DNA packaged into viral coat proteins, as is well known for AAV administration. Simply dissolving an AAV vector in phosphate buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the AAV vector as a free acid (DNA contains acidic phosphate groups) or a pharmacologically acceptable salt can be prepared in water suitably mixed with a surfactant such as hydroxypropylcellulose. A dispersion of AAV viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the AAV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for incorporation into a transdermal patch, and can include known carriers, such as pharmaceutical grade dimethylsulfoxide (DMSO).

Of particular interest is the correction of the genetic defect of cystic fibrosis, by supplying a properly functioning cystic fibrosis transmembrane conductance regulator (CFTR) to the airway epithelium. Thus, rAAV vectors encoding native CFTR protein, and mutants and fragments thereof, are all preferred embodiments of this invention.

Compositions of this invention may be used in vivo as well as ex vivo. In vivo gene therapy comprises administering the vectors of this invention directly to a subject. Pharmaceutical compositions can be supplied as liquid solutions or suspensions, as emulsions, or as solid forms suitable for dissolution or suspension in liquid prior to use. For administration into the respiratory tract, a preferred mode of administration is by aerosol, using a composition that provides either a solid or liquid aerosol when used with an appropriate aerosolubilizer device. Another preferred mode of administration into the respiratory tract is using a flexible fiberoptic bronchoscope to instill the vectors. Typically, the viral vectors are in a pharmaceutically suitable pyrogen-free buffer such as Ringer's balanced salt solution (pH 7.4). Although not required, pharmaceutical compositions may optionally be supplied in unit dosage form suitable for administration of a precise amount.

An effective amount of virus is administered, depending on the objectives of treatment. An effective amount may be given in single or divided doses. Where a low percentage of transduction can cure a genetic deficiency, then the objective of treatment is generally to meet or exceed this level of transduction. In some instances, this level of transduction can be achieved by transduction of only about 1 to 5% of the target cells, but is more typically 20% of the cells of the desired tissue type, usually at least about 50%, preferably at least about 80%, more preferably at least about 95%, and even more preferably at least about 99% of the cells of the desired tissue type. As a guide, the number of vector particles present in a single dose given by bronchoscopy will generally be at least about $1 \times 10^8$, and is more typically $5 \times 10^8$, $1 \times 10^{10}$, and on some occasions $1 \times 10^{11}$ particles, including both DNAse-resistant and DNAse-susceptible particles. In terms of DNAse-resistant particles, the dose will generally be between $1 \times 10^6$ and $1 \times 10^{14}$ particles, more generally between about $1 \times 10^8$ and $1 \times 10^{12}$ particles. The treatment can be repeated as often as every two or three weeks, as required, although treatment once in 180 days may be sufficient.

To confirm the presence of the desired DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence of a polypeptide expressed from a gene present in the vector, e.g., by immunological means (immunoprecipitations, immunoaffinity columns, ELISAs and Western blots) or by any other assay useful to identify the presence and/or expression of a particular nucleic acid molecule falling within the scope of the invention.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the DNA segment in question, they do not provide information as to whether the DNA segment is being expressed. Expression may be evaluated by specifically identifying the polypeptide products of the introduced DNA sequences or evaluating the phenotypic changes brought about by the expression of the introduced DNA segment in the host cell.

Thus, the effectiveness of the genetic alteration can be monitored by several criteria, including analysis of physiological fluid samples, e.g., urine, plasma, serum, blood, cerebrospinal fluid or nasal or lung washes. Samples removed by biopsy or surgical excision may be analyzed by in situ hybridization, PCR amplification using vector-specific probes, RNAse protection, immunohistology, or immunofluorescent cell counting. When the vector is administered by bronchoscopy, lung function tests may be performed, and bronchial lavage may be assessed for the presence of inflammatory cytokines. The treated subject may also be monitored for clinical features, and to determine whether the cells express the function intended to be conveyed by the therapeutic or prophylactic polynucleotide.

The decision of whether to use in vivo or ex vivo therapy, and the selection of a particular composition, dose, and route of administration will depend on a number of different factors, including but not limited to features of the condition and the subject being treated. The assessment of such features and the design of an appropriate therapeutic or prophylactic regimen is ultimately the responsibility of the prescribing physician.

The foregoing description provides, inter alia, methods for generating high titer preparations of recombinant AAV vectors that are substantially free of helper virus (e.g., adenovirus) and cellular proteins. It is understood that variations may be applied to these methods by those of skill in this art without departing from the spirit of this invention.

VII. Exemplary Methods to Identify Useful Agents

The utility of rAAV as a gene therapy vector is based on its transduction properties. Methods to detect AAV transduction are known in the art, including those described herein, and are useful to screen libraries, types and classes of agents for the ability to improve AAV transduction by means other than by affecting binding to cell surface receptors, or the rate of intra-nuclear genome conversion of the single stranded rAAV vector to a double stranded genome.

Transduction may be defined by protein expression of a heterologous transgene contained in the vector or steady state levels thereof. Hence, transduction is a measurable functional endpoint of successful gene delivery with a viral vector, e.g., rAAV. A variety of transgenes have been expressed from cells infected with AAV vectors, and include intracellularly expressed proteins such as the green fluorescent protein (GFP), cell membrane associated proteins such as the cystic fibrosis transmembrane protein (CFTR), and secretory proteins such as Epo, FVIII, and FIX. However, not all transgenes are capable of fully assessing the extent of transduction with a given vector and tissue target. For example, secreted proteins do not give indication of the number of cell types expressing a given transgene. Furthermore, functional markers of gene expression are dependent on the ability of a given transgene protein product to function properly within a given target cell type.

VIII. Agents Useful in the Practice of the Invention rAAV must undergo a number of complex intracellular events between binding and conversion to dsDNA that may be rate limiting for transduction efficiency including but not limited to rAAV endocytosis, trafficking and processing of the rAAV through the appropriate intracellular compartments (including without limitation proteosomes, endosomes, and trans-golgi), transport into the nucleus, and viral uncoating. Furthermore, agents that alter the efficiency of these intracellular processing events can also have an end result of increasing the amount of viral DNA in the nucleus and hence, through steady state, the abundance of gene conversion products. Thus, an increase in genome conversion products following enhancement of rAAV intracellular processing does not necessarily indicate an increased rate of gene conversion. Methods of enhancing transduction with rAAV are expected to increase the extent of double stranded genome conversion products in the nucleus. This is an important distinction with previous methods aimed at directly enhancing genome conversion using DNA damaging agents, topoisomerase inhibitors, or adenoviral early gene products (Alexander et al., 1997; Alexander et al., 1996; Ferrari et al., 1996; Fisher et al., 1996; Halbert et al., 1997; Russel et al., 1995) which essentially change the level of gene conversion enzymes in the nucleus. However, in cases where gene conversion in the nucleus is not rate limiting, intracellular viral processing events that limit transduction may predominate.

Thus, agents useful in the practice of the invention include agents which alter rAAV transduction efficiency, e.g., rAAV endocytosis, trafficking and processing of rAAV through the intracellular compartment, viral nucleic acid or protein degradation, viral uncoating and nuclear transport of virus or viral genomes or otherwise modulate proteosomes. Preferred agents are those which enhance or increase rAAV transduction. Classes of agents useful in the invention include but are not limited to antibiotics, chemotherapeutics, e.g., anthracyclines, proteosome modulators, lipid lowering agents, and food additives. Exemplary agents include proteasomes (Wagner et al., 2002; Young et al., 2000; Seisenberger et al., 2001), as well as agents that modulate the proteosome and ubiquitin pathways, e.g., bind to proteosomes and/or modulate the activity of proteosomes, ubiquitin, ubiquitin carrier protein, or ubiquitin ligase, but do not substantially alter the activity of the proteosome, e.g., the proteolytic activity of the proteasome or of ubiquitin, ubiquitin carrier protein, or ubiquitin ligase. Examples of these agents include without limitation antibiotics, e.g., epoxomicin, lipid lowering drugs, e.g., simvastatin, food additives, e.g., tannic acid, and chemotherapeutics, e.g., cisplatin, anthracyclines such as doxorubicin, and camptothecin.

IX. Dosages, Formulations and Routes of Administration of the Agents of the Invention Administration of the agents identified in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. When the agents of the invention are employed for prophylactic purposes, agents of the invention are amenable to chronic use, preferably by systemic administration.

One or more suitable unit dosage forms comprising the agents of the invention, which, as discussed below, may optionally be formulated for sustained release, can be administered by a variety of routes including oral, or parenteral, including by rectal, transdermal, subcutaneous, intravenous, intramuscular, intraperitoneal, intrathoracic, intrapulmonary and intranasal routes. For example, for administration to the liver, intravenous administration is preferred. For administration to the lung, airway administration is preferred. The formulations may, where appropriate, be conveniently presented in discrete unit dosage forms and may be prepared by any of the methods well known to pharmacy. Such methods may include the step of bringing into association the agent with liquid carriers, solid matrices, semi-solid carriers, finely divided solid carriers or combinations thereof, and then, if necessary, introducing or shaping the product into the desired delivery system.

When the agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The agents of the invention can also be formulated as elixirs or solutions for convenient oral administration or as solutions appropriate for parenteral administration, for instance by intramuscular, subcutaneous or intravenous routes.

The pharmaceutical formulations of the agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$-$C_4$ alkyl esters of short-chain acids, preferably ethyl or isopropyl lactate, fatty acid triglycerides such as the products marketed under the name MIGLYOL®, isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactideglycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The agents of the invention can be delivered via patches for transdermal administration. See U.S. Pat. No. 5,560,922 for examples of patches suitable for transdermal delivery of an agent. Patches for transdermal delivery can comprise a backing layer and a polymer matrix which has dispersed or dissolved therein an agent, along with one or more skin permeation enhancers. The backing layer can be made of any suitable material which is impermeable to the agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylene vinyl alcohol copolymers, ethylene-vinyloxyethanol copolymers; silicone copolymers, for example, polysiloxane-polycarbonate copolymers, polysiloxane-polyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Agents released from a transdermal delivery system must be capable of penetrating each layer of skin. In order to increase the rate of permeation of an agent, a transdermal drug delivery system must be able in particular to increase the permeability of the outermost layer of skin, the stratum corneum, which provides the most resistance to the penetration of molecules. The fabrication of patches for transdermal delivery of agents is well known to the art.

For administration to the upper (nasal) or lower respiratory tract by inhalation, the agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the agent may be administered via nose drops, a liquid spray, such as via a plastic bottle atomizer or metered-dose inhaler. Typical of atomizers are the Mistometer (Wintrop) and the Medihaler (Riker).

The local delivery of the agents of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of an agent of the invention present in a topical formulation will depend on various factors, but generally will be from 0.01% to 95% of the total weight of the formulation, and typically 0.1-25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The formulations and compositions described herein may also contain other ingredients such as antimicrobial agents, or preservatives. Furthermore, the active ingredients may also be used in combination with other agents, for example, bronchodilators.

The agents of this invention may be administered to a mammal alone or in combination with pharmaceutically acceptable carriers. As noted above, the relative proportions of active ingredient and carrier are determined by the solubility and chemical nature of the compound, chosen route of administration and standard pharmaceutical practice.

The dosage of the present agents will vary with the form of administration, the particular compound chosen and the physiological characteristics of the particular patient under treatment. Generally, small dosages will be used initially and, if necessary, will be increased by small increments until the optimum effect under the circumstances is reached.

The invention will be further described by, but is not limited to, the following examples. In particular, the following Examples are provided to exemplify various methods to detect rAAV transduction, which methods are described in WO 00/75365.

Example 1

Endosomal Processing Inhibitors May Increase rAAV Transduction in Polarized Airway Cells Materials and Methods Primary culture of human bronchial epithelia and reagents utilized. Primary human airway epithelial cells were collected by enzymatic digestion of bronchial samples from lung transplants, as previously described (Kondo et al., 1991; Zabner et al., 1996). Isolated primary airway cells were seeded at a density of $5 \times 10^5$ cells/cm$^2$ onto collagen-coated Millicell-HA culture inserts (Millipore Corp., Bedford, Mass.). Primary cultures were grown at the air-liquid interface for more than 2 weeks, by which time differentiation into a mucociliary epithelium occurs. The culture medium, used to feed only the basolateral side of the cells, contained 49% DMEM, 49% Ham's F12 and 2% Ultraser G (BioSepra, Cedex, France). Dimethyl Sulphoxide (DMSO), camptothecin (Camp), etoposide (Etop), aphidicolin (Aphi), hydroxyurea (HU) and genistein (Geni) were purchased from Sigma (St. Louis, Mo.). Tripeptidyl aldehyde proteasome inhibitors N-Acetyl-L-Leucyl-L-Leucyl-Norleucine (LLnL) and benzyloxycarbonyl-L-leucyl-L-leucyl-L-leucinal (Z-LLL) were purchased from Calbiochem-Novabiochem Corporation (La Jolla, Calif.). Ubiquitin ligase (E3) inhibitors were obtained from Bachem Bioscience Inc. (King of Prussia, Pa.). Anti-AAV capsid monoclonal antibody (Anti-VP1, 2 and 3) was purchased from American Research Products (Belmont, Mass.) and anti-ubiquitin antibody was purchased from Santa Cruz Biotechnology Inc. (Santa Cruz, Calif.).

Production of recombinant AAV viral stocks. Recombinant AAV was produced by a CaPO$_4$ co-transfection protocol and purified through three rounds of isopycnic cesium chloride ultracentrifugation. The proviral plasmid pCisAV.GFP3ori is described in Duan et al. (1998). The proviral plasmid pCisRSV.Alkphos, which encodes the alkaline phosphatase reporter gene under the transcriptional control of the RSV promoter and SV40 poly-adenylation signal, was used to generate AV.Alkphos (Yang et al., 1999). The proviral plasmid pCisRSV.LacZ used for AV.LacZ production was generated by first inserting 3474 bp Not I digested β-galactosidase gene (from pCMVβ, Clontech) into the Not I site of the pRep4 (Invitrogene). The entire β-galactosidase expression cassette, including the RSV promoter, β-galactosidase reporter gene and SV40 polyA signal, was excised by Sal I and subsequently cloned into the pSub201 backbone by blunt end ligation (Samulski et al., 1987). Recombinant viral stocks were heated at 58° C. for 60 minutes to inactivate contaminating helper adenovirus. Typical yields were $5 \times 10^5$ to $5 \times 10^9$ particles/μl based on DNA slot blot hybridization assays against plasmid standards. The level of adenoviral contamination, as based on a second reporter assay (Duan et al., 1997) for the recombinant adenovirus used for propagation (Ad.CMVAlkphos for AV.GFP3ori, and Ad.CMVLacZ for AV.Alkphos, Ad.CMVGFP for AV.LacZ), was less than one functional particle per $1 \times 10^{10}$ rAAV particles used for infection of 293 cells in the presence of adenovirus. Transfection with Rep/Cap encoding plasmids served as controls for antibody staining of Rep protein. Virus was dialyzed in PBS prior to in vitro or in vivo infections.

Transduction of polarized airway epithelial cells and primary human fibroblasts. rAAV infection of fully differentiated bronchial cells was performed as described in Duan et al. (1998). For infections from the apical surface of the airway cells, 5 μl rAAV was mixed with 50 μl of culture media and applied directly onto the apical compartment of Millicell inserts (MOI=10,000 particles/cell). During apical infection, the basolateral side of the Millicell was continuously bathed in culture media. Gene transfer to the basal side was performed by inverting Millicell inserts and applying viral vector to the bottom of the supporting filter membrane in a 50 µl volume for 2 hours. Subsequently, Millicell inserts were returned to the upright position, in the continued presence of the original viral inoculum plus an additional 450 µl of media. For both apical and basolateral infections, rAAV containing media was removed after 24 hours and replaced with either fresh culture media (for the basal side) or exposed to air (for the apical side). To test the effect of different agents on the efficiency of AAV transduction in polarized airway cells, 1 µl of each solution was mixed with AAV prior to infection of airway epithelia. Agents were usually presented during the 24 hours AAV infection period unless indicated otherwise. Most of the agents were dissolved in DMSO except for hydroxyurea (dissolved in phosphate buffered saline), H-Leu-Ala-OH (dissolved in 0.9% glacial acetic acid) and H-His-Ala-OH (dissolved in 50% methanol). The working concentrations of the agents were as follows: 0.1 µM camptothecin, 10 µM etoposide, 5 µg/ml aphidicolin, 40 mM hydroxyurea, 50 µM genistein, 40 µM LLnL and 4 µM Z-LLL. When the ubiquitin ligase (E3) inhibitors (H-Leu-Ala-OH and H-His-Ala-OH) were used, airway cells were pretreated with a combination of both inhibitors at a final concentration of 2 mM for 60 minutes prior to infection, followed by the continued presence of inhibitor (0.2 mM) during the entire 24 hours infection period from the basolateral surface. Studies involving EGTA treatment were performed by transiently treating the apical membrane of polarized airway epithelia with 3 mM EGTA in water for 10 minutes (Duan et al., 1998). Following hypotonic EGTA treatment, cultures were washed twice with culture medium and infected with rAAV in the presence or absence of 40 µM LLnL. Human primary fibroblast cells (P4) were maintained in 10% fetal bovine serum (FBS), 1% penicillin and streptomycin, and 89% DMEM. Infection with AV.GFP3ori was performed with 80% confluent fibroblasts at an MOI of 1000 DNA particles/cell in 2% FBS DMEM for 24 hours.

$S^{35}$ labeling of rAAV. The methionine residue in the capsid protein of rAV.GFP3ori was labeled during the generation of radioactive viral stocks according to a previously published protocol with modifications (Mizukami et al., 1996). Briefly, twenty 150 mm plates of subconfluent 293 cells were infected with Ad.LacZ (5 pfu/cell) for 1 hour followed by calcium phosphate transfection of pCisAV.GFP3ori (250 µg) and pRepCap (750 µg). Cells were incubated for an additional 10 hours, at which time the medium was changed to 2% FBS Methionine-free DMEM for 45 to 60 minutes. The medium was changed once again to labeling medium containing 15 mCi of $S^{35}$-methionine per 400 ml of 2% FBS Methionine-free DMEM (final=1.49 MBq/ml), and cells were pulsed for 1.5 hours at 37° C. Following labeling, L-methionine was added back to a final concentration of 30 mg/L, and cells were incubated for an additional 30 hours at 37° C. Cell lysates were prepared and virus was purified by isopycnic cesium chloride ultracentrifugation as described above. Typical specific activities of labeled virus preparations were $5 \times 10^{-6}$ cpm/particle, which is slightly higher than the $5.5 \times 10^{-7}$ cpm/particle specific activity reported by other investigators (Bartlet et al., 1999).

Viral binding/entry assays and in situ localization of viral particles. To assess the binding of rAAV to polarized bronchial epithelia cells, $S^{35}$-labeled AV.GFP3ori was applied to either the apical or basal surface (MOI=50,000 particles/cell), followed by incubation at 4° C. for 60 minutes. Combined binding/entry of rAAV into differentiated airway epithelia was measured under the same conditions, except that the cultures were incubated at 37° C. for an additional 2-24 hours before they were harvested. These combined viral binding/entry assays were performed under identical infection conditions to those used for functional studies of rAAV transduction with transgene expression as an endpoint. After washing three times in PBS, cells were lysed in situ by the addition of 5 ml of liquid scintillation cocktail at room temperature for 5 minutes, and the radioactivity was quantitated in a scintillation counter.

To analyze the subcellular localization of the rAAV particles within polarized human bronchial epithelial cells, infection was performed by applying $S^{35}$ labeled virus (MOI=50,000 particles/cell) to either the mucosal or serosal surface. At 2 hours post-infection, transwells were washed with medium three times and fixed in 4% paraformaldehyde overnight prior to cryoprotection and embedding for frozen sectioning. 10 µm frozen sections were overlaid with photoemulsion and developed for 5 weeks according to a previously published protocol (Duan et al., 1998).

Molecular analysis of rAAV viral genomes following infection of polarized airway epithelial cultures. The molecular state of bound and endocytosed virus was assayed at different times following rAAV infection. To examine the amount of virus attached to the cell surface, rAAV infection was performed at 4° C. for 1 hour. Following binding, the extent of viral internalization was assessed by continuing incubations in the presence of virus at 37° C. for 4-24 hours. Viral DNA was extracted according to a modified Hirt protocol and Southern blots performed with Hybond N+ nylon membrane (Amersham) (Duan et al., 1997). The 1.6 kb single stranded viral DNA, the 2.7 kb double stranded circular intermediate, and the 4.7 kb double stranded replication from viral genome were detected with a transgene EGFP specific probe at $5 \times 10^6$ cpm/ml. Blots were washed at a stringency of 0.2× SSC/0.1% SDS at 55° C. for 20 minutes twice. In studies aimed at evaluating viral internalization, virus attached to the cell surface was removed by trypsinization with 1 ml of buffer containing 0.5% trypsin, and 5.3 mM EDTA at 37° C. for 10 minutes (500 µl buffer was added to the apical and basolateral compartment of the Millicell inserts), followed by washing with ice-cold PBS twice. Externally bound AAV virus was determined by the intensity of the 1.6 kb viral genome band in Hirt DNA extracted from cells infected at 4° C. for 60 minutes. The internalized virus was determined by the intensity of the 1.6 kb viral genome band in Hirt DNA extracted from trypsinized cells after infection at 37° C. for 4 and 24 hours. The dynamic changes in the molecular structure of the internalized virus were assayed at 2, 10, 30 and 50 days after virus was removed from culture medium.

Detection of ubiquitinated AAV capsid proteins by immunoprecipitation. To analyze the effect of the proteasome inhibitor on AAV ubiquitination, human primary fibroblasts were lysed at 6 hours post-viral infection in 1×RIPA buffer. Cell lysates were then cleared with 30 µl Protein A-Agarose. The supernatant was incubated with 10 µl of monoclonal anti-VP 1, 2, and 3 antibody (Clone B 1, ARP) followed by the addition of 30 µl Protein A-Agarose. The pellets were washed 4 times with IX RIPA buffer and resolved on a 10% SDS-PAGE. After transfer to a nitrocellulose filter, blots were probed with a 1:1000 dilution of anti-ubiquitin monoclonal antibody (clone P4D1, Santa Cruz, catalogue #sc-8017), followed by 1:500 HRP-conjugated secondary antibody (BMB). After the final washings, immunoreactivity was visualized using the ECL system (Amersham).

In vivo studies in mice. Animal studies were performed in accordance with the institutional guidelines of the University of Iowa. To determine the effect of the proteasome inhibitor on AAV mediated gene transfer in mouse lung, 6 week-old BALB/c mice were lightly anesthetized using a methoxyflurane chamber. AV.LacZ ($5 \times 10^{10}$ particles) was administered alone or with 400 µM Z-LLL in a 10 µl instillation by nasal aspiration as described by Walters et al. (2000). To prevent unforeseen toxicity of DMSO solvent, the proteasome inhibitor Z-LLL was dissolved in ethanol as a 40 mM stock solution and was included in the viral inoculum at 1% final concentration. Viral infection controls in the absence of Z-LLL also contained a 1% final concentration of ethanol. Since studies in both primary cultured human airway cells and fibroblasts have demonstrated similar enhancement efficiency between 40 µM LLnL and 4 µM Z-LLL, and also due to the poor solubility of LLnL in ethanol (a low dose in DMSO had previously been administered to the trachea), only Z-LLL was tested in this particular mouse lung study. The animals were euthanized at 2, 10 and 150 days post infection and PBS (10 ml) was instilled into the right ventricle, followed by removal of the lungs and heart as an intact cassette. The trachea was intubated and instilled at 10 cm of water pressure with the following solutions in order: PBS, 0.5% glutaraldehyde, 1 mM $MgCl_2$/PBS, and finally X-gal staining reagent for an overnight incubation at room temperature. The X-gal stained mouse lungs were then post fixed in 10% neutral buffered formalin for 48 hours at room temperature and cryopreserved in serial 10%, 20% and 30% sucrose/PBS solutions. Lungs (N=3 for each condition) were embedded in OCT (optimal cutting temperature; Baxter, Warrendale, Pa.) and 15 µm serially sections were analyzed for gene transfer by calculating the percentage of positive cells in the airway epithelium. The diameter of the airway was recorded for classification (>360 µm, 260-350 µm, 160-250 µm, <150 µm) of results following morphometric analysis. Greater than 150 airway cross-sections were quantified for each experimental condition.

Results

Molecular analysis of rAAV genomes in polarized airway epithelia. Recent studies revealed a lack of AAV-2 receptor, heparin sulfate proteoglycan, and co-receptors, FGFR-1 and $\alpha V \beta 5$ integrin, at the apical surface of differentiated airway epithelia (Duan et al., 1998; Duan et al., 1999; Hughes et al., 1993; Goldman et al., 1999). However, differences in the binding of radioactive virus at the apical and basolateral membranes were only 4-7 fold (basolateral>apical) (Duan et al., 1998). These differences in binding are insufficient to explain the 200-fold variance observed in the polarity of infection (basolateral>>apical) with rAAV-2 (Duan et al., 1998). These findings suggested that viral binding and/or uptake were not the sole limiting factors contributing to inefficient mucosal transduction in airway epithelia. To this end, the molecular state of rAAV DNA at 50 days following apical and basolateral infection of air-liquid interface cultured human bronchial epithelia was evaluated. At this time point, gene expression measured from an EGFP reporter was >200-fold higher in basolaterally infected cultures (data not shown) (Duan et al., 1998). Hirt DNA from the cultures was evaluated by Southern blot hybridization with $^{32}$P-labeled EGFP probes. A significant amount of apically applied rAAV was able to infect airway cells. However, only single stranded viral genomes (ssDNA) were detected at this time point (50 days). This result clearly suggests that rAAV can be endocytosed from the mucosal surface and that the endocytosed viral ssDNA was stably sequestered in some unknown subcellular compartment. In contrast, the majority of basolaterally applied rAAV was converted into double stranded forms that migrated at 2.8 kb and >12 kb in 1% non-denaturing agarose gels. Consistent with previous reports (Sanlioglu et al., 1999; Duan et al., 1999), subsequent restriction enzyme mapping of Hirt DNA and Southern blots confirmed this 2.8 kb band to be a supercoiled, circular episomal molecule (data not shown). The identity of the >12 kb band, which is significantly more intense following basolateral infection, is currently unknown but may represent episomal circular concatamers of the AAV genome. Taken together, these results suggest that inefficient molecular conversion of AAV viral DNA to circular genomes represents a significant obstacle for rAAV mediated gene transfer from the apical surface of the airway. Furthermore, circularization, not linear replication though self-priming, is the predominant pathway for rAAV gene conversion in polarized airway epithelia.

Proteasome inhibitors dramatically enhance rAAV infection in polarized airway epithelia. Given the fact that rAAV appears to remain latent within some cellular compartment(s) following apical infection in the airway, and that agents that alter the molecular conversion of the viral genome might enhance rAAV transduction in airway epithelia, several agents were tested in this regard, including DNA damaging agents (Alexander et al., 1994), DNA synthesis and topoisomerase inhibitors (Russell et al., 1995), and cellular tyrosine kinases inhibitors (Qing et al., 1997; Man et al., 1998). Application of camptothecin, etoposide, hydroxyurea, and genistein resulted a 10 to 60 fold enhancement in rAAV transduction from the basolateral surface. Interestingly, however, none of these agents facilitated rAAV transduction from the apical surface (data not shown). Since chemicals known to affect intra-nuclear events involved in rAAV transduction in other cell types (Sanlioglu et al., 1999) did not enhance rAAV apical infection in the airway, other agents affecting endocytic processing, such as the ubiquitin-proteosome pathway, were tested. Proteasome systems are known to modulate the intracellular processing of many foreign and endogenous molecules, including viruses such as HIV (Schwartz et al., 1998). Several specific, cell permeable, peptide aldehyde inhibitors of proteasome pathways have recently been discovered (Rock et al., 1994; Fenteany et al., 1995). These inhibitors bind to the active sites of proteolytic enzymes within the proteasome core and reversibly block their function (Rubin et al., 1995). To test whether proteasomes represent an intracellular compartment that sequesters rAAV following infection, the tripeptidyl aldehyde proteasome inhibitor (a cysteine protease inhibitor) N-acetyl-L-leucinyl-L-leucinal-L-norleucinal (LLnL, also called Calpain inhibitor I) was applied to polarized cultures of human bronchial epithelial cells at the time of rAAV infection. Surprisingly, a greater than 200 fold augmentation in transgene expression was obtained at 2 days post infection when 40 µM LLnL was applied to the serosal surface along with rAAV. A similar result was achieved when another ubiquitin-proteasome pathway inhibitor, N-carbobenzoxyl-L-leucinyl-L-leucinyl-L-leucinal (Z-LLL, also called MG132) (Jensen et al., 1995), was tested (data not shown). However, the most important finding was that these proteasome inhibitors also substantially increased rAAV transduction from the mucosal surface (see below). When compared with other agents, proteasome inhibitors were found to be the most potent enhancers of rAAV transduction in airway epithelium.

Proteasome inhibitors augment rAAV transduction in airway epithelia in a polarized fashion. Although proteosome inhibitors appear to significantly increase the efficacy of rAAV transduction from the serosal surface, the route most germane to clinical application of gene delivery in the airway is the mucosal surface. To test the effect of proteasome inhibitors on rAAV transduction from apical membrane, a side-by-side kinetic comparison of rAAV transduction from both mucosal and serosal surfaces of airway epithelia following treatment with LLnL was performed. Co-administration of LLnL and rAAV to the mucosal surface resulted a sustained augmentation in AAV transduction, which peaked at 22 days post-infection. In contrast to mucosal infection, rAAV infection from the serosal surface in the presence of LLnL resulted only in a transient peak in gene expression at 72 hours post-infection, which returned to the levels equivalent to that of the untreated samples by 22 days. These results suggested that the proteasome inhibitor LLnL produces different augmentation profiles when AAV virus is applied to either the apical or the basolateral membranes. To exclude potential effects caused by polarized uptake of LLnL by airway epithelia, different combinations of rAAV and LLnL administration from both apical and basolateral surfaces were tested. Similar augmentation patterns for AAV transduction were achieved, regardless of whether LLnL was applied to the same or opposite surface as rAAV during infections (data not shown).

To determine whether LLnL administration augmented rAAV transduction of particular airway cell types, a rAAV vector encoding the alkaline phosphatase gene (Alkphos) was utilized. Transduced cell types were evaluated by standard histochemical staining for Alkphos to address this question. In the absence of LLnL, rAAV preferentially transduced basal cells at 3 days following serosal application of virus. Consistent with previous findings utilizing AV.GFP3ori virus, co-administration of LLnL resulted in a dramatic increase in AV.Alkphos transduction. Interestingly, ciliated cell transduction was most significantly increased by treatment with LLnL at the time of rAAV infection. In contrast, basal cells were the least responsive to LLnL treatment. These findings indicated that the mechanisms of LLnL action may have some cell specific components, which differs in polarized (i.e., ciliated) and non-polarized (i.e., basal) cell types.

Optimization of LLnL enhanced rAAV transduction. With the aim of further improving the enhancement in rAAV transduction achieved in the presence of LLnL, several detailed kinetic studies were performed which altered the timing and number of LLnL administrations following rAAV infection. Several important conclusions arose from these studies. First, following basolateral infection, administration of LLnL once every three days increased length of peak transgene expression, despite the fact that by the end of 30 days levels were similar to that of cultures treated once at the time of infection. Second, continual administration of LLnL was toxic to cells and ablated transgene expression by 10 days. Third, re-infection of cultures with rAAV in the presence of LLnL at 7, 10 and 15 days resulted in a similar pattern of augmentation and, as expected, elevated the final level of transgene expression observed at 30 days (only data from the second infection at 15 days are shown). Most notably however, all the cultures infected from the basolateral side produced similar long-term transgene expression levels within 2 to 3 fold of each other, regardless of whether LLnL was administered.

Despite the fact that LLnL administration at the time of the viral infection augmented rAAV transduction from both the apical and basolateral surfaces, the kinetics of this induction were significantly different. Enhancement following basolateral infection was transient, while enhancement following apical infection was long-term. Furthermore, although induction with LLnL from the apical membrane was long-lasting, by 30 days the maximal level of transgene expression was only one eighth of that resulting from basal infection. The application of hypotonic EGTA solution has been shown to increase AAV transduction from the apical surface by 7 to 10 fold (Duan et al., 1998; Walters et al., 2000). Therefore the combined administration of EGTA and LLnL could provide yet a further increase in rAAV transduction from the apical surface. Interestingly, treatment of airway cultures with EGTA prior to infection with rAAV in the presence of LLnL gave a transient peak in transduction within the first three days, and a significantly increased (200-fold), prolonged level of transgene expression out to 30 days. This prolonged level of transgene expression, while comparable to rAAV infection from the basal surface, was much above the level observed in apically infected epithelia treated with EGTA alone. In summary, these results demonstrate that EGTA and LLnL have synergistic effects on rAAV transduction, allowing for transduction from the apical surface at levels normally only seen following basolateral infection.

Viral binding and internalization are not affected by LLNL treatment. The action of LLnL has been typically attributed to it selective and reversible inhibition of the proteasome system. However, it was important to rule out any possible effect on viral binding and/or endocytosis. As has been found for type 1 herpes simplex virus (Everett et al., 1998), LLnL treatment had no significant effect on 4° C. rAAV binding. Similarly, the uptake of $S^{35}$ labeled rAAV for a 2 hour infection period at 37° C. was not altered by LLnL treatment. Given these results, LLnL acts at points distal to virus binding and entry. Interestingly, at 24 hours post-infection a very significant decrease in the amount of intracellular radioactivity was observed in epithelia treated with LLnL, regardless of which surface was infected. Given the concordant increase in transgene expression at this time point, LLnL may be accelerating processing and routing of the virus to the nucleus, wherein uncoating and clearance of $S^{35}$ labeled capsid proteins occur. By this mechanism, $S^{35}$ isotope would be diluted into the culture medium and could explain the decrease in cell-associated counts.

LLnL enhances endosomal processing and nuclear trafficking of rAAV. To test the hypothesis that LLnL increases trafficking of rAAV to the nucleus, in situ localization of the $S^{35}$-labeled rAAV particles following infection from the apical and basolateral surfaces was performed in the presence and absence of LLnL. Since loss of intact radiolabeled capsid proteins occurred at 24 hours post-infection, a 2 hour time point was chosen for this analysis. Using photoemulsion overlay, the subcellular distribution of $S^{35}$-labeled rAAV particles was evaluated by blinded morphometric analysis. The majority of viral particles localized to the cytoplasm in the absence of LLnL. This was the case regardless of whether infection was performed from the apical or basolateral surface. In contrast, LLnL treatment substantially changed the intracellular distribution of radiolabeled rAAV particles, resulting in a significant shift to nuclear associated grains. These results substantiated the findings from whole cell counts at 24 hours post-infection, which suggested that LLnL increases viral uncoating and the subsequent loss of $S^{35}$ isotope into the media.

LLnL augment rAAV transduction within a specific time frame after infection. Evidence thus far has suggested that LLnL may act to increase intracellular routing of rAAV to the nucleus. Additionally, LLnL action is independent of the epithelial surface to which it is administered (i.e., serosal application of LLnL augments mucosal infection and vice versa). This indicates that LLnL need not be endocytosed with AAV particles to enhance transduction. Thus, LLnL may act at a specific time following rAAV endocytosis but during endosomal processing. To provide functional support for this hypothesis, a kinetic analysis of LLnL action at various times after infection from the basolateral surface was performed. In these experiments, LLnL was added to the culture medium either at the time of AAV infection or at various time points after infection. Viral-mediated transgene expression was quantified at 24 hour intervals following infection. Augmentation was achieved regardless of whether LLnL was administrated at 0, 24, 48, and 72 hours after viral infection. However, addition of LLnL at 24 or 48 hours gave the strongest level of augmentation. The ability of LLnL to reduce AAV expression appeared to decline by 72 hour post-infection and was completely lost by 15 days after the initial AAV infection (data not shown). Taken together, it appears that after rAAV enters the cell, it may be targeted to an intracellular compartment that is sensitive to proteasome inhibitor-facilitated liberation. In addition, the loss of an LLnL augmentation effect at 15 days post-infection suggests that enhanced transcription, translation, and/or stability of the transgene products do not likely contribute to the mechanism responsible for this observation.

Combined treatment of LLnL and EGTA prevents degradation of internalized rAAV. To further clarify the molecular mechanism(s) responsible for augmentation of rAAV transduction by LLnL, rAAV genomes in infected cells were analyzed by Southern blotting Hirt DNA. Consistent with studies using $S^{35}$ labeled virus, rAAV binding to either surface of polarized airway epithelia was not affected by LLnL treatment. Southern blotting also demonstrated 2 to 7 fold higher viral binding from the basal surface, which varied among different tissue samples (data not shown). The extent of virus internalization was compared after stripping surface bound virus with trypsin. Confirming previous results, a significant amount of rAAV was endocytosed from the apical surface during the infection period, although viral uptake was more active from basolateral surface. LLnL alone also did not substantially prevent enzymatic degradation of the internalized AAV viral DNA, indicating that enhanced viral trafficking into the nucleus might be more important in the observed augmentation by LLnL. However, treatment with both hypotonic EGTA and LLnL substantially increased the amount of virus internalized from apical surface. Since hypotonic EGTA treatment alone only slightly increased persistence of AAV DNA or AAV-mediated gene expression (Duan et al., 1998; Walters et al., 2000) following apical infection, the predominant mechanism responsible for the combined effects of EGTA and LLnL might be due to reduced degradation of the internalized virus and an increased rate of endocytosis. These synergistic effects of EGTA and LLnL augment rAAV transduction from the apical membrane more than 200-fold. Additionally, the conversion of single stranded viral genomes to linear replication or circular forms has been associated with enhanced AAV transduction by adenoviral early gene products or UV irradiation, respectively (Fisher et al., 1996; Sanlioglu et al., 1999; Duan et al., 1999). Southern blots of Hirt DNA from cultures co-infected with Ad.dl802 and rAAV showed LLnL enhanced AAV transduction was clearly not mediated through the formation of linear replication intermediates (4.7 kb band) as seen in the presence of adenoviral E4orf6 protein produced by Ad.dl802 co-infection.

Ubiquitination of viral capsid proteins following rAAV infection in the airway alters the efficiency of transduction. Proteasome-dependent degradation of ubiquitinated molecules represents a major pathway for disposal of both endogenous and foreign proteins (Schwartz et al., 1999). Several distinct steps in the regulation of this pathway have been identified, including: activation of ubiquitin by its activating enzyme (E1), transfer of the activated ubiquitin to the ubiquitin carrier protein (E2), and subsequent delivery of the activated ubiquitin to the protein substance by ubiquitin ligase (E3). Ultimately, ubiquitinated proteins are degraded by the 26S proteasome through an ATP-dependent process. To test whether enhancement of rAAV transduction by proteasome inhibitors involves liberation of ubiquitinated virus from an endosomal compartment, the extent of ubiquitin side chains on AAV capsid proteins following infection was examined as well as whether treatment with proteasome inhibitors altered the extent of ubiquitination. AAV capsid proteins were immunoprecipitated using anti-VP 1, 2, 3 antibody from rAAV infected human polarized airway cells and confluent human fibroblasts at 6 hours post-viral infection. Subsequent Western analysis with anti-ubiquitin specific antibodies demonstrated a significant increase in the cellular level of ubiquitinated AAV capsid in fibroblasts following proteasome treatment. Ubiquitination significantly increased the molecular weight of capsid proteins (63 kd, 73 kd, and 87 kd) to 220-250 kd and is consistent with the size change following ubiquitination for other molecules (Bregman et al., 1996). Unfortunately, the limited amount of virus retrievable from air-liquid interface cultured human airway cells precluded the ability to detect ubiquitinated capsid in this system (data not shown). Nonetheless, confluent primary fibroblasts also demonstrated augmentation (10-fold) of transgene expression following treatment with proteasome inhibitors. Thus, proteasome inhibitors increase rAAV transduction by decreasing the targeting and/or degradation of ubiquitinated AAV in the proteosome. The net result of such proteasome inhibition would be expected to increase the abundance of ubiquitinated viral capsid.

Because a technical limitation in polarized airway model prevented direct detection of ubiquitinated viral capsid, it was determined whether modulation of other steps in the ubiquitin proteasome pathway could also increase rAAV transduction similarly to that seen with proteasome inhibitors LLnL and Z-LLL. Several dipeptides, such as H-Leu-Ala-OH and H-His-Ala-OH, are known to inhibit ubiquitin ligase E3 (Obin et al., 1999). Application of these ubiquitin ligase inhibitors indeed enhanced rAAV transduction from the basolateral surface of human airway cells. Taken together, data in both fibroblasts and polarized airway epithelia suggest that AAV capsid is ubiquitinated following endocytosis, and that this process is a barrier to rAAV transduction. The most plausible mechanism responsible for the augmentation of rAAV transduction by tripeptide proteasome inhibitors involves the prevention of ubiquitinated virus degradation and/or targeting to the proteasome.

Long-term enhancement of rAAV transduction by proteasome inhibitor in vivo. To evaluate the potential utility of proteasome inhibitors for in vivo gene therapy, both the toxicity and efficacy of these agents for in vivo rAAV mediated gene transfer in the mouse lung was tested. To assess the toxicity of these proteasome inhibitors in mice, 10, 100, and 1000 fold higher effective doses of LLnL or Z-LLL were administered than used to induce gene transfer in polarized airway cells, using both intra-tracheal and systemic (IV) delivery. No toxicity was indicated by histologic evaluation of the lung and liver or was evidenced by the death of animals. To investigate whether these proteasome inhibitors could improve rAAV transduction in vivo, AV.LacZ ($5 \times 10^{10}$ particles) was delivered either alone or in the presence of 400 μM Z-LLL by intranasal administration. Mouse lungs were harvested at 3, 10 and 150 days post-infection to evaluate short and long term effects. Proteasome inhibitor treatment from basal surface, or in conjunction with EGTA from apical surface, resulted in pronounced, immediate enhancement on rAAV transduction, however, X-gal staining of the lung tissues at 3 and 10 days post infection demonstrated no detectable transgene expression in either proteasome inhibitor treated or untreated groups. In contrast, significant transduction was achieved at 150 days in Z-LLL treated samples. Targeted transgene expression was predominantly confined to the conducting airways, rather than in the parenchyma. Alveolar cells were rarely transduced. Although on average only about 5.88% of airway cells were transduced by AV.LacZ, and LacZ positive cells were observed throughout the entire conducting airway, a characteristic transduction profile was evident. The transduction efficiency in larger bronchioles (>350 mm) reached a mean of 10.36±1.63% of the airway epithelium, while 1.37±0.41% of airways cells in the smaller bronchioles (<150 mm) expressed the β-galactosidase transgene. The range of transgene expression in distal and proximal airways was 0 to 4% and 5 to 18%, respectively. This transduction profile demonstrating a higher and more consistent transduction in larger airways likely reflects a more uneven delivery of virus to regions of the lung encompassing the smaller airways. Examination of cryo-sections from lungs infected by AV.LacZ alone revealed only 2 lacZ positive cells in a total of 315 airway sections (n=3 animals).

Discussion

Inefficient gene transfer from the apical surface of the airway has been a major obstacle in numerous gene therapy approaches for cystic fibrosis utilizing recombinant adenovirus (Walters et al., 1999; Pickles et al., 1998), adeno-associated virus (Duan et al., 1998), retrovirus (Wang et al., 1998), and non-viral liposome vectors (Chu et al., 1999). It has been generally thought that inefficient viral mediated gene delivery through the apical membrane of airway epithelia is predominantly due to the lack of receptors or co-receptors on this surface.

Molecular analysis of rAAV infection in polarized airway epithelia has revealed several unique findings. First, there is conclusive evidence that the previously reported lack of known AAV-2 receptor and co-receptors (Duan et al., 1999) at the apical membrane of airway epithelia does not abrogate AAV infection. Although transduction (as determined by transgene expression) from the basolateral surface is 200-fold more efficient than from the apical membrane, quantitative and semi-quantitative analyses of viral endocytosis with either $S^{35}$-labeled virus or Southern blotting have demonstrated that viral uptake from the apical surface is only 2-7 fold less efficient than from the basolateral membrane. Therefore, it is reasonable to assume that previously unidentified alternative receptor/co-receptors and/or receptor-independent mechanism(s) might be involved in AAV uptake from the mucosal surface of the airway.

Polarity is widely recognized to significantly influence endosomal processing of many proteins, and distinct sorting mechanisms have been described for the apical and basolateral compartments (Odorizzi et al., 1996; Rodriguez-Boulan et al., 1993). The lack of a direct correlation between the efficiency of viral uptake and transgene expression following basolateral and apical infection suggest that additional post-endocytic barriers exist for rAAV mediated gene transfer. Differences in the extent of AAV nuclear trafficking following basolateral versus apical routes of infection suggest that basal and apical cellular compartments possess distinct biologic properties that may influence the polarity of AAV transduction. Endosomal processing barriers to rAAV transduction may not be limited to polarized epithelial cells. In support of this notion, impaired intracellular trafficking of viral particles to the nucleus has been observed in NIH 3T3 cells. In addition, rAAV can remain in an inactive state for as long as 7 days in confluent primary fibroblast cells until rescued by UV irradiation to a functionally active state. Thus, post-endocytic barriers to infection exist in multiple cell types.

In the airway, the major rate-limiting steps in rAAV transduction from the mucosal surface appear to involve inefficient endosomal processing of the internalized virus. Regulated intracellular proteolysis through proteasomes plays a critical role in many physiological and pathological conditions (Schwartz et. al., 1999; Kato, 1999). Recent identifications of many specific proteasome inhibitors has set the foundation for pharmacologic intervention in this cellular enzymatic system as a novel therapeutic approach. For example, several cell permeable synthetic tripeptide aldehydes (such as LLnL and Z-LLL used in this study) have been demonstrated to be promising cancer therapy agents or anti-inflammatory drugs (Goldberg et al., 1995; Kloetzel, 1998; Wojcik, 1999). Additionally, the proteasome has been suggested to have antiviral functions in HIV infection (Schwartz et al., 1998), implying that the inhibition of proteosome function could be beneficial in promoting transduction with recombinant viruses. Based on the molecular evidence that apical infection of rAAV in the airway is significantly limited by post-entry events, ubiquitin/proteasome pathways appear to be instrumental in this blockage. The proteasome is commonly know as a compartment for clearance of endogenous and foreign proteins. However, recent studies also suggested that the proteasome system is involved in regulating endocytosis (Bonifacino et al., 1998; Strous et al., 1999). From the standpoint of gene delivery, proteasome inhibitors have been shown to protect transfected plasmid DNA from degradation (Coonrod et al., 1997). The results described herein clearly demonstrate that rAAV mediated gene transfer to the airway epithelia is also significantly enhanced by proteasome inhibitors. Furthermore, this enhancement is correlated with proteasome inhibitor stimulated viral trafficking to the nucleus. Although proteasome inhibitors increased long-term levels of AAV transduction form the apical surface, their effect on basolateral infection appeared predominantly to alter the rate, rather than the long-term levels, of transduction. These differences highlight fundamentally distinct pathways involved in rAAV transduction from apical and basolateral surfaces.

Several findings also support the notion that ubiquitination of virus following endocytosis may be a critical mechanism for sorting incoming AAV. First, treatment of airway epithelia with proteasome inhibitors know to block ubiquitin-dependent degradation of proteins enhances rAAV gene transfer. Second, inhibition of ubiquitin E3 ligase activity in airway epithelia also enhances transduction. Lastly, rAAV capsid proteins are ubiquitinated following infection in confluent human fibroblasts, and that the extent of this ubiquitination is increased by inhibition of ubiquitin-proteasome degradative pathways.

From an applied standpoint, one of the most important findings in this study is the persistent high level of rAAV transduction induced by proteasome inhibitor in mouse lung. Co-administration of Z-LLL with rAAV increased transgene expression from undetectable levels to 10.36+/−1.63% of proximal bronchial epithelial cells at 150 days post-infection. This level of gene expression is thought to be sufficient for therapeutic correction of CFTR deficiency (Crystal, 1999). The feasibility of this strategy for clinical application is further supported by the lack of a detectable local or systemic toxicity following proteasome inhibitor administration to mice. Furthermore, preliminary studies in several other organs, e.g., heart skeletal muscle and liver, have suggested that ubiquitination of rAAV2 may occur in an organ-specific fashion. The application of proteasome inhibitors in skeletal and cardiac muscle had no effect on either short-term or long-term rAAV mediated gene transfer. However, application of Z-LLL in the liver led to a 7-fold increase in rAAV transduction at 1 month post-infection. These findings suggest that tripeptide proteasome inhibitors could be used to increase gene transfer in organs other than the lung, depending on the cell biology of virus processing.

In conclusion, a significant barrier to apical infection in the airway with rAAV-2 lies at the level of endosomal processing and ubiquitination. Modulation of the ubiquitin-proteasome system has revealed innovative strategies to enhance rAAV transduction from the mucosal surface of the airway for gene therapy of cystic fibrosis.

Example 2

Expression of the LacZ Gene in Lung Airway Epithelium and Liver in Vivo

The in vivo activity of rAAV in the presence or absence of an agent of the invention in the lung or liver may be tested using the LacZ gene. A rAAV vector containing the LacZ gene, recombinant AV.LacZ (about $5 \times 10^{10}$ particles), was administered to mouse lung either as virus alone in PBS or virus in combination with 40 µM LLnL in PBS. Virus was directly instilled into C57Balb/c mice trachea with a 30 G needle in a total volume of 30 µl. To insure the spread of the virus in mouse lung, 50 µl air was pumped into lung through the same syringe immediately after virus was administrated. Ninety days after infection, lungs were harvested intact and fixed in 4% paraformaldehyde followed by cryosection. AAV-mediated transgene expression was evaluated by 10 µm tissue sections staining for LacZ.

Recombinant AV.LacZ (about $5 \times 10^{10}$ particles) was also administered to mouse liver either as virus alone in PBS, virus in combination with 40 µM Z-LLL in PBS, or virus in combination with 20 µM LLnL in PBS. Virus was directly instilled into portal vein of the C57B6 mice. AAV-mediated LacZ transgene expression was evaluated by histology staining at 2 and 4 weeks post infection in frozen tissue sections.

Example 3

Methods to Determine Additional Agents Useful to Enhance rAAV Transduction

A. To screen for agents that enhance rAAV transduction, any number of cells can be used. A range of concentrations of the agent to be tested can be determined based on, for instance desirable profiles of the agent, desirable toxicity profiles of the agent and/or concentration of the agents employed in vivo. The usefulness of the cell type chosen for the screen can be confirmed by testing compounds, e.g., proteosome inhibitors described in Example 1 such as LLnL and ZLL which are known to increase rAAV transduction. For example, a AAV2 FLAG-Luc vector was employed to transduce HeLa, ferret fibroblasts, IB3 and Huh (liver) cells in the presence or absence of the proteosome inhibitor MG132. MG132 was confirmed to enhance AAV transduction in all cell types tested: HeLa cell transduction was enhanced about 500-fold at 80 µM, and 200-fold at 40 µM, MG132; ferret fibroblast cell transduction was enhanced about 200-fold at 20 µM, and 17-fold at 4 µM, MG132; IB3-1 cell transduction was enhanced about 30 to 70-fold at 20 to 80 µM MG132; and Huh-7 cell transduction was enhanced about 15-fold at 20 to 80 µM MG132. There was no difference in rAAV transduction efficiency in HeLa cells when either DMSO or ETOH was used as a vehicle for MG132.

B. HeLa cells were selected to screen for additional agents that enhance rAAV transduction, although any cell strain or line; or primary cells, may be employed. Agents were selected from various classes, such as anti-inflammatories (e.g., dexamethasone and cyclosporin A), NSAIDs (e.g., ibuprofen), β-adrenergics (e.g., albuterol), antibiotics (e.g., ciprofloxacin, colison, gentamycin, tobramycin, and epoxomycin), lipid lowering agents (e.g., lovastatin, simvastatin and eicosapentaenoic acid), food additives (e.g., tannic acid), viral protease inhibitors (e.g., NORVIR®, KALETRA® and VIRACEPT), chemotherapeutics (e.g., aclacinomycin A, doxorubicin, doxil, camptothecin, taxol and cisplatin) and protease inhibitors (e.g., chymostatin, bestatin and chloroquine). The range of concentrations of the agents to be tested were selected based on solubility profiles, toxicity profiles and/or concentrations previously employed in vivo.

HeLa cells were infected for 2 hours with an MOI of 100 rAAV in the presence of agents, e.g., ritonavir (Norvir) (1, 10 and 100 µM), cyclosporin A (2.5, 25 and 250 µg/ml), epoxomicin (1, 10 and 50 µM), alcacinomycin A (5, 50 or 500 µM), chymostatin (1, 10 and 100 µM), bestatin (1, 10 and 100 µM), doxorubicin (adriamycin) (0.1, 1 and 10 µM), camptothecin (camptosar) (1, 10 and 100 µM), eicosapentanoic acid (1, 10 and 100 µM), tannic acid (2, 20, 200 and 2000 µM), simvastatin, prodrug (2, 20 and 200 µM), cisplatin (0.2, 2 and 20 µg/mL), and chloroquine (4, 40 and 400 µM). Forty-eight hours after infection, cells were harvested for analysis. rAAV transduction was measured by removing the media from the cell cultures, adding 100 µL reporter lysis buffer (RLB) and freezing. The supernatant was thawed and transferred to microfuge tubes, freeze thawed an additional 2 times, clarified by centrifugation for 10 minutes and then analyzed for reporter gene expression on the luminometer. Protein was determined by Bradford analysis and results were expressed as relative light units per mg protein (RLU/mg). Data is presented in FIGS. 1A-E.

Doxorubicin, epoxomicin, and camptothecin all showed a dose-dependent increase in transduction at the dose ranges tested. At the doses tested doxorubicin and epoxomicin increased transduction efficiency up to 169-fold and 120-fold, respectively, camptothecin increased transduction efficiency by 15-fold, tannic acid increased transduction efficiency by 17-fold, cisplatin increased transduction efficiency by 16-fold, and simvastatin increased transduction efficiency by 4-fold.

It should be noted with respect to simvstatin and the lovastatin, that these drugs are formulated as prodrugs and conversion to the activated open ring forms was not confirmed which may have contribute to the negative results. Similarly, the liposomal formulation of doxorubicin, DOXIL® could not be confirmed to be bioavailable to cell culture cells. Thus, agents which initially screened as statistically negative may be reflective of formulations that are not readily bioavailable to cell culture cells or may be reflective of the limited dose range or exposure time.

Epoxomicin, a naturally occurring antibiotic isolated from Actinomycetes known to inhibit NF-KB-mediated signaling in vivo and in vitro, inhibits proteosomes by inhibiting a proteosome-specific chymotrypsin-like protease. Doxorubicin, an anti-tumor antibiotic which inhibits topoisomerase II and inhibits nucleic acid synthesis, is translocated by a 20S proteosome from the cytoplasm to the nucleus. Camptothecin, a reversible DNA topoisomerase inhibitor, down regulates topoisomerase via an ubiquitin/26S proteosome pathway. Simvastatin is an agent that modulates proteosome activity, tannic acid inhibits chymotrypsin-like activity and is a cancer chemopreventative, and cisplatin is a chemotherapeutic which crosslinks DNA.

C. To determine whether combinations of agents that enhance rAAV transduction efficiency have synergistic or additive effects when used in combination, cells were contacted with the proteosome modulator, doxorubicin, and the proteosome inhibitor Z-LLL or LLnL. Different AAV vectors were tested, including splicing vectors and pseudotyped rAAV. Viral stocks utilized were as follows: Av2RSVluc, $5 \times 10^8$ particle/µl; Av2RSVlucCap5 (also referred to as Av2/5 CMVLuc), $2 \times 10^9$ particle/µl; Av2CMVluc, $1.3 \times 10^9$ particle/µl; and Av2CMVlucCap5, $1.1 \times 10^9$ particle/µl. Combinations of agents were compared to the agents used alone to determine the efficiency of transduction. LLnL was used at 40, 200 or 400 µM, Z-LLL at 4 µM and doxorubicin at 0.5 or 1 µM when employed alone. When a combination of LLnL and doxorubicin was used, LLnL was used at 4, 10, 20, 40, 200 or 400 µM and doxorubicin at 1 or 5 µM. The apical surface of polarized airway epithelia, HeLa cells or ferret fibroblast was contacted with the agents and rAAV ($5 \times 10^9$ particles per well).

The results showed that LLnL enhances transduction in HeLa, ferret fibroblast and polarized epithelial cells at 40 µM and A549 cells at 200 to 400 µM. Doxorubicin enhanced transduction in HeLa and ferret fibroblast cells at 1 µM and A549 or polarized airway cells at 5 µM, and enhanced transduction about 100 fold when ferret fibroblasts were infected with lacZ splicing vectors. Doxorubicin also enhanced AAV2 and AAV5 transduction to a greater extent than LLnL. Synergistic effects were noted when doxorubicin and LLnL were co-administered.

In the absence of agent administration, transduction from the apical surface of polarized epithelial cells was greater with AAV vectors with AAV5 capsid than AAV vectors with AAV2 capsid. In the presence of doxorubicin, a 200 to 600-fold induction was observed for AAV2 and AAV5 apical infection of polarized cells. Thus, agents of the invention can enhance rAAV transduction, including in serotype, pseudotype and multiple vector strategies.

D. Endotracheal administration of $10^{11}$ AV2FLAG-luc rAAV particles to male Balb/c mice in conjunction with intravenous administration of DOXIL® (dosed in a range of 2, 10, or 20 mg/kg), a liposomal preparation of doxorubicin, to mice enhanced AV2FLAG-luc transduction by 2 logs by day 7 at the 20 mk/kg dose of DOXIL®. Specifically, at 20 mg/kg DOXIL®, transduction was enhanced on the average of 67-fold by day 7 and 4-fold by day 30. It is worth noting that DOXIL® previously tested negative in cell line screening while the free compound doxorubicin tested positive in cell line screening (FIGS. 1A-E). Liposomal formulations have desirable properties for in vivo use including their increased stability or circulation half life making them more bioavailable in vivo. Those same characteristics make liposomal formulations less desirable for in vitro screening as described above. Thus, one skilled in the art can design formulation strategies for agents of the invention to tailor them to the desired application. In addition to formulation design, one skilled in the art can tailor routes of delivery in order to maximize rAAV transduction efficiencies.

Figure 3:
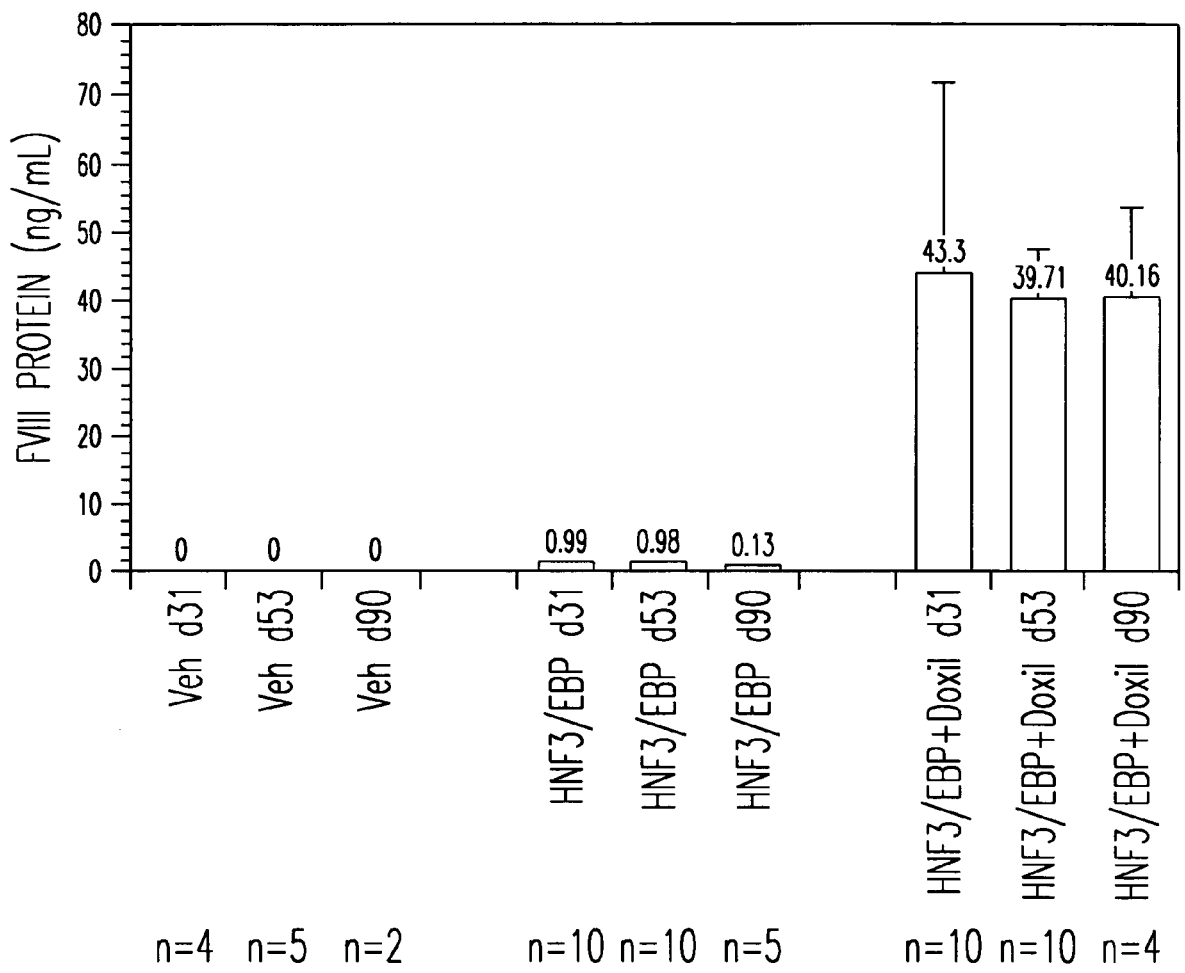
FIG. 3. In vivo enhancement of rAAV transduction of Factor VIII in Rag-1 mice treated with Doxil. Rag-1 mice intravenously administered Doxil (20 mg/kg) were infected with $1\times10^{12}$ DRP AAV5-FVIII, and Factor VIII levels at sacrifice determined. Data are the average±standard deviation.
Figure 4A:
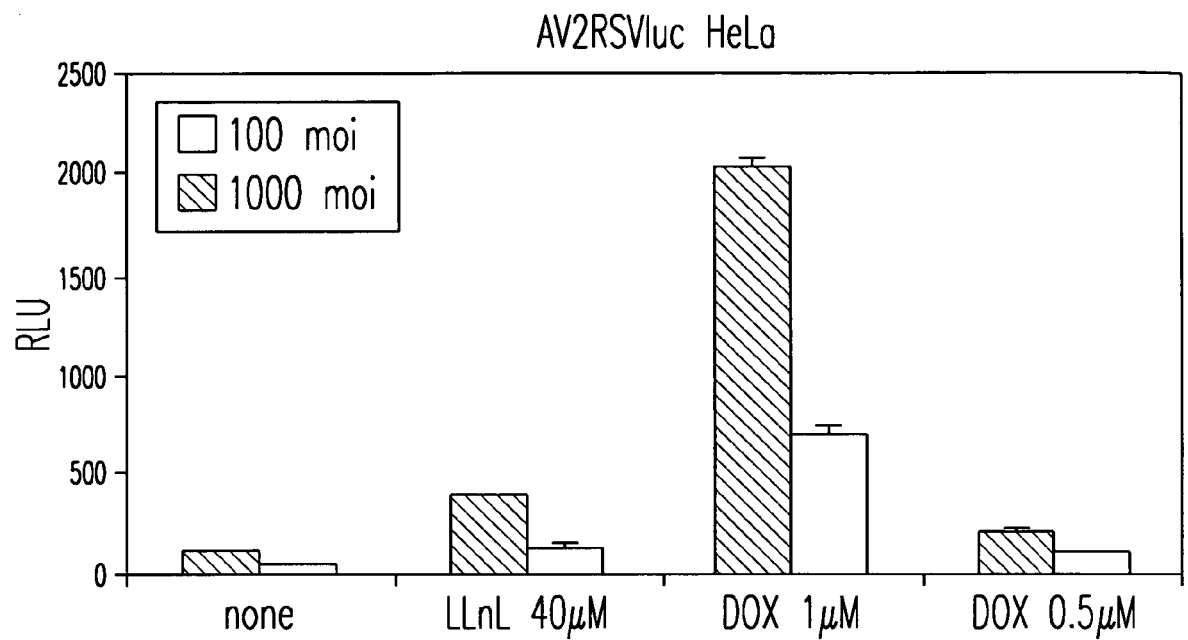
FIGS. 4A-E. Luciferase activity in HeLa cells after infection with A) AV2.RSVLuc or B) AV2.RSVlucCap5 (100 or 1000 moi) in the absence or presence of LLnL (40 μM) or doxorubicin (0.5 or 1.0 μM) administration. C) Luciferase activity after infection with AV2CMVluc and AV2CMVluc Cap5 (500 ppc), and LLnL (40 μM), Z-LLL (4 μM), or doxorubicin (0.5 or 1.0 μM) administration. D) and E) Comparison of CMV and RSV promoters in AAV-2 vectors (1000 ppc and 100 ppc, respectively) in HeLa cells in the absence or presence of LLnL (40 μM) or doxorubicin (0.5 or 1.0 μM) administration.
Figure 4B:
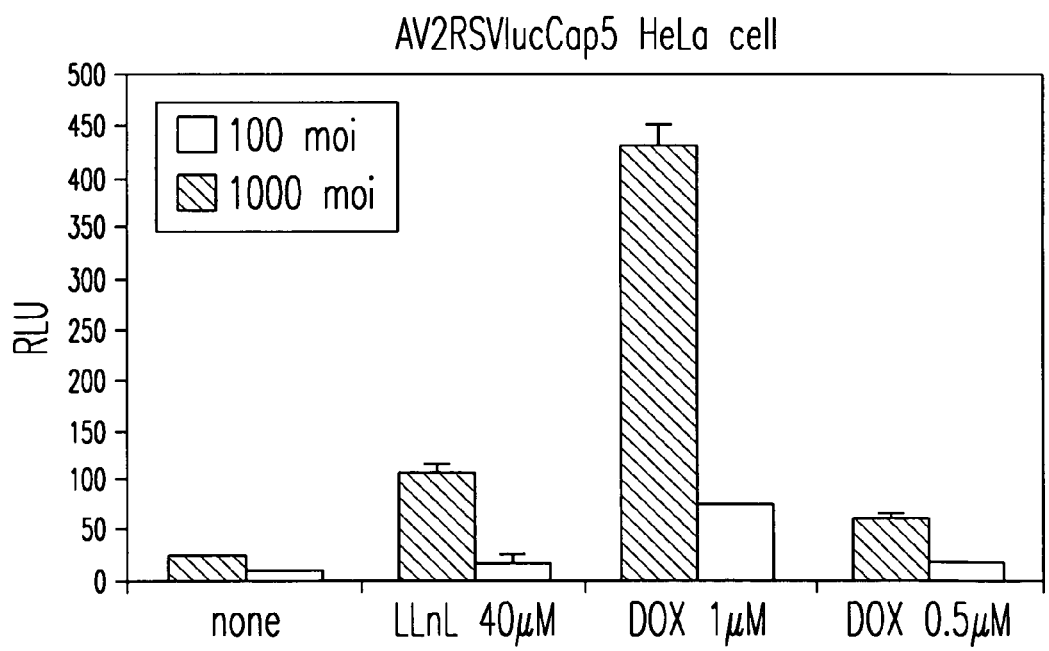
Figure 4C:
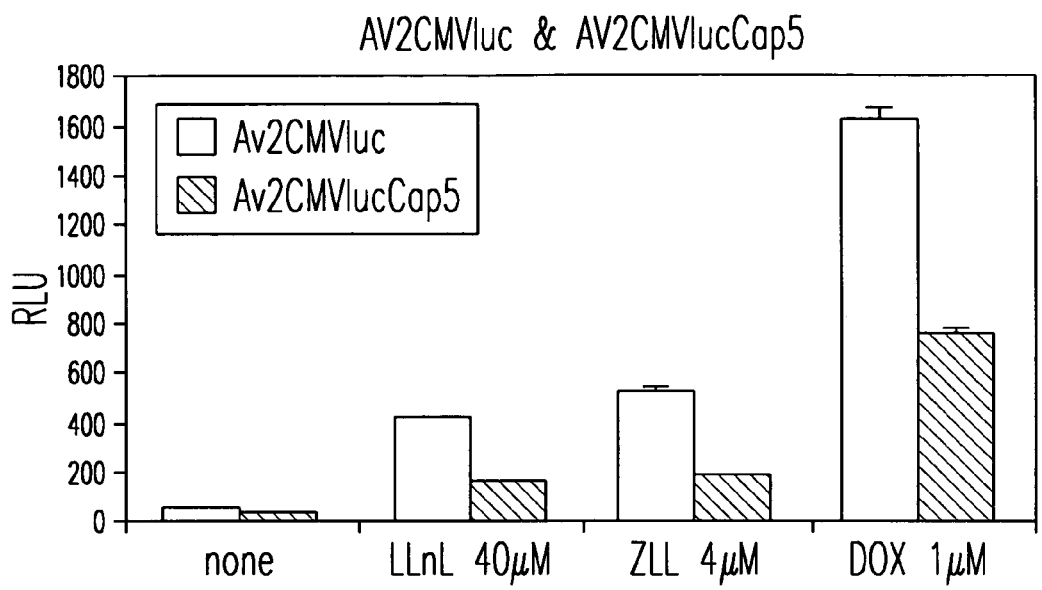
Figure 4D:
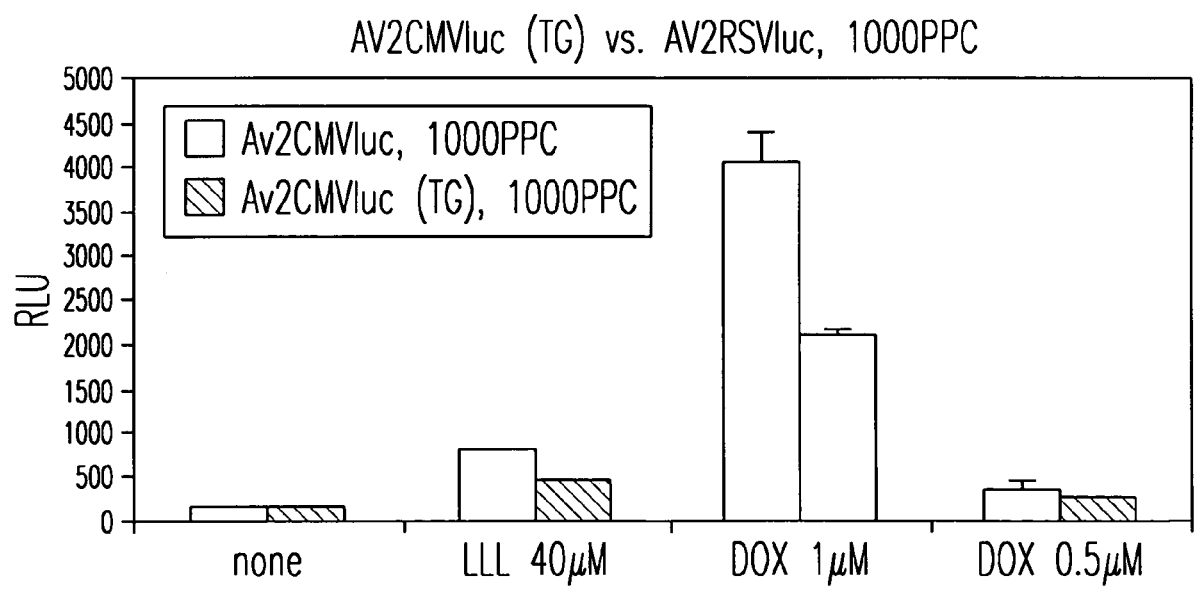
Figure 4E:
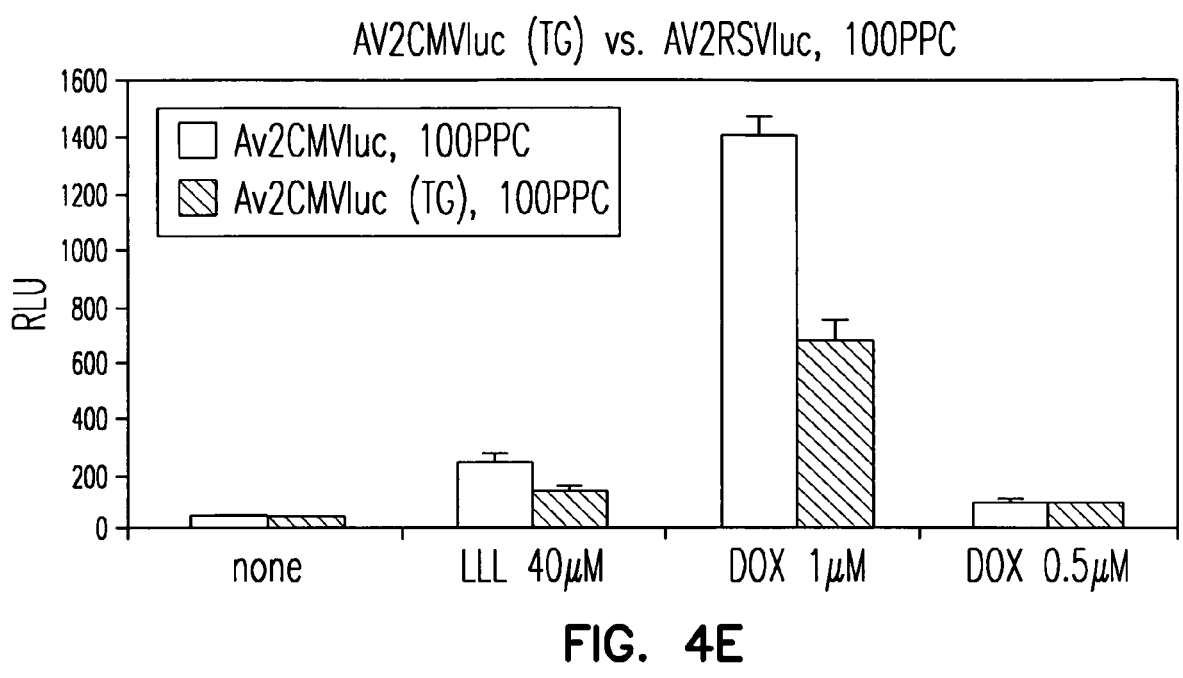

In additional experiments, a pseudotyped rAAV vector encoding FVIII was tested in male Rag-1 mice. Rag-1 mice were used because as described in the art, normal mice produce inhibitors of human FVIII that can obscure protein detection in the serum. Rag-1 mice are known to be deficient in the pathways necessary to produce these inhibitors and thus will either produce no inhibitors, lower levels of inhibitors or have extended time periods for development of inhibitors. The rAAV vector was constructed containing serotype 5 capsid proteins and 5'-3' ITRs of AAV-2 flanking a heterologous transgene comprised of the minimal liver specific element HNF3/EBP and a human B-domain deleted FVIII gene (a second construct was identical except it contained a B-domain deleted canine FVIII gene). Animals were administered $10^{12}$ rAAV vector particles intravenously via the lateral teil vein concurrently with 20 mg/kg of DOXIL® at day 0. Circulating, bioavailable FVIII activity was measured from the serum at days 31, 53 and 90 by techniques known in the art including ELISA and Coatest. Data presented in FIG. 3 demonstrate that animals not treated with DOXIL® had barely detectable levels of FVIII in the range of 0.99 ng/ml for days 31 and 53 which decreased to 0.13 ng/ml by day 90. In contrast, animals dosed with 20 mg/kg of DOXIL® had over 40 times the levels of FVIII protein. Interestingly, the decline in FVIII protein seen in animals not treated with DOXIL® at day 90 (0.13 ng/ml) was not evident in animals treated with DOXIL® (40.16 ng/ml) indicating that DOXIL® not only enhanced rAAV transduction as evident at the shorter time period, but the agent of the invention also prolonged expression. In order to demonstrate that DOXIL® was affecting rAAV transduction and not merely affecting the FVIII protein translation or stability, RS-PCR was performed on liver tissue at the day 53 time point. The data presented for individual animals in Table 1 demonstrates that the increase in FVIII protein noted in animals treated with DOXIL® correlates with the levels of mRNA detected.

The increase in vivo rAAV transduction produced by DOXIL® was further confirmed utilizing the same vectors and protocol described above in male FVIII knockout mice tolerized to the human FVIII protein utilizing a cytoxan mediated tolerization strategy as described in the art. Animals were treated with weekly injection of 50 mg/kg cytoxan beginning at the time of rAAV vector delivery. Data presented in Table 2 confirmed the previously described results when tested by ELISA or Coatest at days 14 and 25, namely animals dosed with DOXIL® demonstrated at least a ten-fold enhancement of rAAV transduction.

TABLE 1

| Animal Number | Treatment | Molecules FVIII mRNA/cell | FVIII Protein (ng/mL) |
|---|---|---|---|
| #26 | AAV2/5 HNF3/EBP | 2.15 | 0.68 |
| #27 | | 0.91 | <0.63 |
| #28 | | 1.98 | 0.97 |
| #29 | | 2.06 | 1.45 |
| #30 | | 2.45 | 0.77 |
| #31 | | 2.29 | <0.63 |
| #59 | AAV2/5 HNF3/EBP | 65.47 | 31.85 |
| #60 | FVIII + Doxil | 41.4 | 37.75 |
| #61 | | 99.43 | 51.9 |
| #62 | | 49.44 | 38.65 |
| #63 | | 43.9 | 40.55 |
| #64 | | 57.54 | 31.55 |
| #26 | | 2.15 | 0.68 |
| #27 | | 0.91 | <0.63 |
| #28 | | 1.98 | 0.97 |
| #29 | | 2.06 | 1.45 |
| #30 | | 2.45 | 0.77 |
| #31 | | 2.29 | <0.63 |
| #59 | AAV2/5 HNF3/EBP | 65.47 | 31.85 |
| #60 | FVIII + Doxil | 41.4 | 37.75 |
| #61 | | 99.43 | 51.9 |
| #62 | | 49.44 | 38.65 |

TABLE 1-continued

| Animal Number | Treatment | Molecules FVIII mRNA/cell | FVIII Protein (ng/mL) |
|---|---|---|---|
| #63 | | 43.9 | 40.55 |
| #64 | | 57.54 | 31.55 |

TABLE 2

In Vivo Enhancement of FVIII rAAV Transduction

| Sample | Animal # and Final Result (ng/mL) | Coatest (mU/mL) |
|---|---|---|
| Day 14 Results | | |
| Group 1 Vehicle | 801 < 0.63 | 0 |
| | 804 < 0.63 | 0 |
| | 805 < 0.63 | 0 |
| | 847 < 0.63 | 0 |
| Group 2 AAV2/5-HFN3/EBP-FVIII | 816 < 0.63 | 0 |
| | 817 < 0.63 | 0 |
| | 818 0.92 | 0 |
| | 819 < 0.63 | 0 |
| | 820 < .63 | 0 |
| | 834 0.9 | 0 |
| Group 2 AAV2/5-HFN3/EBP-FVIII + Doxil | 870 60.45 | 171 |
| | 871 26.29 | 0 |
| | 872 12.395 | 14 |
| | 873 44.3 | 30 |
| | 874 12.135 | 122 |
| | 875 31.04 | 94 |
| 2.X.10, Day 25 FVIII ELISA | | |
| Group 1 Vehicle | 806 < 0.63 | 0 |
| | 807 < 0.63 | 0 |
| | 808 < 0.63 | 0 |
| | 849 < 0.63 | 0 |
| Group 2 AAV2/5-HFN3/EBP-FVIII | 821 < 0.63 | 0 |
| | 822 < 0.63 | 0 |
| | 823 < 0.63 | 0 |
| | 824 1.27 | 0 |
| | 825 0.72 | 0 |
| | 833 0.74 | 0 |
| Group 3 AAV2/5-HFN3/EBP-FVIII + Doxil (no spikes) | 841 16.785 | 49.833 |
| | 842 12.425 | 37.282 |
| | 843 13.685 | 41.466 |
| | 844 35.225 | 91.842 |
| | 845 7.815 | 12.974 |
| | 846 24.02 | 54.853 |

Thus, agents that interact with molecules in intracellular AAV trafficking pathways, such as proteosomes or molecules in the ubiquitin pathway, by binding to those molecules and/or inhibiting their activity, are useful to enhance rAAV transduction.

Example 4

Figure 5A:
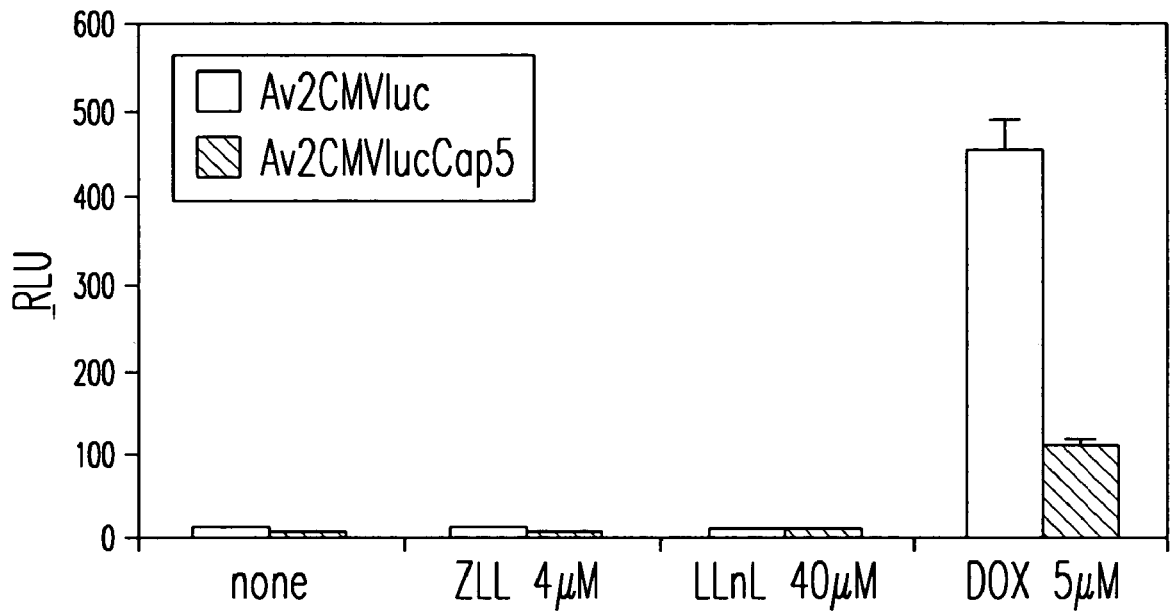
FIG. 5. Luciferase activity in A549 cells after infection with AV2CMVluc or AV2CMVluc Cap5 (500 ppc), and co-administration of LLnL (40, 200 or 400 μM), Z-LLL (4 μM), or doxorubicin (5 μM). A) Comparison of AV2CMVluc and AV2CMVlucCap5. B) Dose response for varying amounts of LLnL in A549 cells infected with AV2CMVluc.
Figure 5B:
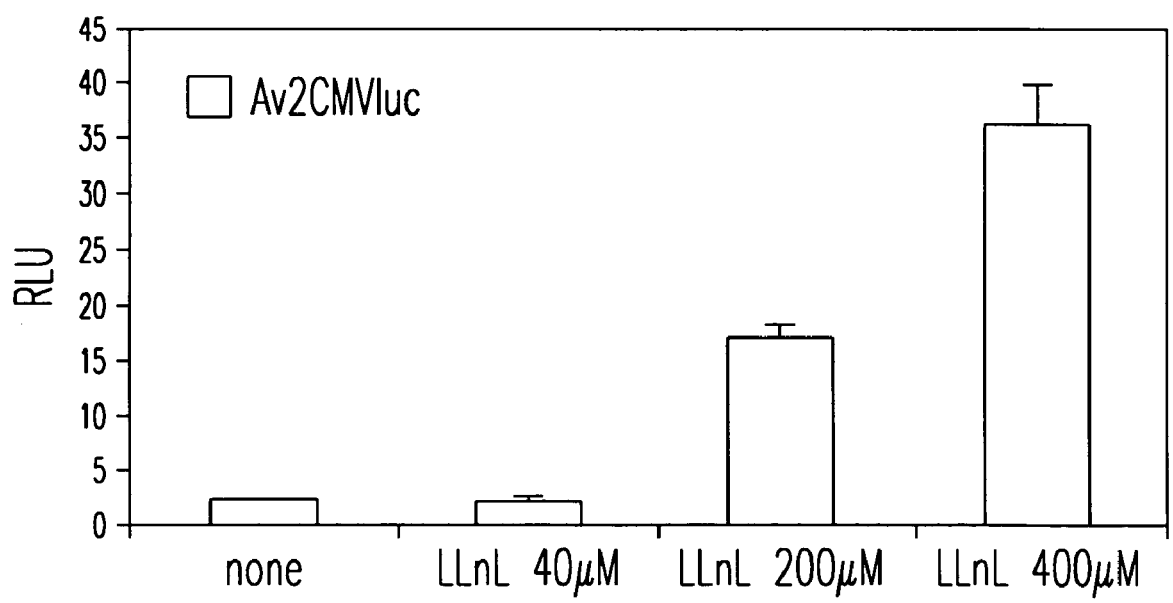
Figure 6A:
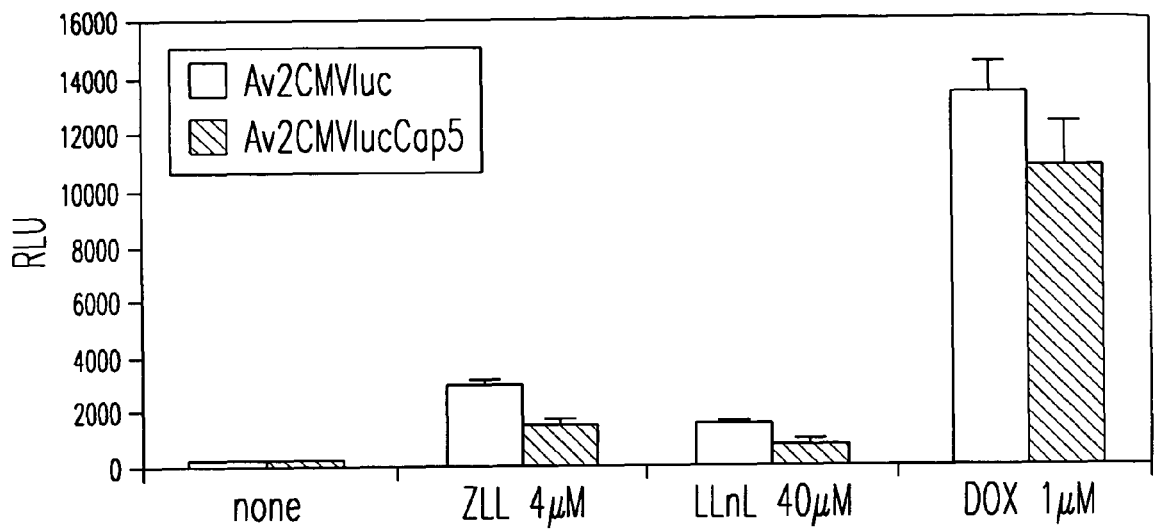
FIGS. 6A-C. A) Luciferase activity in ferret fibroblasts after infection with AV2CMVluc or AV2CMVluc Cap5 (500 ppc), and administration of LLnL (40 µM), Z-LLL (4 µM), or doxorubicin (1 µM). B)-C) RLU at 1 and 5 days for AV2CMVluc (FIG. 6B) and AV2CMVlucCap5 (FIG. 6C) in ferret fibroblasts in the absence or presence of LLL or doxorubicin.
Figures 6B, 6C:
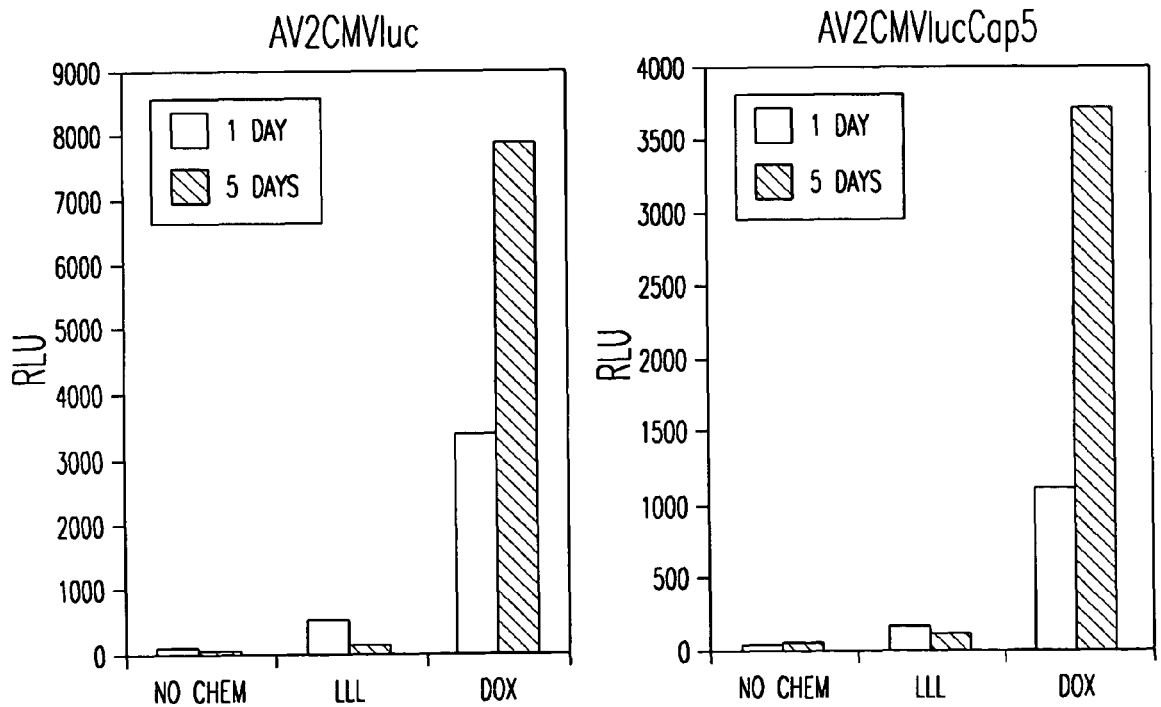
Figure 7A:
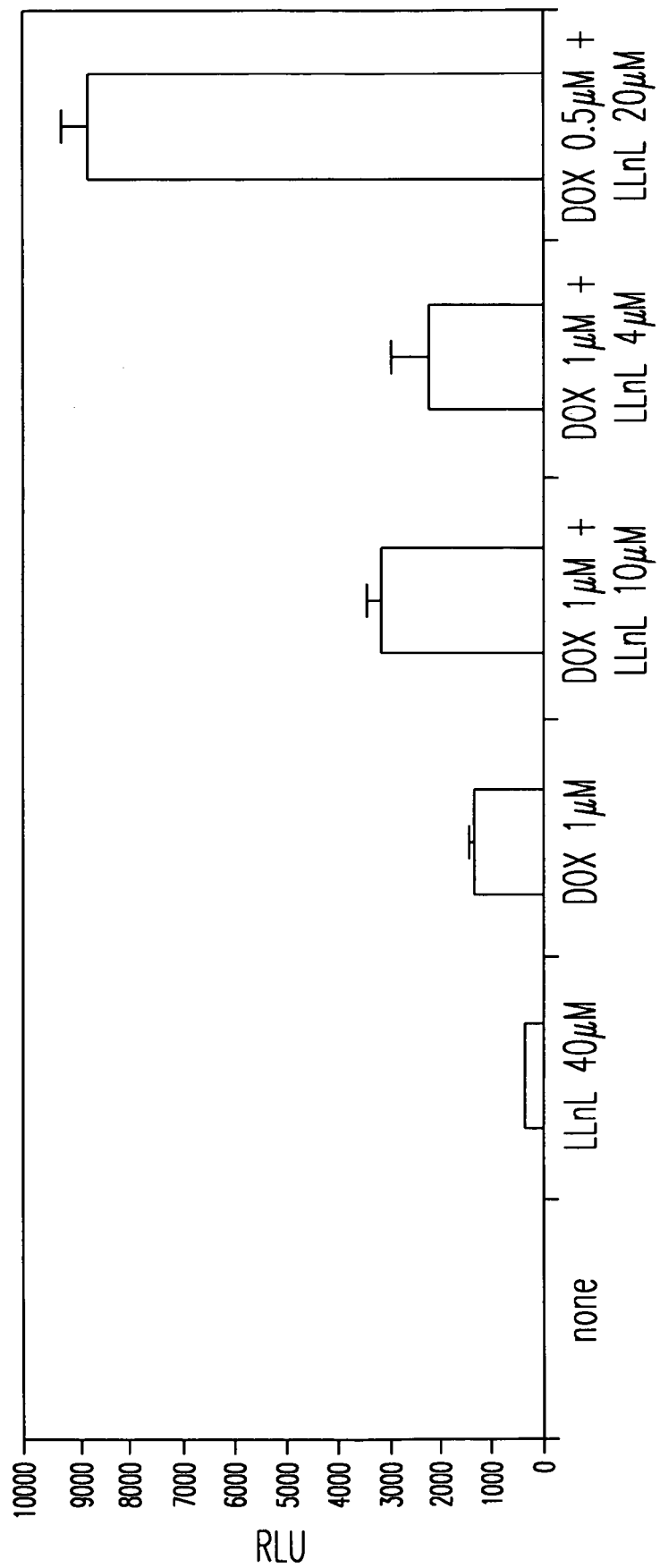
FIG. 7. Comparison of luciferase activity in HeLa (A), ferret fibroblast (B) and A549 (C) cells with one or two proteosome modulators.
Figure 7B:
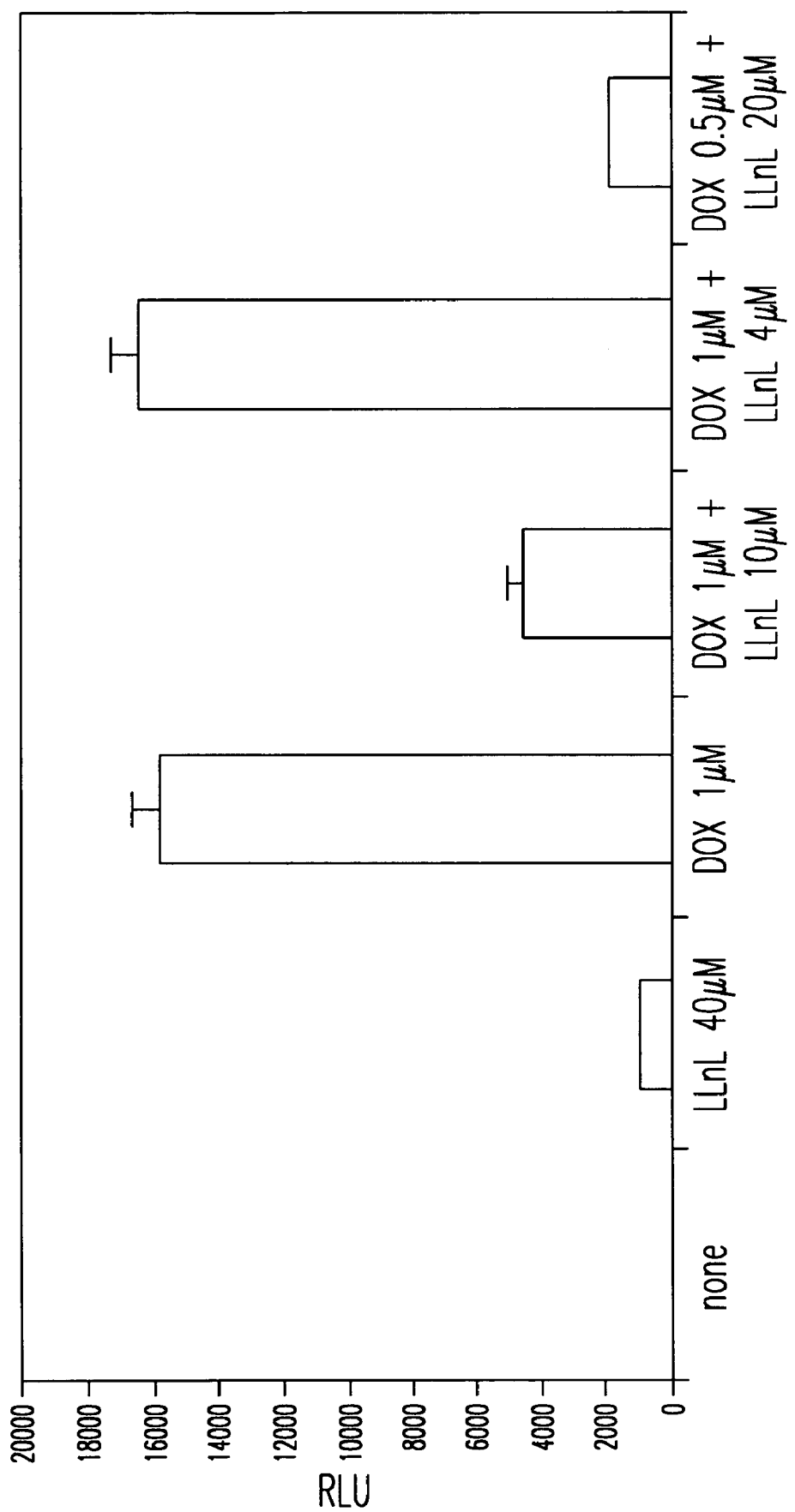
Figure 7C:
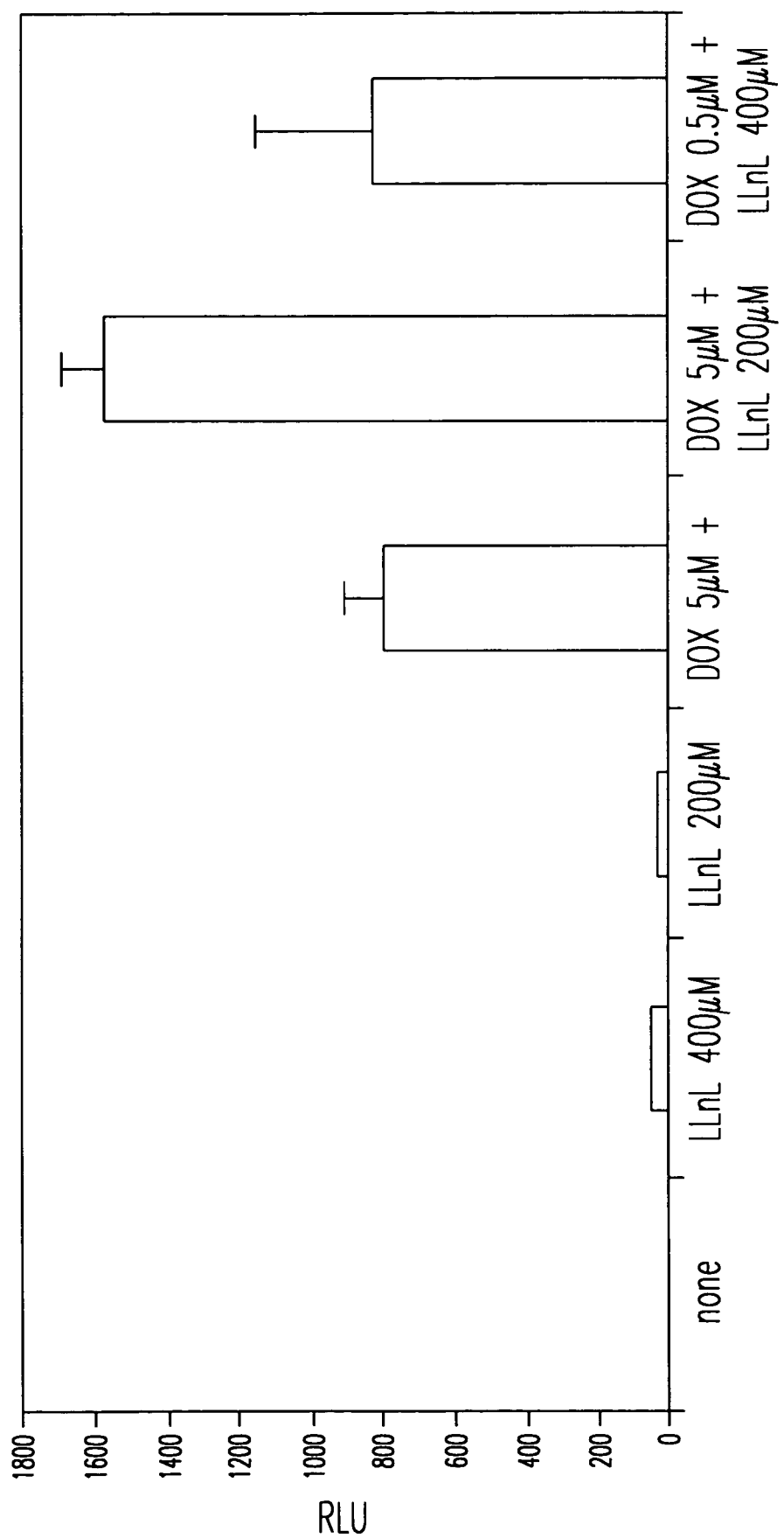

Proteasome Involvement in rAAV-2 and rAAV-5 Transduction of Polarized Airway Epithelia in Vitro and in Vivo Inhibition of the proteasome with small tripeptide inhibitors such as LLnL can significantly augment rAAV-2 transduction from the apical membrane of both polarized human airway epithelia in vitro and mouse lung in vivo (Duan et al., 2000). As AAV-5 has been reported to have higher tropism for, and alternate receptors on, the apical membrane of airway epithelia, increased transduction of airway epithelia from the apical membrane with rAAV-5 might be due to altered proteasome involvement. Co-administration of a proteasome modulator and a proteosome inhibitor was found to augment transduction of both serotypes in a cell type dependent manner (FIGS. 4-6).

Figure 8A:
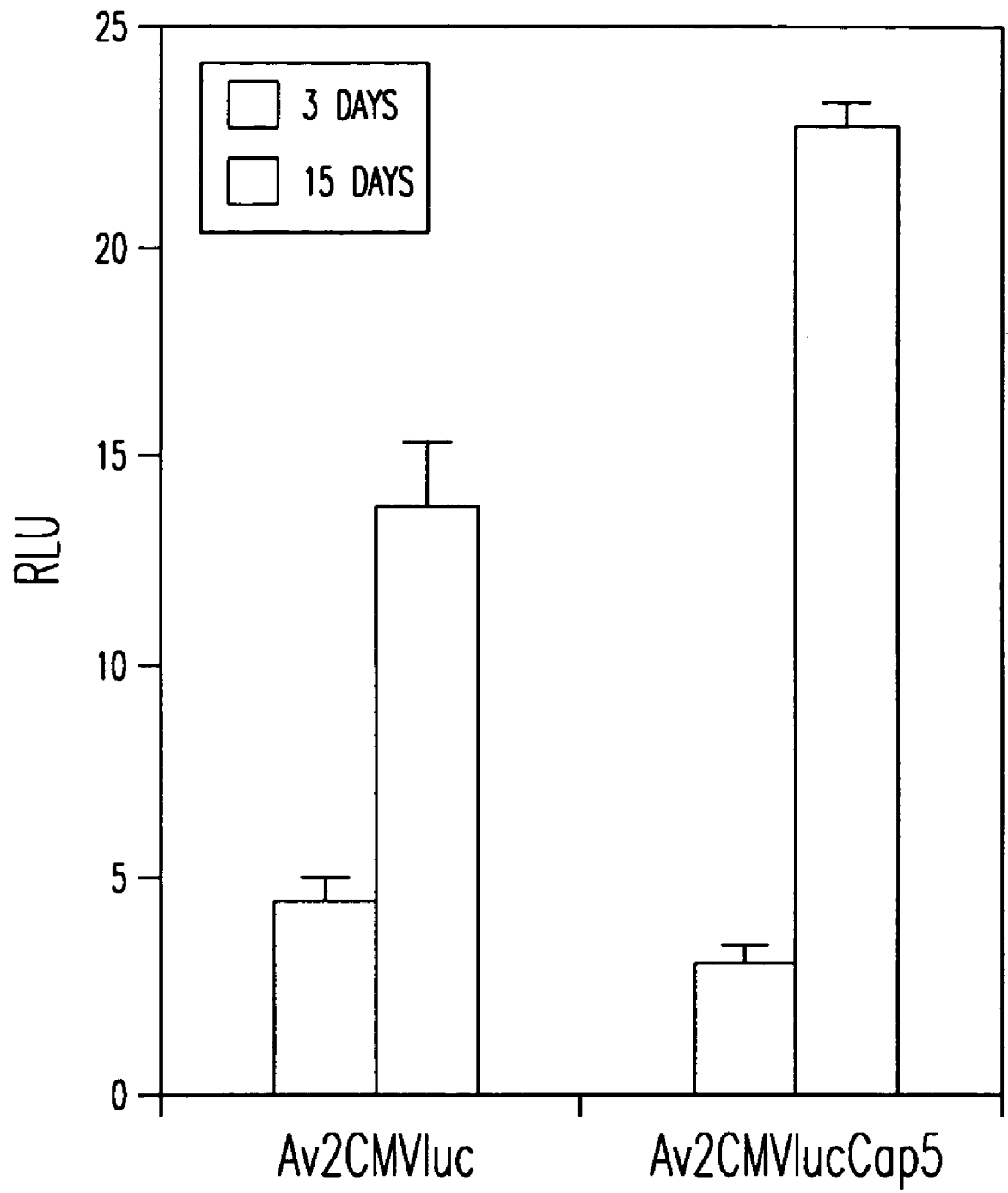
FIGS. 8A-C. Luciferase activity in polarized airway epithelial cells at 3 days (FIGS. 8A and 8B) and 15 days (FIGS. 8A and 8C) after apical infection with $5\times10^9$ AV2CMVluc or AV2CMVlucCap5 and administration of LLnL (40 µM) or doxorubicin (1.0 or 5.0 µM) or a combination of LLnL (40 µM) and doxorubicin (1.0 or 5.0 µM).
Figure 8B:
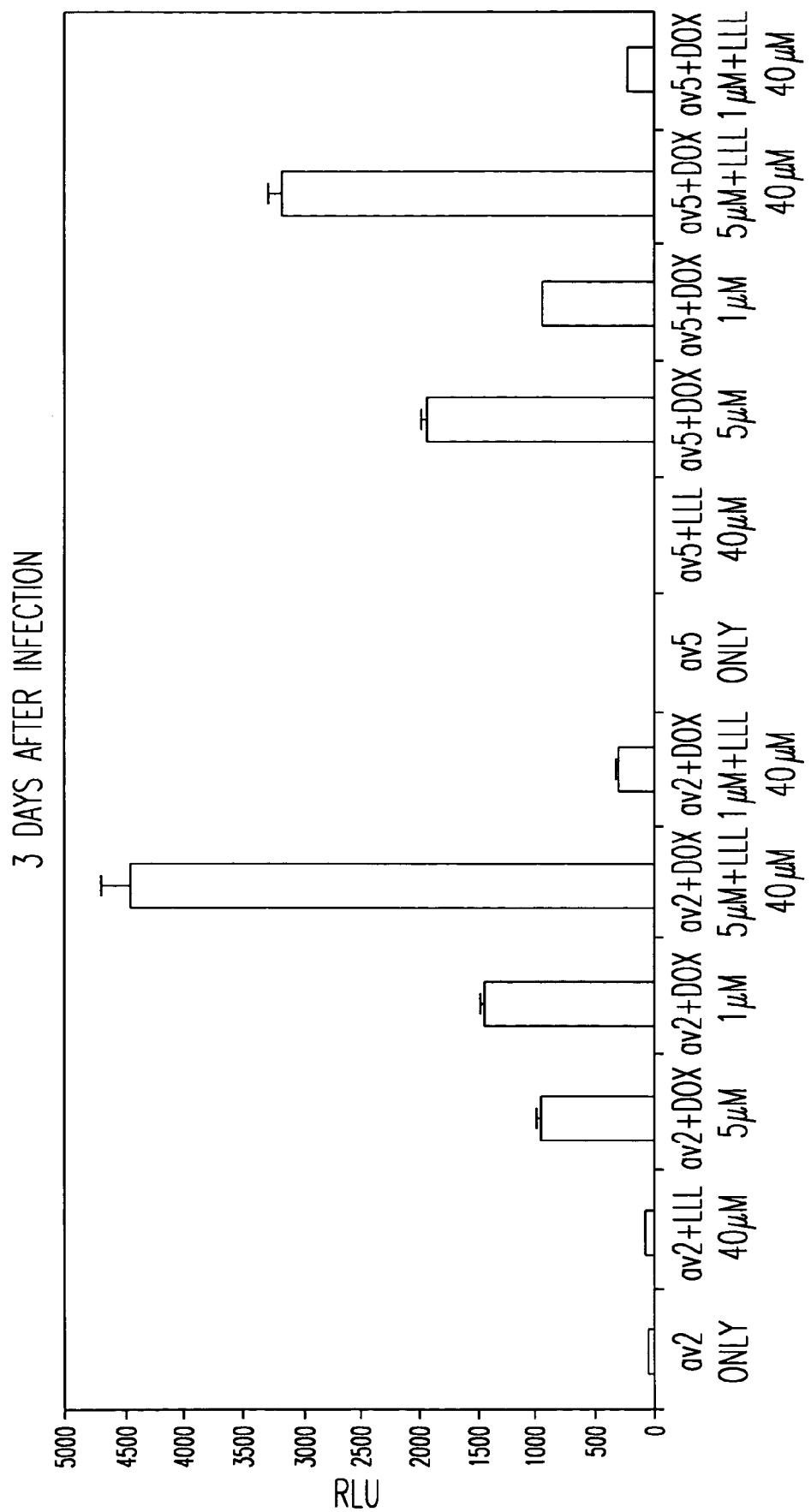
Figure 8C:
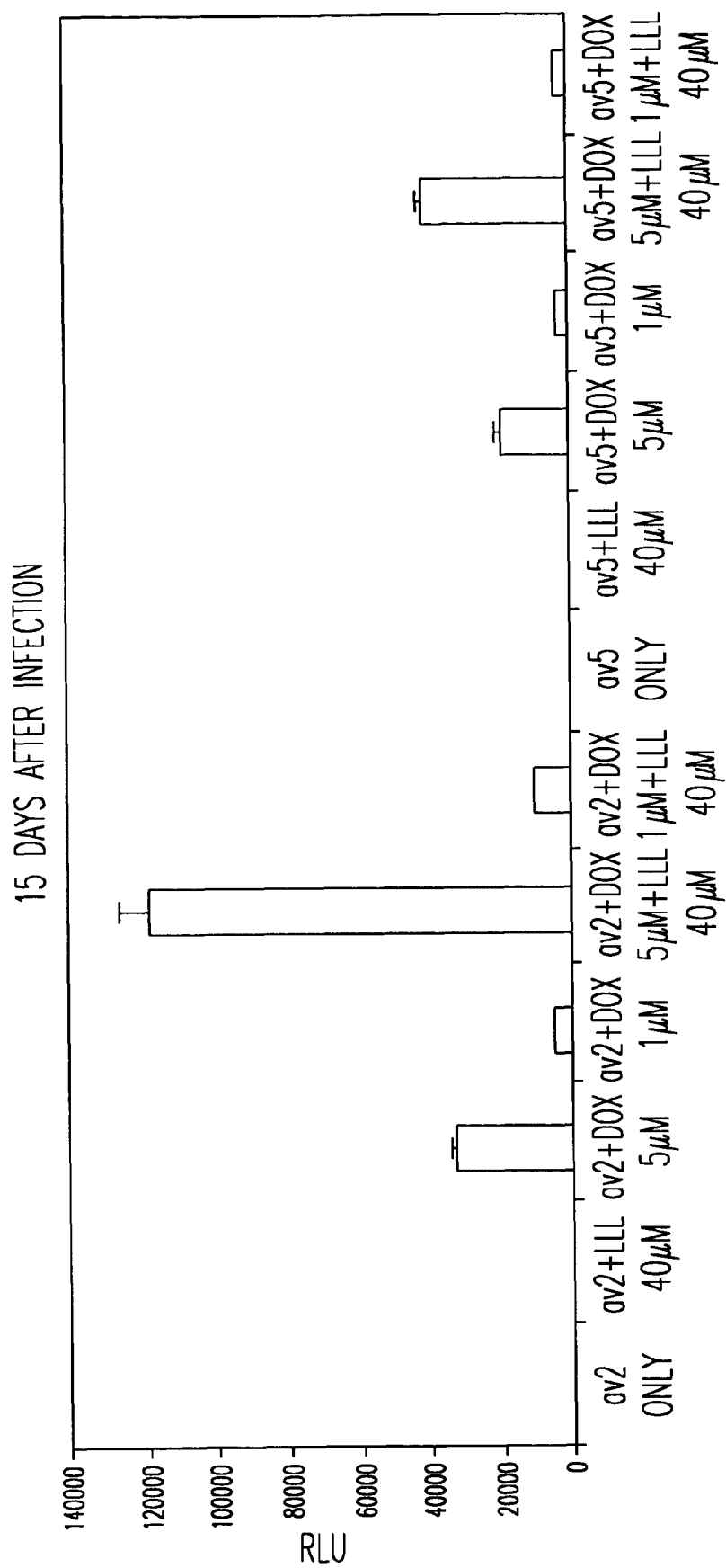
Figure 9A:
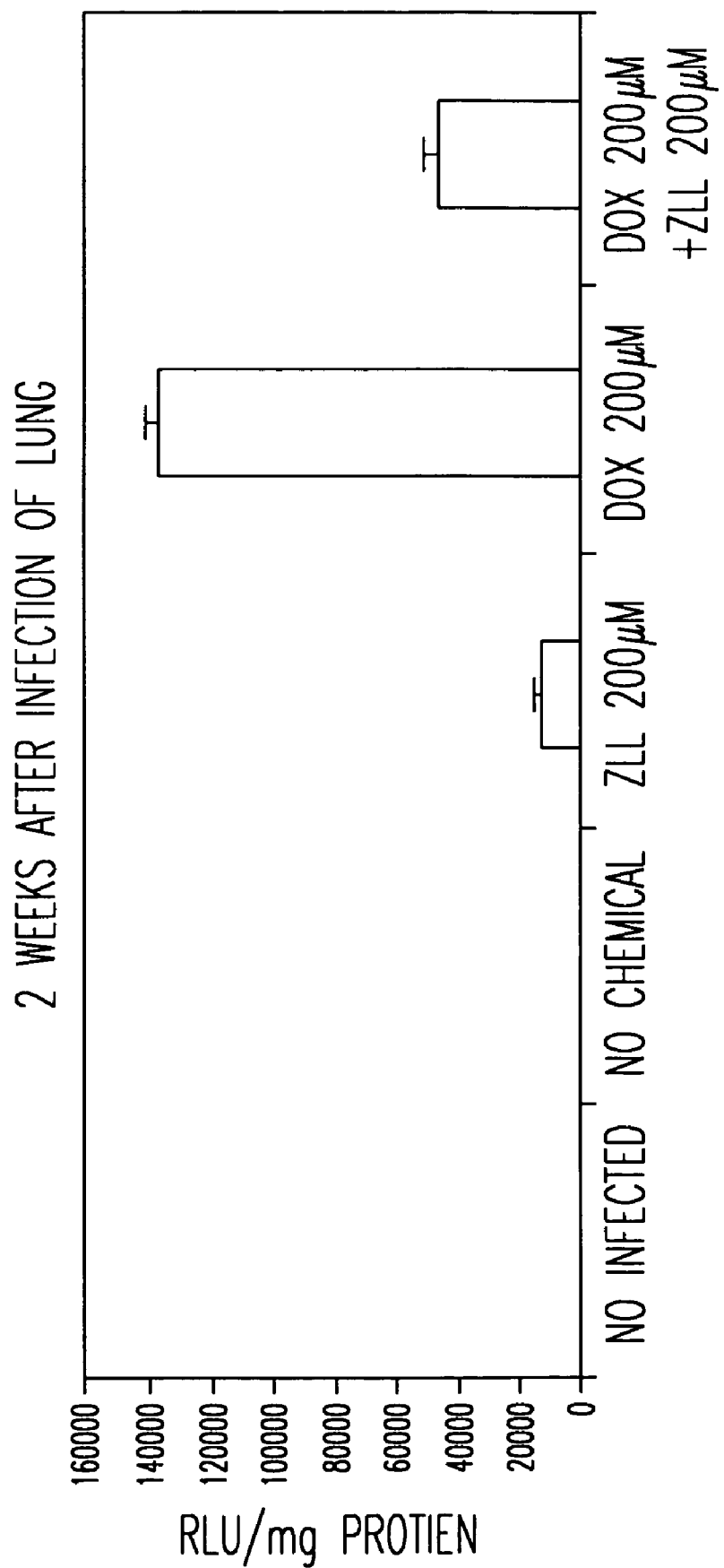
FIGS. 9A-D. Luciferase activity in C57B16 mouse lung (FIGS. 9A and C) or trachea and bronchi (FIGS. 9B and D) at 2 weeks (FIGS. 9A-B) or at 6 weeks (FIGS. 9C-D) after infection (via nasal aspiration) with AV2RSVlucCap5 (3 times with 10 µl of $2\times10^9$ particles/µl in 40 µl, for a total of $6\times10^{10}$ particles) and administration of Z-LLL (200 µM), doxorubicin (200 µM), or a combination of Z-LLL (200 µM) and doxorubicin (200 µM). For each group, n=12. Lung and trachea with some bronchial tissue was isolated and, after extraction, luciferase activity/total protein in the tissue extraction determined.
Figure 9B:
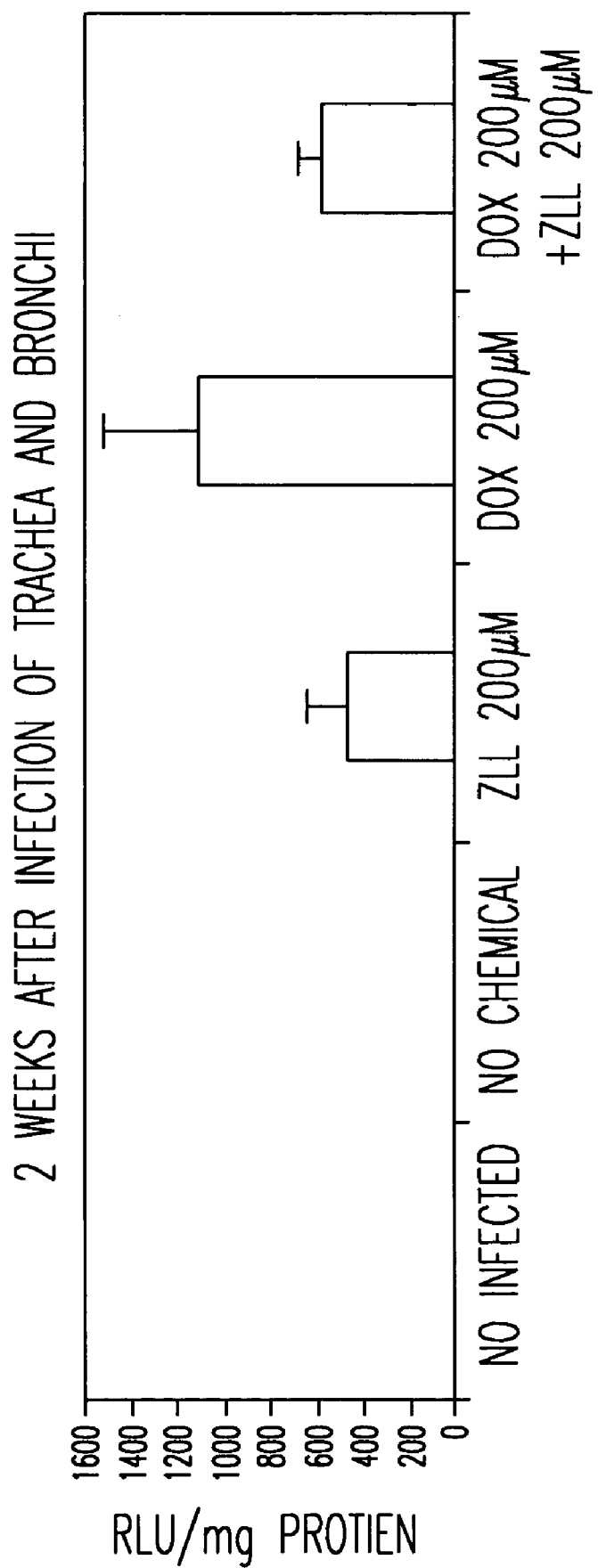
Figure 9C:
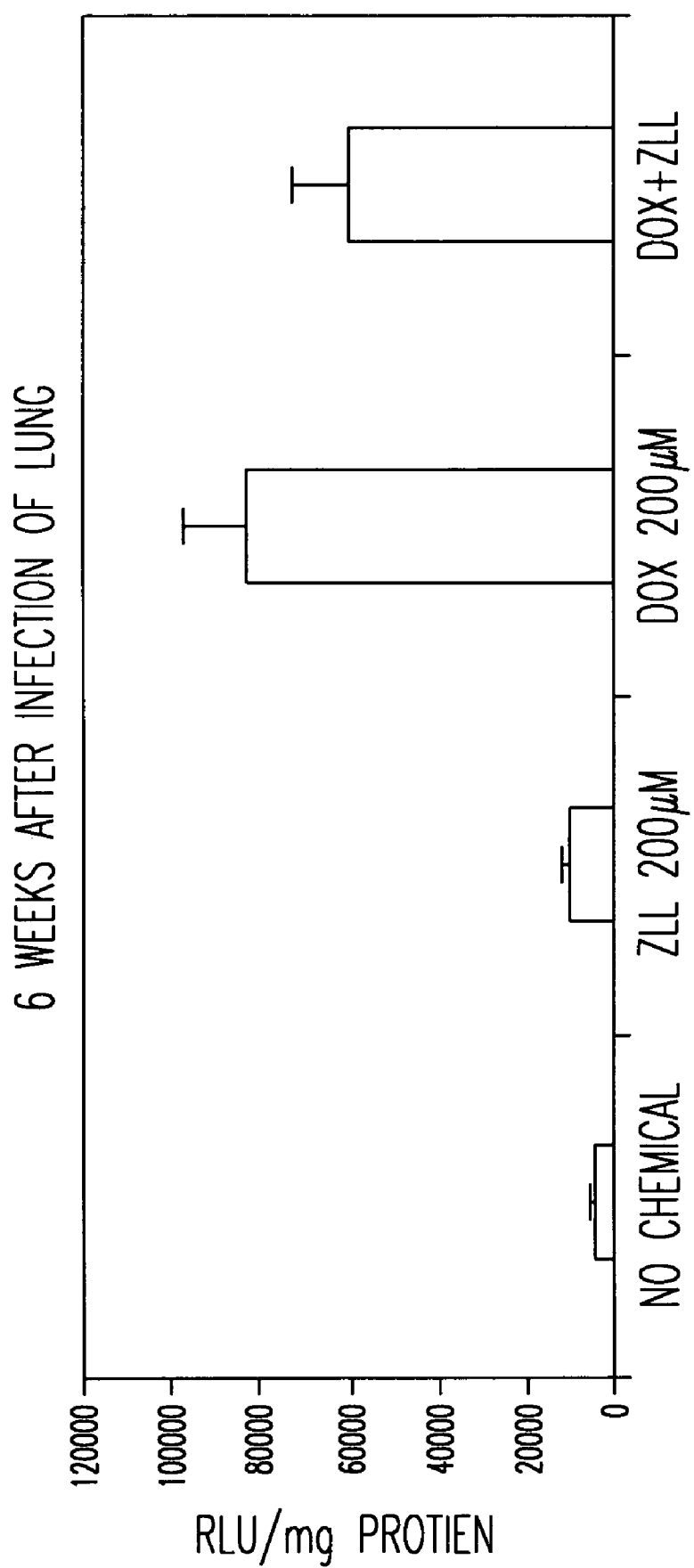
Figure 9D:
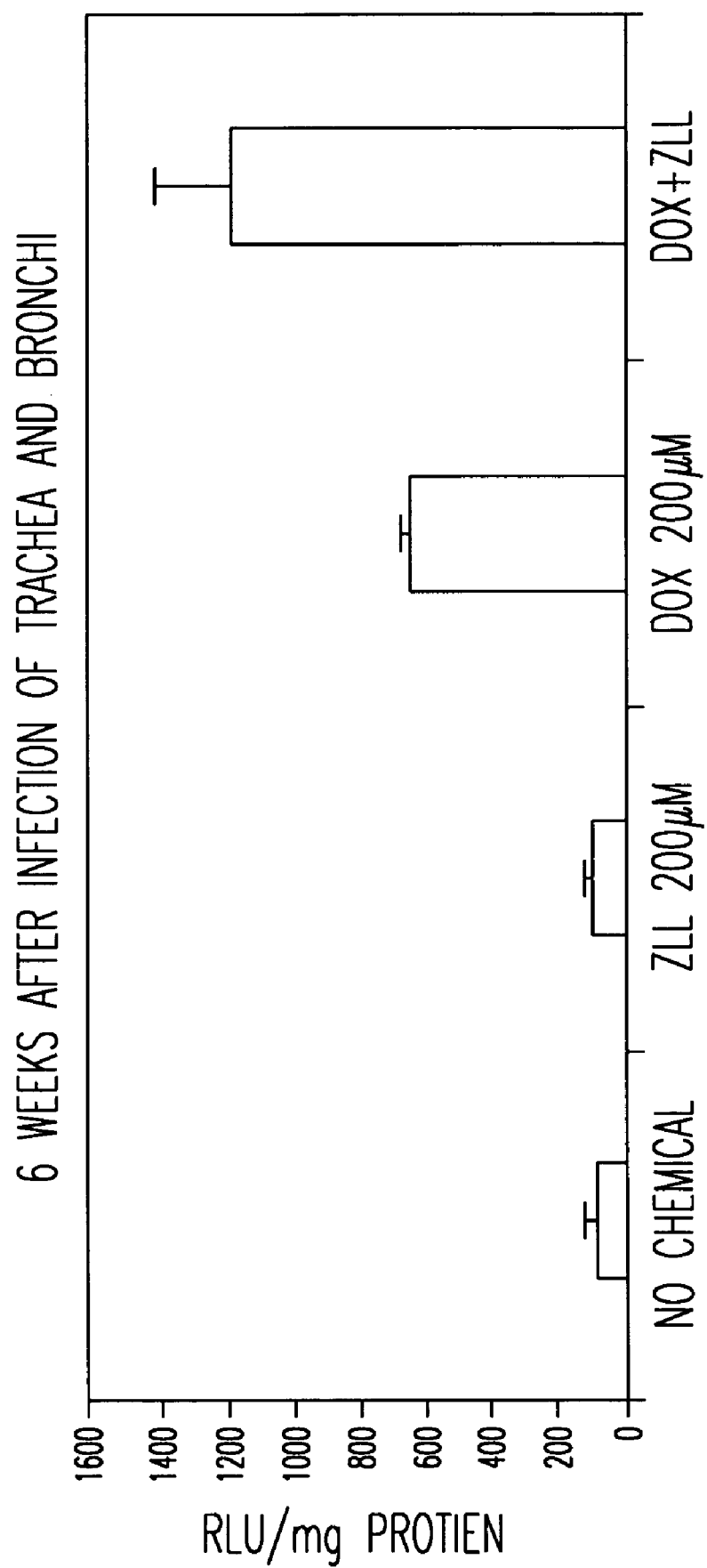

To better understand serotype-specific differences in airway transduction, the effect of proteasome inhibitors on rAAV-2 and rAAV-5 transduction in polarized human airway epithelial cultures and mouse lung was examined (FIG. 8). A proviral construct containing 5' and 3' ITRs from AAV-2 flanking a transgene was packaged into both AAV-2 and AAV-5 capsid to generate AV2.RSVluc and AV2.RSVlucCap5 viruses which express the luciferase transgene. rAAV-2, but not rAVV-5, demonstrated a significant difference in transduction from the apical versus basolateral surface. Transduction with AV2.RSVluc was 36- and 103-fold greater from the basolateral membrane at 5 and 14 days post-infection, respectively. In contrast, AV2.RSVlucCap5 transduced epithelia from the apical and basolateral membranes with similar efficiencies at both time points.

LLnL augments AV2.RSVluc transduction from the apical and basolateral surfaces. However, application of LLnL selectively increased AV2.RSVlucCap5 transduction 12-fold only when virus was applied to the apical surface. These results suggest an interesting difference in the involvement of the proteasome for various AAV capsid entry pathways that are effected by cell polarity.

Figure 10A:
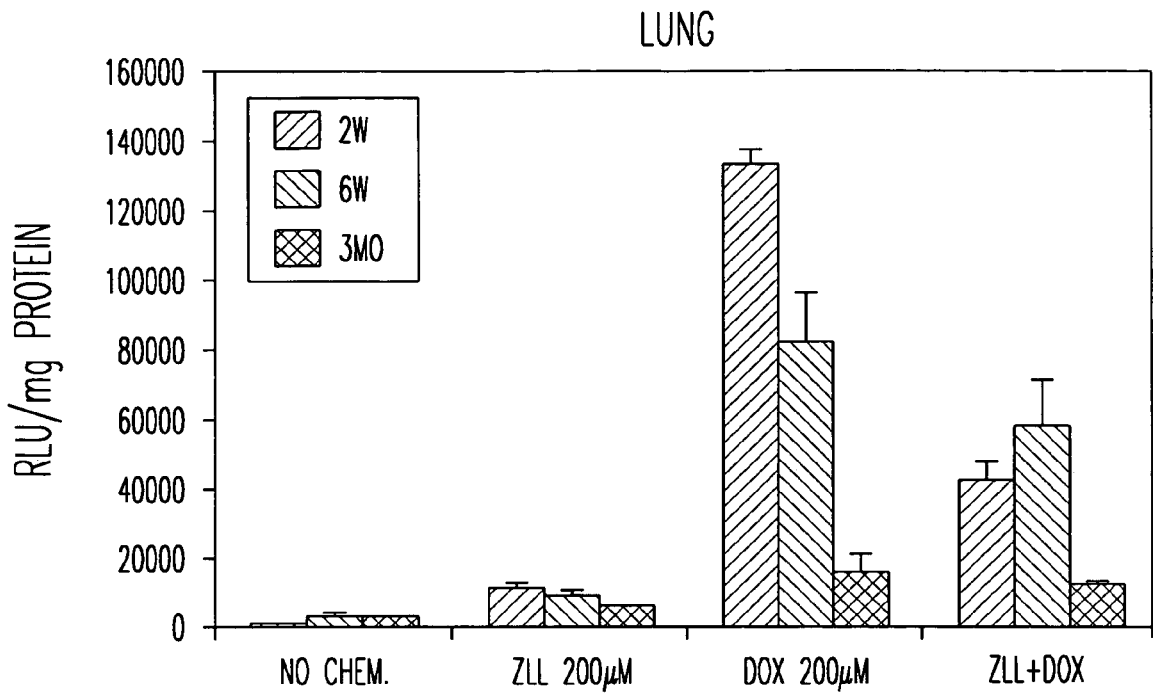
FIG. 10. Luciferase activity in mouse lung (upper panel) or trachea and bronchi (lower panel) at 2 weeks, 6 weeks or 3 months after infection with AV2RSVlucCap5 and administration of Z-LLL (200 µM), doxorubicin (200 µM) or a combination of Z-LLL (200 µM) and doxorubicin (200 µM). The luciferase assay was performed at 80% sensitivity. Lung and trachea with some bronchial tissue was isolated and, after extraction, luciferase activity/total protein in the tissue extraction determined.
Figure 10B:
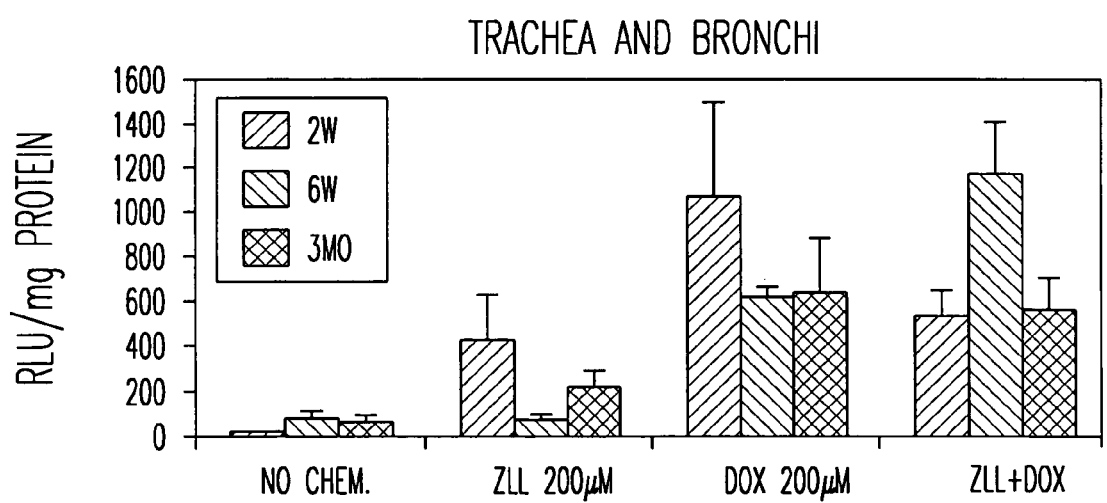
Figure 11A:
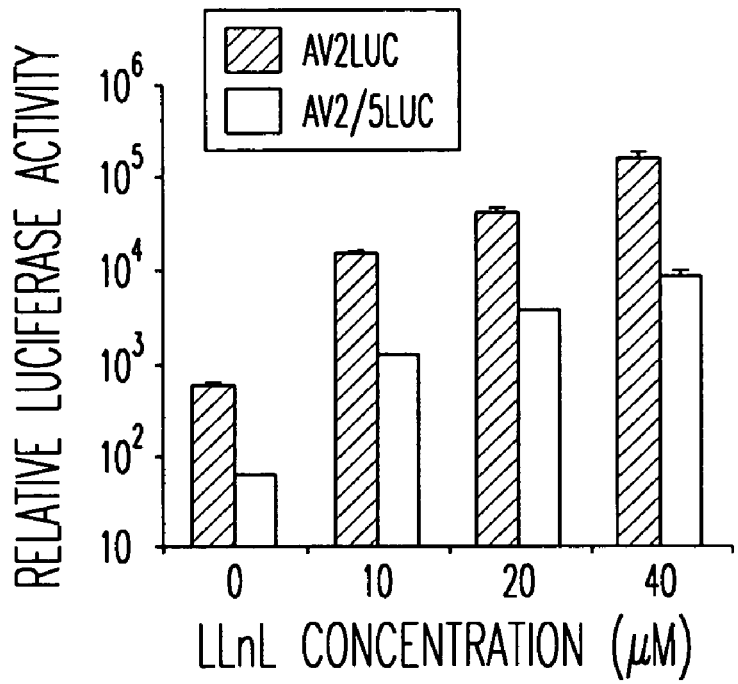
FIGS. 11A-D. The effects of proteasome inhibitors LLnL (FIGS. 11A and C) and Doxorubicin (Dox) (FIGS. 11B and D) on AV2Luc and AV2/5Luc transduction of immortalized human airway cell lines IB3 (FIGS. 11A-B) and A549 cells (FIGS. 11C-D) were evaluated. Proteasome-modulating agents were co-administered with each rAAV vector (MOI of 500 particles per cell) at the time of infection and transduction was evaluated 24 hours later. Various concentrations of each chemical were evaluated as indicated in each graph. Data represent the mean (+/−SEM) relative luciferase activity experiment (N=4).
Figure 11B:
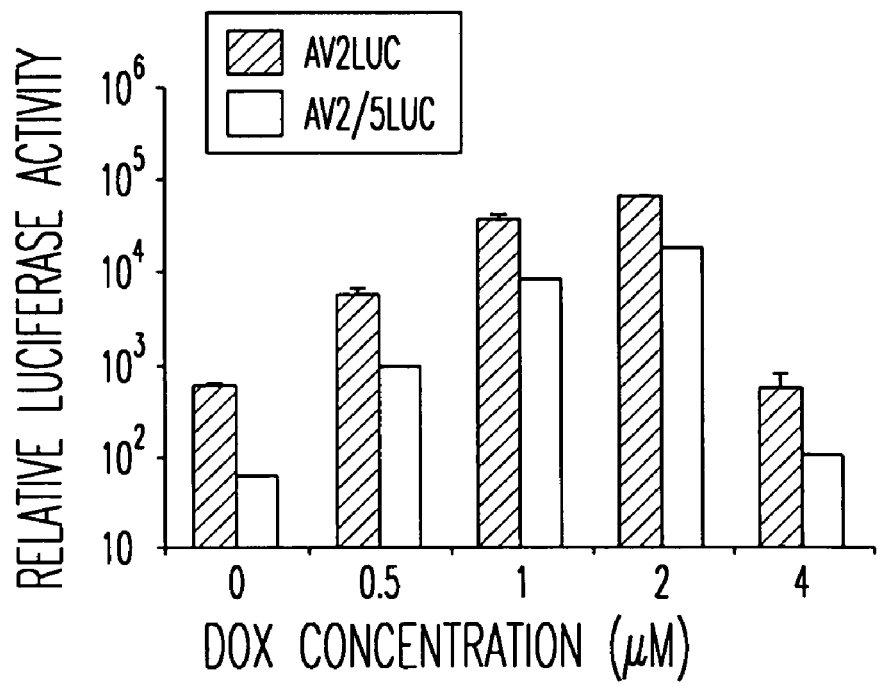
Figure 11C:
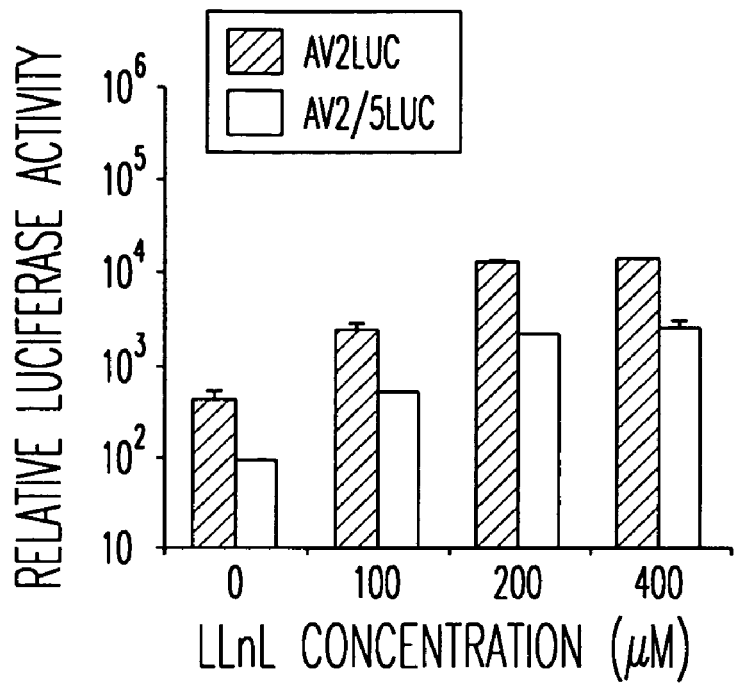
Figure 11D:
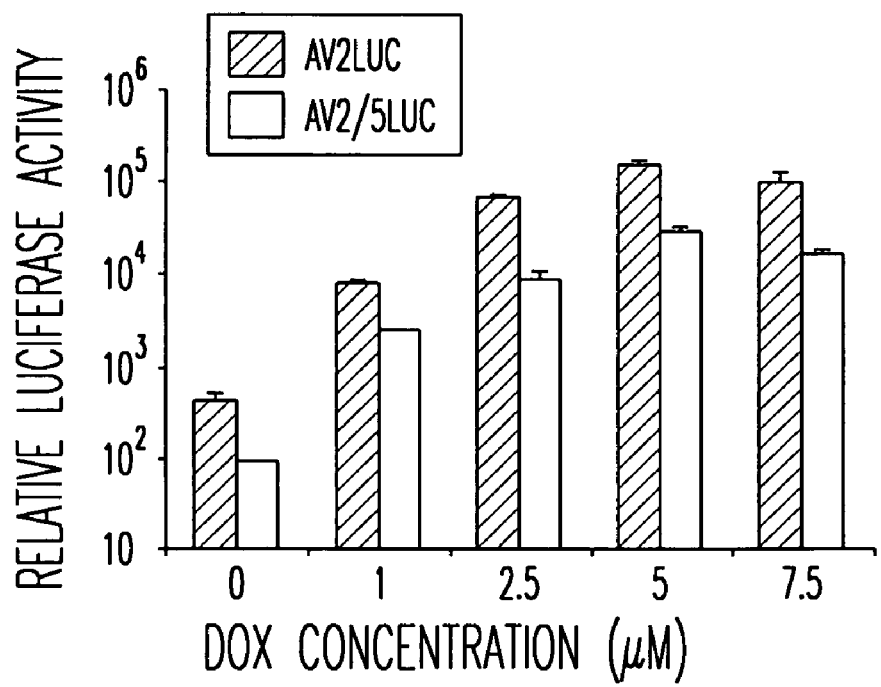

The proteasome inhibitor Z-LLL was found to induce long-term (5 month) transduction with rAAV-2 in mouse lung. To determine in vivo transduction efficiency of AV2.RSVlucCap5, mice were infected with $6 \times 10^{10}$ particles of AV2.RSVlucCap5 by nasal aspiration alone (control) or in combination with 200 µM Z-LLL, 200 µM doxorubicin or 200 µM Z-LLL and 200 µM doxorubicin (12 mice per group). Co-administration of Z-LLL induced whole lung luciferase expression 17.2- and 2.1-fold at 14 (2 weeks) and 42 (6 weeks) days post-infection, respectively (FIG. 9). Interestingly, luciferase expression was further reduced at 3 months post-infection (FIG. 10).

Co-administration of doxorubicin induced whole lung luciferase expression at levels almost ten times higher than those for Z-LLL at 2 weeks. Doxorubicin also induced tracheal and bronchi luciferase expression at higher levels than Z-LLL at 2 weeks. At six-weeks, a similar pattern was observed for Z-LLL and doxorubicin alone, however, luciferase levels were more than additive in trachea and bronchi in mice co-administered virus, Z-LLL and doxorubicin. By three months post-infection, the synergism was no longer observed. These observations suggest a striking difference in the kinetics and longevity of induction by Z-LLL between in vivo studies with rAAV-2 and rAAV-5. Since in vivo transduction is significantly more efficient with rAAV-5 compared to rAAV-2, altering proteasome activity may simply enhance the rate of transduction with rAAV-5. In the case of rAAV-2, this basal rate may be significantly reduced from the apical membrane in vivo rendering more sustained augmentation of transduction by proteasome inhibitors.

These results also highlight the use of different agents and vectors to achieve different results. For example, agents and vectors that result in a steady increase in transgene expression in particular cells over time may be useful for certain disorders or conditions while agents and vectors that result in a high burst of transgene expression may be useful for metabolic disorders such as hemophilia.

Ubiquitination and proteasome activity can influence a myriad of intracellular processes that control protein degradation and intracellular trafficking. The following examples are designed to identify the molecular mechanisms of rAAV transduction that are controlled by the ubiquitin/proteasome system. These studies may lead to a clearer understanding of pathways and/or molecules that influence rate-limiting steps in rAAV transduction and can also be used to identify further useful agents to enhance processing of rAAV (i.e., endosomal escape, trafficking to the nucleus, and uncoating) and hence transduction.

Example 5

Endosomal Pathways for Serotypes of rAAV

To delineate the intracellular pathway(s) of rAAV trafficking in airway epithelial cell lines, the pathway of intracellular trafficking for type 2 and 5 rAAV is determined using co-localization techniques with fluorescently-labeled rAAV and intracellular endosomal markers, biochemical purification of various endosomal compartments, and inhibition of endosomal movement using exogenously-expressed specific dominant negative Rab proteins. Rabs are small GTPases that provide for programmed delivery of endosomal compartments to various subcellular domains, and facilitate membrane fusion through GTP-dependent mechanism. Single cell microinjection of fluorochrome-quenching antibodies was used to determine the endosomal compartment from which rAAV escapes based on a color changes of dually-labeled rAAV. rAAV2 and rAAV5 may traffic through multiple endocytic compartments (Late endosome [LE], golgi, perinuclear recycling endosome [PNRE]), but only one of these compartments is the point of exit into the cytoplasm.

A. Intracellular Accumulation of rAAV2

Previous studies have demonstrated that Cy3-labeled rAAV2 co-localizes with FITC-labeled transferrin but not FITC-labeled Dextran when visualized in Hela cells (Bartlett et al., 2000; Duan et al., 1999; Sanlioglu et al., 2000). Although virus begins to accumulate in the nucleus by 1 hour post-infection, a significant amount accumulates in a perinuclear organization. Transferrin is known to traffic through the PNRE (also called pericentriolar recycling endosome), which is an intracellular warehouse for intracellular sorting of receptors. Thus, rAAV2 may also traffic through this compartment.

Rab proteins encompass a group of small GTPases that are well known for their importance in vesicular sorting and membrane fusion. Many of these Rab proteins have been extensively characterized as markers for various intracellular sorting pathways. GFP-Rab fusion proteins as intracellular markers by which to compare rAAV2 trafficking to the transferrin sorting pathway (Rab5→Rab4→Rab11) (Ren et al., 1998; Trischler et al., 1996).

Methods

Labeling. rAAV was labeled with a monovalent Cy3 fluorochrome as previously described in Duan et al. (1999) and Sanlioglu et al. (2000). Typically about 2 fluorochromes label the rAAV capsid with greater than 85% retention of functional activity. To facilitate quality control analysis of labeled rAAV, rAAV that expresses the luciferase genes was used. For all labeling procedures, rAAV is generated by triple transfection as previously described in Duan et al. (2001). The labeling procedure was modified to include a G50 Sephadex gel-filtration step to isolate virus from free fluorochrome. Fractions were then assessed by slot blot and functional activity, and peak fractions were then analyzed by EM.

Intracellular GFP-tagged endosomal markers. cDNAs that express N-terminal GFP-tagged proteins that mark various intracellular compartments including Rab4, 5, 7, 9, and 11 endosomes, golgi, and the proteasome were obtained, as well as dominant negative constructs for each of these Rabs that prevents GTP hydrolysis (a function required for endosomal fusion mediated by each Rab) (Table 3).

TABLE 3

| Construct | Protein Expressed | Endosomal Compartment and Use | cDNA Source (Ref) |
|---|---|---|---|
| Rab5-GFP | GFP-tagged Rab5a | Marks Early Endosome | Sonnichsen et al. (2000) |
| dnRab5 | Rab5a(S34N) | Block Movement out of Early Endosome | Li et al. (1993) |
| Rab5-HA | HA-tagged Rab5a | Immunoaffinity Isolation of Rab5 Endosomes | |
| Rab4-GFP | GFP-tagged Rab4 | Block Movement into the Rab4 compartment | Sonnichsen et al. (2000) |
| dnRab4 | Rab4(S22N) | Immunoaffinity Isolation of Rab4 Endosomes | Sonnichsen et al. (2000) |
| Rab4-HA | HA-tagged Rab4 | Immunoaffinity Isolation of Rab4 Endosomes | |
| Rab11-GFP | GFP-tagged Rab11a | Marks the PNRE | Sonnichsen et al. (2000) |
| dnRab11 | Rab11a(S25N) | Block Movement through the PNRE | |
| Rab11-HA | HA-tagged Rab11a | Immunoaffinity Isolation of Rab11 Endosomes | |
| Rab7-GFP | GFP-tagged Rab7 | Marks the Late Endosome to Lysosome pathway | Bucci et al. (2000) |
| dnRab7 | Rab7(T22N) | Block Movement through the late endosome | Bucci et al. (2000) |
| Rab7-HA | HA-tagged Rab7 | Immunoaffinity Isolation of Rab7 Endosomes | |
| Rab9-GFP | GFP-tagged Rab9 | Marks Rab7 Late Endosome to Golgi Movement | Barbero et al. (2002) |
| dnRab9 | Rab(S21N) | Blocks endosomal movement to the golgi | Iversen et al. (2001) |
| Rab9-HA | HA-tagged Rab9 | Immunoaffinity Isolation of Rab9 Endosomes | |
| TGN38-GFP | GFP-tagged TGN38 | Marks the trans-golgi network | Girotti et al. (1996) |
| TGN38-HA | HA-tagged TGN38 | Immunoaffinity Isolation trans-golgi network | |
| LMP2-GFP | GFP-tagged LMP2 | Marks the proteasome subunit LMP2 | Reits et al. (1997) |

Co-localization of Cy3-rAAV2 with GFP-labeled Rab compartments. HeLa cells were transfected with GFP-tagged Rab4, Rab5, and Rab11 expression constructs using standard protocols and lipofectamine/DNA complexes. At 48 hours following transfection, HeLa cells were infected with Cy3-rAAV2 at an MOI of 50,000 particles/cell on glass coverslips at 4° C. for 1 hour. Cells were then washed extensively and either fixed for analysis or shifted to 37° C. for 1 hour. Samples were then evaluated by confocal microscopy for the co-localization of Cy3 and GFP signal.

Results and Conclusions

GFP-tagged Rab5 and Rab4 show similar patterns of distribution in HeLa cells at 48 hours post-transfection consistent with their overlapping distribution within the early endosomal recycling compartment (Trischler et al., 1999). In contrast, Rab11-GFP, which marks the PNRE, demonstrated a very unique distribution within the cell. Co-localization experiments with Cy3-rAAV2 and Rab11-GFP demonstrate a large percentage of overlap at 1 hour following infection.

However, as expected, no overlap in signal was detected with bound Cy3-rAAV prior to initiated endocytosis at 37° C. These findings suggest that rAAV2 traffics through the Rab11 compartment. In HeLa cells, this compartment predominantly demarcates the PNRE. However, some overlap exists with trans-golgi as Rab11 has also been shown to control movement from the PNRE to the golgi. The Golgi-specific marker TGN-38 is employed to evaluate this possibility. Although a large extent of overlap between Cy3 and Rab11 signals was observed, specific intracellular and intranuclear domains contained regions of no overlap in signal. The intracellular domains are other potential endosomal compartments through which rAAV2 may migrate (i.e., late endosome, golgi, lysosome).

B. Localization of rAAV with Rab5 and Rab11

Endosomal purification techniques were employed to evaluate the trafficking patterns of rAAV and the effect to which proteasome inhibitors alter the manner in which virus moves through the cell.

Methods

Density gradients. Density gradient centrifugation was used to isolate mixed populations of endosomes according to their size and buoyant density. Iodixanol is used as the medium for fractionation since it can provide an iso-osmotic condition with low viscosity over a wide range of density.

Vesicular isolation. Confluent monolayers of IB2, Hela, or A549 cells grown on one 150 mm dish were incubated with 0.8 mg/ml biotin-transferrin (Sigma Co., St. Louis, Mo.) or AV2Luc (MOI=10,000) in prewarmed MEM supplemented with 10 mM Hepes for 30 minutes at 37° C. The cells were harvested by trypsinization (which removes external, membrane-bound rAAV2 (Duan et al., 2001; Duan et al., 2000), washed in ice-cold PBS three times, and harvested into ice-cold homogenization buffer (0.25 M sucrose, 10 mM triethanolamine, 1 mM EDTA, 1 mM PMSF, 100 µg aprotinin). Cells were then homogenized in a Duall tissue grinder and centrifuged at 1000×g at 4° C. for 10 minutes. The supernatant, which contains intracellular vesicular compartments and membranes, but not the nuclei, was designated the post-nuclear supernatant (PNS). The PNS was subsequently combined with 60% iodixanol solution to obtain a final concentration of 32% and then loaded into an SW55Ti centrifuge tube and overlaid with two-step gradients of 24% and 20% iodixanol. All iodixanol solutions were prepared in homogenization buffer. Samples were centrifuged at 30,500 rpm for 1 hour at 4° C. Fractions were collected from the top to bottom of the centrifuge tube at 4° C. (320-500 ul/fraction) since vesicular fractions migrate at the interphase between 24%/20% iodixanol.

Western blot analysis. 50 µl of each fraction was loaded on SDS-PAGE gel and Western blotted for Rab5 (Santa Cruz Biotechnology), Rab11 (Transduction Laboratories), and/or biotin-transferrin (Zymed Laboratories). Western blots were developed using ECL chemiluminescence using HRP conjugated streptavidin or secondary antibodies.

TaqMan PCR quantification of viral DNA. PCR primers and the Taqman probe for AV2Luc DNA quantification were selected using the Primer Express software program. The forward primer, P1 (5'-TTTTTGAAGCGAAGGTTGTGG-3'; SEQ ID NO:1), and the reverse primer, P2 (5'-CACACA-CAGTTCGCCTCTTTG-3'; SEQ ID NO:2), were chosen to amplify a 32-bp fragment in the promoter region of AV2Luc DNA. The Taqman probe (5'-ATCTGGATACCGG-GAAAACGCTGGGCGTTAAT-3'; SEQ ID NO:3) was designed following the general rules outlined by the manufacturer. The Taqman probe carried a 5' reporter dye, 6-carboxy fluorescein (FAM), and a 3' quencher dye, 6-carboxy tetramethyl rhodamine, and was synthesized by Genosys. The 25 µl PCR mixture consisted of 10 µl AV2Luc gradient sample, primers P1 and P2 (final concentration 500 nM), Taqman probe (final concentration 100 nM), and 12.5 µl Taqman Universal Master Mix (PE Applied Biosystems). For AV2Luc DNA amplification, 1 cycle at 50° C. for 2 minutes and 1 cycle at 95° C. for 10 minutes were followed by a two-step PCR procedure consisting of 15 seconds at 95° C. and 1 minutes at 60° C. for 40 cycles. Amplification, data acquisition, and analysis were performed using the ABI Prism 7700 Sequence Detector System (PE applied Biosystems). All standard dilutions of purified AV2Luc, controls, and samples from the subcellular fractionation were run in duplicate, and the average value of the copy number was used to quantify AV2Luc. The standard curve for AV2Luc was accepted when the slope was between −3.74 and −3.32 and the coefficient of correlation was >0.990.

Results and Conclusions

Subcellular fractionation of purified endosomes was shown by isolating intact endosomes containing preloaded biotin-transferrin. As expected, transferrin immunoreactivity co-fractionates with the Rab5 and Rab11 compartments as detected by Western blotting (fraction 3 and 4). The remaining immunoreactivity in the bottom of the tube represents lysed endosomes and free Rabs or transferrin in the PNS. The addition of free biotin-transferrin to the PNS of unloaded cells does not lead to detectable immunoreactivity in peak vesicular fractions (data not shown).

To investigate whether this method could be used to isolate viral-containing endosomes, similar evaluations were performed on AV2Luc-infected Hela cells (MOI=10,000). Peak Rab5/Rab11 positive vesicular fractions (#2-4) co-isolate with internalized rAAV genomes, following a 30 minute infection at 37° C. Approximately 50% of rAAV DNA was contained within the endosomal fraction. There was also a significant portion of rAAV DNA in the PNS at the bottom of the tube. This likely represents either free rAAV that has exited the endosome or endosomal lysis during the processing. However, without the use of more refined methods proposed in the experimental plan, the interpretation that vector remaining in the PNS had exited the endosome should be interpreted cautiously.

C. Use of HA-tagged Rab Proteins for Purification

Based on a previous report describing the immuno-affinity isolation of Rab5 and Rab11 endosomal compartments to study transferrin movement through cells (Trischler et al., 1999), a novel approach was developed to immuno-isolate numerous endosomal compartments using HA-tagged Rab marker proteins. These HA-tagged constructs as described below, partition to the endogenous sites of their Rab counterparts as well as our ability to immuno-isolate the Rab5 compartment.

Methods

N-terminal HA-tagged Rabs were generated by PCR for Rab5, Rab7, and Rab11 using a forward primer containing the HA epitope. A CMV-driven plasmid expression construct was employed to express HA-Rab5 and HA-Rab11 in Hela cells following lipofectamine transfection. At 72 hours post-transfection, endosomal fractions were purified and various fractions from the Iodixanol gradient were evaluated by Western blotting for HA, Rab5, and Rab11. Mixed populations of endosomes were then used for the immuno-affinity isolation strategy described below.

Immuno-affinity isolation of HA-tagged Rab5 endosomal compartments. Rab5 endosomes were isolated based on a previous method (Trischler et al., 1999) with modifications. Hela cells were transfected with HA-Rab5 expression plasmid and peak vesicular fractions (#3, 4, and 5) were combined from the Iodixanol gradient and immuno-affinity-purified using Dynabeads M-500 (Dynal Inc) bound to anti-HA antibodies. Secondary antibody (40 ug anti-rabbit) was conjugated to Dynabeads (200 µl containing $4 \times 10^8$ beads/ml) in 0.1 M borate buffer (pH 9.5) for 24 hours at 25° C. with slow rocking. The beads were then placed into the magnet for 3 minutes to remove the supernatant and washed three times in 0.1% (w/v) BSA/PBS for 5 minutes at 4° C. A final wash in 0.2 M Tris (pH 8.5)/BSA was performed for 24 hours. Finally, the beads were resuspended in BSA/PBS and conjugated to 4 µg primary anti-HA antibody per $10^7$ beads O/N at 4° C. and washed in BSA/PBS. Vesicular fractions (300 µl) from $2 \times 10^7$ cells expressing the various HA-tagged Rabs were mixed with 700 µl coated beads in PBS containing 2 mM EDTA, 5% BSA, and protease inhibitors. The mixture was then incubated for 6 hours at 4° C. with slow rocking, followed by magnetic capture and washing in the same tube three times (15 minutes each). Beads and enriched endosomes were then resuspended in PBS for Western blotting to assess enrichment of the Rab5 compartment.

Results and Conclusions

Exogenously-expressed HA-Rab5 and HA-Rab11 partition in an Iodixanol gradient to fractions typically containing the endosome. To assess the co-localization of endogenous Rab counterparts with the exogenously-expressed HA-tagged fusion, Western blots of peak vesicular fractions using anti-HA, anti-Rab5, and anti-Rab11 were performed. HA immunoreactivity was only seen in endosomes from cells transfected with the HA-tagged Rabs. This immunoreactivity coincided with the peak immunoreactivity for each of the Rab proteins. These results demonstrated that the tagged Rabs properly incorporate into endosomes and partition with the endogenous membrane-bound Rab counterparts.

Using an immuno-affinity isolation strategy with anti-HA bound Dynabeads beads, the peak endosomal fraction from HA-Rab5-transfected Hela cells (#4) was used for Rab5 endosomal isolation. Immuno-isolation was performed in the presence of 1° anti-HA and 2° anti-rabbit antibodies or with 2° anti-rabbit antibody alone as a control for specificity. The results demonstrate approximately 30% immuno-isolation of Rab5-containing vesicles using the HA-Rab5 marker and undetectable contamination when 2° anti-rabbit antibody was used alone.

D. Dual Fluorochrome Labeling of rAAV to Follow Endosomal Escape

One of the most challenging but important aspects of intracellular trafficking of rAAV is determining the exact endosomal compartment from which virions exit into the cytoplasm. Proteasome inhibitors may modulate this aspect of the rAAV life cycle by either changing the rate of endosomal escape and/or the compartment from which rAAV enters into the cytoplasm.

Methods

To study endosomal escape, single-cell imaging and microinjection of quenching antibodies against one of two fluorochromes on a dual-labeled rAAV capsid were performed. The Alexa Fluor system from Molecular Probes was chosen as a system for which multiple fluorochromes could be linked to the rAAV capsid at similar efficiencies. Three dyes (Alexa Fluor® 488 [green], Alexa Fluor® 568 [Red] and Alexa Fluor® 647 [blue]) were selected as useful in this regard. Preferably, dual labeling of rAAV does not change the infection pattern. Also preferably, microinjection of quenching antibodies against Alexa-488 (Molecular Probes) can shift fluorescence of dual-labeled rAAV. The general approach to assess endosomal escape is to inject the cytoplasm of living cells with anti-Alexa-488 following infection with rAAV that is dual labeled with Alexa-488 and one of the other dyes. Alexa-488/568 dual-labeled rAAV, a shift in fluorescence of virus from yellow to red (i.e., quenching of the green fluorochrome) indicates movement of virus into the cytoplasm. This approach is used in combination with GFP-tagged endosomal compartments and/or dominant negative Rabs to evaluate the compartment from which rAAV moves into the cytoplasm.

Alexa labeling of rAAV. The monovalent Alexa succinimidyl ester reactive dye (Alexa-488 and/or Alexa-568) was dissolved in 50 µl of 1 M bicarbonate. $0.5 \times 10^{12}$ particles (determined by slot blot) of purified AV2Luc in 0.5 ml Hepes buffer was added to the reaction mixture and incubated for 2 hours. When dual labeling was performed, equal molar amounts of the two fluorochromes was used and the reaction time was extended to 3 hours. The labeled rAAV2 was separated from the free dye by exclusion chromatography. The fractions were tested for infectious titers on HeLa cells using luciferase assays. The 5 peak fractions were then combined and used for fluorescent imaging studies. Imaging studies were performed.

Results and Conclusions

Assessment of functional particles demonstrated that greater than 85% activity was retained following label with Alexa dyes (data not shown). This was similar to results observed with Cy3 labeling. Results from Hela cells infected with Alex-568-labeled rAAV2 demonstrated a significant overlap in signal with the GFP-tagged Rab11 compartment. The distribution observed was very similar to that seen with Cy3-labeled rAAV2. From these studies, it was concluded that Alexa-labeling of rAAV can be performed, and it was slightly more sensitive than Cy3-labeling. In these studies, approximately 3-4 fluorochromes were labeled on each rAAV capsid. To investigate whether dual labeling procedures could also be adapted to efficiently label rAAV, studies were conducted that compared dual Alexa-488/568 and Alexa-568-labeled rAAV2 following a 1 hour infection of Hela cells. These studies, which demonstrate overlap in the Alexa-488/568 signal, as compared to Alexa-568 alone, confirm that the predominance of rAAV virions are dual-labeled when both dyes are added to the conjugation reaction.

Figure 17A:
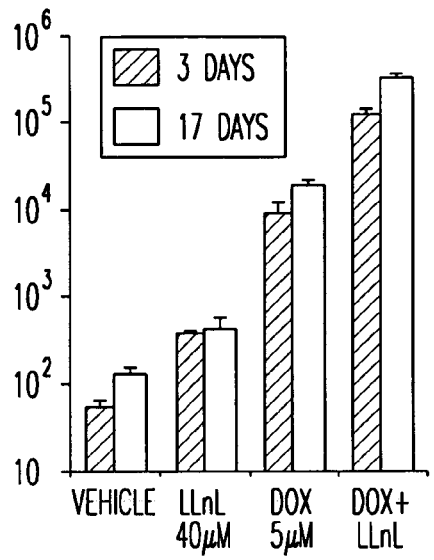
FIG. 17. Combined administration of proteasome-modulating agents can synergistically induce rAAV transduction from the apical surface of polarized human airway epithelia. (A) $1\times10^9$ particles of AV2Luc were applied to the apical surface of polarized human airway epithelia cultures in the absence and presence of various combinations of LLnL (40 µM) and/or Dox (5 µM). Luciferase expression was assayed at 3 and 17 days post-infection (B-E). Similar results were observed following apical infection with a self complementary (2.3 kb) scAV2eGFP vector at 15 days post-infection. (F) Combined administration of LLnL and Dox augments dual vector heterodimer-mediated delivery of a trans-spliced LacZ gene product. $10^{10}$ particles of AV2LacZdonor (indicated by D) and/or AV2LacZacceptor (indicated by A) were used to infect each transwell of the polarized airway epithelia in the presence or absence of co-administered LLnL (40 µM) and Dox (5 µM). β-galactosidase activity was evaluated at 15 days post-infection. Data represents the mean (+/−SEM) relative luciferase or β-galactosidase activity (per 1/10 sample) for 3 independent experiments.
Figure 17B:
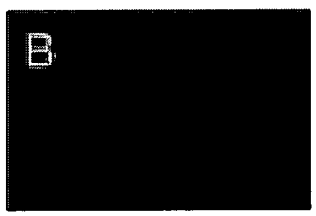
Figure 17C:
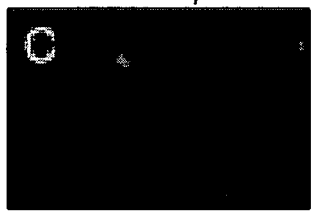
Figure 17D:
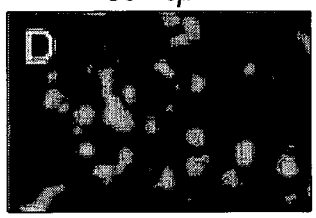
Figure 17E:

To begin to develop assays for visualizing endosomal release of rAAV into the cytoplasm, it was determined single cell injection of Anti-Alexa-488 could quench green fluorescence from dual-labeled Alexa-488/568 once rAAV entered into the cytoplasm. Results from these experiments are show in FIG. 17C and depict the fluorescence of Alexa-488/568 dual-labeled AV2Luc in Hela cells at 2 hour post-infection following injection with Anti-Alexa-488. Three cells are shown in the field, of which two were microinjected with antibody (closed arrowheads). From this study, it is obvious that the level of Alexa-488 fluorescence is significantly quenched by injection of anti-Alexa-488 while leaving red channel fluorescence of Alexa-568 intact. In contrast, fluorescence of both fluorochromes remains quite high in uninjected cells (open arrow). The remaining Alexa-488 fluorescence in injected cells is interpreted as virus still remaining in the endosomal compartment protected from antibody binding. These findings suggest that a significant portion of rAAV may be free in the cytoplasm by two hrs post-infection.

E. Intracellular Trafficking Patterns of rAAV-2 Demonstrate Significant Cell-Type Specificity To further investigate the intracellular mechanisms of rAAV-2 transduction that might vary between cell types, immunofluorescent localization of Cy3-rAAV-2 was performed following transduction of HeLa and IB3 cells. Despite the fact that rAAV-2 enters these two cell types with similar efficiency, HeLa cells are much more transducible with rAAV-2 than IB3 cells. However, IB3 cells demonstrate a much higher responsiveness to tripeptidyl proteosome inhibitor induction of transduction than HeLa cells. These differences in transduction may be reflected by variations in the intracellular trafficking patterns of rAAV-2 between HeLa and IB3 cells.

Methods

Luciferase-expressing rAAV2 was labeled with Cy3 and purified by column chromatography. Rab11, Rab7, and Rab9 were cloned into a pEGFP-C3 vector such that N-terminal EGFP-Rab fusions were generated. IB3 and HeLa cells were transfected with various EGFP-tagged Rabs using lipofectamine and infected with Cy3-labeled rAAV-2 at 4° C. for 30 minutes with an MOI of 10,000 particles/cell. Cells were then washed and shifted to 37° C. for 30 minutes to 2 hours. Cells were fixed and evaluated by fluorescent microscopy.

Results

Fluorescent microscopy was used to evaluate the primary vesicular compartments in which Cy3-labeled rAAV-2 accumulated following infection of HeLa and IB3 cells. A substantial degree of co-localization of Cy3-AAV-2 and EGFP-Rab11 was observed in HeLa cells from 30 minutes to 2 hours post-infection. This pattern, however, was not observed in IB3 cells. In contrast, the Cy3-labeled rAAV-2 was primarily co-localized with EGFP-Rab9 in IB3 cells. In HeLa cells, the degree of co-localization of Cy3-AAV and EGFP-Rab9 was not predominant. These findings suggest that rAAV-2 traffics through a diversity of intracellular compartments in a cell type specific manner.

Example 6

Altered Trafficking of rAAV

Proteasome-modulating agents act to increase rAAV transduction through one or more of the following mechanisms: 1) increasing the rate at which rAAV accumulates in the primary compartment through which it emerges to the cytoplasm without changing the pathway of intracellular trafficking; 2) altering the pathway of rAAV intracellular trafficking in a manner that leads to more efficient accumulation in a compartment through which it emerges to the cytoplasm; 3) increasing the efficiency at which rAAV breaks out of the endosomal compartment; and/or 4) enhancing the rate of nuclear trafficking of free rAAV in the cytoplasm.

Several lines of evidence suggest that proteasome inhibitors may act to enhance rAAV transduction by increasing the rate of viral transport to the nucleus (Duan et al., 2000) and/or enhancing viral processing of the capsid (Yan et al., 2002). First, proteasome inhibitors such as the tripeptides LLnL and Z-LLL enhance transduction of both rAAV2 or rAAV5, viruses without enhancing 1) endocytosis of virus, 2) stability of viral DNA within the cell, or 3) promoter activity which drives transgene expression (Duan et al., 2000; Yan et al., 2002). Second, proteasome inhibitors can be added up to a week following infection of polarized human airway epithelia and still enhance transduction (i.e., gene expression). Third, viral capsids for type 2 and type 5 show enhanced ubiquitination in vivo in the presence of proteasome inhibitors, and purified virus can also be ubiquitinated in vitro (Yan et al., 2002). Together, these findings strongly suggest that modulating proteasome activity enhances rAAV transduction for at least two serotypes and that the mechanism of enhancement involves some aspect of intracellular viral processing.

A. Proteasome Inhibitors Increase Transport of rAAV2 and rAAV2/5 Cell to the Nucleus A large number of various classes of proteasome inhibitors were screened to identify those that had the largest effect. Two classes of compounds (the tripeptidyl aldehyde LLnL and an anthracycline derivative doxorubicin), and their ability to induce rAAV2 and rAAV2/5 transduction in two airway cell lines (IB3 and A549) are described below.

Methods

LLnL and Z-LLL are two tripeptidyl aldehydes shown to inhibit calpains, cathepsins, cysteine proteases as well as the chymotrypsin-like protease activity of proteasomes (Wagner et al., 2002; Donkor, 2000; Sasaki et al., 1990). Doxorubicin has also been shown to inhibit chymotrypsin-like protease activity of proteasomes (Kiyomiya et al., 2002). Both classes of proteasome inhibitors bind tightly to the proteasome complex. Dose response curves for these two proteasome-modulating agents were evaluated on IB3, A549, Hela, and primary fibroblasts. The responses were consistent for a number of cell lines and for three different promoters driving luciferase expression. For one set, CMV-driven luciferase constructs with an AAV2-based genome were employed that were packaged into AV2 or AV5 capsids. Cells were infected at various doses of AV2Luc and AV2/5Luc (MOIs 100 to 1000 particles/cell). At the time of infection, cells were treated with various concentrations of LLnL or Doxorubicin and gene expression was assayed at 24 hours post-infection. The effect of proteasome inhibitors on nuclear uptake of virus was evaluated using a previously-described protocol for fractionating viral DNA in the cytoplasm and nucleus (Xiao et al., 2002). Viral DNA content in the cytoplasmic and nuclear fractions was then evaluated by slot blot hybridization against a Luciferase DNA probe.

Results and Conclusions

Results from this analysis demonstrated that both LLnL and Dox can significantly augment rAAV2 and rAAV2/5 transduction in two independent airway cell lines (FIG. 11). Although the trends were similar between these two cell lines and the two serotypes of rAAV, several features of the induction are worth noting. First, transduction in IB3 cells was most significantly inducible (>200-fold) by LLnL, while A549 cells required much higher concentration of LLnL to achieve 10-fold lower levels of induction. Hence, IB3 cells appear to be particularly sensitive to LLnL induction of rAAV. Second, rAAV transduction in both cell lines was highly inducible (200-fold) by Dox.

Figure 12A:
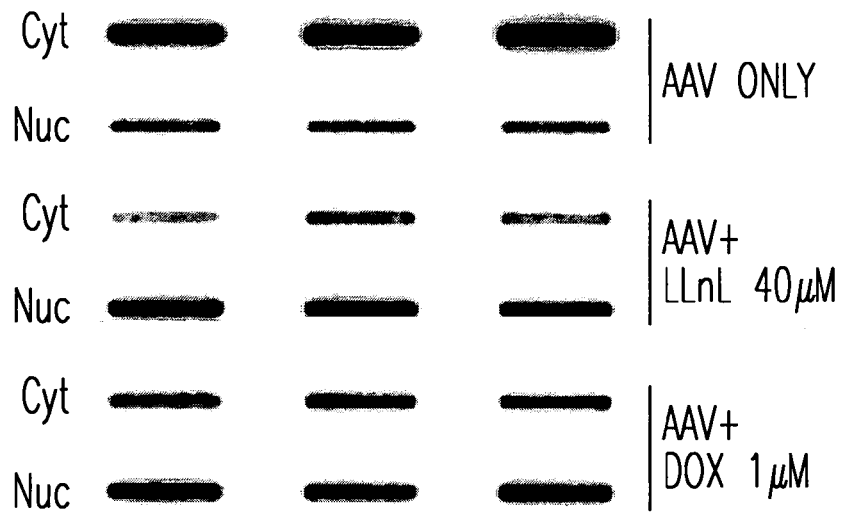
FIG. 12. LLnL and Dox both facilitate translocation of rAAV to the nucleus. IB3 cells were infected with AV2eGFP (MOI=1000 particles/cell) in the presence or absence 40 µM LLnL or 1 µM Dox. At 24 hours post-infection, cytoplasmic (Cyt) and nuclear (Nuc) fractions were isolated. (A) Viral DNA in each fraction was detected by slot-blot hybridization against a $P^{32}$ labeled eGFP probe and visualized using a BioRad phosphoimager (N=3 isolations are shown for each condition). $P^{32}$ signal was quantified using BioRad software. (B) The percentage distribution of the signals in nuclear and cytoplasmic fractions was calculated based on the mean signal for the three experimental points. (C) Results of $S^{35}$-capsid labeled rAAV2 localization in polarized human airway epithelia by in situ autoradiography. Infections were performed in the presence and absence of LLnL treatment.
Figure 12B:
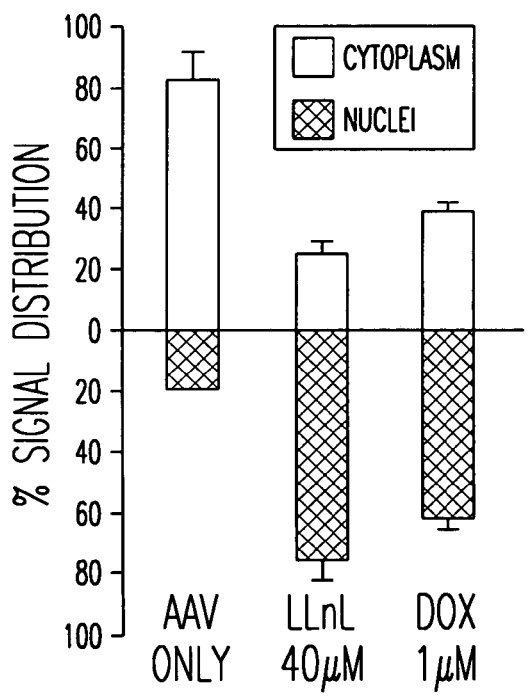
Figure 12C:
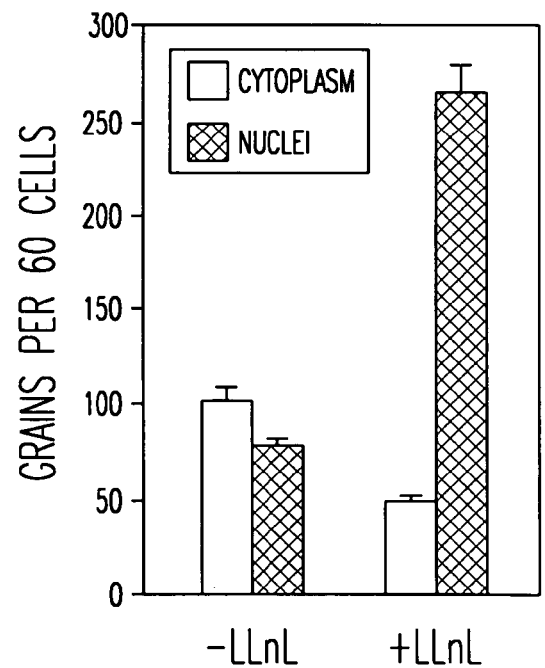

Given previous findings in polarized human airway epithelial cells that treatment with LLnL increased movement of rAAV to the nucleus (Duan et al., 2000), it was determined whether LLnL and Dox treatment at the time of infection also enhanced rAAV movement to the nucleus. Subcellular fractionation of nuclei and cytoplasmic extracts from rAAV2-infected IB3 cells, demonstrated that both Dox and LLnL significantly increased the fraction of viral DNA in the nuclear compartment (FIGS. 12A and B). These findings suggest that these two proteasome-modulating agents act to increase rAAV transduction by mobilizing virus to the nucleus. In summary, these findings support a growing body of work that the ubiquitin/proteasome system acts in some manner to control intracellular processing of rAAV and its movement to the nucleus.

B. LLnL and Dox Act through Distinct Mechanisms to Modulate the Proteasome and Enhance rAAV Transduction To test the hypothesis that LLnL and Dox might augment rAAV transduction through distinct mechanistic interactions with the proteasome, their effects on rAAV transduction were assessed when added in combination. If each of these drugs acted to augment transduction by distinct mechanistic interactions with the proteasome, then their cumulative effect would be greater than either individually.

Methods

Hela, A549, IB3, and primary fetal fibroblasts were evaluated for AV2Luc and AV2/5Luc transduction in the presence of LLnL, Dox, or LLnL+Dox at various concentrations. The data shown is from Hela and A549 cells at the most optimal dose combination that induces rAV2Luc transduction to a greater extent than each compound alone.

Results and Conclusions

Figure 13A:
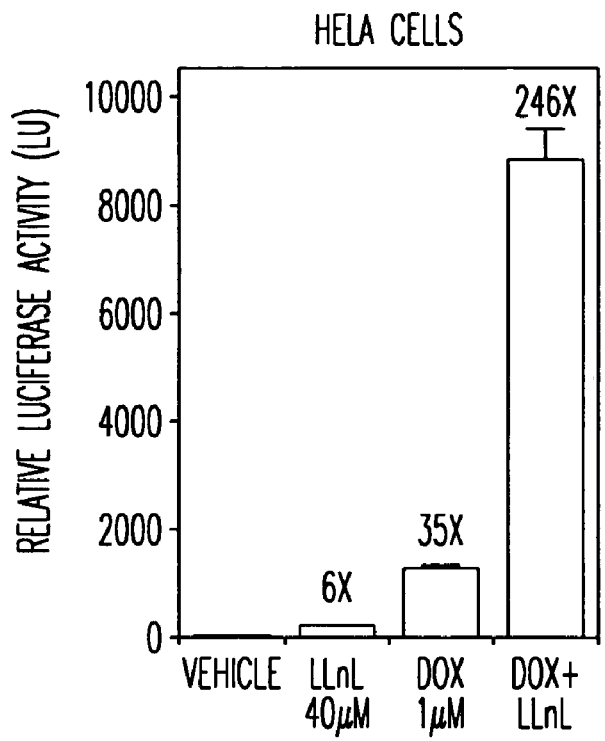
FIGS. 13A-B. Dox and LLnL provide more than additive induction of rAV2 transduction. Hela cells (A) and A549 cells (B) were infected with rAAV (MOI 500 particles/cell) in the presence of the indicated drug combinations and the expressed transgene was assessed at 24 hours post-infection (Mean+/−SEM, N=4). Fold induction relative to vehicle-treated rAAV-infected cells is indicated above each bar.
Figure 13B:
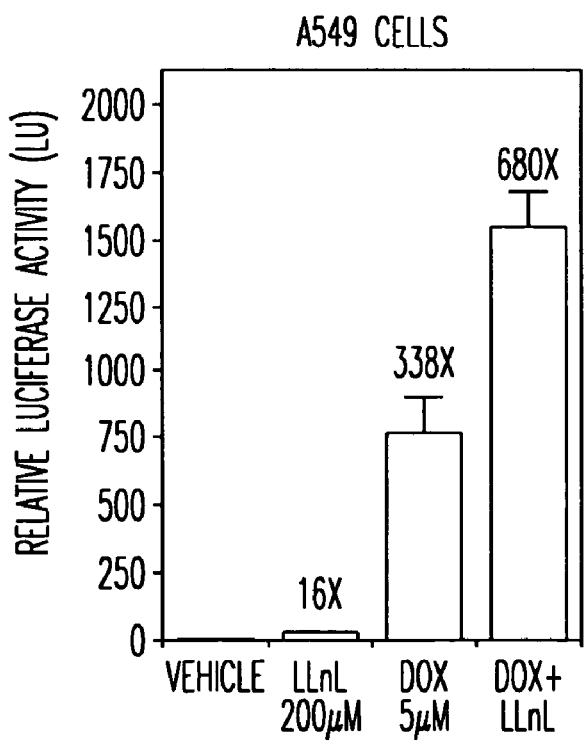

Cooperative inhibition of the proteasome by multiple proteasome inhibitors can provide increased augmentation in rAAV transduction (FIG. 13). The observation that combined Dox and LLnL treatment enhances rAAV transduction greater than either compound alone does not, in and of itself, prove that the mechanisms of induction are independent of one another. There are several potential reasons why such drugs might cooperatively enhance rAAV transduction. First LLnL and/or Dox might alter endosomal routing of rAAV, enhance endosomal escape, and/or mobilize rAAV in the cytoplasm to the nuclear pore. Each of these compounds might affect any one or more of these processes to differing extents and allow for additive or synergistic affects on rAAV transduction. Hela cells appear to provide a greater additive effects of Dox and LLnL on rAAV transduction than A549 cells. Furthermore, it should be noted that in primary fetal fibroblasts, no additive effect on transduction is seen (data not shown). In this cell line, Dox most significantly enhances transduction of rAAV2 and rAAV5, and LLnL provides no additional induction despite the fact it induced transduction 10-fold by itself. These interesting cell-specific differences also imply that certain cellular processes that alter rAAV transduction may be uniquely controlled by LLnL and Dox interactions with the proteasome.

Example 7

The mechanism(s) by which proteasome inhibitors augment rAAV transduction from the apical membrane of airway epithelia may be reflected in the biologic differences in intracellular trafficking in apical and basolateral compartments. Co-infection studies from the apical and basolateral membranes of epithelia with two different fluorochrome-labeled rAAV viruses were used to directly visualize how polarity alters intracellular trafficking, as endocytic pathways from the apical and basolateral membranes of polarized airway epithelia may differentially utilize the ubiquitin/proteasome system to modulate vesicular trafficking and processing of rAAV. Endosomal trafficking pathways for rAAV2 and rAAV5 identified using cell lines and polarized airway models may be in vivo using human and mouse bronchial xenograft models with recombinant adenoviruses expressing either GFP-tagged intracellular markers or dominant negative Rab proteins.

A. Epithelial Polarity and the Ubiquitin/Proteasome System Uniquely Affect rAAV Transduction from Apical and Basolateral Membranes Of particular importance to understanding the intracellular barriers to rAAV transduction from the apical membrane is an appreciation of how epithelial polarity alters intracellular trafficking of virus from the apical and basolateral membranes. It was previously reported that rAAV2 transduces from the basolateral membrane of polarized human airway epithelia 200-fold more effectively then from the apical membrane (Duan et al., 1998). Interestingly, this reduced transduction from the apical membrane correlated with the partitioning of high-affinity heparan sulfate proteoglycan (HSPG) AAV2 receptor to the basolateral membrane, but did not correlate with a substantial difference in viral endocytosis from the apical vs basolateral membranes (Duan et al. 1999, Duan et al., 2000). These findings suggest that an unidentified alternative apical receptor for AAV2 may be present on the apical surface of human airway epithelia which leads to endocytosis but also to poor intracellular processing of rAAV2 in the absence of applied proteasome inhibitors (Duan et al., 2000). In contrast, rAAV5 has been suggested to infect the apical surface of airway epithelia more effectively than rAAV2 due to its use of an alternative receptor that resides on both the apical and basolateral surfaces (Walters et al., 2001; Zabner et al., 2000). This finding raises the possibility that the different receptors for rAAV2 and rAAV5 may also utilize different endosomal processing pathways.

Methods

Polarized human airway epithelia were generated as previously described in Duan et al. (1998), Duan et al. (2000), and Duan et al. (1998). Both AV2Luc and pseudotyped AV2/5Luc viruses were utilized in these studies. Infections were performed by applying equal amounts of virus, in 500 µl of cell culture media, to the apical or basolateral membrane in the presence of LLnL (40 µM) for 16 hours as previously described in Duan et al. (1998). After infection, the epithelia were washed and re-fed with media lacking LLnL or virus and harvested for luciferase assays at 5 and 14 days post-infection.

Results and Conclusions

Figure 14A:
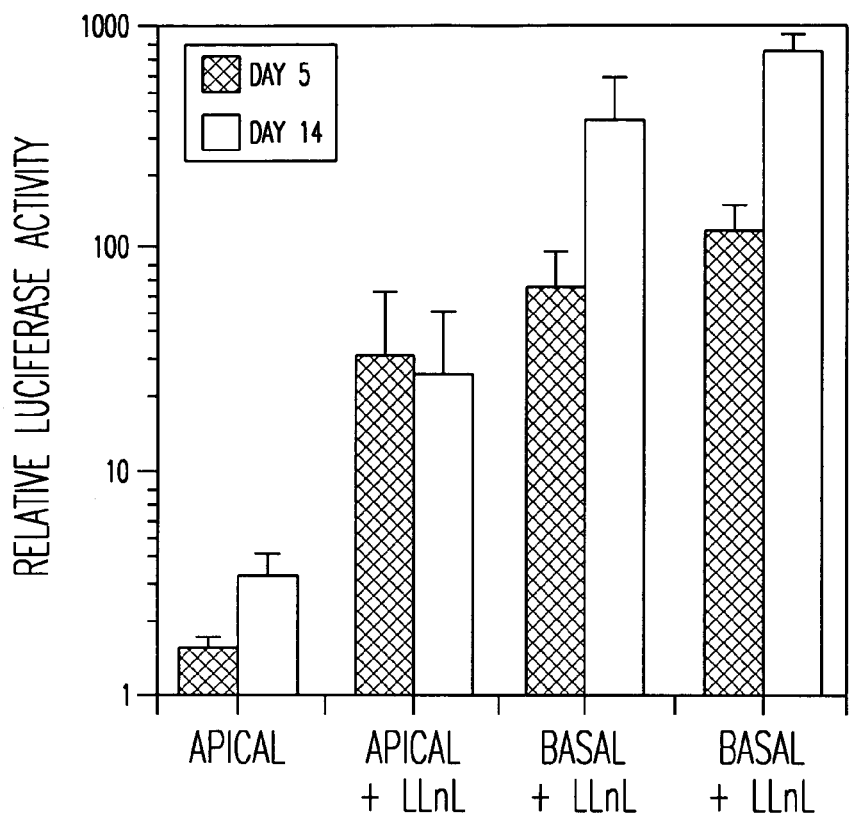
FIG. 14. The effect of proteasome inhibitor LLnL on (A) AV2Luc and (B) AV2/5Luc transduction was evaluated following apical and basolateral infection of human polarized airway epithelia at an MOI of 10,000 particles/cell in the presence and absence of LLnL (40 µM). Luciferase activity was measured at 5 and 14 days post-infection. Values represent the mean (+/−SEM) relative luciferase activity for three independent tissue samples (N=6-9 total transwells).
Figure 14B:
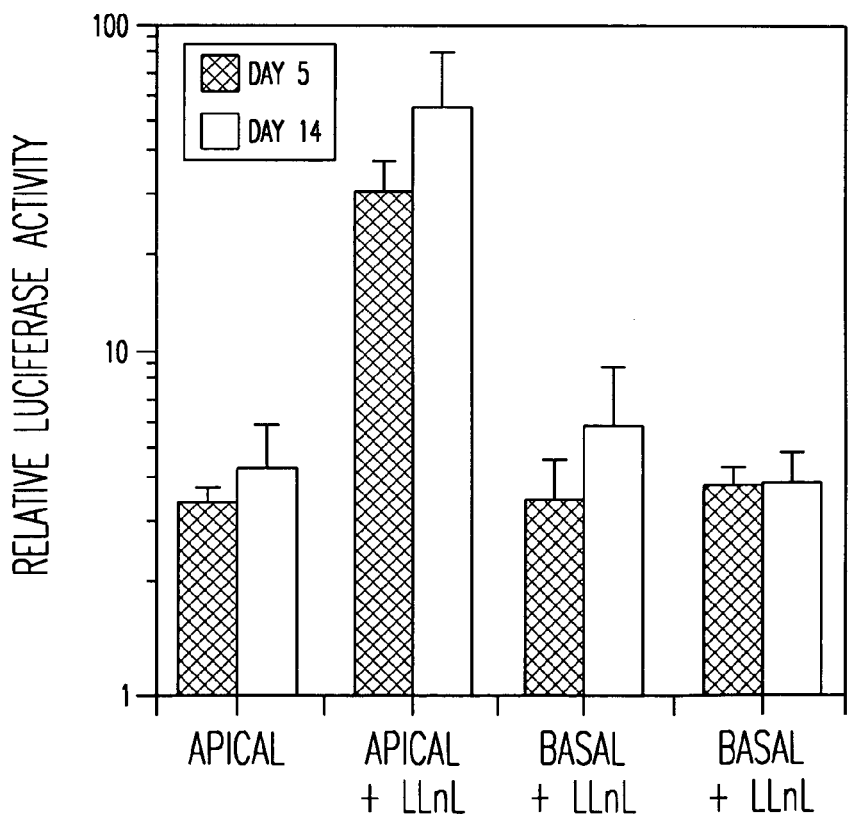

Comparison of AV2Luc and AV2/5Luc transduction from the apical and basolateral membrane of airway epithelia yielded several interesting findings (FIG. 14). First, these studies confirmed previous findings demonstrating a >200 fold higher efficiency of rAAV2 transducing from the basolateral as compared to the apical membrane. Second, they also demonstrated a slightly higher level of transduction from the apical membrane with AV2/5Luc as compared with AV2Luc, although the difference was not as great as previously reported by Zabner et al. (2000). Third, only rAAV2 demonstrated a polarity of infection from the apical and basolateral membranes. Lastly, only apical transduction for both AAV serotypes was enhanced by the addition of the proteasome inhibitor LLnL. Thus, the data suggest a common link between rAAV transduction and the proteasome independent of the receptor entry pathway.

B. rAAV Gene Conversion is not a Rate-Limiting Step in Transduction of Polarized Airway Epithelium from the Apical Membrane Thus far the data suggests that inhibition of the proteasome increases the ability of rAAV to migrate to the nucleus and express its encoded gene. Since rAAV is a single-stranded DNA virus which packages + or − stands, it must convert its genome to duplex double-stranded form in order to express encoded transgenes. If proteasome inhibition also affects this process, the mechanism of action could be more complicated than proposed. Since increased nuclear uptake of virus in the presence of proteasome inhibitors will undoubtedly also increase genome conversion of rAAV, differentiating between a direct proteasome inhibitor effect on the level of conversion enzymes and increased nuclear transport of virus or viral genome, e.g., via cytoskeletal components such as microtubules or microfilaments.

To address whether second strand synthesis might also be rate-limiting in the airway epithelia and enhanced by the proteasome inhibition, self-complementary AAV vectors (scAAV, also known as double-stranded AAV or dsAAV) that do not require second strand synthesis were used. These viruses which contain half-length genomes (<2.5 kb) have been shown to package either two annealed single-strand genomes (══ i.e., dsAAV) or replication form (Rf) monomer genomes composed of a covalently joined end (⟹ i.e., scAAV) (McCarty et al., 2001). Since scAAV vectors have been shown to not require second strand synthesis to express an encoded transgene, their onset of gene expression is much more rapid. scAAV vectors and full-length AAV vectors were employed to demonstrate that intracellular processing, and not second strand synthesis, is the primary rate-limiting step in apical transduction of human airway epithelia.

Methods

A set of viral vectors was prepared of half-genome length was prepared. Four GFP-based viruses were generated for this analysis (AV2eGFP, scAV2eGFP, AV2/5eGFP, and scAV2/5eGFP that had either 4.7 kb or 2.4 kb length genomes packaged into AAV2 or AAV5 capsids. The data AAV2 capsid viruses were identical to data for rAAV5 viruses. Functional confirmation of scAAV/dsAAV structure was performed by analysis of gene conversion and gene expression rates in Hela cells, sensitivity of transduction in Hela cells to the DNA synthesis inhibitor hydroxyurea (HU), and by denaturing NaHO gel electrophoresis. Polarized airway epithelia were infected with the various vector constructs from the apical membrane in the presence and absence of applied LLnL at the time of infection. Gene expression was monitored by quantitative morphometry of GFP fluorescence at various post-infection time points.

Results and Conclusions

Figure 16:
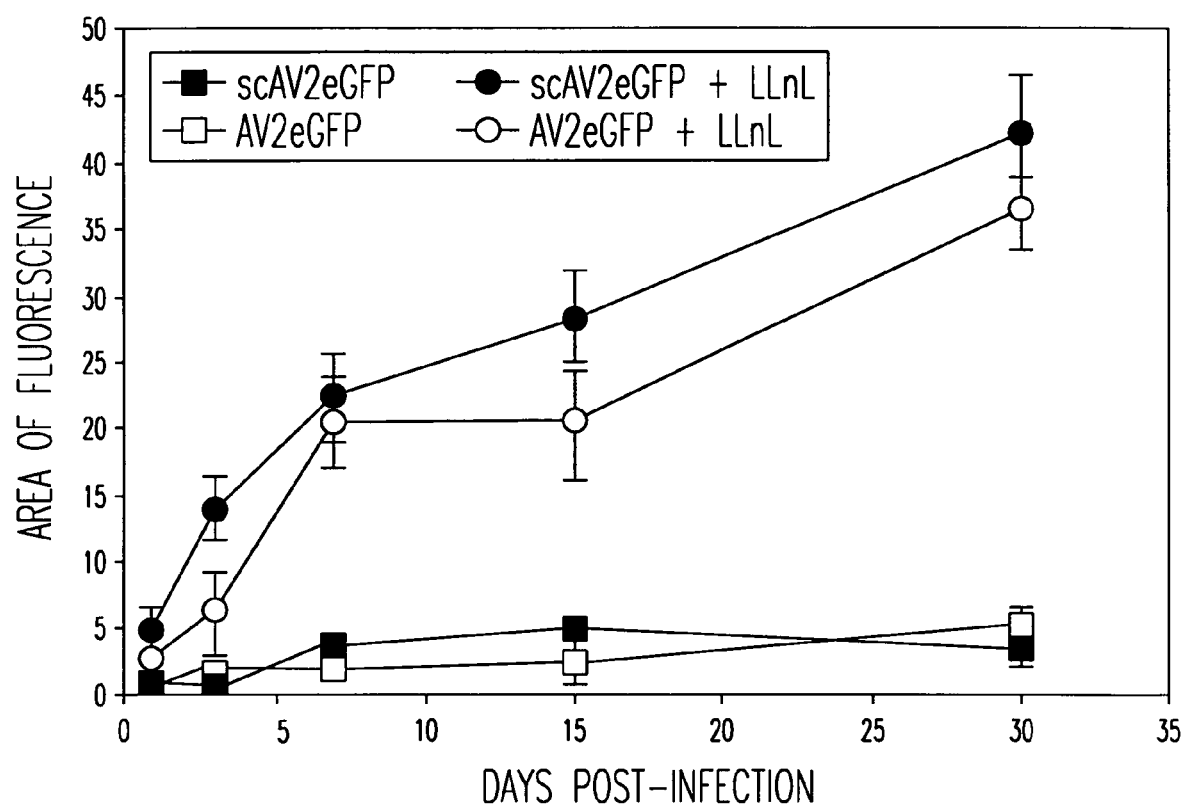
FIG. 16. Quantification of eGFP expression following apical infection of polarized human airway epithelia with self-complementary and full-length eGFP vectors. The relative mean area of fluorescence was evaluated following transduction with AV2eGFP and scAV2eGFP vectors in the presence or absence of LLnL (40 µM) at an MOI of 10,000 particles/cell on 1, 3, 7, 15 and 30 days post-infection. The values represent the mean (+/−SEM) for three independent tissue samples. For each tissue sample, 3 transwells were evaluated by imaging 10 random fields in each sample at the various time points (N=9 total transwells for each experimental point).

Evaluation of full-length rAAV and scAAV vectors on Hela cells demonstrated the previously reported faster rate of onset and higher levels of gene expression for scAV2eGFP as compared to AV2eGFP (FIG. 15A) (McCarty et al., 2001). Furthermore, pretreatment of Hela cells with 5 mM HU significantly decreased gene expression from AV2eGFP but not scAV2eGFP virus (FIG. 15B). These findings support the notion that scAAV vectors do not require DNA synthesis to express encoded transgenes (McCarty et al., 2001). Furthermore, molecular characterization of Hirt DNA from infected Hela cells demonstrated a much higher percentage of full-length scAV2eGFP genomes (2.4 kb) at 24 hours post-infection as compared to AV2eGFP, which was predominantly single-stranded migrating at 1.6 kb in a native gel (FIG. 15C). Additionally, denaturing NaHO gel analysis of viral DNA demonstrated that approximately 75% was Rf (data not shown). Given the Hirt DNA analysis, we assume the remainder is likely dsAAV. In contrast to the clear enhancement of gene expression seen with scAV2eGFP vector on Hela cells, results from analysis of scAV2eGFP and full-length AV2eGFP vector on airway epithelia demonstrated no discernable difference in apical transduction in the presence or absence of proteasome inhibitor (FIGS. 16-17). Although data is only shown for rAAV2 serotypes, the results were identical for rAAV2/5. These findings strongly suggest that second strand synthesis is not the major rate-limiting step in rAAV transduction of human airway epithelia. Additionally, the finding that LLnL did not alter the profile of expression between scAV2eGFP and full-length AV2eGFP viruses also suggests that this proteasome inhibitor does not alter the rate of second strand synthesis in airway epithelia.

Figure 18:
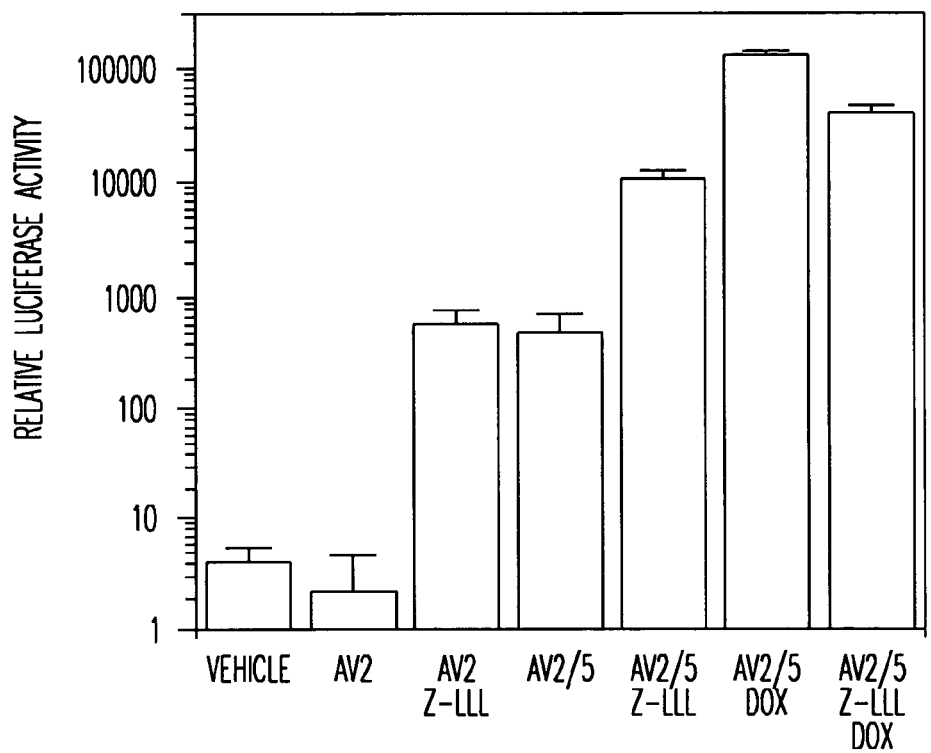
FIG. 18. In vivo gene transfer to the mouse lung. AV2 and AV2/5 luciferase vectors were used to evaluate the ability of proteasome-modulating agents to induce transduction. Results depict the mean (+/−SEM) luciferase expression from (N=5) mouse lungs at 14 days post-infection for each condition.

C. Proteasome Inhibitors Enhance the Efficacy of rAAV-Mediated Functional Correction of CFTR in Polarized Human Airway Epithelia As described below, combined administration of LLnL and Dox synergistically act to augment rAAV transduction from the apical membrane of human polarized airway epithelia to a level which can restore near normal levels of CFTR-mediated chloride current. Furthermore, analysis of type 5 and type 2 rAAV vectors in mouse lung using these approaches suggest species-specific differences in both the synergistic response to proteasome inhibitors and the optimal AAV serotype when compared to human airway epithelia (FIG. 18).

Methods

Several vectors were used for this analysis including, AV2.Luc, AV2/5Luc, scAV2eGFP, AV2LacZdonor, AV2LacZacceptor, AV2tgCF, AV2/5tgCF, AV2CF83, and AV2/5CF83. AV2LacZdonor and AV2LacZacceptor virus are two trans-splicing vectors that reconstitute LacZ expression following intermolecular recombination and have been previously described in Duan et al. (2001). These vectors were used to establish the utility of combined proteasome inhibitor treatment to augment delivery using this approach. AV2tgCF is the current clinically-used AAV2-based full-length CFTR vector in which expression of CFTR is driven off the ITR (Aitken et al., 2001; Wagner et al., 2002). AV2/5tgCF virus has the identical proviral structure to AV2tgCF but is packaged into AAV5 capsid. AV2CF83 and AV2/5CF83 viruses have an additional 83 bp minimal promoter inserted into the AV2tgCF proviral genome to increase gene expression and are packaged into AAV2 and AAV5 capsids, respectively. All the CFTR vectors used in the current study were provided by Target Genetics Incorporated. Infections of polarized human CF and non-CF airway epithelia were all performed from the apical membrane at a dose of 10,000 particles/cell for 24 hours in the presence of Dox and LLnL.

Figure 19:
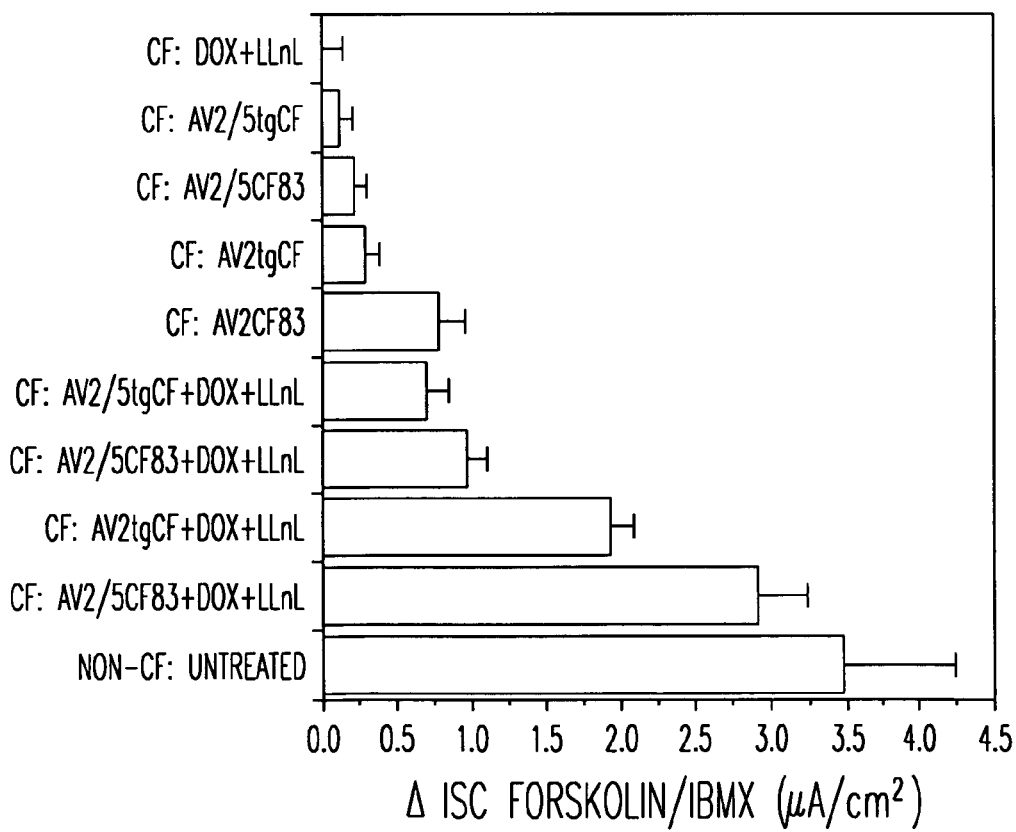
FIG. 19. Complementation of CFTR chloride transport abnormalities in CF airway epithelia using combined CFTR rAAV and proteasome inhibitor treatment. Results depict the mean+/−SEM (N=9) delta Isc response to IBMX/forskolin in CF airway epithelia treated under the indicated conditions. Assays were performed at 15 days post-infection and a non-CF untreated control is given as a reference for fully functional CFTR.

In vivo Assessment of Gene Transfer in Mouse Lung. In vivo gene delivery to the lung of BL6 mice was performed by nasal inhalation of $1 \times 10^{11}$ particles of AV2Luc or AV2/5Luc in the presence of proteasome inhibitor (200 µM Z-LLL and/or 200 µM Dox) as previously described in Duan et al. (2000). For in vivo studies, it is necessary to use the tripeptide Z-LLL was employed in place of LLnL because solubility in ethanol is much higher for Z-LLL. LLnL and Z-LLL perform similarly to augment rAAV in human polarized airway epithelia (Duan et al., 2000). For in vivo use, the concentration of tripeptide proteasome inhibitor is 5 to 10-fold higher to augment rAAV transduction and LLnL is insoluble in ethanol at 200 µM. Mouse lung and tracheas were harvested separately for analysis at various post-infection time points and assayed for luciferase activity as previously described in Duan et al. (2000). Data presented here shows only 14-day time points for comparison to studies with human polarized airway epithelia (FIG. 19).

Functional assays for CFTR complementation. Complementation of CFTR chloride transport abnormalities in polarized CF airway epithelia was performed as previously described in Liu et al. (2002). Short circuit currents of epithelia were measured in Ussing chambers at 15 days following a 24 hour apical infection in the presence of Dox and LLnL. CFTR-mediated transport of chloride was interpreted as the increase in current generated following addition of 0.1 mM IBMX/10 µM Forskolin to the luminal bath of epithelia equilibrated with low luminal chloride and 100 µM amiloride. All CFTR-mediated current was reversibly blocked by the addition of 100 µM bumetanide to the basolateral bath.

Results and Conclusion

Figure 17F:
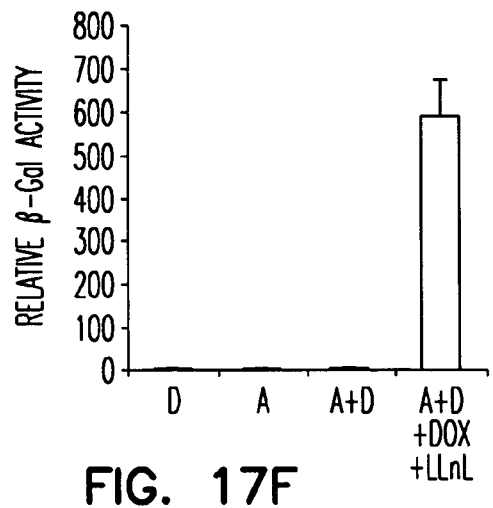

Experiments evaluating the affect of LLnL and/or Dox treatment of polarized airway epithelia demonstrated a dramatic synergistic affect on transduction efficiency with rAAV transduction. As seen in FIG. 15, enhancement of transduction from the apical surface increased 10 and 100-fold in the presence of LLnL and Dox, respectively. Remarkably, the combined addition of Dox and LLnL at the time of infection enhanced transduction 1000-fold with both full-length AV2Luc (FIG. 17A) or self-complementary scAV2eGFP (FIGS. 17B-E). This high level of augmentation was also capable of facilitating high level dual vector trans-splicing reconstitution of LacZ (FIG. 17F). Expression of the reconstituted LacZ gene product was only seen in epithelia co-infected with both AV2LacZdonor and AV2LacZacceptor viruses.

CFTR complementation studies in CF polarized airway epithelia using CFTR rAAV vectors, which compared both AAV2 and AAV5 capsid-mediated transduction in the presence and absence of optimal proteasome inhibitor combinations (Dox and LLnL), demonstrated several interesting findings (FIG. 19). First, it was evident that rAAV2 capsid vectors performed as well or slightly better than rAAV5 in the absence of proteasome inhibitor. These findings are similar to those previously discussed using luciferase vectors (FIG. 19) but differ from one previous report (Zabner et al., 2000). Second, as seen with luciferase-based vectors, rAAV2-mediated CFTR delivery performed dramatically better in the presence of proteasome inhibitors than that seen with rAAV5. These findings suggest that in the presence of proteasome inhibitors, rAAV2 capsid-based vectors are perhaps the better vector for gene therapy of CF. Third, there was a tangible increase in correction seen with the AV2CF83 minimal promoter as compared to the current clinical vector AV2tgCF that utilizes the ITR as a promoter. Cumulatively, these findings demonstrate the need to circumvent intracellular barriers by modulating the proteasome to achieve functional expression of CFTR and support the current clinical observations with AV2tgCF (also called tgAAVCF) that substantial vector DNA can be found in airway epithelia without RT PCR detectable mRNA (Aitken et al., 2001). Thus far, results have demonstrated a direct correlation of CFTR functional correction with mRNA expression from the vectors.

Studies comparing transduction of rAAV2 and rAAV2/5 vectors and the effect of Dox and Z-LLL on transduction in mouse lung have demonstrated several notable differences to those seen in human polarized airway model. First, AV2/5 vectors perform substantially better (100-fold) in mouse lung and trachea as compared to AV2 vectors. This finding in mice supports several other reports in the field comparing AV2 to AV2/5 (Aurrichio et al., 2002; Zabner et al., 2000), but is notably different than observations in polarized human airway epithelia that demonstrate near equivalent transduction with these two serotypes. Second, Z-LLL and Dox both substantially increased transgene expression from AV2/5 vectors to a level of 10 and 100-fold induction, respectively. Third, the lack of synergism in the induction of AV2/5 vectors when both Dox and Z-LLL were given at the time of infection. In fact, the combination of the two drugs appeared to inhibit overall transduction (FIG. 19).

These differences between rAV2 and rAV2/5 transduction in mouse and human airways are relevant to evaluating mechanisms of proteasome involvement in rAAV transduction in the airway for several reasons. First, the mouse is extensively used as a preclinical model and knowledge about differences in transduction biology between humans is made. Second, tripeptidyl aldehyde (i.e., LLnL and Z-LLL) and anthracycline derivatives (i.e., Dox) may enhance intracellular processing of rAAV through overlapping yet distinct mechanisms. Hence, the lack of synergism in the induction of rAAV transduction in the mouse airway may provide clues as to the mechanism of action of these compounds.

Example 8

In vitro and In vivo Activities of Additional Proteasome Modulators

Figure 20A:
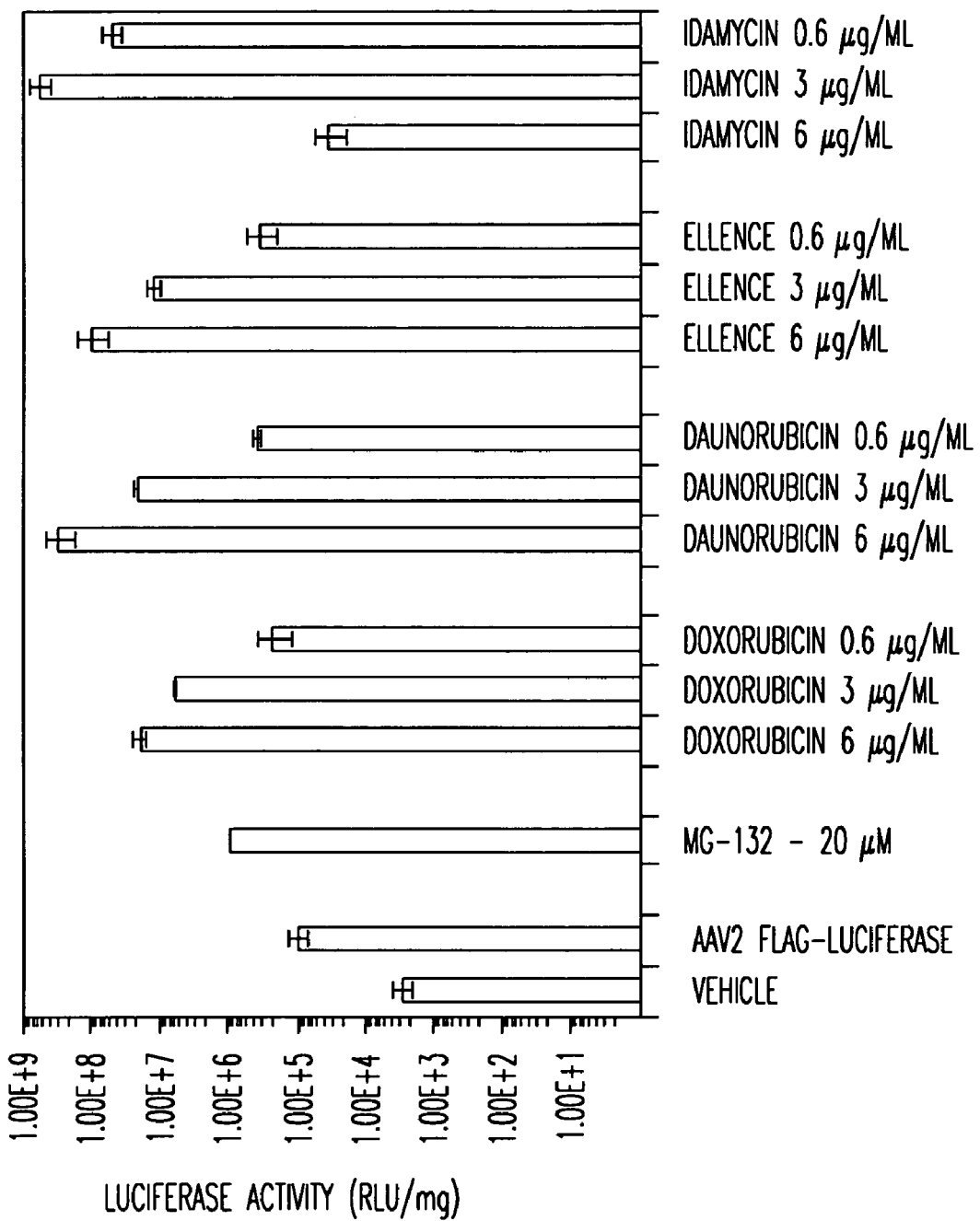
FIG. 20. Screening for anthracycline proteosome modulators. A) Graph of luciferase activity versus concentration of tested agent. B) Fold change in luciferase activity for various treatments.

Based on results with doxorubicin, a small number of FDA approved anthracyclines were tested for their relative in vitro and in vivo activities on AAV transduction. HeLa cells were infected with 100 ppc AAV2FLAG-Luc for 2 hours in the presence of different anthracyclines, e.g., doxorubicin, daunarubicin (Cerubidine), epirubicin (Ellence™), and idarubicin (Idamycin®), and cells harvested 48 hours later. The anthracyclines were pharmaceutical grade, and prepared according to the manufacturer's instructions. Prior to use, the agents were diluted in sterile water to an equal mass, e.g., 0.6 µg/mL, 3 µg/mL and 6 µg/mL. The results are shown in FIG. 20. For example, 3 µg/mL idamycin increased luciferase expression by over 5000-fold while doxorubin increased luciferase expression by 58-fold. Generally, the potency was as follows: idarubicin>daunarubicin>epirubicin>doxorubicin.

Six groups of ten, five-to-seven week-old, Balb/c mice (5 male and 5 female per group) were employed in a comparison of the relative in vivo potency and safety of different anthracycline derivatives at a single dose after intranasal delivery. Treatment was administered as shown in Table 4. Animals were followed for seven days post dose.

TABLE 4

| Group | $R_x$ | rAAV Treatment (Dose in DRP) | Proteasome Modulator | Proteasome Modulator Dose (% of HDE) | Route of Administration (rAAV/Inhibitor) | Day of Sacrifice |
|---|---|---|---|---|---|---|
| 1 | No $R_x$ control | Vehicle | Vehicle | 0 | Intranasal/ Intranasal | 7 |
| 2 | Vector control | 1 × 10$^{12}$ AAV2- | Vehicle | 0 | Intranasal/ Intranasal | 7 |

TABLE 4-continued

| Group | Rx | rAAV Treatment (Dose in DRP) | Proteasome Modulator | Proteasome Modulator Dose (% of HDE) | Route of Administration (rAAV/Inhibitor) | Day of Sacrifice |
|---|---|---|---|---|---|---|
| 3 | Test 1 | GFP + 1 × 10$^{11}$ AAV2-Luc 1 × 10$^{12}$ AAV2-GFP + 1 × 10$^{11}$ AAV2-Luc | Doxorubicin | 10 | Intranasal/Intranasal | 7 |
| 4 | Test 2 | 1 × 10$^{12}$ AAV2-GFP + 1 × 10$^{11}$ AAV2-Luc | Idamycin | 10 | Intranasal/Intranasal | 7 |
| 5 | Test 3 | 1 × 10$^{12}$ AAV2-GFP + 1 × 10$^{11}$ AAV2-Luc | Doxil | 10 | Intranasal/Intranasal | 7 |
| 6 | Positive control | 1 × 10$^{12}$ AAV2-GFP + 1 × 10$^{11}$ AAV2-Luc | Doxil | 75 | Intranasal/Intravenous | 7 |

The dose of modulator was based on the Human Dose Equivalent (HDE) and is summarized below in Table 5. For intranasal dose administration, the dose was held constant at 10% of the HDE. For the intravenous positive control (Doxil), a dose of 10 mg/kg (75%) of the HDE was used. This represented the lowest dose that gave a 10% increase in mean and median luciferase expression in earlier studies.

TABLE 5

Human dose equivalent calculations

| Drug | Drug Concentration (mg/mL) | Human dose (mg/m$^2$) | 10% Human Dose (mg/m$^2$) | 10% of Human dose in mg/kg for a mouse (dose mg/m$^2$/3) | 10% of human dose per 20 gram mouse (mg) | Volume of stock drug (mL) per mouse |
|---|---|---|---|---|---|---|
| Adriamycin | 2 | 40-75 | 7.5 | 2.5 mg/kg | 0.05 mg | 0.025 mL |
| Idamycin | 1 | 10-12 | 1.2 | 0.4 mg/kg | 0.008 mg | 0.008 mL |
| Doxil | 2 | 10-40 | 4.0 | 1.3 mg/kg | 0.026 mg | 0.013 mL |

Dose calculation: Animal (mouse) dose in mg/kg × 3 (mouse km) = dose in mg/m$^2$.
mg per mouse = Dose in mg/kg × 0.02 kg mouse Safety endpoints included morbidity and mortality, clinical observations, body weights, gross necropsy observations and histopathology. Transduction endpoints included luciferase and GFP analysis.

On the day of sacrifice, the left lung was clamped off at the level of the extrapulmonary bronchi, removed and frozen on dry ice. The left lung was homogenized and processed for luciferase expression using Promega's luciferase assay system (Madison, Wis.). Luminescence was measured using the Berthold AutoLumat LB953 instrument. Samples were normalized for total protein using Pierce's Coomassie Plus Protein Assay Reagent (Rockford, Ill.).

Intranasal administration of doxorubicin and idamycin at 10% HDE were both associated with early mortality of some animals, ruffled hair coats and sick mice. In addition, those animals that survived also lost considerable body weight over the week. The intranasally DOXIL® treated mice did better than the doxorubicin- or idamycin-treated animals in that there was no early mortality and they appeared clinically normal. However, they also lost weight. The intravenously DOXIL® treated mice fared the best.

Figure 21:
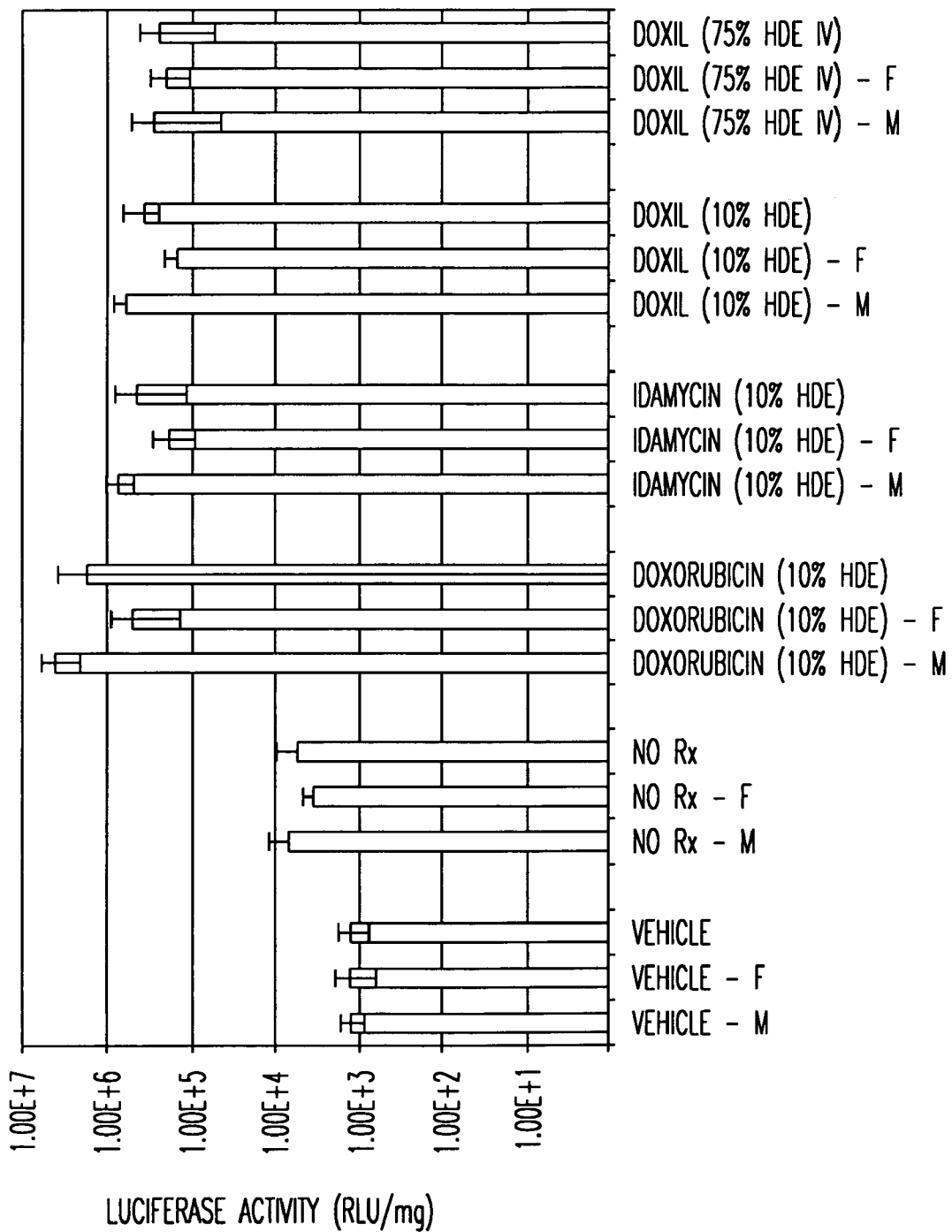
FIG. 21. In vivo results for anthracycline proteosome modulators.

Intranasal treatment of doxorubicin and idamycin resulted in increased luciferase expression (FIG. 21 and Table 6). Treatment with DOXIL® at a 10% HDE (both intravenously and intranasally) resulted in an average increase in luciferase expression by 49- and 74-fold, respectively, 7 days post-dose.

TABLE 6

Fold increase in luciferase expression

| Rx | Average | Standard Deviation | Fold Increase |
|---|---|---|---|
| Vehicle - M | 1.28E+03 | 4.05E+02 | |
| Vehicle - F | 1.32E+03 | 6.64E+02 | |
| Vehicle | 1.30E+03 | 5.19E+02 | |
| No Rx - M | 7.28E+03 | 5.01E+03 | 1 |
| No Rx - F | 3.56E+03 | 1.27E+03 | 1 |
| No Rx | 5.63E+03 | 4.12E+03 | 1 |
| Doxorubicin (10% HDE) - M | *4.21E+06 | *2.06E+06 | 578 |
| Doxorubicin (10% HDE) - F | 5.44E+05 | 4.00E+05 | 153 |
| Doxorubicin (10% HDE) | 1.77E+06 | 2.13E+06 | 314 |
| Idamycin (10% HDE) - M | 8.11E+05 | 2.81E+05 | 111 |
| Idamycin (10% HDE) - F | 2.02E+05 | 1.05E+05 | 57 |
| Idamycin (10% HDE) | 5.06E+05 | 3.80E+05 | 90 |
| Doxil (10% HDE) - M | 6.68E+05 | 2.57E+05 | 92 |
| Doxil (10% HDE) - F | 1.65E+05 | 7.15E+04 | 46 |

TABLE 6-continued

Fold increase in luciferase expression

| Rx | Average | Standard Deviation | Fold Increase |
|---|---|---|---|
| Doxil (10% HDE) | 4.16E+05 | 3.19E+05 | 74 |
| Doxil (75% HDE iv) - M | 3.16E+05 | 2.69E+05 | 43 |
| Doxil (75% HDE iv) - F | 2.31E+05 | 1.21E+05 | 65 |
| Doxil (75% HDE iv) | 2.73E+05 | 2.02E+05 | 49 |

*Average and standard deviation were calculated from two numbers

REFERENCES

Afione et al., *J. Virol.*, 70:3235 (1996).
Aitken et al., *Hum. Gene Ther.*, 12:1907 (2001).
Alexander et al., *Hum. Gene Ther.*, 7:841 (1996).
Alexander et al., *J. Virol.*, 68:8282 (1994).
*Animal Cell Culture* (R. I. Freshney, Ed., 1987).
Aurichio et al., *J. Clin. Invest.*, 110:499 (2002).
Aurrichio et al., *Hum. Mol. Genetics*, 10:3075 (2001).
Bantel-Schaal et al., *J. Virol.*, 73:939 (1999).
Bantel-Schaal et al., *J. Virol.*, 76:2340 (2002).
Barbero et al., *J. Cell Biol.*, 156:511 (2002).
Bartlett et al., *Hum. Gene Ther.*, 9:1181 (1998).
Bartlett et al., *J. Virol.*, 74:2777 (2000).
Bartlett et al., *Nat. Biotechnol.*, 17:181 (1999).
Basak et al., *J. Virol.*, 63:3164 (1989).
Basak et al., *Virology*, 186:368 (1992).
Benson et al., *J. Virol.*, 74:9184 (2000).
Berg et al., *J. Biol. Chem.*, 273:21883 (1998).
Bertran et al., *Ann. N.Y. Acad. Sci.*, 850:163 (1998).
Blacklow, *Parvoviruses and Human Disease*, J. R. Pattison, ed., pp. 165-174 (1988).
Blau et al., *Virology*, 210:91 (1995).
Blommaart et al., *Eur. J. Biochem.*, 243:240 (1997).
Bonifacino et al., *Ann. Rev. Cell Dev. Biol.*, 14:19 (1998).
Bregman et al., *Proc. Natl. Acad. Sci. USA*, 93:11586 (1996).
Britten et al., *Radiat. Res.*, 148:308 (1997).
Bucci et al., *Mol. Biol. Cell*, 11, 467 (2000).
Ceresa et al., *Mol. Cell Biol.*, 18:3862 (1998).
Chao et al., *Mol. Ther.*, 2:619 (2000).
Chen et al., *J. Cell Biol.*, 101:85 (1985).
Chiorini et al., *J. Virol.*, 68:797 (1994).
Chiorini et al., *J. Virol.*, 71:6823 (1967).
Chiorini et al., *J. Virol.*, 73:1309 (1999).
Chorini et al., *J. Virol.*, 73:4293 (1999).
Chu et al., *Hum. Gene Ther.*, 10:25 (1999).
Clayson et al., *Mol. Cell Biol.*, 8:3391 (1988).
Conforti et al., *Cell Adhes. Commun.*, 1:279 (1994).
Conrad et al., *Gene Ther.*, 3:658 (1996).
Coonrod et al., *Gene Ther.*, 4:1313 (1997).
Crystal et al., *J. Clin. Invest.*, 104:1491 (1999).
*Current Protocols in Immunology* (J. E. Coligan, A. M. Kruisbeek, D. H. Margulies, E. M. Shevach and W. Strober, eds., 1991).
*Current Protocols in Molecular Biology* (F. M. Ausubel, R. Brent, R. E. Kingston, D. D. Moore, J. G. Siedman, J. A. Smith, and K. Struhl, eds., 1987).
*Current Protocols in Protein Science* (John E. Coligan et al., eds., Wiley and Sons, 1995).
Davidson et al., *Proc. Natl. Acad. Sci. USA*, 97:3428 (2000).
Duan et al., *Am. J. Respir. Cell Mol. Biol.*, 18:750 (1998).
Duan et al., *Hum. Gene Ther.*, 10:1553 (1998).
Duan et al., *Hum. Gene Ther.*, 10:1553 (1999).
Duan et al., *Hum. Gene Ther.*, 9:2761 (1998).
Duan et al., *J. Clin. Invest.*, 105:1573 (2000).
Duan et al., *J. Virol.*, 72:8568 (1998).
Duan et al., *J. Virol.*, 73:10371 (1999).
Duan et al., *J. Virol.*, 73:161 (1999).
Duan et al., *Virus Res.*, 48:41 (1997).
Engelhard et al., *J. Clin. Invest.*, 90:2598 (1992).
Engelhardt et al., *Development*, 121:2031 (1995).
Engelhardt et al., *Nat. Genet.*, 2:240 (1992).
Engelhardt et al., *Nat. Genet.*, 4:27 (1993).
Everett et al., *EMBO J.*, 17:161 (1998).
Fenteany et al., *Science*, 268:726 (1995).
Ferrari et al., *J. Virol.*, 70:3227 (1996).
Fisher et al., *J. Virol.*, 70:520 (1996).
Flotte et al., *Gene Ther.*, 2:357 (1995).
Flotte et al., *Hum. Gene Ther.*, 7:1145 (1996).
Flotte et al., *Proc. Natl. Acad. Sci. USA*, 90:10613 (1993).
Flotte et al., *Proc. Natl. Acad. Sci. USA*, 93:10163 (1993).
Folli et al., *Gastroenterology*, 113:954 (1997).
Fuller et al., *Cell*, 38:65 (1984).
Gao et al., *Proc. Natl. Acad. Sci. USA*, 99:11854 (2002).
*Gene Transfer Vectors for Mammalian Cells* (J. M. Miller and M. P. Calos eds. 1987).
Gibson et al., *J. Cell Biol.*, 143:81 (1998).
Girotti et al., *J. Cell Sci.*, 109:2915 (1996).
Goldberg et al., *Chem. Biol.*, 2:503 (1995).
Goldenthal et al., *J. Histochem. Cytochem.*, 36:391 (1988).
Goldman et al., *Gene Ther.*, 3:811 (1996).
Goldman et al., *J. Virol.*, 69:5951 (1995).
Gommerman et al., *J. Biol. Chem.*, 272:30519 (1997).
Gottlieb et al., *J. Cell Biol.*, 120:695 (1993).
Griffiths et al., *Cell*, 52:329 (1988).
Halbert et al., *J. Virol.*, 71:5932 (1997).
Halbert et al., *J. Virol.*, 74:1524 (2000).
Halbert et al., *J. Virol.*, 75:6615 (2001).
*Handbook of Experimental Immunology*, (D. M. Weir and C. C. Blackwell, Eds.).
Hansen et al., *J. Virol.*, 74:992 (2000).
Hansen et al., *J. Virol.*, 75:4080 (2001).
Hansen et al., Mol. Ther., 4:289 (2001).
Hildinger et al., *J. Virol.*, 75:6199 (2001).
Hirt, *J. Mol. Biol.*, 26:365 (1967).
Hoggan et al., Proceedings of the Fourth Lepetit Colloqium, pp. 41-47, North Holland, Amsterdam.
Horowitz, *Fundamental Virology*, Fields et al., eds., pp. 771-816 (1985).
Hughes et al., *Lab Invest.*, 69:173 (1993).
Iqbal et al., *J. Med. Chem.*, 38, 2276 (1995).
Iversen et al., *Mol. Biol. Cell*, 12:2099 (2001).
Janson et al., *Hum. Gene Ther.*, 13:1391 (2002).
Jeggo et al., *Int. J. Radiat. Biol.*, 66:573 (1994).
Jensen et al., *Cell*, 83:129 (1995).
Jiang et al., *J. Cell Biol.*, 143:645 (1998).
Kao et al., *J. Biol. Chem.*, 273:25450 (1998).
Kaplitt et al., *Nat. Genet.*, 8:148 (1994).
Kato, *Hum. Mutat.*, 13:87 (1999).
Kay et al., *Nat. Genetics*, 24:257 (2000).
Kloetzel, *Gene Ther.*, 5:1297 (1998).
Kondo et al., *Am. J. Physiol.*, 261:L106 (1991).
Kotin et al., *Proc. Natl. Acad. Sci. USA*, 87:2211 (1990).
Lebkowski et al., *Mol. Cell Biol.*, 8:3988 (1988).
Lee et al., Ch. 10 in Proteosomes: The World of Regulatory Proteolysis, Hut et al., eds (2000).
Li et al., *J. Biol. Chem.*, 268:24475 (1993).
Li et al., *J. Virol.*, 72:2055 (1998).
Li et al., *J. Virol.*, 72:8806 (1998).
Lim et al., *Proc. Natl. Acad. Sci. USA*, 95:10146 (1998).

Linden et al., *Proc. Natl. Sci. USA*, 93:11288 (1996).
Mah et al., *J. Virol.*, 72:9835 (1998).
Martys et al., *J. Biol. Chem.*, 271:10953 (1996).
Memmo et al., *J. Cell Sci.*, 111:425 (1998).
Meresse et al., *J. Cell Sci.*, 108:3349 (1995).
Mingozzi et al., *J. Virol.*, 76:10497 (2002).
Minutes of Recombinant DNA Advisory Committee Meeting of June 14015, 2002. *Hum. Gene Ther.*, 12:2129 (2001).
Miramatsu et al., *Virology*, 221:208 (1996).
Mizukami et al., *Virology*, 217:124 (1996).
Mu et al., *J. Biol. Chem.*, 270:13503 (1995).
Muzyczka et al., In: B N Fields, D M Knipe, P M Howley, eds., Virology, New York, Raven Press, 2327-2360 (2001).
Muzyczka, *Curr. Top. Microbiol. Immunol.*, 158, 97 (1992).
Naim et al., *J. Cell Biol.*, 129:1241 (1995).
Obin et al., *J. Biol. Chem.*, 274:11789 (1999).
Odorizzi et al., *J. Cell Biol.*, 135:139 (1996).
Odorizzi et al., *J. Cell Biol.*, 137:1255 (1997).
*Oligonucleotide Synthesis* (M. J. Gait Ed., 1984).
Paillard, *Hum. Gene Ther.*, 10:337 (1999).
Park et al., *Proc. Natl. Acad. Sci. USA*, 89:11416 (1992).
Parker et al., *J. Virol.*, 74:1919 (2000).
Peters et al., *Embo J.*, 13:3296 (1994).
Pickles et al., *J. Virol.*, 72:6014 (1998).
Ponnazhagan et al., *Hum. Gene Ther.*, 8:275 (1997).
Powell et al., *Am. J. Respir. Cell Mol. Biol.*, 19:563 (1998).
Prasad et al., *Virology*, 214:360 (1995).
*Protein Purification: Principles and Practice* (Robert K. Scopes, Springer-Verlag, 1994).
Prydz et al., *J. Cell Biol.*, 119:259 (1992).
Qing et al., *J. Virol.*, 71:5663 (1997).
Qing et al., *J. Virol.*, 75:8968 (2001).
Qing et al., *J. Virol.*, 77:2741 (2003).
Qing et al., *Nat. Med.*, 5:71 (1999).
Qing et al., *Proc. Natl. Acad. Sci. USA*, 94:10879 (1997).
Rabinowitz et al., *J. Virol.*, 76:791 (2002).
Rabinowitz et al., *Virology*, 278:301 (2000).
Recchia et al., *Proc. Natl. Acad. Sci. USA*, 96:2615 (1999).
Reits et al., *EMBO J.*, 16:6087 (1997).
Ren et al., *PNAS USA*, 95:6187 (1998).
Rock et al., *Cell*, 78:761 (1994).
Rodriguez et al., *J. Virol.*, 65:494 (1991).
Rodriguez-Boulan et al., *J. Cell Sci. Suppl.*, 17:9 (1993).
Rose, *Comprehensive Virology*, 3:1 (1974).
Rose, *Comprehensive Virology*, 3:1 (1974).
Rubin et al., *Curr. Biol.*, 5:854 (1995).
Russell et al., *Proc. Natl. Acad. Sci. USA*, 91:8915 (1994).
Russell et al., *Proc. Natl. Acad. Sci. USA*, 92:5719 (1995).
Rutledge et al., *J. Virol.*, 72:309 (1998).
Sambrook, Fritsch, and Maniatis, *Molecular Cloning: A Laboratory Manual*, Second Edition (1989).
Samulski et al., *EMBO J.*, 10:3941 (1991).
Samulski et al., *EMBO J.*, 11:1228 (1992).
Samulski et al., *J. Virol.*, 61:3096 (1987).
Samulski, In Press, 2003.
Sanlioglu et al., *Gene Ther.*, 6:1427 (1999).
Sanlioglu et al., *Human Gene Therapy*, 10:591 (1999).
Sanlioglu et al., *Virology*, 74:9184 (2000).
Sato et al., *J. Biochem.* (Tokyo), 119:887 (1996).
Schwartz et al., *Annu. Rev. Med.*, 50:57 (1999).
Schwartz et al., *J. Virol.*, 72:3845 (1998).
Seglen, *Methods Enzymol.*, 96:737 (1983).
Seisenberger et al., *Science*, 294:1029 (2001).
Sharma et al., *Am. J. Respir. Cell Mol. Biol.*, 19:30 (1998).
Shiomi et al., *Mutat. Res.*, 314:167 (1994).
Snyder et al., *Nat. Genet.*, 16:270 (1997).
Sonnichsen et al., *J. Cell Biol.*, 149:901 (2000).
Srivastava et al., *J. Virol.*, 45:555 (1983).
Strouss et al., *J. Cell Sci.*, 112:1417 (1999).
Summerford et al., *J. Virol.*, 72:1438 (1998).
Summerford et al., *Nat. Med.*, 5:78 (1999).
Teramoto et al., *J. Virol.*, 72:8904 (1998).
Thompson et al., *Mol. Cell Biol.*, 10:6160 (1990).
Thompson et al., *Proc. Natl. Acad. Sci. USA*, 91:6855 (1994).
Tomkinson et al., *Mutat. Res.*, 407:1 (1998).
Tugizov et al., *J. Gen. Virol.*, 77:61 (1996).
Vihinen-Ranta et al., *J. Virol.*, 72:802 (1998).
Wacher et al., *J. Pharma. Sci.*, 87, 1322 (1998).
Wagner et al., *Hum. Gene Ther.*, 13:1349 (2002).
Wagner et al., *Laryngoscope*, 109:266 (1999).
Waite et al., *Clin. Immunol. Immunopathol.*, 86:81 (1998).
Walters et al., *J. Biol. Chem.*, 274:10219 (1999).
Walters et al., *J. Biol. Chem.*, 276:20610 (2001).
Walters et al., *J. Virol.*, 74:535 (2000).
Wang et al., *J. Virol.*, 72:3455 (1998).
Wang et al., *J. Virol.*, 72:9818 (1998).
Weber et al., *Mol. Cell Biol.*, 8:1137 (1988).
Westerveld et al., *Nature*, 310:425 (1984).
Wickham et al., *J. Virol.*, 70:6831 (1996).
Wickham et al., *Nat. Biotechnol.*, 14:1570 (1996).
Wills et al., *Epithelial transport: a guide to methods and experimental analysis*, $1^{st}$ ed., Chapman & Hall, London; New York (1996).
Wojcik, *Drug Discovery Today*, 4:188 (1999).
Xiao et al., *J. Virol.*, 70:8098 (1996).
Xiao et al., *J. Virol.*, 71:941 (1997).
Xiao et al., *J. Virol.*, 72:10222 (1998).
Xiao et al., *J. Virol.*, 73:3994 (1999).
Xiao et al., *J. Virol.*, 76:11505 (2002).
Yan et al., *J. Virol.*, 76:2043 (2002).
Yang et al., *J. Virol.*, 73:9468 (1999).
Yang et al., *J. Virol.*, 76:7651 (2002).
Young et al., *J. Virol.*, 74:3953 (2000).
Yukawa et al., *Atherosclerosis*, 141:125 (1998).
Zabner et al., *Gene Ther.*, 3:458 (1996).
Zabner et al., *J. Clin. Invest.*, 100:1144 (1997).
Zabner et al., *J. Virol.*, 70:6994 (1996).
Zabner et al., *J. Virol.*, 74:3652 (2000).
Zhang et al., *Am. J. Physiol.*, 270:C1326 (1996).
Zhang et al., *Hum. Gene Ther.*, 9:635 (1998).
Zhang et al., *J. Clin. Invest.*, 96:2997 (1995).
Zwacka et al., *Nat. Med.*, 4:698 (1998).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. A method to enhance recombinant adeno-associated (rAAV) transduction of a mammalian cell, the method comprising contacting the mammalian cell at the time of rAAV infection with an amount of an anthracycline and an amount of a tripeptide aldehyde that inhibits proteosome proteolytic activity that together more than additively enhance rAAV transduction.

2. The method of claim 1 wherein the rAAV comprises a marker gene or a selectable gene.

3. The method of claim 1 wherein one rAAV comprises a first recombinant DNA molecule comprising linked:

i) a first DNA segment comprising a 5' inverted terminal repeat (ITR) of AAV;
ii) a second DNA segment comprising a heterologous DNA; and
iii) a third DNA segment comprising a 3' ITR of AAV.

4. The method of claim 3 further comprising a second rAAV comprising a second recombinant DNA molecule comprising linked:
i) a first DNA segment comprising a 5' ITR of AAV, and
ii) a second DNA segment comprising a heterologous DNA which has sequences that are different than the sequences in the second DNA segment of the first recombinant DNA molecule; and
iii) a third DNA segment comprising a 3' ITR of AAV.

5. The method of claim 4 wherein the second DNA segment of the first recombinant DNA molecule comprises a portion of an open reading frame for a gene product, optionally operably linked to at least one transcriptional regulatory element, and a splice donor site 3' to the portion of the open reading frame, and wherein the second DNA segment of the second recombinant DNA molecule comprises a splice acceptor site 5' to the remainder of an open reading frame, which together with the second DNA segment of the first recombinant DNA molecule encodes a functional gene product.

6. The method of claim 5 wherein the transcriptional regulatory element is a promoter.

7. The method of claim 5 wherein the transcriptional regulatory element is an enhancer.

8. The method of claim 4 wherein the second DNA segment of the first recombinant DNA molecule comprises an enhancer and the second DNA segment of the second recombinant DNA molecule comprises an open reading frame encoding a functional gene product.

9. The method of claim 4 wherein the second DNA segment of the first recombinant DNA molecule comprises a promoter and the second DNA segment of the second recombinant DNA molecule comprises an open reading frame encoding a functional gene product.

10. The method of claim 1 wherein the cell is a lung cell, an epithelial cell, a liver cell, a muscle cell, a hematopoietic cell, a heart cell, or a neuronal cell.

11. The method of claim 5, 8 or 9 wherein the expression of the functional gene product is enhanced.

12. The method of claim 3 wherein the second DNA segment encodes a functional gene product.

13. The method of claim 5, 8, 9 or 12 wherein the functional gene product is a therapeutic peptide or polypeptide or a prophylactic peptide or polypeptide.

14. The method of claim 13 wherein the functional polypeptide is cystic fibrosis transmembrane conductance regulator, β-globin, γ-globin, tyrosine hydroxylase, glucocerebrosidase, aryl sulfatase A, factor VIII, dystrophin or erythropoietin.

15. The method of claim 1 wherein the anthracycline is doxorubicin, daunorubicin, idarubicin, or epirubicin, or the tripeptidyl aldehyde is LLnL or Z-LLL.

16. The method of claim 1 wherein the cell is a human cell, canine cell, murine cell, rat cell or rabbit cell.

17. The method of claim 1 wherein the cell is contacted with the anthracycline or the tripeptidyl aldehyde or a combination thereof before the cell is contacted with the virus.

18. The method of claim 1 wherein the cell is contacted with the virus before the cell is contacted with the anthracycline or the tripeptidyl aldehyde or a combination thereof.

19. The method of claim wherein the anthracycline or tripeptide aldehyde modulates rAAV trafficking in the cell.

20. The method of claim 1 wherein the anthracycline or tripeptide aldehyde modulates rAAV nucleic acid degradation in the cell.

21. The method of claim 1 wherein the anthracycline or tripeptide aldehyde modulates rAAV protein degradation in the cell.

22. The method of claim 1 wherein the anthracycline or tripeptide aldehyde modulates rAAV transport to the nucleus.

23. The method of claim 1 wherein the anthracycline or tripeptide aldehyde modulates viral genome transport to the nucleus.

24. A method to enhance rAAV transduction of a mammalian cell, the method comprising contacting the mammalian cell at the time of rAAV infection with an amount of a peptide that inhibits proteosome proteolytic activity and an amount of an anthracycline, selected from the group consisting of doxorubicin, duanorubicin, idarubicin and epirubicin, that together more than additively enhance rAAV transduction.

25. The method of claim 24 wherein the rAAV comprises a marker gene or a selectable gene.

26. The method of claim 24 wherein the cell is a lung cell, an epithelial cell, a liver cell, a heart cell, a hematopoietic cell, a muscle cell or a neuronal cell.

27. The method of claim 24 wherein the rAAV expresses a therapeutic or prophylactic gene product.

28. The method of claim 24 wherein the cell is a human cell, canine cell, murine cell, rat cell or rabbit cell.

29. The method of claim 24 wherein the anthracycline or peptide modulates microfilaments or microtubules.

30. The method of claim 24 wherein the anthracycline or peptide modulates rAAV trafficking in the cell.

31. The method of claim 24 wherein the anthracycline or peptide modulates rAAV nucleic acid degradation in the cell.

32. The method of claim 24 wherein the anthracycline or peptide modulates rAAV protein degradation in the cell.

33. The method of claim 24 wherein the anthracycline or peptide modulates rAAV transport to the nucleus.

34. The method of claim 24 wherein the anthracycline or peptide modulates viral genome transport to the nucleus.

35. The method of claim 24 wherein the anthracycline or peptide modulates subcellular localization of proteosomes.

36. The method of claim 1 wherein the anthracycline that is contacted with the mammalian cell is in a liposomal formulation.

37. The method of claim 36 wherein the anthracycline is doxorubicin.

38. The method of claim 24 wherein the doxorubicin, daunorubicin, idarubicin, or epirubicin is in a liposomal formulation.

* * * * *

UNITED STATES PATENT AND TRADEMARK OFFICE
CERTIFICATE OF CORRECTION

PATENT NO. : 7,749,491 B2  Page 1 of 1
APPLICATION NO. : 10/815262
DATED : July 6, 2010
INVENTOR(S) : John F. Engelhardt et al.

It is certified that error appears in the above-identified patent and that said Letters Patent is hereby corrected as shown below:

In column 1, lines 14-17, delete "This invention was made, at least in part, with a grant from the Government of the United States of America (grant HL58340 from the National Institutes of Health). The Government may have certain rights in the invention." and
insert -- This invention was made with a grant from the Government of the United States of America (grant HL58340 from the National Institutes of Health). The government has certain rights in the invention. --, therefor.

Signed and Sealed this

Seventeenth Day of August, 2010

David J. Kappos
*Director of the United States Patent and Trademark Office*

UNITED STATES PATENT AND TRADEMARK OFFICE
CERTIFICATE OF CORRECTION

Page 1 of 1

PATENT NO. : 7,749,491 B2
APPLICATION NO. : 10/815262
DATED : July 6, 2010
INVENTOR(S) : Engelhardt et al.

It is certified that error appears in the above-identified patent and that said Letters Patent is hereby corrected as shown below:

In Column 1, Lines 14-17, delete "This invention was made, at least in part, with a grant from the Government of the United States of America (grant HL58340 from the National Institutes of Health). The Government may have certain rights in the invention." and insert --This invention was made with government support under HL058340 awarded by the National Institutes of Health. The government has certain rights in the invention.-- therefor This certificate supersedes the Certificate of Correction issued August 17, 2010.

Signed and Sealed this
Twenty-first Day of April, 2020

Andrei Iancu
*Director of the United States Patent and Trademark Office*